us011369624B2

United States Patent
Ueda et al.

(10) Patent No.: US 11,369,624 B2
(45) Date of Patent: Jun. 28, 2022

(54) SALTS OF PRODRUGS OF PIPERAZINE AND SUBSTITUTED PIPERIDINE ANTIVIRAL AGENTS

(71) Applicant: VIIV HEALTHCARE UK (NO. 4) LIMITED, Middlesex (GB)

(72) Inventors: Yasutsugu Ueda, Wallingford, CT (US); Timothy P. Connolly, Wallingford, CT (US); John F. Kadow, Branford, CT (US); Nicholas A. Meanwell, Wallingford, CT (US); Tao Wang, Wallingford, CT (US); Chung-Pin H. Chen, Wallingford, CT (US); Kap-Sun Yeung, Wallingford, CT (US); Zhongxing Zhang, Wallingford, CT (US); David Kenneth Leahy, Somerset, NJ (US); Shawn K. Pack, Plainsboro, NJ (US); Nachimuthu Soundararajan, Kendall Park, NJ (US); Pierre Sirard, St. Jean sur Richelieu (CA); Kathia Levesque, Ste-Catherine (CA); Dominique Thoraval, Candiac (CA)

(73) Assignee: VIIV HEALTHCARE UK (No. 4) LIMITED

( * ) Notice: Subject to any disclaimer, the term of this patent is extended or adjusted under 35 U.S.C. 154(b) by 65 days.

(21) Appl. No.: 17/068,902

(22) Filed: Oct. 13, 2020

(65) Prior Publication Data

US 2021/0023098 A1   Jan. 28, 2021

Related U.S. Application Data

(63) Continuation of application No. 16/659,786, filed on Oct. 22, 2019, now abandoned, which is a
(Continued)

(51) Int. Cl.
*C07D 471/04* (2006.01)
*A61K 31/675* (2006.01)
(Continued)

(52) U.S. Cl.
CPC .......... *A61K 31/675* (2013.01); *A61K 31/497* (2013.01); *A61K 31/519* (2013.01);
(Continued)

(58) Field of Classification Search
CPC .......................... C07D 471/04; A61K 31/4545
(Continued)

(56) References Cited

U.S. PATENT DOCUMENTS 6,476,034 B2   11/2002   Wang et al.
7,354,924 B2   4/2008    Wang et al.
(Continued)

FOREIGN PATENT DOCUMENTS

WO   WO 00/76521 A   12/2000
WO   WO 01/62255 A   8/2001
(Continued)

OTHER PUBLICATIONS

Heimbach, et al. Pharmaceutical Research, 20(6): 848-856 (2003).
Stella, et al. Handbook of Experimental Pharmacology, Chapter 4, pp. 71-103 (1991).
Stella, et al. Drugs, 29(5): 455-473 (1985).
Stella, et al. Pharmacy International, 5(11): 276-279 (1984).
F. A. Dorwald. Side Reactions in Organic Synthesis, 2005, Wiley: VCH, Weinheim, p. IX of Preface.
Berge, et al. Journal of Pharmaceutical Sciences, 66(1): 132-150 (Jan. 1977).
Sriram, et al. Bioorganic & Medicinal Chemistry Letters, 14: 1085-1087 (2004).
(Continued)

*Primary Examiner* — Jeffrey H Murray
(74) *Attorney, Agent, or Firm* — Nora L. Stein; Scott S. Young

(57) ABSTRACT

This invention provides for prodrug Compounds I, pharmaceutical compositions thereof, and their use in treating HIV infection.

wherein:
X is C or N with the proviso that when X is N, $R^1$ does not exist;
W is C or N with the proviso that when W is N, $R^2$ does not exist;
V is C;
E is hydrogen or a pharmaceutically acceptable salt thereof; and
Y is selected from the group consisting of (Continued)

Also, this invention provides for intermediate Compounds II useful in making prodrug Compounds I.

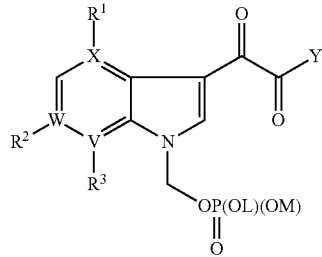

wherein:
L and M are independently selected from the group consisting of $C_1$-$C_6$ alkyl, phenyl, benzyl, trialkylsilyl, -2,2,2-trichloroethoxy and 2-trimethylsilylethoxy.

1 Claim, 23 Drawing Sheets

Related U.S. Application Data continuation of application No. 16/190,632, filed on Nov. 14, 2018, now abandoned, which is a continuation of application No. 15/704,100, filed on Sep. 14, 2017, now abandoned, which is a continuation of application No. 15/249,827, filed on Aug. 29, 2016, now abandoned, which is a continuation of application No. 14/704,183, filed on May 5, 2015, now abandoned, which is a continuation of application No. 14/249,638, filed on Apr. 10, 2014, now abandoned, which is a continuation of application No. 13/861,804, filed on Apr. 12, 2013, now Pat. No. 8,871,771, which is a continuation of application No. 13/429,838, filed on Mar. 26, 2012, now Pat. No. 8,461,333, which is a continuation of application No. 12/767,222, filed on Apr. 26, 2010, now Pat. No. 8,168,615, which is a continuation of application No. 11/066,745, filed on Feb. 25, 2005, now Pat. No. 7,745,625.

(60) Provisional application No. 60/635,231, filed on Dec. 10, 2004, provisional application No. 60/553,320, filed on Mar. 15, 2004.

(51) Int. Cl.
| | |
|---|---|
| *A61K 31/497* | (2006.01) |
| *C07F 9/572* | (2006.01) |
| *C07F 9/655* | (2006.01) |
| *C07F 9/6558* | (2006.01) |
| *C07F 9/6561* | (2006.01) |
| *C07F 9/06* | (2006.01) |
| *A61K 45/06* | (2006.01) |
| *A61K 31/519* | (2006.01) |
| *C07C 215/10* | (2006.01) |

(52) U.S. Cl.
CPC ............ *A61K 45/06* (2013.01); *C07C 215/10* (2013.01); *C07D 471/04* (2013.01); *C07F 9/062* (2013.01); *C07F 9/5728* (2013.01); *C07F 9/6561* (2013.01); *C07F 9/65515* (2013.01); *C07F 9/65586* (2013.01)

(58) Field of Classification Search
USPC ......................................... 546/193; 514/300
See application file for complete search history.

(56) References Cited

U.S. PATENT DOCUMENTS

| | | |
|---|---|---|
| 7,723,338 B2 | 5/2010 | Chen et al. |
| 7,745,625 B2 | 6/2010 | Ueda et al. |
| 7,776,863 B2 | 8/2010 | Lin et al. |
| 7,851,476 B2 | 12/2010 | Chen et al. |
| 8,168,615 B2 | 5/2012 | Ueda |
| 8,436,168 B2 | 5/2013 | Tripp |
| 8,461,333 B2 | 6/2013 | Ueda |
| 8,871,771 B2 | 10/2014 | Ueda |
| 9,249,168 B2 | 2/2016 | Eastgate |
| 2002/0061892 A1 | 5/2002 | Wang et al. |
| 2003/0069266 A1 | 4/2003 | Wang et al. |
| 2003/0020791 A1 | 11/2003 | Wang et al. |
| 2013/0253196 A1 | 9/2013 | Ueda et al. |

FOREIGN PATENT DOCUMENTS

| | | |
|---|---|---|
| WO | WO 02/04440 | 1/2002 |
| WO | WO 03/082881 A | 10/2003 |

OTHER PUBLICATIONS

Borisy, et al. Proceedings of the National Academy of Sciences of the United States of America, 100(13): 7977-7982 (Jun. 24, 2003).
Berge, et al. Journal of Pharmaceutical Sciences, 66(1): 1-19 (Jan. 1977).
Bastin, et al. Organic Process Research & Development, 4: 427-435 (2000).
Stahl, et al. Handbook of Pharmaceutical Salts, Properties, Selection and Use, 1-374 (2002).

SALTS OF PRODRUGS OF PIPERAZINE AND SUBSTITUTED PIPERIDINE ANTIVIRAL AGENTS

CROSS-REFERENCE TO RELATED APPLICATIONS

This application is a continuation application of U.S. Ser. No. 16/190,632, filed Nov. 14, 2018, now pending, which is a continuation application of U.S. Ser. No. 15/704,100, filed Sep. 14, 2017, now pending, which is a continuation application of U.S. Ser. No. 15/249,827, filed Aug. 29, 2016, abandoned, which is a continuation application of U.S. Ser. No. 14/704,183 filed May 5, 2015, abandoned, which is a continuation application of U.S. Ser. No. 14/249,638 filed Apr. 10, 2014, abandoned, which is a continuation application of U.S. Ser. No. 13/861,804 filed Apr. 12, 2013, now U.S. Pat. No. 8,871,771, which is a continuation application of U.S. Ser. No. 13/429,838 filed Mar. 26, 2012, now U.S. Pat. No. 8,461,333, which is a continuation application of U.S. Ser. No. 12/767,222 filed Apr. 26, 2010, now U.S. Pat. No. 8,168,615, which is a continuation application of U.S. Ser. No. 11/066,745 filed Feb. 25, 2005, now U.S. Pat. No. 7,745,625, which claims the benefit of U.S. Provisional Application Ser. No. 60/635,231 filed Dec. 10, 2004 and 60/553,320 filed Mar. 15, 2004. The entire teachings of the referenced applications are herein incorporated by reference in their entirety.

FIELD OF THE INVENTION

This invention provides compounds having drug and bio-affecting properties, their pharmaceutical compositions and method of use. In particular, the invention is concerned with new prodrug derivatives with antiviral activity. More particularly, the present invention relates to compounds useful for the treatment of HIV and AIDS.

BACKGROUND ART

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include ten nucleoside reverse transcriptase (RT) inhibitors or approved single pill combinations (zidovudine or AZT (or RETROVIR®), didanosine (or VIDEX®), stavudine (or ZERIT®), lamivudine (or 3TC or EPIVIR®), zalcitabine (or DDC or HMD®), abacavir succinate (or ZIAGEN®), tenofovir disoproxil fumarate salt (or VIREAD®), COMBIVIR® (contains −3TC plus AZT), TRIZIVIR® (contains abacavir, lamivudine, and zidovudine) and EMTRIVA® (emtricitabine); three non-nucleoside reverse transcriptase inhibitors: nevirapine (or VIRAMUNE®), delavirdine (or RESCRIPTOR®) and efavirenz (or SUSTIVA®), nine peptidomimetic protease inhibitors or approved formulations: saquinavir, indinavir, ritonavir, nelfinavir, amprenavir, lopinavir, KALETRA® (lopinavir and ritonavir), atazanavir (REYATAZ®), FOSAMPRENAVIR® and one fusion inhibitor which targets viral gp41 T-20 (FUZEON®). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6-14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref 15). A recent overview of non-nucleoside reverse transcriptase inhibitors: "Perspectives on novel therapeutic compounds and strategies for the treatment of HIV infection". has appeared (Buckheit, reference 99). A review covering both NRTI and NNRTIs has appeared (De Clercq, reference 100). An overview of the current state of the HIV drugs has been published (De Clercq, reference 101).

Several indole derivatives including indole-3-sulfones, piperazino indoles, pyrazino indoles, and 5H-indolo[3,2-b][1,5]benzothiazepine derivatives have been reported as HIV-1 reverse transcriptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref. 4). 3-Substituted indole natural products (Semicochliodinol A and B, didemethylasterriquinone and isocochliodinol) were disclosed as inhibitors of HIV-1 protease (Fredenhagen et al, Ref. 22).

Structurally related aza-indole amide derivatives have been disclosed previously (Kato et al, Ref. 23(a); Levacher et al, Ref. 23(b); Dompe Spa, WO-09504742, Ref. 5(a); SmithKline Beecham PLC, WO-09611929, Ref. 5(b); Schering Corp., U.S. Pat. No. 5,023,265, Ref. 5(c)). However, these structures differ from those claimed herein in that they are monoaza-indole mono-amide rather than oxoacetamide derivatives, and there is no mention of the use of these compounds for treating viral infections, particularly HIV.

New drugs for the treatment of HIV are needed for the treatment of patients who become resistant to the currently approved drugs described above which target reverse transcriptase or the protease. One approach to obtaining these drugs is to find molecules which inhibit new and different targets of the virus. A general class of inhibitors which are under active study are HIV entry inhibitors. This general classification includes drugs aimed at several targets which include chemokine receptor (CCR5 or CXCR4) inhibitors, fusion inhibitors targeting viral gp41, and inhibitors which prevent attachment of the viral envelope, gp120, the its human cellular target CD4. A number of reviews or general papers on viral entry inhibitors have recently appeared and some selected references are:

*Chemokine receptor antagonists as HIV entry inhibitors.* Expert Opinion on Therapeutic Patents (2004), 14(2), 251-255.

*Inhibitors of the entry of HIV into host cells.* Meanwell, Nicholas A.; Kadow, John F. Current Opinion in Drug Discovery & Development (2003), 6(4), 451-461.

*Virus entry as a target for anti-HIV intervention.* Este, Jose A. Retrovirology Laboratory irsiCaixa, Hospital Universitari Germans Trias i Pujol, Universitat Autonoma de Barcelona, Badalona, Spain. Current Medicinal Chemistry (2003), 10(17), 1617-1632.

*New antiretroviral agents.* Rachline, A.; Joly, V. Service de Maladies Infectieuses et Tropicales A, Hopital Bichat-Claude Bernard, Paris, Fr. Antibiotiques (2003), 5(2), 77-82.

*New antiretroviral drugs.* Gulick, R. M. Cornell HIV Clinical Trials Unit, Division of International Medicine and Infectious Diseases, Weill Medical College of Cornell University, New York, N.Y., USA. Clinical Microbiology and Infection (2003), 9(3), 186-193.

*Sensitivity of HIV-1 to entry inhibitors correlates with envelope/coreceptor affinity, receptor density, and fusion kinetics.* Reeves, Jacqueline D.; Gallo, Stephen A.; Ahmad, Navid; Miamidian, John L.; Harvey, Phoebe E.; Sharron, Matthew; Pohlmann, Stefan; Sfakianos, Jeffrey N.; Derdeyn, Cynthia A.; Blumenthal, Robert; Hunter, Eric; Doms, Robert W. Department of Microbiology, University of Pennsylvania, Philadelphia, Pa., USA. Proceedings of the National Academy of Sciences of the United States of America (2002), 99(25), 16249-16254. CODEN: PNASA6 ISSN: 0027-8424.

*Opportunities and challenges in targeting HIV entry.* Biscone, Mark J.; Pierson, Theodore C.; Doms, Robert W. Department of Microbiology, University of Pennsylvania, Philadelphia, Pa., USA. Current Opinion in Pharmacology (2002), 2(5), 529-533.

*HIV entry inhibitors in clinical development.* O'Hara, Bryan M.; Olson, William C. Progenics Pharmaceuticals, Inc., Tarrytown, N.Y., USA. Current Opinion in Pharmacology (2002), 2(5), 523-528.

*Resistance mutation in HIV entry inhibitors.* Hanna, Sheri L.; Yang, Chunfu; Owen, Sherry M.; Lal, Renu B. HIV Immunology and Diagnostics Branch, Division of AIDS, STD, Atlanta, Ga., USA. AIDS (London, United Kingdom) (2002), 16(12), 1603-1608.

*HIV entry: are all receptors created equal?* Goldsmith, Mark A.; Doms, Robert W. Genencor International, Inc., Palo Alto, Calif., USA. Nature Immunology (2002), 3(8), 709-710. CODEN: NIAMCZ ISSN: 1529-2908.

*Peptide and non-peptide HIV fusion inhibitors.* Jiang, Shibo; Zhao, Qian; Debnath, Asim K. The New York Blood Center, Lindsley F. Kimball Research Institute, New York, N.Y., USA. Current Pharmaceutical Design (2002), 8(8), 563-580.

There are two general approaches for preventing the initial attachment of viral membrane, gp120, to cellular CD4 which are a) inhibitors which bind to human CD4 and block attachment of viral envelope (gp120) and b) inhibitors which bind to viral gp120 and prevent the binding of cellular CD4. The second approach has the advantage that it inhibits a viral target and, if selective, minimizes the chances of perturbing normal human physiology or causing side effects. With this approach, in order to overcome a spectrum in susceptability to drug caused by variability in the sequences of viral envelope and to suppress the development of resistance, it is important to achieve plasma levels of drug that is as many multiples as possible over the EC50 or other measure of the concentration of drug needed to kill virus. As discussed later, these inhibitors appear safe so to be of wide utility in man they, therefore, must be able to achieve exposure levels sufficient to enable virus suppression. The higher the multiple of drug levels over the level needed to inhibit viral growth, the more efficiently and completely the suppression of viral replication and the lower the chance for viral mutation and subsequent development of resistance to treatment. Thus, important aspects contributing to the efficacy of viral attachment inhibitors include not only intrinsic potency and safety, but also pharmacokinetics and pharmaceutical properties which allow attainment of high plasma exposure at a physically feasible dose and an acceptable, preferably convenient, administration schedule. This invention describes a prodrug approach which greatly enhances the maximum exposure and the ability to increase exposure multiples (i.e., multiples of drug exposure greater than $EC_{50}$ or $EC_{90}$) upon dose escalation of efficacious members of a previously disclosed class of HIV attachment inhibitors.

A series of recent publications and disclosures characterize and describe a compound labelled as BMS-806, an initial member of a class of viral entry inhibitors which target viral gp-120 and prevent attachment of virus to host CD4.

*A small molecule HIV-1 inhibitor that targets the HIV-1 envelope and inhibits CD4 receptor binding*. Lin, Pin-Fang; Blair, Wade; Wang, Tao; Spicer, Timothy; Guo, Qi; Zhou, Nannan; Gong, Yi-Fei; Wang, H.-G. Heidi; Rose, Ronald; Yamanaka, Gregory; Robinson, Brett; Li, Chang-Ben; Fridell, Robert; Deminie, Carol; Demers, Gwendeline; Yang, Zheng; Zadjura, Lisa; Meanwell, Nicholas; Colonno, Richard. Proceedings of the National Academy of Sciences of the United States of America (2003), 100(19), 11013-11018.

*Biochemical and genetic characterizations of a novel human immunodeficiency virus type 1 inhibitor that blocks gp120-CD4 interactions*. Guo, Qi; Ho, Hsu-Tso; Dicker, Ira; Fan, Li; Zhou, Nannan; Friborg, Jacques; Wang, Tao; McAuliffe, Brian V.; Wang, Hwei-gene Heidi; Rose, Ronald E.; Fang, Hua; Scamati, Helen T.; Langley, David R.; Meanwell, Nicholas A.; Abraham, Ralph; Colonno, Richard J.; Lin, Pin-fang. Journal of Virology (2003), 77(19), 10528-10536.

*Method using small heterocyclic compounds for treating HIV infection by preventing interaction of CD4 and gp120*. Ho, Hsu-Tso; Dalterio, Richard A.; Guo, Qi; Lin, Pin-Fang. PCT Int. Appl. (2003), WO 2003072028A2.

*Discovery of 4-benzoyl-1-[(4-methoxy-1H-pyrrolo[2.3-b]pyridin-3-yl)oxoacetyl]-2-(R)*-methylpiperazine *(BMS-378806): A Novel HIV-1 Attachment Inhibitor That Interferes with CD4-gp120 Interactions*. Wang, Tao; Zhang, Zhongxing; Wallace, Owen B.; Deshpande, Milind; Fang, Haiquan; Yang, Zheng; Zadjura, Lisa M.; Tweedie, Donald L.; Huang, Stella; Zhao, Fang; Ranadive, Sunanda; Robinson, Brett S.; Gong, Yi-Fei; Ricarrdi, Keith; Spicer, Timothy P.; Deminie, Carol; Rose, Ronald; Wang, Hwei-Gene Heidi; Blair, Wade S.; Shi, Pei-Yong; Lin, Pin-fang; Colonno, Richard J.; Meanwell, Nicholas A. Journal of Medicinal Chemistry (2003), 46(20), 4236-4239.

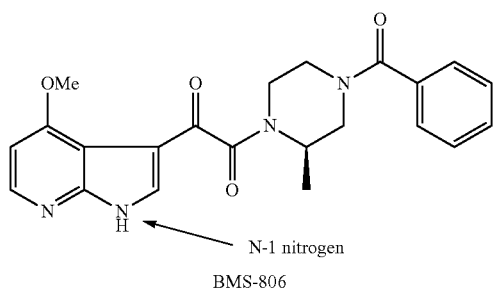 [SMILES: COc1ccnc2[nH]cc(C(=O)C(=O)N3CCN(C(=O)c4ccccc4)C[C@H]3C)c12]

BMS-806

Indole, azaindole and other oxo amide containing derivatives from this class have been disclosed in a number of different PCT and issued U.S. patent applications (Reference 93-95, 106, 108, 109, 110, 111, and 112) and these references directly relate to the compounds in this patent application. None of the compounds in these references of prior art contain a methyl dihydrogen phosphate (or salt or mono or di ester of the phosphate group) group appended to the N−1 nitrogen and thus the compounds of this current invention represent new compositions of matter. This moiety dramatically increases the utility of the parent compounds by functioning as a prodrug modification which dramatically increases the maximum systemic exposure of the parent molecules in preclinical models of human exposure. We believe nothing in the prior art references can be construed to disclose or suggest the novel compounds of this invention and their use to inhibit HIV infection.

This invention describes prodrugs of specific indole and azaindole ketopiperazine amides which are extremely effective at improving the oral utility of the parent molecules as antiviral agents particularly as anti HIV drugs. The parent molecules are relatively insoluble, and suffer from dissolution-limited or solubility limited absorption which means as the dose is increased above a maximum level, less and less of the drug dissolves in time to be absorbed into the circulation and they are instead passed through the body to be eliminated as waste. The improvements offered by the prodrug are necessary, for they allow drug levels in the body to be increased significantly, which provides greater efficacy vs HIV virus and in particular vs less sensitive or more resistant strains. Prodrugs are especially important for this class of drugs since the drugs target the envelope of the HIV virus, a target which varies from strain to strain and thus in which maximum exposure multiples are desired. Because with a prodrug, more of the drug will be absorbed and reach the target, pill burden, cost to the patient and dosing intervals could be reduced. The identification of prodrugs with these properties is difficult and neither straightforward, nor is a clear path to successful prodrug design disclosed in the literature. There is no clear prior art teaching of which prodrug chemistry to employ nor which will be most effective. The following discussion and data will show that the prodrugs described in this invention work surprisingly well. They release parent drug extremely quickly and efficiently and enhance the exposure to levels which are higher than reported for many prodrugs.

The use of prodrug strategies or methodologies to markedly enhance properties of a drug or to overcome an inherent deficiency in the pharmaceutic or pharmacokinetic properties of a drug can be used in certain circumstances to markedly enhance the utility of a drug. Prodrugs differ from formulations in that chemical modifications lead to an entirely new chemical entity which upon administration to the patient, regenerates the parent molecule within the body. A myriad of prodrug strategies exist which provide choices in modulating the conditions for regeneration of the parent drug, the physical, pharmaceutic, or pharmacokinetic properties of the prodrug, and the functionality to which the prodrug modifications may be attached. However, none of these publications teach what approach to use that result in the specific prodrugs herein invented. A number of reviews or discussions on prodrug strategies have been published and a nonexhaustive list is provided below:

*Hydrolysis in Drug and prodrug Metabolism.* Richard Testa and Joachim Mayer, 2003 Wiley-VCH publisher, ISBN 3-906390-25-x.

*Design of Prodrugs*, Bundgard, H. Editor, Elsevier, Amsterdam, 1985.

*Pharmacokinetics of drug targeting: specific implications for targeting via prodrugs.* Stella, V. J.; Kearney, A. S. Dep. Pharm. Chem., Univ. Kansas, Lawrence, Kans., USA. Handbook of Experimental Pharmacology (1991), 100 (Targeted Drug Delivery), 71-103. CODEN: HEPHD2 ISSN: 0171-2004. Journal; General Review written in English. CAN 116:158649 AN 1992:158649 CAPLUS (Copyright 2004 ACS on SciFinder (R)).

*Prodrugs. Do they have advantages in clinical practice?* Stella, V. J.; Charman, W. N. A.; Naringrekar, V. H. Dep. Pharm. Chem., Univ. Kansas, Lawrence, Kans., USA. Drugs (1985), 29(5), 455-73. CODEN: DRUGAY ISSN: 0012-6667. Journal; General Review written in English. CAN 103:115407 AN 1985:515407 CAPLUS (Copyright 2004 ACS on SciFinder (R)).

*Trends in prodrug research.* Stella, V. J.; Naringrekar, V. H.; Charman, W. N. A. Dep. Pharm. Chem., Univ. Kansas, Lawrence, Kans., USA. Pharmacy International (1984), 5(11), 276-9. CODEN: PHINDQ ISSN: 0167-3157. Journal; General Review written in English. CAN 102:72143 AN 1985:72143 CAPLUS (Copyright 2004 ACS on SciFinder (R)).

While some technologies are known to have specific applications, ie to improve solubility or absorption for example, the development of prodrugs remains, to a great extent, an empirical exercise. Thus a number of strategies or chemical modifications must usually be surveyed and the resulting compounds evaluated in biological models in order to ascertain and gauge the success of prodrug strategies.

A successful prodrug strategy requires that a chemically reactive site in a molecule be modified via addition of the prodrug moiety and that later under the desired conditions in the patients the prodrug moiety will unmask and release parent drug. The prodrug molecule must have suitable stability in an acceptable dosage form prior to dosing. In addition, the release mechanism must allow the prodrug to regenerate parent drug efficiently and with kinetics that provide therapeutic levels of parent drug at the disease target. In our molecules, the indole or azaindole nitrogen represents an acceptable point of attachment for a prodrug moiety.

The suggestion that a phosphate group joined by an appropriate chemistry or linker can enhance oral exposure of a parent drug is a concept known in the art. However, as will be discussed below, it is unpredictable to know that if using a phosphate group to create a prodrug will work with a given drug substance. The phosphate group temporarily alters the physical properties of the drug and is, thus, a prodrug which increases the aqueous solubility of the resulting molecule, until it is cleaved by alkaline phosphatase in the body or other chemical reaction of a rationally designed linker. For example, in the following reference, the authors conclude phosphates may improve oral efficacy. In this reference a phosphate derivative of an alcohol group in a poorly water soluble, lipophilic drug displayed better oral bioavailbility than two other prodrugs and appeared to offer an advantage over the parent molecule which possessed low oral bioavailability.

*Evaluation of a targeted prodrug strategy to enhance oral absorption of poorly water-soluble compounds*. Chan, O. Helen; Schmid, Heidi L.; Stilgenbauer, Linda A.; Howson, William; Horwell, David C.; Stewart, Barbra H. Pharmaceutical Research (1998), 15(7), 1012-1018.

Two very pertinent and recent papers have published which discuss the difficulties of identifying phosphate prodrugs with significant advantages over the parent molecule for oral use.

A paper entitled "Absorption Rate Limit Considerations for Oral Phosphate Prodrugs" by Tycho Heimbach et. al. in *Pharmaceutical Research* 2003, Vol 20, No. 6 pages 848-856 states "The surprising inability to use phosphate prodrugs by the oral route prompted a study in a system being used to screen drug candidates for absorption potential." This paper also reviews the reasons many phosphate prodrugs were unsuitable for oral use and discusses several potential rate limiting factors in the drug absorption process. The paper also identifies the few successful applications. The paper attempts to identify properties which may make some drugs suitable for oral delivery as phosphate prodrugs but the message is clear that this is still an empirical science. This is emphasized by the conclusions of a second paper by the same authors entitled "Enzyme mediated precipitation of parent drugs from their phosphate prodrugs" by Tycho Heimbach et. al in *International Journal of Pharmaceutics* 2003, 261, 81-92. The authors state in the Abstract that many oral phosphate prodrugs have failed to improve the rate or extent of absorption compared to their insoluble parent drugs. Rapid parent drug generation via intestinal alkaline phosphatase can result in supersaturated solutions, leading to parent drug precipitation. This would limit utility of the oral phopshates. The conclusions of this paper state (quoted) "In summary, precipitation of parent drugs from phosphate prodrugs can be enzyme mediated. Precipitation of certain drugs can also be observed for certain drugs in the Caco-2 model. Since induction times decrease and nucleation times increase with high supersaturation ratios, parent drugs can precipitate when targeted prodrugs concentration are much higher than the parent drug's solubility ie for parent drugs with high supersaturation ratios. The extent to which a parent drug precipitates during conversion of the prodrug is dependent on the prodrug to parent conversion rates, prodrug effect on the precipitation of parent drug, and the solubilization of the parent drug." As can be seen by the author's conclusion, the process is a complex one and is dependent on many factors which are impossible to predict in advance such as supersaturation ratios, rate of prodrug conversions in vivo, and ability of the intestinal milieu to solubilize parent and prodrug mixtures.

The two references by Heimbach describe the clinical status of phosphate prodrugs and discuss the many failures and few successful examples. One example of a clinical failure and one example of a success are provided below:

ETOPOSIDE® is an anticancer drug which is administered either via iv or oral routes. Etoposide phosphate prodrugs are used clinically, but these structures differ from the derivatives of the current application as this prodrug contains a phosphate formed by direct attachment to a phenol moiety of the parent drug. The main reasons for preparing a phosphate prodrug of the drug etoposide were to improve intravenous use via increased solubility and reduction of excipients. Although the phosphate prodrug was evaluated orally both preclinically and clinically it is only used clinically for iv administration.

*Synthesis of etoposide phosphate. BMY-40481: a water-soluble clinically active prodrug of etoposide*. Saulnier, Mark G.; Langley, David R.; Kadow, John F.; Senter, Peter D.; Knipe, Jay O.; Tun, Min Min; Vyas, Dolatrai M.; Doyle, Terrence W. Bristol-Myers Squibb Co., Wallingford, Conn., USA. Bioorganic & Medicinal Chemistry Letters (1994), 4(21), 2567-72 and references therein.

As can be seen from the following two references, the benefits of the phosphate moiety for oral dosing were not clear.

*Randomized comparison of etoposide pharmacokinetics after oral etoposide phosphate and oral etoposide*. De Jong, R. S.; Mulder, N. H.; Uges, D. R. A.; Kaul, S.; Winograd, B.; Sleijfer, D. Th.; Groen, H. J. M.; Willemse, P. H. B.; van der Graaf, W. T. A.; de Vries, E. G. E. Department of Medical Oncology, University Hospital Groningen, Groningen, Neth. British Journal of Cancer (1997), 75(11), 1660-1666. This paper compared parent and prodrug directly and concluded that oral etoposide phosphate does not offer a clinically relevant benefit over oral etoposide.

*Etoposide bioavailability after oral administration of the prodrug etoposide phosphate in cancer patients during a phase I study*. Chabot, G. G.; Armand, J.-P.; Terref, C.; De Fomi, M.; Abigerges, D.; Winograd, B.; Igwemezie, L.; Schacter, L.; Kaul, S.; et al. Department Medicine, Gustave-Roussy Institute, Villejuif, Fr. Journal of Clinical Oncology (1996), 14(7), 2020-2030.

This earlier paper found that compared with literature data, oral EP had a 19% higher F value compared with oral E either at low or high doses. They concluded this higher F in E from oral prodrug EP appears to be a pharmacological advantage that could be of potential pharmacodynamic importance for this drug. However the previously mentioned study which reached opposite conclusions was done later and it appears that the direct comparison data was more valid. Thus adding a phosphate group to improve solubility is not a guarantee of improved oral efficacy.

A phosphate prodrug of the HIV protease inhibitor Amprenavir was prepared and is the active ingredient of what has now become an improved drug for oral use. This is an example of a rare success from this approach. The phosphate is directly attached to a hydroxy moiety and serves to enhance solubility. Fosamprenavir alone or in combination with another protease inhibitor ritonavir, which serves to inhibit Cytochrome P450 3A4-mediated metabolic deactivation, allow patients to receive fewer pills, smaller pills (due to the need for less excipients), and to employ a less frequent dosing schedule. Clearly, the structure of Amprenavir is significantly different than the molecules of the present invention and does not predict success with other classes of drugs or phosphate linker chemistry. Two references on Fosamprenavir are included below but most recent data can be found by searching a database well known in the art such as IDDB (A commercial database called Investigational Drugs Database produced by Current Drugs Ltd.).

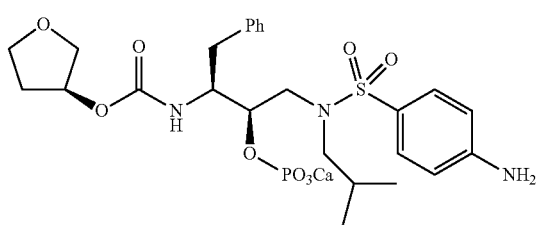

*Fosamprenavir vertex Pharmaceuticals/GlaxoSmithKline.* [*Erratum to document cited in CA*138:130388]. Corbett, Amanda H.; Kashuba, Angela D. M. School of Pharmacy, The University of North Carolina Hospitals, Chapel Hill, N.C., USA. Current Opinion in Investigational Drugs (PharmaPress Ltd.) (2002), 3(5), 824.

*Fosamprenavir Vertex Pharmaceuticals/GlaxoSmithKline.* Corbett, Amanda H.; Kashuba, Angela D. M. School of Pharmacy, The University of North Carolina Hospitals, Chapel Hill, N.C., USA. Current Opinion in Investigational Drugs (PharmaPress Ltd.) (2002), 3(3), 384-390.

Searching the literature for examples which can be found listed under keywords "prodrugs of indoles" or "prodrugs of azaindoles" identify a number of references that have been described. We are not aware of any references in which azaindole prodrugs were prepared via use of a methyl dihydrogen phosphate (or salt or mono or di ester of the phosphate group) moiety attached to N-1.

Regarding indole phosphate prodrugs, the publication by Zhu et. al. describes a study to find an effective phosphate prodrug of PD 154075. In this molecule, either the direct indole phosphate or a methyl dihydrogen phosphate or salt prodrug of the indole nitrogen were unsuitable prodrugs due to a slow rate of regenerating the parent molecule. Thus the novel and complex linker depicted below was developed to incorporate a solubilizing phosphate.

*Phosphate prodrugs of PD 154075.* Zhu, Zhijian; Chen, Huai-Gu; Goel, Om P.; Chan, O. Helen; Stilgenbauer, Linda A.; Stewart, Barbra H. Division of Warner-Lambert Company, Chemical Development, Parke-Davis Pharmaceutical Research, Ann Arbor, Mich., USA. Bioorganic & Medicinal Chemistry Letters (2000), 10(10), 1121-1124.

I

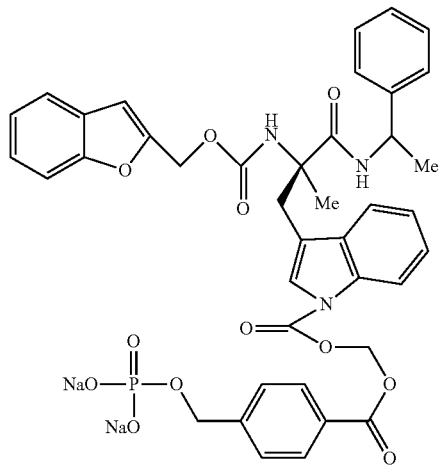

Many of the references describe the design of prodrugs for purposes other than overcoming dissolution-limited absorption. A number of the prodrugs are not attached to the indole or azaindole nitrogen or are designed to release radical intermediates rather than the parent drug. The prodrugs described in this art and their properties do not provide obvious solutions for improving the properties of the parent HIV attachment inhibitors.

It has now been found that new methyl dihydrogen phosphate prodrugs and pharmaceutically acceptable salts of the general structure shown below are useful as anti HIV agents with a new mechanism that is currently not employed by existing drugs. The need for drugs with new mechanisms is great since patients are left with no options if they become resistant to the current drug classes. In addition, drugs with new mechanisms can be used in combinations with known classes of inhibitors to cover the emergence of resistance to these drugs since strains of resistant virus are likely still susceptible to drugs with an alternative mechanism.

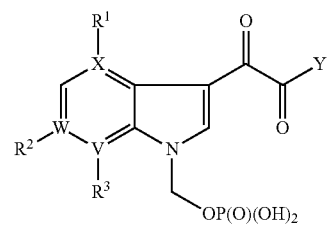

We have found that these prodrugs are more water soluble than the parent molecules, and rapidly convert to the parents after oral dosing in rodents or in in vitro assays with human enzymes or tissues. In addition, in one oral dose escalation study, a prodrug provided surprising enhancements in drug exposure (AUC) and maximum concentration (Cmax) as the dose increased. These predictive studies suggest these prodrugs should provide advantages in dogs and humans.

IVa

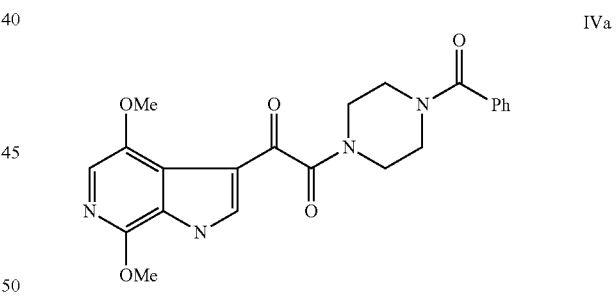

The parent compound IVa has been studied in human clinical trials. The compound was dosed in healthy human volunteers. A graph of the exposure vs dose is shown in FIG. 1.

As can be seen, single doses of a capsule formulation (red triangles) ranged in size from 200-2400 mgs in 200 mg increments. It is also readily apparent from the oral AUCs, that increases in drug exposure increased much more slowly and less than proportionally with dose. In fact the differences or increase in exposure above 800 mgs is minimal. With the dose ratios of 1:2:4:6:9:12 for capsule treatment under fasted condition, the ratios of mean Cmax and AUC values are 1:1.3:2.4:2.3:2.1:2.7 and 1:1.5:2.3:2.0:1.9:2.4, respectively. Between 200-800 mg dose range the increases in systemic exposure is dose-related although less than dose-proportional, while such exposure is dose independent above dose of 800 mg. This phenomenon indicates that the absorption of Compound IVa with the capsule formulation used is saturable under fasted conditions.

The dose proportionality in systemic exposure seems to be much better presented under fed condition (high fat meal) as ratios of Cmax and AUC are 1.6 and 1.5, respectively, when the dose ratio is 1:2.3 (800 mg vs. 1800 mg). As can be seen by comparing the single 200 mg dose of a solution of IVa (dark red square) with that of the 200 mg capsule dose, exposure from the solution was higher. Dosing with a solution increased Compound IVa exposure. The Cmax and AUC of the solution were approximately 8- and 3-fold, respectively, of those of the capsule (200 mg). The relative bioavailability (32%) of the capsule to the solution formulation suggests absorption is dissolution rate-limited, suggesting a potential to enhance systemic exposure by improving the formulation.

A high fat meal had a positive food-effect on the compound. The Cmax after a fed treatment were approximately 2.6 and 4.6 fold for 800 and 1800 mg doses, respectively, of those of the fast treatment. The AUCs after a fed treatment were approximately 2.5 and 4.7 fold for 800 and 1800 mg doses, respectively, of those of the fasted treatment. The relative bioavailability (fed vs. fasted) values were 293% and 509% for 800 mg and 1800 mg doses, respectively. The median Tmax changed from 1.25 or 2 (fasted) to 4 (fed) hours.

For the 800 mg capsule with food, the average plasma concentration is 1001 and 218 ng/mL at 8 and 12 hours post dose, respectively. The results supported a q12 h or q8 h dosing regimen for a targeted Cmin value of at least 200 ng/mL after multiple doses. This value was selected based on preclinical data. A further summary of some of this data presented as a bar graph is shown in the second bar graph in FIG. 2B.

Multiple Dose Study in Healthy Humans

A placebo-controlled, ascending multiple-dose study to evaluate the safety, tolerability and pharmacokinetics of Compound IVa in healthy human subjects was carried out. Dosing was continued at 12 h intervals for 14 days. In summary, the preliminary PK results indicated that, after single and multiple Q12H doses of Compound IVa, the exposure is generally dose proportional over the dose ranges of 400 to 1200 mg and 400 to 800 mg with high fat meal and light meal, respectively, the exposure seems to be dose independent above these dose levels with the different meal types, the accumulation is low to moderate (up to ~1.5 fold), and that there is a diurnal variation in the exposure in that exposure is higher after an evening dose than that after a morning dose. Thus, the exposure was better when dosing was combined with a high fat meal and exposure increases with dose were higher with a high fat meal.

This is similar to the results obtained in the above single dose study.

Multiple Dose Study in HIV Patients

Based on the exposure data from the studies in normal volunteers, an efficacy study was carried out in HIV patients. An initial disclosure of this data has been made in a talk and published abstract. "Antiviral Activity, Safety, and Tolerability of a Novel, Oral Small-Molecule HIV-1 Attachment Inhibitor, IVa, in HIV-1-Infected Subjects" G. Hanna, J. Lalezari, J. Hellinger, D. Wohl, T. Masterson, W. Fiske, J. Kadow, P-F. Lin, M. Giordano, R. Colonno, D. Grasela. Abstract J-32, Feb. 11, 2004, 11th Conference on Retroviruses and Opportunistic Infections (CROI), San Francisco, Calif. The study design included HIV+ adults who were either antiretroviral therapy naïve or off antiretroviral therapy for ≥16 weeks. Their CD4 counts were required to be ≥250 cells/mm3 and plasma HIV-1 RNA needed to be in the range 5,000-500,000 c/mL. There were 15 subjects in each dose arm and the ratio of patients receiving drug: placebo was 4:1.

The placebo-controlled, sequential study of IVa utilized an initial dose arm of 800 mg PO every 12 h followed by a second dosing arm of 1800 mg PO administered every 12 h. It is important to note that drug was administered in a capsule and in combination with a high fat meal to increase exposure and plasma levels. Study drug was administered for 7 days and the morning of Day 8. Subjects were followed for 14 days.

| Study Results (for 18 of the 24 Patients Receiving Drug IVa) | | | |
|---|---|---|---|
| | | Compound IVa | Placebo |
| Day 8 Change in HIV RNA | Mean (SD) | −0.72 (0.51) | −0.02 (0.40) |
| Over 14 days, log10 c/mL | Range | +0.34 to −1.37 | +0.45 to −0.26 |
| Maximal change in HIV RNA | Mean (SD) | −1.00 (0.50) | −0.30 (0.08) |
| Over 14 days, log10 c/mL | Range | −0.32 to −1.60 | −.22 to −0.38 |
| Day 8 Change in CD4, | Mean (SD) | 106 (151) | 6 (57) |
| cells/mm3 | Range | −214 to +272 | −35 to +47 |

| Study Results (for 18 of the 24 Patients Receiving Drug IVa) | | | |
|---|---|---|---|
| | | Compound IVa | Placebo |
| Maximal Change in | >0.5 log10 c/mL | 8 (67%) | 0 |
| HIV RNA Over 14 | >1.0 log10 c/mL | 7 (58%) | 0 |
| days n (%) | >1.5 log10 c/mL | 3 (25%) | |

1. As can be seen by the data for the 800 mg dosing level in combination with a high fat meal, significant antiviral activity was observed. However, only 58% of patients had >1.0 log drop in viral load. A more robust antiviral response was seen with the 1800 mg dosing regimen with a high fat meal where the mean response was a −0.96 log 10 drop in viral load. This data shows that this drug has significant antiviral activity at doses of 800 mg and 1800 mg (and thus in between) every 12 hours in combination with a high fat meal and therefore it could play a significant role in combination therapy. An updated summary of the results with BMS-043 in man can be obtained by viewing the abstract or slides from the oral presentation: "Antiviral Activity, Safety, and Tolerability of a Novel, Oral Small-Molecule HIV-1 Attachment Inhibitor, BMS-488043, in HIV-1-Infected Subjects" G. Hanna, J. Lalezari, J. Hellinger, D. Wohl, T. Masterson, W. Fiske, J. Kadow, P-F. Lin, M. Giordano, R. Colonno, D. Grasela. Abstract J-32, Feb. 11, 2004, 11th Conference on Retroviruses and Opportunistic Infections (CROI), San Francisco, Calif.

Unfortunately, it will be unfeasible to deliver this drug chronically over many months involving administration of a total of 9 capsules of 200 mg each, twice a day in combination with a high fat meal for obvious health reasons so a new formulation will be needed which provides increased exposure from a lower dose and which eliminates the need for a high fat meal.

Thus the clinical data shows that a method for improving the exposure of this drug from lower doses and in the absence of a high fat meal is necessary.

Thus the initial data on the prodrugs of this invention surprisingly predicts they will improve the exposure of molecules such as IVa and deliver the parent drugs in concentrations that will allow the drugs to be used in the absence of high fat meals, with lower capsule burden, and chronically as a component of antiretroviral therapy.

Initial data obtained from dosing solid capsules of either the prodrug Iab (lysine salt) or solid parent molecule (IVa) to dogs are summarized in the first bar graph FIG. 2A of FIG. 2. As can be seen, after dosing prodrug Iab (mono lysine salt) either in fasted or dogs fed a high fat meal, the exposure is surprisingly high when compared to dosing parent molecule. Also, the effect of fed vs fasted state is minimal if any for the prodrug yet has an obvious effect on the exposure after dosing the solid parent molecule. Thus, surprisingly, the exposure of parent molecule after dosing of prodrug, shows no dependence on a high fat meal which predicts for more consistent exposure levels after dosing than those from parent molecule. The bar graph in FIG. 2B summarizes the previously discussed human data for parent molecule IVa and shows the dependence of exposure for the molecule on the high fat meal, the non proportional increases in exposure vs dose, and the better exposure from dosing a solution rather than solid formulation. As discussed below, this shows dissolution or absorption rate limited exposure which in preclinical models, appears to be surprisingly improved via use of the phosphate prodrug. The use of phosphate prodrugs also increased exposure in fasted dogs vs parent for two other prodrugs. Details of these experiments are contained in the experimental section. In addition, details from various studies in rats, dogs, and monkeys for two additional prodrug examples and in rats for another two prodrugs demonstrate the surprising utility of these prodrugs to increase exposure over that obtained parent molecule at doses which correlate to those likely to be of utility for the treatment and inhibition of HIV viral replication.

REFERENCES CITED

Patent Documents

1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.
3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxyamides as antitussive agents. PCT WO 95/04742 (Dompe Spa). (b) Cassidy, F.; Hughes, I.; Rahman, S.; Hunter, D. J. Bisheteroaryl-carbonyl and carboxamide derivatives with 5HT 2C/2B antagonists activity. PCT WO 96/11929. (c) Scherlock, M. H.; Tom, W. C. Substituted 1H-pyrrolopyridine-3-carboxamides. U.S. Pat. No. 5,023,265. (d) Hutchison, D. R.; Martinelli, M. J.; Wilson, T. M. Preparation or pyrrolo[2,3-d]pyrimidines as sPLA2 inhibitors PCT WO 00/00201.

OTHER PUBLICATIONS

6. Larder, B. A.; Kemp, S. D. Multiple mutations in the HIV-1 reverse transcriptase confer high-level resistance to zidovudine (AZT). *Science*, 1989, 246, 1155-1158.
7. Gulick, R. M. Current antiretroviral therapy: An overview. *Quality of Life Research*, 1997, 6, 471-474.
8. Kuritzkes, D. R. HIV resistance to current therapies. *Antiviral Therapy*, 1997, 2 (Supplement 3), 61-67.
9. Morris-Jones, S.; Moyle, G.; Easterbrook, P. J. Antiretroviral therapies in HIV-1 infection. *Expert Opinion on Investigational Drugs*, 1997, 6(8), 1049-1061.
10. Schinazi, R. F.; Larder, B. A.; Mellors, J. W. Mutations in retroviral genes associated with drug resistance. *International Antiviral News*, 1997, 5, 129-142.
11. Vacca, J. P.; Condra, J. H. Clinically effective HIV-1 protease inhibitors. *Drug Discovery Today*, 1997, 2, 261-272.
12. Flexner, D. HIV-protease inhibitors. *Drug Therapy*, 1998, 338, 1281-1292.
13. Berkhout, B. HIV-1 evolution under pressure of protease inhibitors: Climbing the stairs of viral fitness. *J. Biomed. Sci.*, 1999, 6, 298-305.
14. Ren, S.; Lien, E. J. Development of HIV protease inhibitors: A survey. *Prog. Drug Res.*, 1998, 51, 1-31.
15. Pedersen, O. S.; Pedersen, E. B. Non-nucleoside reverse transcriptase inhibitors: the NNRTI boom. *Antiviral Chem. Chemother.* 1999, 10, 285-314.
16. (a) De Clercq, E. The role of non-nucleoside reverse transcriptase inhibitors (NNRTIs) in the therapy of HIV-1 infection. *Antiviral Research*, 1998, 38, 153-179. (b) De Clercq, E. Perspectives of non-nucleoside reverse transcriptase inhibitors (NNRTIs) in the therapy of HIV infection. IL. *Farmaco*, 1999, 54, 26-45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino[4,5-b]indoles as nonnucleoside analog inhibitors of HIV-1 reverse transcriptase. *Eur. J. Med. Chem.* 1995, 30, 963-971.
18. Romero, D. L.; Morge, R. A.; Genin, M. J.; Biles, C.; Busso, M; Resnick, L.; Althaus, I. W.; Reusser, F.; homas, R. C and Tarpley, W. G. Bis(heteroaryl)piperazine (BHAP) reverse transcriptase inhibitors: structure-activity relationships of novel substituted indole analogues and the identification of 1-[(5-methanesulfonamido-H-indol-2-yl)-carbonyl]-4-[3-[1-methylethyl)amino]-pyridinyl] piperazine momomethansulfonate (U-90152S), a second generation clinical candidate. *J. Med. Chem.*, 1993, 36, 1505-1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.*, 1995, 5, 491-496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.*, 1996, 39, 5267-5275.
21. Silvestri, R; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother.* 1998, 9, 139-148.

22. Fredenhagen, A.; Petersen, F.; Tintelnot-Blomley, M.; Rosel, J.; Mett, H and Hug, P. J. Semicochliodinol A and B: Inhibitors of HIV-1 protease and EGF-R protein Tyrosine Kinase related to Asterriquinones produced by the fungus *Chrysosporium nerdarium*. *Antibiotics,* 1997, 50, 395-401.

23. (a) Kato, M.; Ito, K.; Nishino, S.; Yamakuni, H.; Takasugi, H. New 5-HT3 (Serotonin-3) receptor antagonists. IV. Synthesis and structure-activity relationships of azabicycloalkaneacetamide derivatives. *Chem. Pharm. Bull.,* 1995, 43, 1351-1357. (b) Levacher, V.; Benoit, R; Duflos, J; Dupas, G.; Bourguignon, J.; Queguiner, G. Broadening the scope of NADH models by using chiral and non chiral pyrrolo [2,3-b]pyridine derivatives. *Tetrahedron,* 1991, 47, 429-440.

24. (a) Resnyanskaya, E. V.; Tverdokhlebov, A. V.; Volovenko, Y. M.; Shishkin, O. V.; Zubatyuk, R. I. A simple synthesis of 1-acyl-3-aryl-3H-pyrrolo[2',3',4,5]pyrimido[6,1-b]benzothiazol-6-ium-2-olates: Betainic derivatives of a novel heterocyclic system. Synthesis, 2002, 18, 2717-2724. (b) Cook, P. D.; Castle, R. N. Pyrrolopyridazines. 1. Synthesis and reactivity of [2,3-d] pyridazine 5-oxides. *J. Het. Chem.* 1973, 10(4), 551-557.

25. Shadrina, L. P.; Dormidontov, Yu. P.; Ponomarev, V. G.; Lapkin, I. I. Reactions of organomagnesium derivatives of 7-aza- and benzoindoles with diethyl oxalate and the reactivity of ethoxalylindoles. *Khim. Geterotsikl. Soedin.,* 1987, 1206-1209.

26. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.,* 1987, 100-106.

27. (a) Desai, M.; Watthey, J. W. H.; Zuckerman, M. A convenient preparation of 1-aroylpiperazines. *Org. Prep. Proced. Int.,* 1976, 8, 85-86. (b) Adamczyk, M.; Fino, J. R. Synthesis of procainamide metabolites. N-acetyl desethylprocainamide and desethylprocainamide. *Org. Prep. Proced. Int.* 1996, 28, 470-474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.,* 1995, 36, 6419-6422. (d) Wang, T.; Zhang, Z.; Meanwell, N. A. Benzoylation of Dianions: Preparation of mono-Benzoylated Symmetric Secondary Diamines. *J. Org. Chem.,* 1999, 64, 7661-7662.

28. Li, H.; Jiang, X.; Ye, Y.-H.; Fan, C.; Romoff, T.; Goodman, M. 3-(Diethoxyphosphoryloxy)-1,2,3-benzotriazin-4(3H)-one (DEPBT): A new coupling reagent with remarkable resistance to racemization. *Organic Lett.,* 1999, 1, 91-93.

29. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.,* 1997, 45, 134-137.

30. Schneller, S. W.; Luo, J.-K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.,* 1980, 45, 4045-4048.

31. Shiotani, S.; Tanigochi, K. Furopyridines. XXII [1]. Elaboration of the C-substitutents alpha to the heteronitrogen atom of furo[2,3-b]-, -[3·2-b]-, -[2,3-c]- and -[3,2-c]pyridine. *J. Het. Chem.,* 1997, 34, 901-907.

32. Minakata, S.; Komatsu, M.; Ohshiro, Y. Regioselective functionalization of 1H-pyrrolo[2,3-b]pyridine via its N-oxide. *Synthesis,* 1992, 661-663.

33. Klemm, L. H.; Hartling, R. Chemistry of thienopyridines. XXIV. Two transformations of thieno[2,3-b]pyridine 7-oxide (1). *J. Het. Chem.,* 1976, 13, 1197-1200.

34. Antonini, I.; Claudi, F.; Cristalli, G.; Franchetti, P.; Crifantini, M.; Martelli, S. Synthesis of 4-amino-1-β-D-ribofuranosyl-1H-pyrrolo[2,3-b]pyridine (1-Deazatubercidin) as a potential antitumor agent. *J. Med. Chem.,* 1982, 25, 1258-1261.

35. (a) Regnouf De Vains, J. B.; Papet, A. L.; Marsura, A. New symmetric and unsymmetric polyfunctionalized 2,2'-bipyridines. *J. Het. Chem.,* 1994, 31, 1069-1077. (b) Miura, Y.; Yoshida, M.; Hamana, M. Synthesis of 2,3-fused quinolines from 3-substituted quinoline 1-oxides. Part II, *Heterocycles,* 1993, 36, 1005-1016. (c) Prof, V. E.; Rolle, W. Uber 4-merkaptoverbindungendes 2-methylpyridins. *J. Prakt. Chem.,* 1960, 283 (11), 22-34.

36. Nesi, R.; Giomi, D.; Turchi, S.; Tedeschi, P., Ponticelli, F. A new one step synthetic approach to the isoxazolo[4,5-b]pyridine system. *Synth. Comm.,* 1992, 22, 2349-2355.

37. (a) Walser, A.; Zenchoff, G.; Fryer, R. I. Quinazolines and 1,4-benzodiazepines. 75. 7-Hydroxyaminobenzodiazepines and derivatives. *J. Med. Chem.,* 1976, 19, 1378-1381. (b) Barker, G.; Ellis, G. P. Benzopyrone. Part I. 6-Amino- and 6-hydroxy-2-substituted chromones. *J. Chem. Soc.,* 1970, 2230-2233.

38. Ayyangar, N. R.; Lahoti, R J.; Daniel, T. An alternate synthesis of 3,4-diaminobenzophenone and mebendazole. *Org. Prep. Proced. Int.,* 1991, 23, 627-631.

39. Mahadevan, I.; Rasmussen, M. Ambident heterocyclic reactivity: The alkylation of pyrrolopyridines (azaindoles, diazaindenes). *Tetrahedron,* 1993, 49, 7337-7352.

40. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.,* 1994, 68, 654-660.

41. Bodanszky, M.; Bodanszky, A. *"The Practice of Peptide Synthesis"* 2$^{nd}$ Ed., Springer-Verlag: Berlin Heidelberg, Germany, 1994.

42. Albericio, F. et al. *J. Org. Chem.* 1998, 63, 9678.

43. Knorr, R. et al. *Tetrahedron Lett.* 1989, 30, 1927.

44. (a) Jaszay Z. M. et al. *Synth. Commun.,* 1998 28, 2761 and references cited therein; (b) Bemasconi, S. et al. *Synthesis,* 1980, 385.

45. (a) Jaszay Z. M. et al. *Synthesis,* 1989, 745 and references cited therein; (b) Nicolaou, K. C. et al. *Angew. Chem. Int. Ed.* 1999, 38, 1669.

46. Ooi, T. et al. *Synlett.* 1999, 729.

47. Ford, R. E. et al. *J. Med. Chem.* 1986, 29, 538.

48. (a) Yeung, K.-S. et al. Bristol-Myers Squibb Unpublished Results. (b) Wang, W. et al. *Tetrahedron Lett.* 1999, 40, 2501.

49. Brook, M. A. et al. *Synthesis,* 1983, 201.

50. Yamazaki, N. et al. *Tetrahedron Lett.* 1972, 5047.

51. Barry A. Bunin "The Combinatorial Index" 1998 Academic Press, San Diego/London pages 78-82.

52. Richard C. Larock Comprehensive Organic Transformations 2nd Ed. 1999, John Wiley and Sons New York.

53. M. D. Mullican et. al. *J. Med. Chem.* 1991, 34, 2186-2194.

54. Protective groups in organic synthesis 3rd ed./Theodora W. Greene and Peter G. M. Wuts. New York: Wiley, 1999.

55. Katritzky, Alan R. Lagowski, Jeanne M. The principles of heterocyclic Chemistry New York: Academic Press, 1968.
56. Paquette, Leo A. Principles of modern heterocyclic chemistry New York: Benjamin.
57. Katritzky, Alan R; Rees, Charles W.; Comprehensive heterocyclic chemistry: the structure, reactions, synthesis, and uses of heterocyclic compounds 1st ed.Oxford (Oxfordshire); New York: Pergamon Press, 1984. 8 v.
58. Katritzky, Alan RHandbook of heterocyclic 1st edOxford (Oxfordshire); New York: Pergamon Press, 1985.
59. Davies, David I Aromatic Heterocyclic Oxford; New York: Oxford University Press, 1991.
60. Ellis, G. P. Synthesis of fused Chichester [Sussex]; New York: Wiley, c1987-c1992. Chemistry of heterocyclic compounds; v. 47.
61. Joule, J. A Mills, K., Smith, G. F. Heterocyclic Chemistry, 3rd ed London; New York Chapman & Hall, 1995.
62. Katritzky, Alan R., Rees, Charles W., Scriven, Eric F. V. Comprehensive heterocyclic chemistry II: a review of the literature 1982-1995.
63. The structure, reactions, synthesis, and uses of heterocyclic compounds 1st ed. Oxford; New York: Pergamon, 1996. 11 v. in 12: ill.; 28 cm.
64. Eicher, Theophil, Hauptmann, Siegfried. The chemistry of heterocycles: structure, reactions, syntheses, and applications Stuttgart; New York: G. Thieme, 1995.
65. Grimmett, M. R. Imidazole and benzimidazole Synthesis London; San Diego: Academic Press, 1997.
66. Advances in heterocyclic chemistry. Published in New York by Academic Press, starting in 1963-present.
67. Gilchrist, T. L. (Thomas Lonsdale) Heterocyclic chemistry 3rd ed. Harlow, Essex: Longman, 1997, 414 p: ill.; 24 cm.
68. Farina, Vittorio; Roth, Gregory P. Recent advances in the Stille reaction; *Adv. Met.-Org. Chem.* 1996, 5, 1-53.
69. Farina, Vittorio; Krishnamurthy, Venkat; Scott, William J. The Stille reaction; Org. React. (N. Y.) (1997), 50, 1-652.
70. Stille, J. K. *Angew. Chem. Int. Ed. Engl.* 1986, 25, 508-524.
71. Norio Miyaura and Akiro Suzuki *Chem Rev.* 1995, 95, 2457.
72. Home, D. A. *Heterocycles* 1994, 39, 139.
73. Kamitori, Y. et. al. *Heterocycles,* 1994, 37(1), 153.
74. Shawali, J. *Heterocyclic Chem.* 1976, 13, 989.
75. a) Kende, A. S. et al. *Org. Photochem. Synth.* 1972, 1, 92. b) Hankes, L. V.; *Biochem. Prep.* 1966, 11, 63. c) *Synth. Meth.* 22, 837.
76. Hulton et. al. *Synth. Comm.* 1979, 9, 789.
77. Pattanayak, B. K. et. al. *Indian J. Chem.* 1978, 16, 1030.
78. *Chemische Berichte* 1902, 35, 1545.
79. *Chemische Berichte* Ibid 1911, 44, 493.
80. Moubarak, I., Vessiere, R. *Synthesis* 1980, Vol. 1, 52-53.
81. *Ind J. Chem.* 1973, 11, 1260.
82. Roomi et. al. *Can J. Chem.* 1970, 48, 1689.
83. Sorrel, T. N. *J. Org. Chem.* 1994, 59, 1589.
84. Nitz, T. J. et. al. *J. Org. Chem.* 1994, 59, 5828-5832.
85. Bowden, K. et. al. *J. Chem. Soc.* 1946, 953.
86. Nitz, T. J. et. al. *J. Org. Chem.* 1994, 59, 5828-5832.
87. Scholkopf et. al. *Angew. Int. Ed. Engl.* 1971, 10(5), 333.
88. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.,* 1995, 36, 6419-6422. (c) Jenneskens, L. W.; Mahy, J.; den Berg, E. M. M. de B.-v.; Van der Hoef, I.; Lugtenburg, J. *Recl. Tra. Chim. Pays-Bas* 1995, 114, 97.
89. Wang, T.; Zhang, Z.; Meanwell, N. A. Benzoylation of Dianions: Preparation of mono-Benzoylated Symmetric Secondary Diamines. *J. Org. Chem.,* 1999, 64, 7661-7662.
90. (a) Adamczyk, M.; Fino, J. R. Synthesis of procainamide metabolites. N-acetyl desethylprocainamide and desethylprocainamide. *Org. Prep. Proced. Int.* 1996, 28, 470-474. (b) Wang, T.; Zhang, Z.; Meanwell, N. A. Regioselective mono-Benzoylation of Unsymmetrical Piperazines. *J. Org. Chem.,* in press.
91. Masuzawa, K.; Kitagawa, M.; Uchida, H. *Bull Chem. Soc. Jpn.* 1967, 40, 244-245.
92. Furber, M.; Cooper, M. E.; Donald, D. K. *Tetrahedron Lett.* 1993, 34, 1351-1354.
93. Blair, Wade S.; Deshpande, Milind; Fang, Haiquan; Lin, Pin-fang; Spicer, Timothy P.; Wallace, Owen B.; Wang, Hui; Wang, Tao; Zhang, Zhongxing; Yeung, Kap-sun. Preparation of antiviral indoleoxoacetyl piperazine derivatives U.S. Pat. No. 6,469,006. Preparation of antiviral indoleoxoacetyl piperazine derivatives. PCT Int. Appl. (PCT/US00/14359), WO 0076521 A1, filed May 24, 2000, published Dec. 21, 2000.
94. Wang, Tao; Wallace, Owen B.; Zhang, Zhongxing; Meanwell, Nicholas A.; Bender, John A. Antiviral azaindole derivatives. U.S. Pat. No. 6,476,034 and Wang, Tao; Wallace, Owen B.; Zhang, Zhongxing; Meanwell, Nicholas A.; Bender, John A. Preparation of antiviral azaindole derivatives. PCT Int. Appl. (PCT/US01/02009), WO 0162255 A1, filed Jan. 19, 2001, published Aug. 30, 2001.
95. Wallace, Owen B.; Wang, Tao; Yeung, Kap-Sun; Pearce, Bradley C.; Meanwell, Nicholas A.; Qiu, Zhilei; Fang, Haiquan; Xue, Qiufen May; Yin, Zhiwei. Composition and antiviral activity of substituted indoleoxoacetic piperazine derivatives. U.S. patent application Ser. No. 10/027,612 filed Dec. 19, 2001, which is a continuation-in-part application of U.S. Ser. No. 09/888,686 filed Jun. 25, 2001 (corresponding to PCT Int. Appl. (PCT/US01/20300), WO 0204440 A1, filed Jun. 26, 2001, published Jan. 17, 2002.
96. J. L. Marco, S. T. Ingate, and P. M. Chinchon Tetrahedron 1999, 55, 7625-7644.
97. C. Thomas, F. Orecher, and P. Gmeiner Synthesis 1998, 1491.
98. M. P. Pavia, S. J. Lobbestael, C. P. Taylor, F. M. Hershenson, and D. W. Miskell.
99. Buckheit, Robert W., Jr. Expert Opinion on Investigational Drugs 2001, 10(8), 1423-1442.
100. Balzarini, J.; De Clercq, E. Antiretroviral Therapy 2001, 31-62.
101. E. De clercq Journal of Clinical Virology, 2001, 22, 73-89.
102. Merour, Jean-Yves; Joseph, Benoit. Curr. Org. Chem. (2001), 5(5), 471-506.
103. T. W. von Geldem et al. J. Med. Chem 1996, 39, 968.
104. M. Abdaoui et al. Tetrahedron 2000, 56, 2427.
105. W. J. Spillane et al. J. Chem. Soc., Perkin Trans. 1, 1982, 3, 677.
106. Wang, Tao; Zhang, Zhongxing; Meanwell, Nicholas A.; Kadow, John F.; Yin, Zhiwei; Xue, Qiufen May. (USA). *Composition and antiviral activity of substituted azaindoleoxoacetic piperazine derivatives.* U.S. Pat. Appl. Publ. (2003), US 20030207910 A1 published Nov. 6, 2003 which is U.S. patent application Ser. No. 10/214,982 filed Aug. 7, 2002, which is a continuation-in-part application of U.S. Ser. No. 10/038,306 filed Jan. 2, 2002 (corresponding to PCT Int. Appl. (PCT/US02/00455), WO 02/062423 A1, filed Jan. 2, 2002, published Aug. 15, 2002.
107. a) Nickel, Bernd; Szelenyi, Istvan; Schmidt, Jurgen; Emig, Peter; Reichert, Dietmar; Gunther, Eckhard; Brune, Kay. *Preparation of indolylglyoxylamides as antitumor agents*. PCT Int. Appl. (1999), 47 pp. CODEN: PIXXD2 WO 9951224 b) Emig, Peter; Bacher, Gerald; Reichert, Dietmar; Baasner, Silke; Aue, Beate; Nickel, Bernd; Guenther, Eckhard. Preparation of N-(6-quinolinyl)-3-indolylglyoxylamides as antitumor agents. PCT Int. Appl. (2002), 4WO 2002010152A2 c) Nickel, Bernd; Klenner, Thomas; Bacher, Gerald; Beckers, Thomas; Emig, Peter; Engel, Juergen; Bruyneel, Erik; Kamp, Guenter; Peters, Kirsten. Indolyl-3-glyoxylic acid derivatives comprising therapeutically valuable properties. PCT Int. Appl. (2001), WO 2001022954A2.
108. Wang, Tao; Wallace, Owen B.; Meanwell, Nicholas A.; Zhang, Zhongxing; Bender, John A.; Kadow, John F.; Yeung, Kap-Sun. *Preparation of indole, azaindole, and related heterocyclic piperazinecarboxamides for treatment of AIDS*. PCT Int. Appl. WO 2002085301A2.
109. Kadow, John F.; Xue, Qiufen May; Wang, Tao; Zhang, Zhongxing; Meanwell, Nicholas A. Preparation of indole, azaindole and related heterocyclic pyrrolidine derivatives as antiviral agents. PCT Int. Appl. WO 2003068221A1.
110. Wang, Tao; Wallace, Owen B.; Meanwell, Nicholas A.; Kadow, John F.; Zhang, Zhongxing; Yang, Zhong. Bicyclo 4.4.0 antiviral derivatives PCT Int. Appl. (2003), WO 2003092695A1.
111. Preparation of indolyl-, azaindolyl-, and related heterocyclic sulfonylureidopiperazines for treatment of HIV and AIDS. Kadow, John F.; Regueiro-Ren, Alicia; Xue, Qiufen May. PCT Int. Appl. (2003), WO2004000210 A2.
112. *Composition and antiviral activity of substituted azaindoleoxoacetic piperazine derivatives*. Wang, Tao; Zhang, Zhongxing; Meanwell, Nicholas A.; Kadow, John F.; Yin, Zhiwei; Xue, Qiufen May; Regueiro-Ren, Alicia; Matiskella, John D.; Ueda, Yasutsugu. U.S. Pat. Appl. Publ. (2004), US 2004110785A1.

SUMMARY OF THE INVENTION

The present invention comprises compounds of Formula I, their pharmaceutical formulations, and their use in patients suffering from or susceptible to a virus such as HIV. The compounds of Formula I, which include nontoxic pharmaceutically acceptable salts thereof, have the formula and meaning as described below.

The present invention comprises a compound of Formula I,

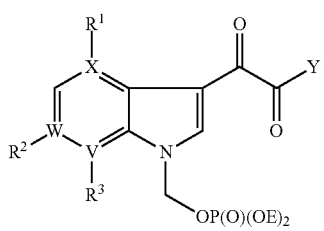

wherein:

X is C or N with the proviso that when X is N, R does not exist;

W is C or N with the proviso that when W is N, $R^2$ does not exist;

V is C;

$R^1$ is hydrogen, methoxy or halogen;

$R^2$ is hydrogen;

$R^3$ is methoxy or heteroaryl, each of which may be independently optionally substituted with one substituent selected from G; wherein heteroaryl is triazolyl, pyrazolyl or oxadiazolyl;

E is hydrogen or a pharmaceutically acceptable mono or bis salt thereof;

Y is selected from the group consisting of

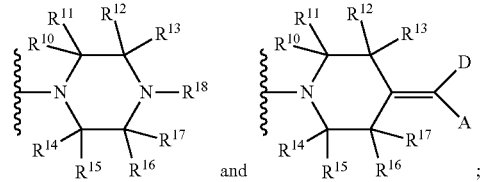

$R^{10}$, $R^{11}$, $R^{12}$, $R^{13}$, $R^{14}$, $R^{15}$, $R^{16}$, $R^{17}$ are each independently H or methyl, with the proviso that not more than two of $R^{10}$-$R^{17}$ are methyl;

$R^{18}$ is selected from the group consisting of C(O)-phenyl, C(O)-pyridinyl, pyridinyl, pyrimidinyl, quinolinyl, isoquinolinyl, quinazolinyl, quinoxalinyl, napthyridinyl, pthalazinyl, azabenzofuryl and azaindolyl, each of which may be independently optionally substituted with from one to two members selected from the group consisting of methyl, -amino, —NHMe, —NMe$_2$, methoxy, hydroxymethyl and halogen;

D is selected from the group consisting of cyano, S(O)$_2$R$^{24}$, halogen, C(O)NR$^{21}$R$^{22}$, phenyl and heteroaryl; wherein said phenyl or heteroaryl is independently optionally substituted with one to three same or different halogens or from one to three same or different substituents selected from G; wherein heteroaryl is selected from the group consisting of pyridinyl and oxadiazolyl;

A is selected from the group consisting of phenyl, pyridinyl, furyl, thienyl, isoxazolyl and oxazolyl wherein said phenyl, pyridinyl, furyl, thienyl, isoxazolyl and oxazolyl are independently optionally substituted with one to three same or different halogens or from one to three same or different substituents selected from G;

G is selected from the group consisting of (C$_{1-6}$)alkyl, (C$_{1-6}$)alkenyl, phenyl, hydroxy, methoxy, halogen, —NR$^{23}$C(O)—(C$_{1-6}$)alkyl, —NR$^{24}$R$^{25}$, —S(O)$_2$NR$^{24}$R$^{25}$, COOR$^{26}$ and —CONR$^{24}$R$^{25}$; wherein said (C$_{1-6}$)alkyl is optionally substituted with hydroxy, dimethylamino or one to three same or different halogen;

R$^{26}$ is selected from the group consisting of hydrogen and (C$_{1-6}$)alkyl;

R$^{20}$, R$^{21}$, R$^{22}$, R$^{23}$, R$^{24}$, R$^{25}$ are independently selected from the group consisting of hydrogen, (C$_{1-6}$)alkyl and —(CH$_2$)$_n$NR$^{27}$R$^{28}$;

n is 0-6; and

R$^{27}$ and R$^{28}$ are each independently H or methyl.

A more preferred embodiment are compounds above wherein:
X and W are each N;
or compounds above wherein:
X is C; and
W is N.

Another preferred embodiment are compounds as described above wherein:
R²⁸ is —C(O)-Ph; and
Y is

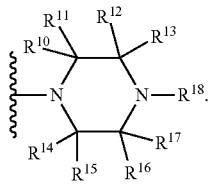

Another preferred embodiment are compounds as described above wherein: R³ is methoxy or triazolyl; wherein said triazolyl is optionally substituted with one substituent selected from G;
R¹⁰-R¹¹ are each H; and
G is methyl.

Another preferred embodiment are compounds as described above wherein:
R¹ is F, and R³ is 1,2,3-triazolyl attached at position N-1.

Another preferred embodiment are compounds as described above wherein:
R¹ is OMe, and R³ is 3-methyl-1,2,4-triazolyl attached at position N-1.

Another preferred embodiment are compounds as described above wherein:
R¹ and R³ are each methoxy.

Another preferred embodiment are compounds as described above wherein the salt is sodium, lysine or tromethamine.

Another preferred embodiment of the invention is a pharmaceutical composition which comprises an antiviral effective amount of a compound of Formula I, including pharmaceutically acceptable salts thereof, and one or more pharmaceutically acceptable carriers, excipients or diluents.

Another preferred embodiment is the pharmaceutical composition from above, useful for treating infection by HIV, which additionally comprises an antiviral effective amount of an AIDS treatment agent selected from the group consisting of:
(a) an AIDS antiviral agent;
(b) an anti-infective agent;
(c) an immunomodulator; and
(d) HIV entry inhibitors.

Also encompassed by the embodiments is a method for treating a mammal infected with the HIV virus comprising administering to said mammal an antiviral effective amount of a compound of Formula I, including pharmaceutically acceptable salts thereof, and one or more pharmaceutically acceptable carriers, excipients or diluents.

Another embodiment is method described above, comprising administering to said mammal an antiviral effective amount of a compound of Formula I, including pharmaceutically acceptable salts thereof, in combination with an antiviral effective amount of an AIDS treatment agent selected from the group consisting of an AIDS antiviral agent; an anti-infective agent; an immunomodulator; and an HIV entry inhibitor.

Another embodiment is the intermediate compounds of Formula II, useful in making compounds I,

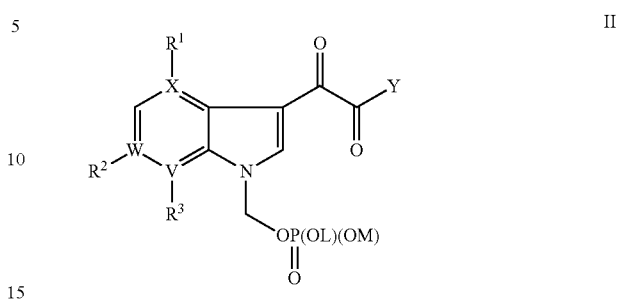

wherein:
X is C or N with the proviso that when X is N, R¹ does not exist;
W is C or N with the proviso that when W is N, R² does not exist;
V is C;
R¹ is hydrogen, methoxy or halogen;
R² is hydrogen;
R³ is methoxy or heteroaryl, each of which may be independently optionally substituted with one substituent selected from G; wherein heteroaryl is triazolyl, pyrazolyl or oxadiazolyl;
L and M are independently selected from the group consisting of hydrogen, $C_1$-$C_6$ alkyl, phenyl, benzyl, trialkylsilyl, -2,2,2-trichloroethoxy and 2-trimethylsilylethoxy with the proviso that not more than one of L and M can be hydrogen;
Y is selected from the group consisting of

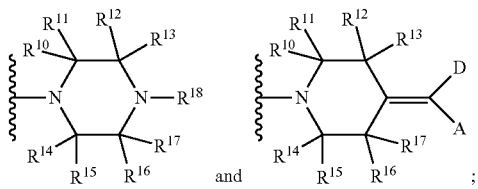

$R^{10}$, $R^{11}$, $R^{12}$, $R^{13}$, $R^{14}$, $R^{15}$, $R^{16}$, $R^{17}$ are each independently H or methyl, with the proviso that not more than two of $R^{10}$-$R^{17}$ are methyl;
R¹⁸ is selected from the group consisting of C(O)-phenyl, C(O)-pyridinyl, pyridinyl, pyrimidinyl, quinolinyl, isoquinolinyl, quinazolinyl, quinoxalinyl, napthyridinyl, pthalazinyl, azabenzofuryl and azaindolyl, each of which may be independently optionally substituted with from one to two members selected from the group consisting of methyl, -amino, —NHMe, —NMe₂, methoxy, hydroxymethyl and halogen;
D is selected from the group consisting of cyano, $S(O)_2R^{24}$, halogen, $C(O)NR^{21}R^{22}$, phenyl and heteroaryl; wherein said phenyl or heteroaryl is independently optionally substituted with one to three same or different halogens or from one to three same or different substituents selected from G; wherein heteroaryl is selected from the group consisting of pyridinyl and oxadiazolyl;
A is selected from the group consisting of phenyl, pyridinyl, furyl, thienyl, isoxazolyl and oxazolyl wherein said phenyl, pyridinyl, furyl, thienyl, isoxazolyl and oxazolyl are independently optionally substituted with one to three same or different halogens or from one to three same or different substituents selected from G;

G is selected from the group consisting of $(C_{1-6})$alkyl, $(C_{1-6})$alkenyl, phenyl, hydroxy, methoxy, halogen, —$NR^{23}C$(O)—$(C_{1-6})$alkyl, —$NR^{24}R^{25}$, —$S(O)_2NR^{24}R^{25}$, $COOR^{26}$ and —$CONR^{24}R^{26}$; wherein said $(C_{1-6})$alkyl is optionally substituted with hydroxy, dimethylamino or one to three same or different halogen;

$R^{26}$ is selected from the group consisting of hydrogen and $(C_{1-6})$alkyl;

$R^{20}$, $R^{21}$, $R^{22}$, $R^{23}$, $R^{24}$, $R^{25}$ are independently selected from the group consisting of hydrogen, $(C_{1-6})$alkyl and —$(CH_2)_nNR^{27}R^{28}$;

$R^{27}$ and $R^{28}$ are each independently H or methyl; and n is 0-6.

DETAILED DESCRIPTION OF THE INVENTION

Figure 1:
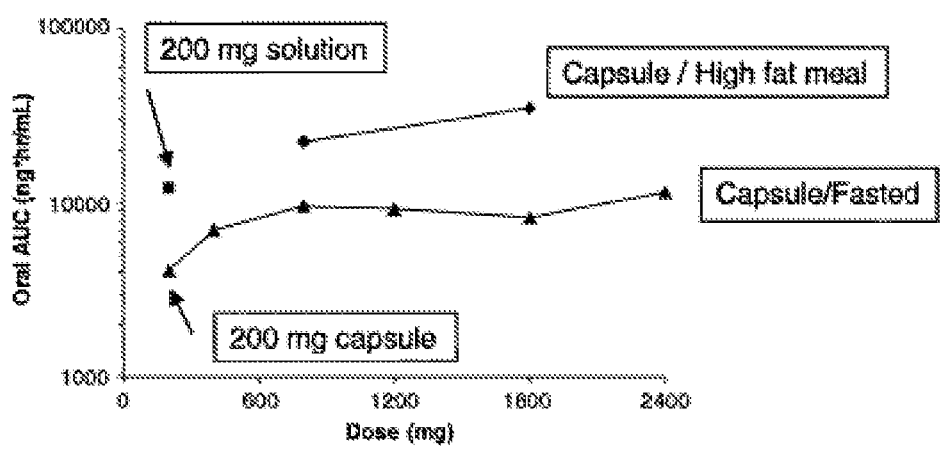
FIG. 1 illustrates AUC (Area Under the Curve) Versus Dosage in Human Clinical Trials for Compound IVa.
Figure 2A:
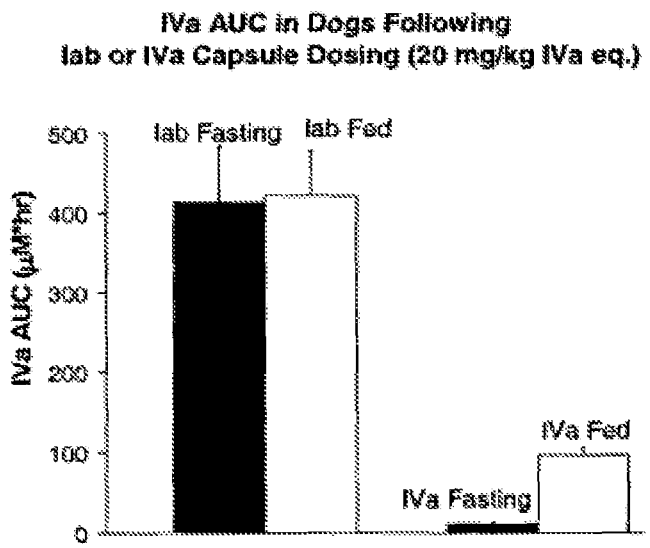
FIGS. 2A and 2B illustrates AUC for Compound IVa and Prodrug Iab Under Fasting and Fed Conditions in Dog and Human Studies.
Figure 2B:
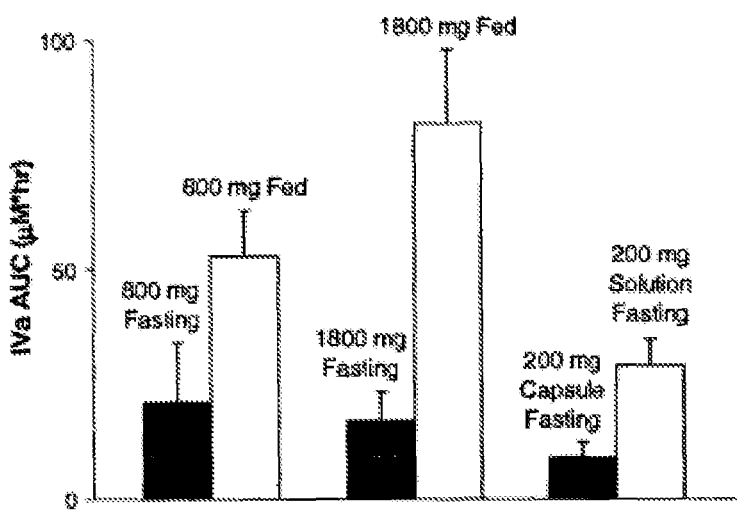

Since the compounds of the present invention, may possess asymmetric centers and therefore occur as mixtures of diastereomers and enantiomers, the present invention includes the individual diastereoisomeric and enantiomeric forms of the compounds of Formula I in addition to the mixtures thereof.

Definitions

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl, diazinyl, pyrazine, triazinyltriazine, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encomplish systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group (s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a $Z_3CC$(=O)— group with said Z being a halogen.

A "C-carboxy" group refers to a —C(=O)O—R" groups, with R" as defined herein.

An "O-carboxy" group refers to a R"C(=O)O— group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS$(=O)$_2$— groups with Z as defined above.

A "trihalomethanesulfonamido" group refers to a $Z_3CS$(=O)$_2NR^x$— group with Z and $R^X$ as defined herein.

A "sulfinyl" group refers to a —S(=O)—R" group, with R" as defined herein and, in addition, as a bond only; i.e., —S(O)—.

A "sulfonyl" group refers to a —S(=O)$_2$R" group with R" as defined herein and, in addition, as a bond only; i.e., —S(O)$_2$—.

A "S-sulfonamido" group refers to a —S(=O)$_2NR^XR^Y$, with $R^X$ and $R^Y$ as defined herein.

A "N-Sulfonamido" group refers to a R"S(=O)$_2$NR$_X$— group with R$_x$ as defined herein.

A "O-carbamyl" group refers to a —OC(=)NR$^x$R$^y$ as defined herein.

A "N-carbamyl" group refers to a R$^x$OC(=O)NR$^y$ group, with R$^x$ and R$^y$ as defined herein.

A "O-thiocarbamyl" group refers to a —OC(=S)NR$^x$R$^y$ group with R$^x$ and R$^y$ as defined herein.

A "N-thiocarbamyl" group refers to a R$^x$OC(=S)NR$^y$— group with R$^x$ and R$^y$ as defined herein.

An "amino" group refers to an —NH$_2$ group.

A "C-amido" group refers to a —C(=O)NR$^x$R$^y$ group with R$^x$ and R$^y$ as defined herein.

A "C-thioamido" group refers to a —C(=S)NR$^x$R$^y$ group, with R$^x$ and R$^y$ as defined herein.

A "N-amido" group refers to a R$^x$C(=O)NR$^y$— group, with R$^x$ and R$^y$ as defined herein.

An "ureido" group refers to a —NR$^x$C(=)NR$^y$R$^{y2}$ group with R$^x$ and R$^y$ as defined herein and R$^{y2}$ defined the same as R$^x$ and R$^y$.

An "thioureido" group refers to a —NR$^x$C(=S)NR$^y$R$^{y2}$ group with R$^x$ and R$^y$ as defined herein and R$^{y2}$ defined the same as R$^x$ and R$^y$.

A "guanidino" group refers to a —R$^x$NC(=N)NR$^y$R$^{y2}$ group, with R$^x$, R$^y$ and R$^{y2}$ as defined herein.

A "guanyl" group refers to a R$^x$R$^y$NC(=N)— group, with R$^x$ and R$^y$ as defined herein.

A "cyano" group refers to a —CN group.

A "silyl" group refers to a —Si(R")$_3$, with R" as defined herein.

A "phosphonyl" group refers to a P(=O)(OR)$_2$ with R$^x$ as defined herein.

A "hydrazino" group refers to a —NR$^x$NR$^y$R$^{y2}$ group with R$^x$, R$^y$ and R$^{y2}$ as defined herein.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts of the prodrug compounds disclosed herein are within the scope of this invention. The term "pharmaceutically acceptable salt" as used herein and in the claims is intended to include nontoxic base addition salts. The term "pharmaceutically acceptable salt" as used herein is also intended to include salts of acidic groups, such as a carboxylate or phosphate or phosphate mono ester, with such counterions as ammonium, alkali metal salts, particularly sodium or potassium, alkaline earth metal salts, particularly calcium or magnesium, transition metal salts such as zinc and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or mono tromethamine (also called TRIS or 2-amino-2-(hydroxymethyl)propane-1, 3-diol) tris(hydroxymethyl)-aminomethane), lysine, arginine, histidine, N-methylglucamine, or with bases such as piperidine or morpholine. It is understood that both pharmaceutically acceptable salts, when isolated in solid or crystalline form, also include hydrates or water molecules entrapped within the resulting Compound I substance. Stoichiometry possibilities are well known to those in the art. Discussions of pharmaceutically acceptable salts and lists of possible salts are contained in the following references:

*Preparation of water-soluble compounds through salt formation.* Stahl, P. Heinrich. Cosmas Consult, Freiburg im Breisgau, Germany. Editor(s): Wermuth, Camille Georges. Practice of Medicinal Chemistry (2nd Edition) (2003), 601-615. Publisher: Elsevier, London, UK CODEN: 69EOEZ.

Handbook of pharmaceutical salts: properties, selection, and use by Stahl, P. Heinrich, Wermuth, Camille G., International Union of Pure and Applied Chemistry. Weinheim; New York: VHCA; Wiley-VCH, 2002.

In another aspect of the invention, novel phosphate ester intermediate Compounds II are disclosed.

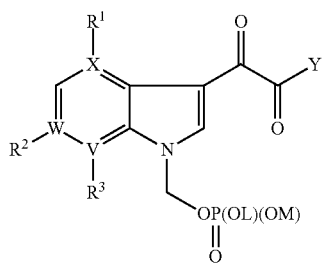

In the case of phosphate esters, the possibility of mono or bis exists and both are covered by this invention.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |

| Drug Name | Manufacturer | Indication |
|---|---|---|
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated Diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |

| Drug Name | Manufacturer | Indication |
|---|---|---|
| Tenofovir disoproxil, fumarate salt (VIREAD ®) | Gilead AIDS, | HIV infection, (reverse transcriptase inhibitor) |
| EMTRIVA ® (Emtricitabine) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REVATAZ ® (or atazanavir) | Bristol-Myers Squibb | HIV infection AIDs, protease inhibitor |
| FUZEON ® (or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Omidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin Intraconazole-R51211 | Rhone-Poulenc Janssen-Pharm. | Cryptosporidial diarrhea Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F. Current Opinion in Drug Discovery & Development (2003), 6(4), 451-461. Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this invention with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is Kaletra®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

ABBREVIATIONS

The following abbreviations, most of which are conventional abbreviations well known to those skilled in the art, are used throughout the description of the invention and the examples. Some of the abbreviations used are as follows:
h=hour(s)
r.t.=room temperature
mol=mole(s)
mmol=millimole(s)
g=gram(s)
mg=milligram(s)
mL=milliliter(s)
TFA=Trifluoroacetic Acid
DCE=1,2-Dichloroethane
$CH_2Cl_2$=Dichloromethane
TPAP=tetrapropylammonium perruthenate
THF=Tetrahydofuran
DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
MCPBA=meta-Chloroperbenzoic Acid
azaindole=1H-Pyrrolo-pyridine
4-azaindole=1H-pyrrolo[3,2-b]pyridine
5-azaindole=1H-Pyrrolo[3,2-c]pyridine
6-azaindole=1H-pyrrolo[2,3-c]pyridine
7-azaindole=1H-Pyrrolo[2,3-b]pyridine
4,6-diazaindole=5H-Pyrrolo[3,2-d]pyrimidine
5,6-diazaindole=1H-Pyrrolo[2,3-d]pyridazine
5,7-diazaindole=7H-Pyrrolo[2,3-d]pyrimidine
PMB=4-Methoxybenzyl
DDQ=2, 3-Dichloro-5, 6-dicyano-1, 4-benzoquinone
OTf=Trifluoromethanesulfonoxy
NMM=4-Methylmorpholine
PIP-COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCE=Dichloroethane
MeOH=Methanol
THF=Tetrahydrofuran
EtOAc=Ethyl Acetate
LDA=Lithium diisopropylamide
TMP-Li=2,2,6,6-tetramethylpiperidinyl lithium
DME=Dimethoxyethane
DIBALH=Diisobutylaluminum hydride
HOBT=1-hydroxybenzotriazole
CBZ=Benzyloxycarbonyl
PCC=Pyridinium chlorochromate
TRIS=Tromethamine or 2-amino-2-(hydroxymethyl)propane-1,3-diol Chemistry The present invention comprises compounds of Formula I, their pharmaceutical formulations, and their use in patients suffering from or susceptible to HIV infection.

Scheme A depicts an overview of the process for preparing the prodrugs I of the invention from the parent molecules IV.

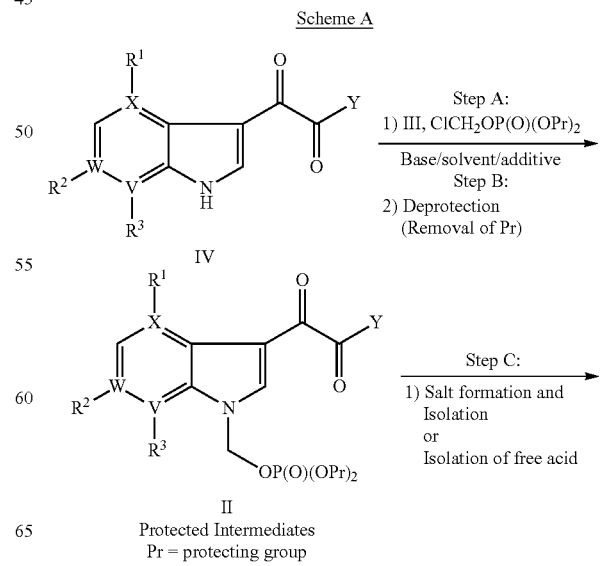

Scheme A

IV

II
Protected Intermediates
Pr = protecting group

Step A:
1) III, $ClCH_2OP(O)(OPr)_2$
Base/solvent/additive
Step B:
2) Deprotection
(Removal of Pr)

Step C:
1) Salt formation and Isolation
or
Isolation of free acid

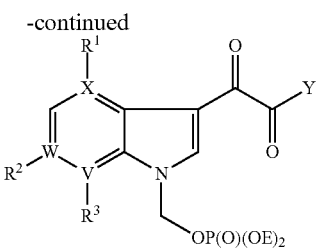

Compounds of Claim 1
E = hydrogen, or as defined to form pharmaceutically acceptable mono or bis salt Scheme B

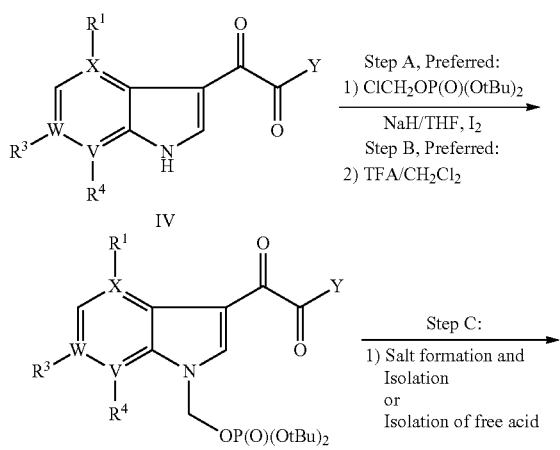

tBu = Pr = Protecting group

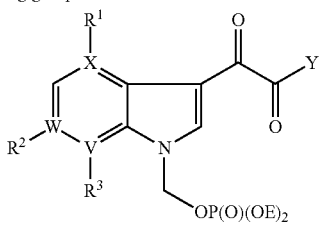

Compounds of Claim 1
E = hydrogen, or as defined to form pharmaceutically acceptable mono or bis salt To elaborate on the method, as shown in Scheme A, the antiviral parent compound of interest, IV, is converted into the phosphate intermediate II, by N-alkylation with chloride intermediate III, in the presence of a suitable base such as sodium hydride, potassium hydride, sodium amide, sodium t-butoxide, sodium (bis trimethylsilyl) amide, potassium (bis trimethyl silyl) amide, or combinations thereof such as sodium hydride plus sodium bis (trimethylsilyl) amide. The preparation of reagent III and the methodology for use in preparing prodrugs by the alkylation hydroxy groups has been described in Y. Ueda et. al. U.S. Pat. No. 6,362,172B2 which is incorporated by reference in its entirety. The alkylation conditions, protecting groups, protecting group removal, and conditions for salt formation are in general applicable to our application despite the fact that we are alkylating an azaindole in the indole ring rather than a hydroxy group. In the current application, from 1.1 to 5.0 equivalents of base may be utilized with between 2 and 4 equivalents being preferred. From 1.1 up to 12 equivalents of reagent III may be used with 5 to 10 being preferred depending on the substrate. The reagent may be added in one portion or incrementally in several portions over time. A source of iodide ion is usually added to the reaction to provide increased yields. Elemental iodine is currently preferred as the source of iodide. 0.1 to 1.5 equivalents of iodine are usually added per azaindole/indole NH being alkylated with 1.0 to 1.2 equivalents of iodine being preferred since yields are highest. Alternate sources of iodide include, for example, sodium iodide, lithium iodide, cesium iodide, copper iodide, or tetrabutyl ammonium iodide. The function of iodine is presumably to generate the corresponding iodomethyl reagent IIIa in situ from the chloro methyl reagent III. The iodo or bromo reagents corresponding to III could likely be used directly in the reaction in place of the chloride III. The alkylation reaction of step A is usually carried out in an inert organic solvent such as tetrahydrofuran at a temperature from about 0° C. to 50° C., more preferably between 20° and 40° C. Other anhydrous organic solvents such as methyl tetrahydrofuran, methyl t-butyl ether, dioxane, ethylene glycol dimethyl ether, dimethyl acetamide, or N,N-dimethylformamide could also find utility. Ester intermediate II is then subjected to a conventional deprotection step to remove the protecting groups Pr. The reagents used in such step will depend on the protecting group used, but will be well known to those skilled in the art. The most preferred protecting group is the t-butyl group which can be removed with trifluoroacetic acid, hydrochloric acid, or formic acid in an appropriate inert organic solvent. The inert solvent can be dichloromethane, or possibly, for example, dichloroethane, toluene, or trifluoromethyl benzene. In methylene chloride, trifluoroacetic acid deprotection may be effected using from 1 to 15 equivalents of acid (or the acid can be measured differently as for example a 5% solution in solvent by volume) and temperatures of between 0° and 40°. In general, the greater excess of TFA employed, the lower the temperature utilized. Exact conditions vary with substrate. Step 3 describes the isolation of the free acid or salts which can be formed via many standard ways which are well known in the art. Generally, following TFA deprotection, an aqueous workup is employed in which the excess acid is neutralized with a base and the organic impurities removed via extraction with an organic solvent such as ethyl acetate or dichloromethane. For example excess aqueous NaOH may be used to basify the reaction mixture. This is well known to any chemist skilled in the art. Reacidification of the aqueous phase to pH 2.5 with aqueous 1N HCl and then extraction with an organic solvent will provide, after removal of solvent in vacuo, the free acid. The free acid may be converted to inorganic salts by the addition of appropriate bases in solvents such as water, methanol, ethanol, etc. For example, addition of sodium carbonate to an aqueous solution of phosphate prodrug and adjustment of the pH to approximately 7.6 provides a solution which upon removal of water via lypohilization leaves the disodium salt of the prodrug. Potassium carbonate could be used similarly. Aqueous solutions of sodium bicarbonate or potassium bicarbonate could be used similarly. Mono potassium or mono sodium salts could be generated via careful titration of phosphate acid solutions with potassium or sodium 2-ethyl hexanoate. Amine salts can be generated by dissolving the free acid in organic solvents such as ethyl acetate or acetonitrile or low molecular weight alcohols or mixtures of these solvents optionally containing water. Some amines potentially useful for salt formation include: lower alkylamines (methylamine, ethylamine, cyclohexylamine, and the like) or substituted lower alkylamines (e.g. hydroxyl-substituted alkylamines such as diethanolamine, triethanolamine or tris(hydroxymethyl)-aminomethane), lysine, arginine, histidine, N-methylglucamine, or bases such as piperidine or morpholine. Slow addition of an amine to a stirring solution at low temperature can provide either the mono of bis amine salt depending on stoichiometry. Amine salts can also be obtained by stirring the solution and removing the solvent in vacuo rather than be crystallization or precipitation. Recrystallization procedures will vary by compound and salt but are available to one skilled in the art. Scheme B depicts a preferred sequence and set of reagents and conditions for carrying out the general sequence shown in Scheme A.

An alternate and in many cases the preferred method for carrying out the sequence in step C which includes the deprotection of the diester to provide the intermediate acid insitu followed by salt formation in the reaction medium may be utilized. For example, heating the diester II in a mixture of water and a water miscible cosolvent such as for example acetone, methanol, ethanol, or isopropanol can produce the free acid of I in the reaction medium (insitu). A preferred solvent is acetone and isopropanol. Temperatures between ambient and the boiling points of the solvents could be utilized. Typically 40° to 60° C. is in the preferred range. Addition of a base or more preferably an amine as described above to the reaction mixture containing the free acid in the water and cosolvent can produce the salt directly. If appropriate conditions are selected, the salt, may crystallize or precipitate directly from the reaction medium and be isolated by filtration and drying. Specific examples are contained in the experimental section.

The preferred method of preparation of intermediates IIa, IIb, and IIc and of the acids Iac, Ibc and Ic offers a number of significant advantages over the procedures used initially for preparation of IIa, IIb, and IIc during exploratory research efforts. The initial discovery routes for the preparation of all three intermediates II used a preparation of di-tertbutyl chloromethyl phosphate that required the use of relatively expensive tetrabutylammonium di tert-butyl phosphate which was reacted with a 10 fold excess of expensive and potentially hazardous chloro iodomethane. The excess volatiles and iodomethane were removed in vacuo to provide the crude reagent which was used without further purification. At least a 5 fold excess of this reagent was used to react with compounds IV meaning that at least 5 equivalents of tetrabutylammonium phosphate and 50 equivalents of chloroiodomethane were used as compared to quantities of either IVa, b or c. In addition, alkylation of compounds IV with this reagent was achieved using NaH as base and iodine as an additive to promote alkylation. These conditions produced a reaction mixture containing the desired compound II as a major product and side products which were removed using silica gel chromatography, a tedious, time consuming, and expensive operation especially on reactions of increasing scale. Failure to remove side products, resulted in products I from the next step, the removal of the protecting groups, that contained impurities which were very difficult to remove in a satisfactory manner in either a reasonable yield or time frame.

The improved preparation of di-tertbutyl chloromethyl phosphate utilizes less expensive ditertbutyl potassium phosphate and only an approximate 2 fold excess of this reagent as compared to the other reactant chloromethyl sulfonyl chloride. The di-tertbutyl chloromethyl phosphate prepared by this method is isolated in pure form via convenient distillation.

For the conversion of IVa to IIa, only 1.2 equivalents of this reagent was used to alkylate compounds IV. In addition, a less reactive and economical base, potassium carbonate, was used in conjunction with DMSO to achieve an alkylation in which the compounds II produced are sufficiently free of side products that they can be used without chromatographic purification as inputs for the deprotection reaction. The free acid Iac or salts such as Iab for example can be obtained in pure form from IIa prepared in this manner without chromatography.

For the synthesis of compounds IIb and IIc which are slower to react than IVa, 2 to 2.5 equivalents of di-tertbutyl chloromethyl phosphate were employed and modified conditions (cesium carbonate as base with KI in the solvent, NMP) were used to alkylate either IVb and IVc and realize high conversion to IIb and IIc respectively.

Again the new conditions provided compounds II in sufficient purity to allow them to be used to produce compounds I without the need for chromatographic purification. Thus the new conditions reduce the quantities and stoichiometry of reagents needed to prepare the compound I of this invention and avoids the need for chromatographic purification of intermediates II. The starting materials employed to prepare the di-tertbutyl chloromethyl phosphate are more economical and less hazardous and the final product is produced in higher purity. Finally, the conditions developed for alkylating IVa, IVb, and IVc eliminate the need for the reactive, flammable sodium hydride base that had been used in excess and employ either potassium or cesium carbonate.

In the alkylation step, a suitable base can be used such as $M_2CO_3$ (M is lithium, sodium, potassium, rubidium or cesium). For converting IVa to IIa, $K_2CO_3$ is preferred (1-5 molar equivalents, preferably 2 molar equivalents per mole of IVa). For converting IVb to IIb or IVc to IIc, cesium carbonate is preferred.

Also, a suitable solvent is needed such as dimethylsulfoxide, N-dimethylformamide, acetone, acetonitrile, N-methylpyrrolidinone, formamide, tetrahydrofuran, etc. (2-50 ml/gram of IV, with 5 ml/gram preferred); dimethylsulfoxide is preferred in converting IVa to IIa; N-methylpyrrolidinone is preferred in converting IVb to IIb or IVc to IIc.

A suitable solvent iodine source includes, but is not limited to, MI (M is, for example, lithium, sodium, potassium, iodine, tetrabutylammonium, etc.); with potassium iodide preferred (0.1-5 molar equivalents/mole of Compound IV; 2 equivalents preferred).

The alkylating agent, di-tert-butyl chloromethyl phosphate, can be used in 1-10 molar equivalents per mole of IV; but about 1.2 molar equivalents is preferred.

The reaction temperature can be 10-60° C. (30° C. preferred).

In the deprotecting step, when the two tert-butyl groups are removed from IIa to form Iac, this is carried out in the presence of a suitable solvent such as dichloromethane (preferred), dichloroethane, chloroform, carbontetrachloride, toluene, benzene, etc. (2-50 ml/gram of IV, preferably 10 ml/gram)

For deprotecting IIb and IIc to obtain Ibc and Ic, respectively, this is accomplished in acetone/water at a temperature of about 40° C.

Additionally, during deprotection of IIa, it is preferred to have an acid present such as trifluoroacetic acid (preferred), hydrochloric, sulfuric, nitric, etc. (2-100 molar equivalents based on IVa, with 15 molar equivalents preferred).

Chemistry
General:

Additional preparations of starting materials and precursors are contained in Wang et. al. U.S. Pat. No. 6,476,034 granted Nov. 5, 2002 which is incorporated by reference in its entirety.

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Method (I.E., Compound Identification)
Column A: YMC ODS-A S7 3.0×50 mm column
Column B: PHX-LUNA C18 4.6×30 mm column
Column C: XTERRA ms C18 4.6×30 mm column
Column D: YMC ODS-A C18 4.6×30 mm column
Column E: YMC ODS-A C18 4.6×33 mm column
Column F: YMC C18 S5 4.6×50 mm column
Column G: XTERRA C18 S7 3.0×50 mm column
Column H: YMC C18 S5 4.6×33 mm column
Column I: YMC ODS-A C18 S7 3.0×50 mm column
Column J: XTERRA C-18 S5 4.6×50 mm column
Column K: YMC ODS-A C18 4.6×33 mm column
Column L: Xterra MS C18 uM 4.6×30 mm column
Column M: YMC ODS-A C18 S3 4.6×33 mm column
Standard LC Run Conditions (Used Unless Otherwise Noted):
Gradient: 100% Solvent A/0% Solvent B to 0% Solvent A/100% Solvent B
Solvent A=10% MeOH-90% H$_2$O-0.1% TFA, Solvent B=90% MeOH-10% H$_2$O-0.1% TFA; and R$_t$ in min.
Gradient time: 2 minutes
Hold time 1 minute
Flow rate: 5 mL/min
Detector Wavelength: 220 nm
Solvent A: 10% MeOH/90% H$_2$O/0.1% Trifluoroacetic Acid
Solvent B: 10% H$_2$O/90% MeOH/0.1% Trifluoroacetic Acid
Alternate LC Run Conditions B:
Gradient: 100% Solvent A/0% Solvent B to 0% Solvent A/100% Solvent B
Solvent A=10% MeOH-90% H$_2$O-0.1% TFA, Solvent B=90% MeOH-10% H$_2$O-0.1% TFA; and R$_t$ in min.
Gradient time: 4 minutes
Hold time 1 minute
Flow rate: 4 mL/min
Detector Wavelength: 220 nm
Solvent A: 10% MeOH/90% H$_2$O/0.1% Trifluoroacetic Acid
Solvent B: 10% H$_2$O/90% MeOH/0.1% Trifluoroacetic Acid Compounds purified by preparative HPLC were diluted in MeOH (1.2 mL) and purified using the following methods on a Shimadzu LC-10A automated preparative HPLC system or on a Shimadzu LC-8A automated preparative HPLC system with detector (SPD-10AV UV-VIS) wavelength and solvent systems (A and B) the same as above.
Preparative HPLC Method (I.E., Compound Purification)

Purification Method: Initial gradient (40% B, 60% A) ramp to final gradient (100% B, 0% A) over 20 minutes, hold for 3 minutes (100% B, 0% A)
Solvent A: 10% MeOH/90% H$_2$O/0.1% Trifluoroacetic Acid
Solvent B: 10% H$_2$O/90% MeOH/0.1% Trifluoroacetic Acid
Column: YMC C18 S5 20×100 mm column
Detector Wavelength: 220 nm For the experimental procedures below the following HPLC conditions or modifications from the standard procedures were employed: HPLC conditions for routine LC purity:
Detection at 254 nm; Gradient 0-100% B/A; A 10% CH$_3$CN-90% H$_2$O-0.1% TFA, B 90% CH$_3$CN-10% H$_2$O-0.1% TFA; Gradient time 4 min; Column YMC ODS-AQ or ORD-A 4.6×50 mm 3 micron.

HPLC conditions for LC/MS analysis:
Column J: XTERRA C-18 S5 4.6×50 mm column, Gradient: 100% Solvent A/0% Solvent B to 0% Solvent A/100% Solvent B
Solvent A=10% MeOH-90% H$_2$O-0.1% TFA, Solvent B=90% MeOH-10% H$_2$O-0.1% TFA; and Rt in min; Gradient time: 3 minutes; Flow rate: 4 mL/min; Detector Wavelength: 220 nm Starting materials, can be purchased from commercial sources or prepared using literature procedures.
Preparation of Parent Compounds IV:

The preparation of parent Compounds IV has been described previously in the following, all of which are herein incorporated by reference in their entirety as follows:

U.S. Pat. No. 6,469,006 granted Oct. 22, 2002 to W. S. Blair et al;

U.S. Pat. No. 6,476,034 granted Nov. 5, 2002 to Wang et al;

U.S. Pat. No. 6,573,262 granted Jun. 3, 2003 to Meanwell et al;

U.S. Ser. No. 10/630,278 filed Jul. 30, 2003 to J. Kadow et al; which is a continuation-in-part of U.S. Ser. No. 10/214,982 filed Aug. 7, 2002, which is a continuation-in-part of U.S. Ser. No. 10/038,306 filed Jan. 2, 2002, which corresponds to PCT WO 02/062423, filed Jan. 2, 2002, published Aug. 15, 2002;

U.S. Ser. No. 10/871,931 filed Jun. 18, 2004 to Yeung et al;

U.S. Ser. No. 10/762,108 filed Jan. 21, 2004 to Wang et al, corresponding to PCT WO 2004/043337 published May 27, 2004.

Select detailed procedures are provided below:
Typical Procedure for the Preparation of Intermediates for the Preparation of Parent Compounds IV
1) Preparation of Azaindole I

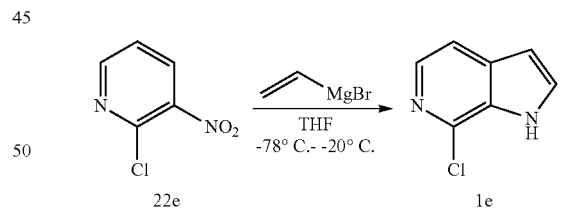

Preparation of azaindole, Method A: Preparation of 7-Chloro-6-azaindole 1e: 2-Chloro-3-nitropyridine 22e (5.0 g) was dissolved in dry THF (200 ml). After the solution was cooled down to −78° C., an excess of vinyl magnesium bromide (1.0 M in THF, 100 ml) was added. Then, the reaction was left at −20° C. for eight hours before being quenched with 20% NH$_4$Cl (150 ml). The aqueous phase was extracted with EtOAc (3×150 ml). The combined organic layer was dried over MgSO$_4$. After filtration and concentration, the crude product was purified by silica gel column chromatography to afford 1.5 g of 7-chloro-6-azaindole 1e in 31% yield.

Compounds 5an, IVa and 5ap are described below.

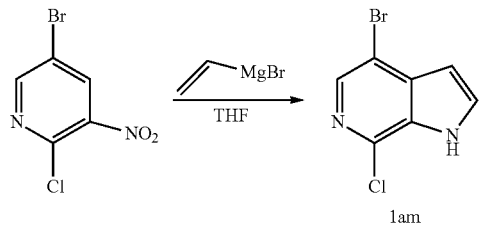

Compound 1am, 4-bromo-7-chloro-6-azaindole (yellow solid) was prepared by the same method used for azaindole 1e but the starting material employed was 5-bromo-2-chloro-3-nitropyridine. (available from Aldrich, Co.). MS m/z: (M+H)$^+$ calcd for $C_7H_5BrClN_2$: 230.93. found 231.15. HPLC retention time: 1.62 minutes (column B).

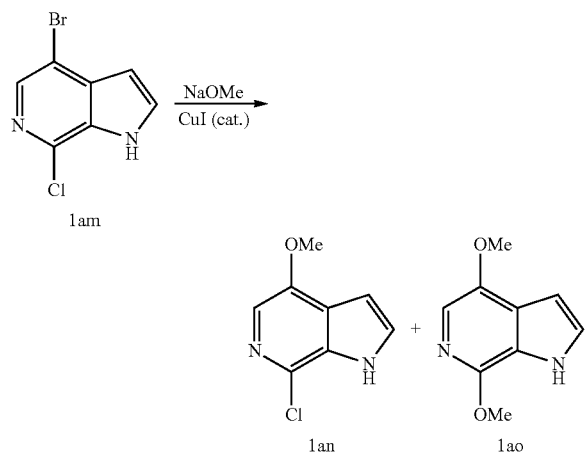

Compound 1an (4-methoxy-7-chloro-6-azaindole) and compound 1ao (4,7-dimethoxy-6-azaindole): A mixture of 4-bromo-7-chloro-6-azaindole (1 g), CuI (0.65 g) and NaOMe (4 ml, 25%) in MeOH (16 ml) was heated at 110-120° C. for 16 hours in a sealed tube. After cooling to ambient temperature, the reaction mixture was neutralized with 1N HCl to achieve pH 7. The aqueous solution was extracted with EtOAc (3×30 ml). Then the combined organic layer was dried over MgSO$_4$ and concentrated in vacuo to afford a residue, which was purified by silica gel (50 g) chromatography using 1:7 EtOAc:hexane as the eluent. (Column dimension: 20 mm×30 cm) to give 0.3 g of 4-methoxy-7-chloro-6-azaindole (white solid) and 0.1 g of 4,7-dimethoxy-6-azaindole (white solid).

Compound 1an (4-methoxy-7-chloro-6-azaindole). MS m/z: (M+H)$^+$ calcd for $C_8H_8ClN_2O$: 183.03. found 183.09. HPLC retention time: 1.02 minutes (column B).

Compound 1ao (4,7-dimethoxy-6-azaindole). $^1$H NMR (500 MHz, CDCl$_3$) δ 7.28 (m, 2H), 6.63 (m, 1H), 4.14 (s, 3H), 3.95 (s, 3H). MS m/z: (M+H)$^+$ calcd for $C_9H_{11}N_2O_2$: 179.08. found 179.05. HPLC retention time: 1.36 minutes (column B).

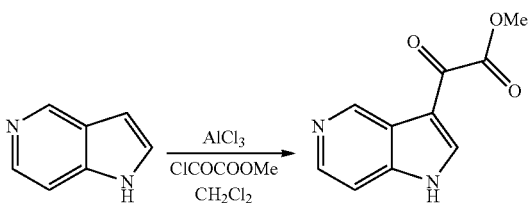

Acylation of azaindole, method B: Preparation of Methyl (5-azaindol-3-yl)-oxoacetate 2b: 5-Azaindole (1b) (0.5 g, 4.2 mmol) was added to a suspension of AlCl$_3$ (2.8 g, 21.0 mmol) in CH$_2$Cl$_2$ (100 ml). Stirring was continued at room temperature for 1 hour before methyl chlorooxoacetate (2.5 g, 21.0 mmol) was added dropwise. The reaction was stirred for 8 hours. After 20 ml of MeOH was added cautiously to quench the reaction, solvents were removed under vacuum. The solid residue was purified by silica gel column chromatography (EtOAc/MeOH=10:1) to afford 0.6 g (70%) of the acylated product 2b.

Characterization of compounds 2:

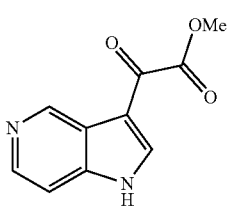

Compound 2b (Methyl (5-azaindol-3-yl)-oxoacetate): 1H NMR (500 MHz, CD$_3$OD) δ 9.61 (s, 1H), 9.02 (s, 1H), 8.59 (d, 1H, J=6.63 Hz), 8.15 (d, 1H, J=6.60 Hz), 4.00 (s, 3H); $^{13}$C NMR (125 MHz, CD$_3$OD) δ 178.9, 163.0, 145.6, 144.2, 138.3, 135.0, 124.7, 116.3, 112.1, 53.8. MS m/z: (M+H)$^+$ calcd for $C_{10}H_9N_2O_3$: 205.06. found 205.04. HPLC retention time: 0.32 minutes (column A).

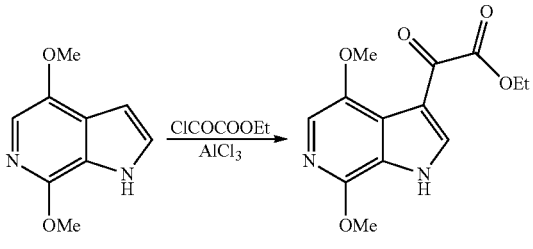

Compound 2ao (Ethyl (4,7-dimethoxy-6-azaindol-3-yl)-oxoacetate) was prepared by the same method as used for compound 2b but the starting material employed was 4,7-dimethoxy-6-azaindole. The compound was purified by silica gel chromatography using 2:3 EtOAc: Hexane as the eluent to give a yellow oil: H NMR (500 MHz, CDCl$_3$) δ 9.50 (s, 1H), 8.21 (s, 1H), 7.47 (s, 1H), 4.39 (q, 2H, d=7.05 Hz), 4.13 (s, 3H), 3.93 (s, 3H), 1.40 (t, 3H, d=7.2 Hz). MS m/z: (M+H)$^+$ calcd for $C_{13}H_{15}N_2O_5$: 279.10. found 279.16. HPLC retention time: 1.28 minutes (column B).

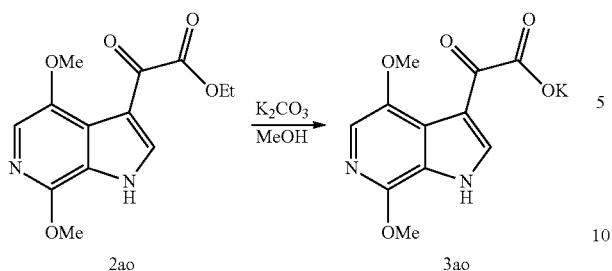

2) Preparation of Potassium Azaindole 3-glyoxylate 3

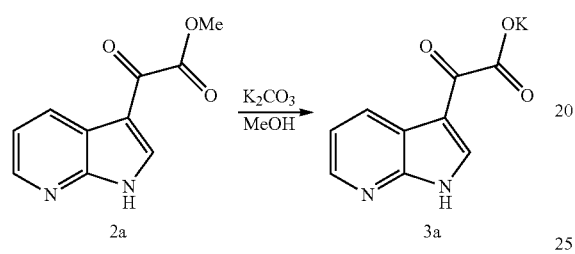

Preparation of Potassium (7-azaindol-3-yl)-oxoacetate 3a: Compound 2a (43 g, 0.21 mol) and K$_2$CO$_3$ (56.9 g, 0.41 mol) were dissolved in MeOH (200 ml) and H$_2$O (200 ml). After 8 hours, product 3a precipitated out from the solution. Filtration afforded 43 g of compound 3a as a white solid in 90.4% yield.

Characterization of compounds 3:

Compound 3a, Potassium (7-azaindol-3-yl)-oxoacetate: $^1$H NMR (300 MHz, DMSO-d) δ 8.42 (d, 1H, J=7.86 Hz), 8.26 (d, 1H, J=4.71 Hz), 8.14 (s, 1H), 7.18 (dd, 1H, J=7.86, 4.71 Hz); $^{13}$C NMR (75 MHz, DMSO-d$_6$) δ 169.4, 148.9, 143.6, 135.1, 129.3, 118.2, 117.5, 112.9. MS m/z: (M+H)$^+$ of the corresponding acid of compound 3a (3a-K+H) calcd for C$_9$H$_7$N$_2$O$_3$: 191.05. found 190.97. HPLC retention time: 0.48 minutes (column A).

Compound 3ao (Potassium (4,7-dimethoxy-6-azaindol-3-yl)-oxoacetate) was prepared (as a yellow solid), by the same method used to prepare compound 3a except Ethyl (4,7-dimethoxy-6-azaindol-3-yl)-oxoacetate was employed as the starting material. MS m/z: (M+H)$^+$ of the corresponding acid of compound 3ao (M-K+H)$^+$ calcd for C$_{11}$H$_{11}$N$_2$O$_5$: 251.07. found 251.09. HPLC retention time: 0.69 minutes (column B).

Example Procedure Prep of 5a

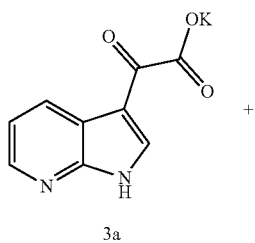

+

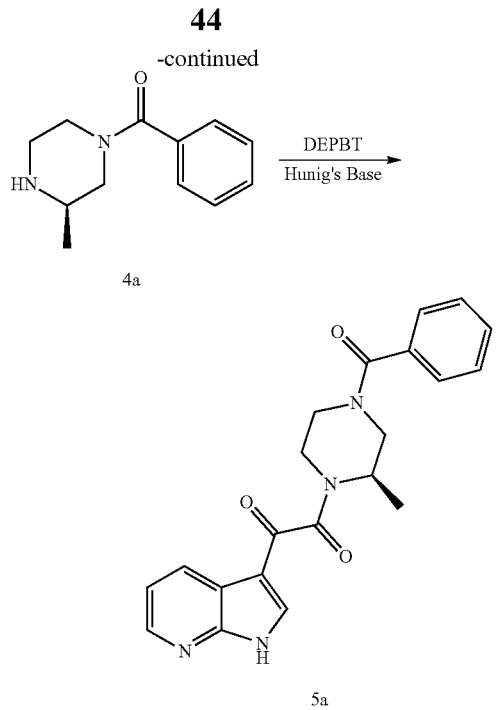

Preparation of (R)—N-(benzoyl)-3-methyl-N'-[(7-azaindol-3-yl)-oxoacetyl]-piperazine 5a: Potassium 7-azaindole 3-glyoxylate 3a (25.4 g, 0.111 mol), (R)-3-methyl-N-benzoylpiperazine 4a (22.7 g, 0.111 mol), 3-(diethoxyphosphoryloxy)-1,2,3-benzotriazin-4(3H)-one (DEPBT) (33.3 g, 0.111 mol) and Hunig's Base (28.6 g, 0.222 mol) were combined in 500 ml of DMF. The mixture was stirred at room temperature for 8 hours.

DMF was removed via evaporation at reduced pressure and the residue was partitioned between ethyl acetate (2000 ml) and 5% Na$_2$CO$_3$ aqueous solution (2×400 ml). The aqueous layer was extracted with ethyl acetate (3×300 ml). The organic phase combined and dried over anhydrous MgSO$_4$. Concentration in vacuo provided a crude product, which was purified by silica gel column chromatography with EtOAc/MeOH (50:1) to give 33 g of product 5a in 81% yield.

Characterization of compounds 5 with the following sub-structure:

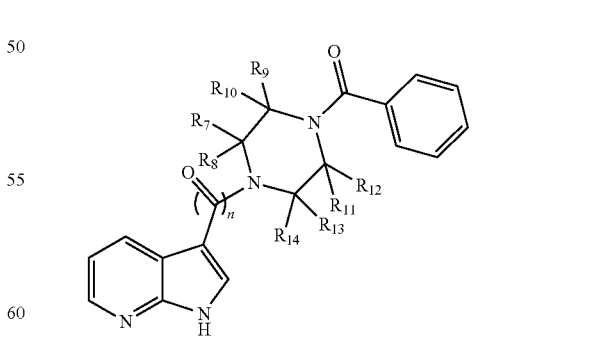

Compound 5a, n=2, R$_{7-13}$=H, R$_{14}$=(R)-Me, (R)—N-(benzoyl)-3-methyl-N'-[(7-azaindol-3-yl)-oxoacetyl]-piperazine: $^1$H NMR (300 MHz, CD$_3$OD) δ □8.57 (d, 1H, J=5.97 Hz), 8.38 (d, 1H, J=4.20 Hz), 8.27 (m, 1H), 7.47 (s, 5H), 7.35 (t, 1H, J=5.13 Hz), 4.75-2.87 (m, 7H), 1.31 (b, 3H); $^{13}$C NMR (75 MHz, CD$_3$OD) δ 185.6, 172.0, 166.3, 148.9, 144.6, 137.0, 134.8, 130.2, 129.9, 128.4, 126.6, 118.6, 118.0, 112.2, 61.3, 50.3, 45.1, 35.5, 14.9, 13.7. MS m/z: (M+H)$^+$ calcd for C$_{21}$H$_{21}$N$_4$O$_3$: 377.16. found 377.18. HPLC retention time: 1.21 minutes (column A). Anal. Calcd for C$_{21}$H$_{20}$N$_4$O$_3$: C, 67.01; H, 5.36; N, 14.88. Found: C, 66.01; H, 5.35; N, 14.61.

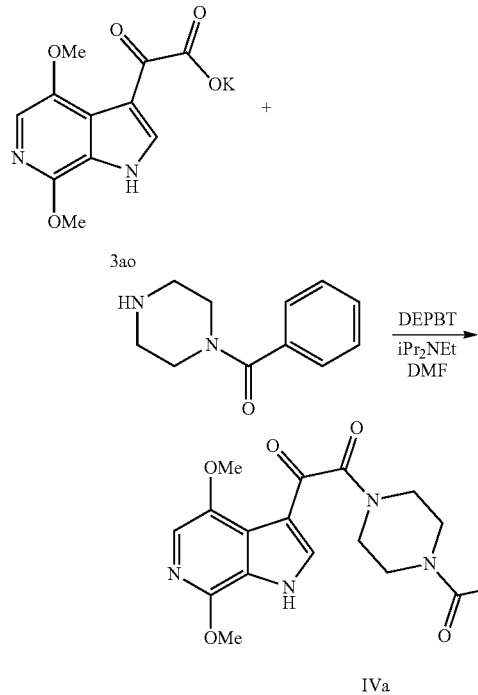

Compound IVa, N-(benzoyl)-N'-[(4,7-dimethoxy-6-azaindol-3-yl)-oxoacetyl]piperazine, was prepared by the same method used to prepare compound 5a but the starting material was Potassium (4,7-dimethoxy-6-azaindol-3-yl)-oxoacetate. The compound was purified by silica gel chromatography using EtOAc as the eluting solvent to give a white solid. $^1$H NMR (500 MHz, DMSO-d$_6$) δ 13.0 (s, 1H), 8.15 (s, 1H), 7.40 (m, 6H), 4.00 (s, 3H), 3.83 (s, 3H), 3.63-3.34 (m, 8H); $^{13}$C NMR (125 MHz, DMSO-d$_6$) □δ 185.5, 169.3, 166.5, 146.2, 145.7, 136.6, 135.3, 129.6, 128.4, 126.9, 122.2, 122.1, 119.2, 114.4, 56.8, 52.9, 45.5, 39.9. MS m/z: (M+H)$^+$ calcd for C$_{22}$H$_{23}$N$_4$O$_5$: 423.17. found 423.19. HPLC retention time: 1.33 minutes (column B). Anal. Calcd. For C$_{22}$H$_{21}$N$_4$O$_5$: C, 62.7; H, 5.02; N, 13.29. Found: C, 61.92; H, 5.41; 13.01. Melting Point: 229.5-232° C.

Procedures for Preparation of Parent Compound IVC

Preparation of 3-methyl-1,2,4-triazole (2-81)

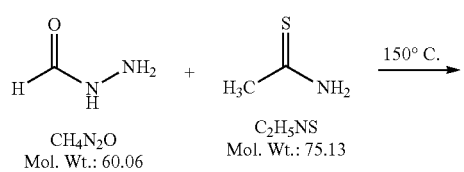

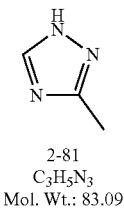

2-81
C$_3$H$_5$N$_3$
Mol. Wt.: 83.09

Procedure: A solid mixture of formic hydrazide (68 g, 1.13 mol) and thioacetamide (85 g, 1.13 mol) in a 500 mL-round bottom flask was heated with stirring at 150° C. (oil bath temp.) for 1.5 hrs with a gentle stream of nitrogen, removing H$_2$S and water (about 18 mL of liquid collected) formed during the reaction. The reaction mixture was distilled under reduced pressure, collecting 60.3 g (0.726 mol, Y. 63.3%) of the title compound at 102° C./0.35-1 mmHg as a white solid after removing a liquid forerun: $^1$H NMR (CDCl$_3$) δ ppm 2.51 (3H, s, 3-Me), 8.03 (1H, s, 5-H), 9.5 (H, br, NH); TLC Rf (10% MeOH/CH$_2$Cl$_2$)=0.3 (phosphomolybdate-charring, white spot).

Reference: Vanek, T.; Velkova, V.; Gut, Jiri *Coll. Czech. Chem. Comm.* 1985, 49, 2492.

Preparation of 3-81

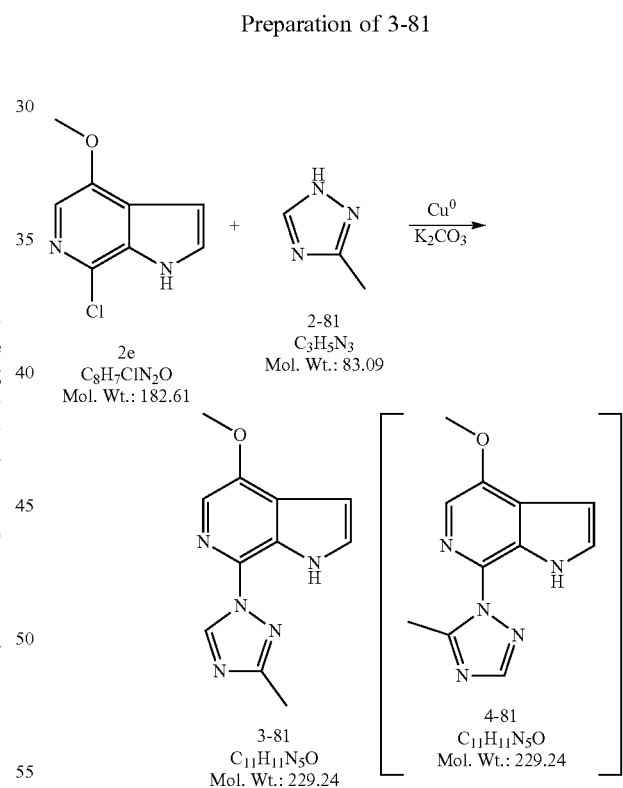

Procedure: A 500 mL round bottom flask was loaded with 4-methoxy-7-chloro-6-azaindole 2e (9.1 g, 50 mmol; dried in vacuo), potassium carbonate (13.8 g, 100 mmol, 2 eq.), copper powder (6.35 g, 100 mmol, 2 eq.), and 3-methyl-1,2,4-triazole (83 g, 1.0 mol, eq.). The solid mixture was heated to melt at 170-175° C. (external oil bath temperature) under a gentle stream of anhydrous nitrogen for 12 h, by which time HPLC analysis indicated that the amount of the peak for the starting material had become 5-30% and the desired product peak becomes about 45% with isomeric by-product peak becomes 15%. As the reaction mixture cooled, MeOH (150 mL) was added slowly to the warm, stirred mixture. Upon cooling, the insoluble material (copper powder) was filtered through a Celite pad, and rinsed with methanol. The filtrate was concentrated in vacuo to a thick paste which was diluted with water (1 L) and extracted with EtOAc (3×150 mL). The EtOAc extracts were dried (MgSO$_4$), filtered and concentrated to obtain about 8 g of crude residue which was crystallized by dissolving in hot CH$_3$CN (50 mL), followed by diluting with water (100 mL) and cooling at 0° C. to collect 1.45 g (12.7%) of the title compound as white solid. The filtrate was purified by C-18 reverse phase silica gel (YMC ODS-A 75 μm) eluted with 15-30% CH$_3$CN/H$_2$O. Appropriate fractions were combined and the aqueous solution after removing CH$_3$CN by rotary evaporator was lyophilized to give additional 1.15 g of the title compound 3-81. The crude aqueous layer was further extracted with EtOAc several times. The ethyl acetate extracts were dried (MgSO$_4$), filtered, concentrated, and crystallized from MeOH to give additional 200 mg of the title compound 3-81. The total yield: 2.8 g (12.2 mmol, Y. 24.5%); MS m/z 230 (MH), HRMS (ESI) m/z calcd for C$_{11}$H$_{12}$N$_5$O (M+H), 230.1042, found 230.1038 (Δ −1.7 ppm); $^1$H NMR (CDCl$_3$) δ ppm 2.54 (3H, s, CH$_3$), 4.05 (3H, s, OCH$_3$), 6.73 (1H, s, H-3), 7.40 (1H, s, H-2), 7.56 (1H, s, H-5), 9.15 (1H, s, triazole-H-5); $^{13}$C NMR (CDCl$_3$, 125.7 MHz) δ ppm 14.2 (triazole-Me), 56.3 (OMe), 100.5 (C-3), 116.9 (C-5), 123.5, 127.2, 127.5 (C-2), 129.5 (C-7), 141.2 (C-5'), 149.5 (C-4), 161.8 (C-3'); Anal. Calcd for C$_{11}$H$_{11}$N$_5$O: C, 57.63, H, 4.83, N, 30.55, found C, 57.37, H, 4.64, N, 30.68.

The structure was confirmed by a single X-ray crystallographic analysis using crystals obtained from C-18 column fractions. A portion of C-18 column fractions containing a mixture of the desired 3-methyl-1,2,4-triazolyl analog 3-81 and isomeric 5-methyl-1,2,4-triazolyl analog 4-81 was further purified by C-18 reverse phase column eluting with 8-10% CH$_3$CN/H$_2$O. Appropriate fractions were extracted with CH$_2$Cl$_2$, and slow evaporation of the solvent gave crystalline material of the isomeric 7-(5-methyl-1,2,4-triazolyl)-4-methoxy-6-azaindole (4-81): MS m/z 230 (MH), $^1$H NMR (CDCl$_3$) δ ppm 3.05 (3H, s, CH$_3$), 4.07 (3H, s, OCH$_3$), 6.74 (1H, q, J=2.4, H-2), 7.37 (1H, t, J=2.4, H-3), 7.65 (1H, s, H-5), 8.07 (1H, s, triazole-H-3). The structure was confirmed by a single X-ray crystallographic analysis.

Preparation of 5-81

Procedure: AlCl$_3$ (40 g, 0.3 mol, 15 eq.) was dissolved in a solution of CH$_2$Cl$_2$ (100 mL) and nitromethane (20 mL) under dry nitrogen. To this solution was added compound 3-81 (4.58 g, 0.02 mol) under stirring and under N$_2$, followed by methyl chlorooxoacetate (9.8 g, 0.08 mol, 4 eq.). The mixture was stirred under N$_2$ at room temperature for 1.5 h. The mixture was added drop-wise to a cold and stirred solution of 20% aqueous ammonium acetate solution (750 mL). The mixture was stirred for 20 min and the resultant precipitate was filtered, washed thoroughly with water and dried in vacuo to obtain 4.7 g (0.015 mol, Y. 75%) of the title compound 5-81 as white solid: MS m/z 316 (MH); HRMS (ESI) m/z calcd for C$_{14}$H$_{14}$N$_5$O$_4$ (M+H), 316.1046. found 316.1041 (Δ −1.6 ppm); $^1$H NMR (CDCl$_3$, 500 MHz) δ ppm 2.58 (3H, s, CH$_3$), 3.96 (3H, s, OCH$_3$), 4.05 (3H, s, OCH$_3$), 7.76 (1H, s, H-5), 8.34 (1H, d, J=3 Hz, H-2), 9.15 (1H, s, triazole-H-5), 11.0 (1H, brs, NH). More title compound 5-81 and hydrolyzed acid 6-81 can be obtained from the filtrate by acid-base extraction with EtOAc.

Preparation of 6-81

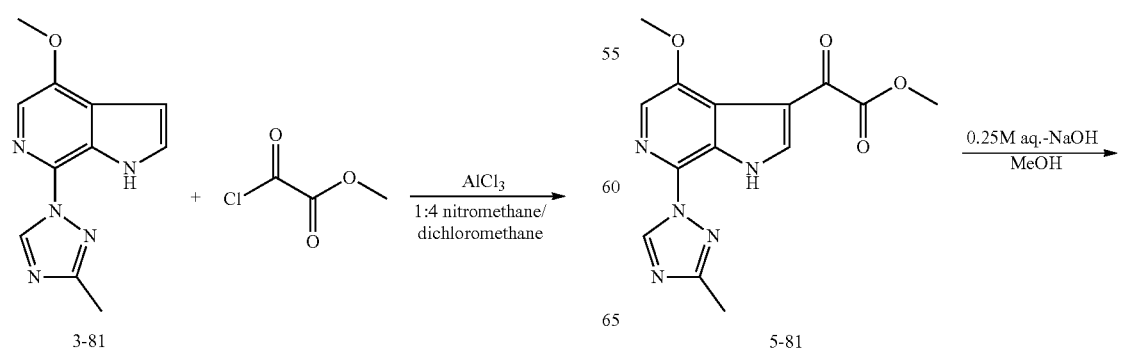

Preparation of Compound IVc

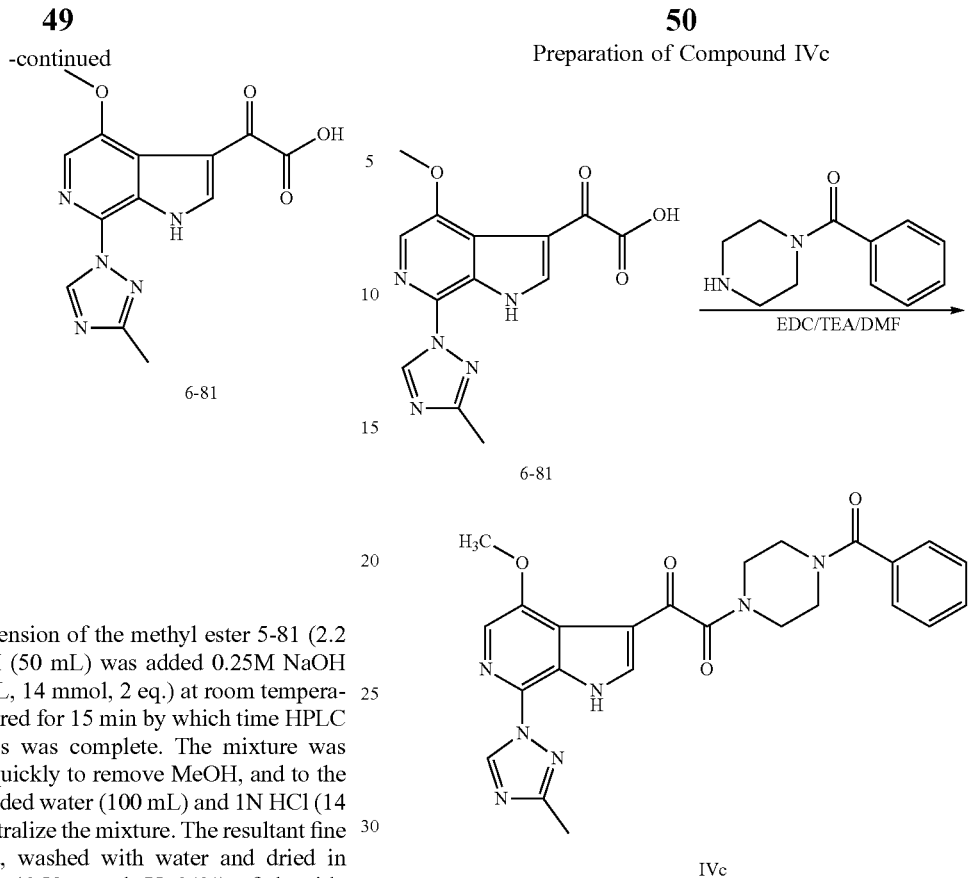

Procedure: To a suspension of the methyl ester 5-81 (2.2 g, 7.0 mmol) in MeOH (50 mL) was added 0.25M NaOH solution in water (56 mL, 14 mmol, 2 eq.) at room temperature and the mixture stirred for 15 min by which time HPLC indicated the hydrolysis was complete. The mixture was concentrated in vacuo quickly to remove MeOH, and to the residual solution was added water (100 mL) and 1N HCl (14 mL) with stirring to neutralize the mixture. The resultant fine precipitate was filtered, washed with water and dried in vacuo to obtain 1.98 g (6.58 mmol, Y. 94%) of the title compound 6-81 as off-white solid: MS m/z 302 (MH); $^1$H NMR (DMSO-$d_6$, 500 MHz) δ ppm 2.50 (3H, s, overlapped with DMSO peaks), 3.98 (3H, s, $CH_{3O}$), 7.87 (1H, s, H-5), 8.29 (1H, d, J=3.5 Hz, H-2), 9.25 (1H, s, triazole-H-5), 12.37 (1H, s, NH).

Alternative procedure: To a suspension of the methyl ester 5-81 (10.7 g, 34 mmol) in MeOH (150 mL) was added 0.25M NaOH solution in water (272 mL, 68 mmol, 2 eq.) at room temperature and the mixture stirred for 20 min by which time HPLC indicated the hydrolysis was complete. The mixture was concentrated in vacuo quickly to remove MeOH, and the residual solution was extracted with EtOAc to remove any neutral impurities. To the aqueous phase was added 1N HCl (68 mL, 68 mmol) to neutralize the product. The resultant mixture was frozen and lyophilized to obtain 14.1 g (33.7 mmol, Y. 99.2%) of the title compound 6-81, containing 2 mole equivalents of NaCl as off-white solid. This material was used in the subsequent reaction without further purification. The disodium salt of the title compound 6-81 was obtained by C-18 reverse phase column chromatography after sodium bicarbonate treatment: HPLC >97% (AP, uv at 254 nm); HRMS (Na salt, ESI$^-$) m/z calcd for $C_{13}H_{10}N_5O_4$ (M−H), 300.0733. found 300.0724 (Δ −3 ppm); $^1$H NMR (Na salt, DMSO-$d_6$, 500 MHz) δ ppm 2.37 (3H, s, Me), 3.83 (3H, s, $CH_{3O}$), 7.56 (1H, s, H-5), 8.03 (1H, s, H-2), 9.32 (1H, s, triazole-H-5); $^{13}$C NMR (Na salt, DMSO-$d_6$, 125.7 MHz) δ ppm 13.8 (triazole-Me), 57.2 (OMe), 114.8 (C-3), 120.0 (C-5), 125.1, 143.5 (C-5'), 149.8 (C-4), 160.0 (C-3'), 171.7, 191.3.

Procedure: To a solution of the acid 6-81 (3.01 g, 10 mmol) and benzoylpiperazine hydrochloride (3.39 g, 15 mmol) in DMF (50 mL) was added triethylamine (10.1 g, 100 mmol, 10 eq.), followed by 1-[3-(dimethylamino)propyl]-3-ethylcarbodiimide hydrochloride (EDC; 5.75 g, 30 mmol) under $N_2$ and the mixture stirred at room temperature for 22 h after sonication and at 40° C. for 2 h. The mixture was concentrated in vacuo to remove DMF and TEA, and to the residual solution was added water (200 mL) under stirring and sonication. The precipitates formed were collected, washed with water and dried in vacuo to obtain 2.8 g (5.9 mmol, Y. 59%) of the title compound IVc as off-white solid. The filtrate was extracted with $CH_2Cl_2$ (×2). The $CH_2Cl_2$ extracts were dried ($Na_2SO_4$), filtered and concentrated to gum which was triturated with $Et_2O$ to obtain a solid. This solid was suspended and triturated with MeOH to obtain 400 mg of the title compound IVc as off-white solid. Total yield: 3.2 g (6.8 mmol, Y. 68%): MS m/z 474 (MH); HRMS (ESI) m/z calcd for $C_{24}H_{24}N_7O_4$ (M+H) 474.1890, found 474.1884 (Δ −1.2 ppm); $^1$H NMR (DMSO-d6) δ ppm 2.50 (3H, s, overlapped with DMSO peaks), 3.43 (4H, br, $CH_2N$), 3.68 (4H, br, $CH_2N$), 3.99 (3H, s, $CH_3O$), 7.46 (5H, br. s, Ar—Hs), 7.88 (1H, s, indole-H-5), 8.25 (1H, s, indole-H-2), 9.25 (1H, s, triazole-H-5), 12.40 (1H, s, NH); $^{13}$C-NMR (DMSO-d6) δ ppm 13.78, 40.58, 45.11, 56.78, 114.11, 120.95, 122.71, 123.60, 126.98, 128.34, 129.6, 135.43, 138.52, 142.10, 149.15, 161.29, 166.17, 169.22, 185.42; UV (MeOH) λmax 233.6 nm (ε 3.43×10$^4$), 314.9 nm (ε 1.73×10$^4$); Anal: Calc for $C_{24}H_{24}N_7O_4 \cdot ⅕H_2O$; C, 60.42, H, 4.94, N, 20.55, Found; C, 60.42, H, 5.03, N, 20.65; KF ($H_2O$) 0.75%.

This reaction can also be performed by use of HATU and DMAP to provide more consistent yield of the title compound: To a suspension of the acid 6-81 (15.6 mmol) and HATU [O-(7-azabenzotriazol-1-yl)-N,N,N',N'-tetramethyluronium hexafluorophos phonate] (8.90 g, 23.4 mmol; 1.5 eq.) in DMF (60 mL) and CH$_2$C$_2$ (60 mL) was added a mixture of DMAP (5.72 g, 46.8 mmol, 3 eq.) and benzoylpiperazine hydrochloride (5.30 g, 23.4 mmol; 1.5 eq.) in DMF (60 mL) at room temperature and the mixture was stirred under nitrogen atmosphere for 4 hrs. The mixture was concentrated in vacuo to remove CH$_2$C$_2$ and most of DMF, and to the residual solution was added water under stirring and sonication. The precipitates formed were collected, washed with water and dried in vacuo to obtain 5.38 g (11.4 mmol, Y. 72.8%) of the title compound IVc as off-white solid: HPLC >95% (AP, uv at 254 nm).

Compound IVb

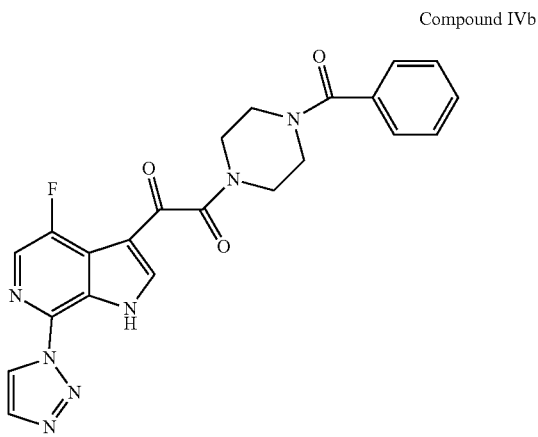 [SMILES: O=C(C(=O)N1CCN(C(=O)c2ccccc2)CC1)c1c[nH]c2c(-n3ccnn3)ncc(F)c12]

Synthetic Experimental Procedures for Best Preparation of Compound IVb

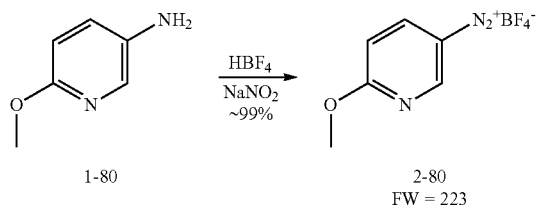

5-Amino 2 methoxypyridine (50 g, 0.4 mol) was added to a stirring mixture of absolute ethanol (280 ml) and HBF$_4$ (48% in water, 172 ml) and cooled to 0° C. Sodium nitrite (129 g) was dissolved in water (52 ml) and added portion-wise over 1 h). The stirring was continued at 0° C. for 2 hr. The reaction mixture was diluted with ether (1 L). The solid product was collected by filtration and washed with 500 ml of 50:50 EtOH/ether and subsequently several times with ether until the product was slightly pinkish in color. The pale pink solid 90 g (~100% yield) was kept in a dessicator over P2O5.

The same procedure was followed to perform the reaction on larger scale:

(1) (200 g. 1.6 mol); HBF$_4$ (688 ml); NaNO$_2$ (116 g); EtOH (1.12 L); H$_2$O (208 ml)

The reaction was run 4 times (total 800 grams (1-80)). The product was dried over P2O5 for 48 hr. (only 24 hr for first batch).

A total of 1,293 g of (2-80) was obtained, (91% yield).

Ref: *J. Heterocyclic Chem.*, 10, 779. 1973 (for above reactions, including analytical data)

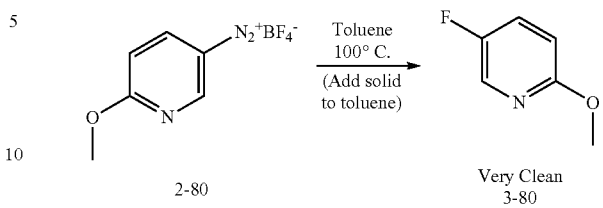

The decomposition of the diazonium salt was run in 3 batches of:

206 g, 219 g and 231 g using 1.3 L, 1.4 L and 1.6 L of anhydrous toluene respectively.

The toluene was preheated under nitrogen to 100° C. (internal temperature) in a 2 L 3-neck round bottom flask provided with a mechanical stirrer. The solid was added solid portion-wise via a scoop through a powder funnel which was attached to an adapter with slight outward positive nitrogen flow. During addition, the temperature was maintained between 99-102° C. (set at 100° C.) and stirred vigorously. Total addition time was 60 min. for the smaller two batches and 70 min. for the last one. After the addition was finished, each stirring reaction was heated at 110° C. for 1 hr. The heating mantle was removed and stirring was stopped. The reactions were allowed to stand for 2 hr (ambient temp achieved). Safety Note: The reaction contains BF3 so working with the reaction hot exposes vapors which caused skin irritation with some people. No incidents were noted at ambient temperature (6 different people). The hot toluene from the reaction was poured into a 4 L Erlenmeyer (a dark brown oil and residue remained in the flask). The residue was washed with 50 ml of toluene and poured into the original toluene extracts.

Add 1.5 L of 1N NaOH to toluene layer, extract and wash with ~100 ml of sat aq. NaCl.

Combine NaCl with NaOH layer, re-extract with 150 ml of toluene, wash with 50 ml of sat NaCl.

Combine toluene layers.

Add 1 L of 1N NaOH to residue in reaction flask and swirl to dissolve as much residue as possible then add 500 ml Et$_2$O and pour into Erlenmeyer.

Add ~500 ml more of 1 N NaOH to reaction flask and swirl ~500 ml of Et$_2$O.

Combine dark Et$_2$O and NaOH washings in erlenmyer flask.

Et2O/NaOH mixture was poured through powder funnel containing plug of glass wool to collect dark viscous solid. (Add ~500 ml more ether to wash) into 6 L sep funnel.

Extract. Wash ether layer with ~200 ml of H$_2$O and then 100 ml of sat NaCl.

Combine all washings with original NaOH aq. Layer and re-extract with 500 ml of ether. Wash with 100 ml H$_2$O and 100 ml of NaCl.

Combine ether extracts. Toluene and ether extracts were checked by LC/MS clean product.

The ether was concentrated on a rotovap and the residue was combined with the toluene extracts to make a homogeneous solution which is taken to next step as is.

The other two runs were combined and worked up in the same way.

All aqueous layers were checked by LC/MS=no product.

Ref *J. Heterocyclic Chem.*, 10, 779, 1973 (for above reactions, including analytical data)

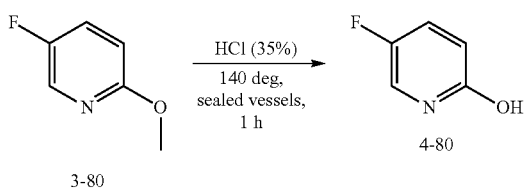

A total of 4.6 L of toluene solution containing 3-80 was placed in several sealed tubes and treated with 900 ml of 35% HCl at 145° C. for 2 hr. LC/MS showed no starting material, only 4. The toluene solution was decanted and discarded. The aqueous phase was washed with EtOAc and concentrated down to remove volatiles to afford a brown solid containing the desired fluoro-hydroxypyridine 4-80.

A total of 244 g of this solid was collected and taken to next step as is (it was not completely dry).

Note: We have subsequently run this by decanting the toluene layer first prior to heating to reduce volumes. Same reaction was carried out using HBr (48% in $H_2O$) at 100° C. for 6 h with similar result to the literature procedure 49% yield.

Ref: *J. Heterocyclic Chem.*, 10, 779, 1973 (for above reactions, including analytical data)

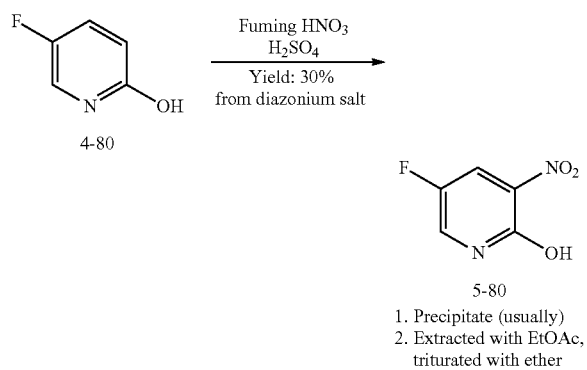

1. Precipitate (usually)
2. Extracted with EtOAc, triturated with ether

The solid from above containing (4-80) was divided in 4 batches and treated with $H_2SO_4$ and fuming $HNO_3$ as shown below. The amounts used were:

|  | batch 1 | batch 2 | batch 3 | batch 4 |
|---|---|---|---|---|
| (1) | 25 g | 54 g | 75 g | 90 g |
| fuming $HNO_3$ | 20.8 ml | 45 ml | 62.4 ml | 75 ml |
| $H_2SO_{4,(for\ addition)}$ | 5.6 ml+ | 12 ml+ | 16.8 ml+ | 20 ml+ |
| (for soln) | 56 ml | 120 ml | 168 ml | 200 ml |

Compound 440 was dissolved in sulfuric acid (the larger amounts indicated above) at rt and then heated to 65° C. A preformed solution of fuming nitric acid and sulfuric acid (the smaller amount indicated above) was added dropwise. The temperature was kept between 65° C. and 80° C. (rxn is exothermic and although the bath is at 65° C., temperature goes higher, usually 75, sometimes 80° C.). After the addition was complete, the reaction mixture was heated at 65° C. for an additional hr. The reaction mixture was then cooled to rt and poured in a flask containing ice) (20 g of ice/gr compound, evolution of gas occurred). A solid precipitated out and it was collected by filtration (¹HNM" showed 4-80 and something else (discarded)).

The aqueous layer was extracted with AcOEt several times (3-5) and concentrated on a rotary evaporator under vacuum to afford a solid that was triturated with ether to afford 5-80 as a bright yellow solid. A total of 117 g of desired product was collected in the first crop (27% yield from diazonium salt). A portion did not crystallize: this oil was triturated with MeOH and $Et_2O$ to afford 3.6 g of 510; another precipitation from the mother liquid afforded an additional 6.23 g of the desired product 5-80.

Total: 117.0+3.6+6.23=126.83. 30.4%). Yield for 3 steps (decomposition of diazonium salt; deprotection and nitration).

Analytical data from Notebook: 53877-115: ¹HNMR (δ, MeOD): 8.56-8.27 (dd, J=7.5, 3.3 Hz, 1H), 8.01 (d, J=3.3 Hz, 1H); LC/MS $(M+1)^+$=158.9; rt=0.15 min.

Note: A portion of the aqueous acidic solution was taken and neutralized with $Na_2CO_3$ until effervescence stopped and then it was extracted with AcOEt⇒A different product was obtained. No desired product in these extracts.

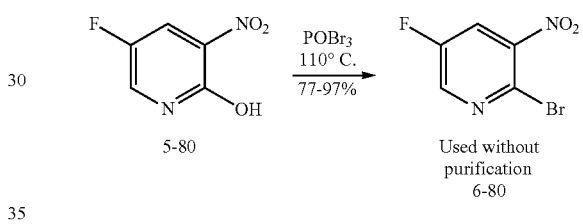

5-80

Used without purification
6-80

A total of 117 g of 5-0 was divided in 4 batches of 30 g×3 and 27 g×1 and treated with $POBr_3$ (3 equiv.; 163 g×3 and 155 g×1) and a catalytic amount of DMF (15 ml) at rt (DMF was added carefully⇒gas evolution). After 5 min. at room temperature, the solutions were heated at 110° C. for 3 hr. LC/MS showed starting material had been consumed. The reaction mixtures were allowed to cool to rt. The reaction flasks were placed in an ice bath; and then ice was added very slowly and carefully portionwise into the flask, gas evolution was due to HBr formation; the liquid and black solid that formed was poured into a beaker with ice. EtOAc was added and the mixture was then extracted several times with EtOAc. The organic layer was washed with saturated aq. $NaHCO_3$; $H_2O$ and brine; dried over $Na_2SO_4$ and filtered. The product was dried in the pump overnight to provide 123 g of 6-80 as a brown solid (77% yield).

Note: Reaction is completed within 1 h.

¹HNMR (δ, $CDCl_3$): 8.52 (m, 1H), 7.93 (m, 1H).

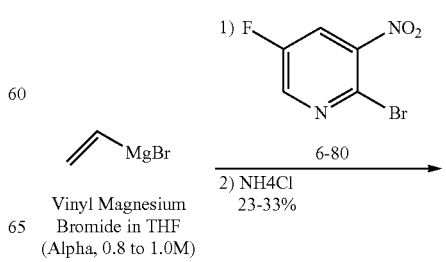

Vinyl Magnesium Bromide in THF (Alpha, 0.8 to 1.0M)

2) NH4Cl
23-33%

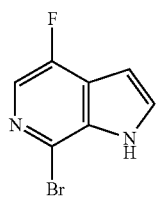

precursor 2i
C₇H₄BrFN₂
Exact Mass: 213.95
Mol. Wt.: 215.02
C, 39.10; H, 1.88; Br, 37.16;
F, 8.84; N, 13.03

800 ml of vinyl magnesium bromide (1M in THF, Aldrich) was cooled below −60° C. with vigorous stirring under N₂. 2-bromo-5-fluoro-3-nitro pyridine (43.3 g, 0.196 mol) in 200 ml THF was added dropwise via addition funnel at such a rate that the temp was kept below −60° C. This took ~1.25 hr. The reaction mixture was warmed to −40 to −50° C. and stirred for 1 hr more. Then 1 L of saturated aqueous NH₄Cl was added slowly and cautiously. At first, foaming occurred and considerable solid was present, but this essentially dissolved as the addition was completed and the material warmed to rt. The layers were separated and the aqueous layer extracted 3 times with ethyl acetate. The organic extracts were washed with brine, dried over Na₂SO₄, filtered and concentrated to afford ~50 g of a black gummy solid. HPLC indicated 57-58% product. To this was added CH₂Cl₂ and the solid was collected by filtration and washed with CH₂Cl₂ to afford 12.5 g of product as a brown solid. The reaction was repeated on exactly the same scale and worked up in the same manner. From CH₂Cl₂ trituration there was obtained 12.4 g of Precursor 2i (HPLC ~97% pure). The crude was recovered and allowed to stand in dichloromethane. Upon standing 3.6 g of additional product separated and was recovered by filtration.

Total yield=29.5 g (35%).

¹HNMR (δ, CDCl₃): 8.69 (bs, 1H), 7.92 (d, J=1.8 Hz, 1H), 7.41 (m, 1H), 6.77 (m, 1H); LC/MS (M+1)⁺=216.-217.9; rt=1.43 min.

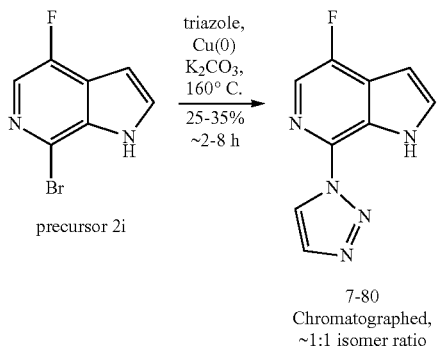 [SMILES: Fc1cnc(Br)c2[nH]ccc12 ; Fc1cnc(-n2ccnn2)c2[nH]ccc12]

7-80
Chromatographed,
~1:1 isomer ratio

Reaction was carried in a 250 ml flask (foaming occurred upon heating and the big size flask is more convenient). A mixture of precursor 2i (3 g, 13.95 mmol), 1,2,3-triazole (15 g, 217.6 mmol, 15 eq), K₂CO₃ (1.9 g, 13.95 mmol, 1 eq) and Cu(0)(0.9 g, 13.9 mmol, 1 eq) was heated at 160° C. for 7 hr (from rt to 160° C. total 7 hr) under N₂ (depending on the Cu(0) lot, reaction time may vary from 2 hr to 7 hr). The resulting mixture was diluted with MeOH, filtered through filter paper (to remove the copper). Washed with MeOH (20 ml) and water (30 ml).

The filtrate was concentrated (remove solvent in rotovap) and diluted with ethylacetate. The aqueous layer was extracted with ethylacetate. The combined organic layer was dried over sodium sulfate, filtered and concentrated. The residue was dissolved in MeOH (20 ml), 7-80 (750 mg) crystallized from the methanol as a white solid and was collected by filtration. (Slow gradient volume, silica gel hex/AcOEt (0-+18%) of the mother liquids usually affords 5-10% more of 7-80.

¹HNMR (δ, CDCl₃): 10.47 (bs, 1H), 8.76 (s, 1H), 7.94 (s, 1H), 7.89 (s, 1H), 7.53 (m, 1H), 6.78 (m, 1H); LCMS (M+1)⁺=204; rt=1.29 min.

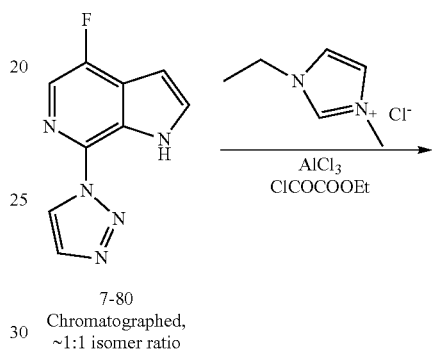

7-80
Chromatographed,
~1:1 isomer ratio

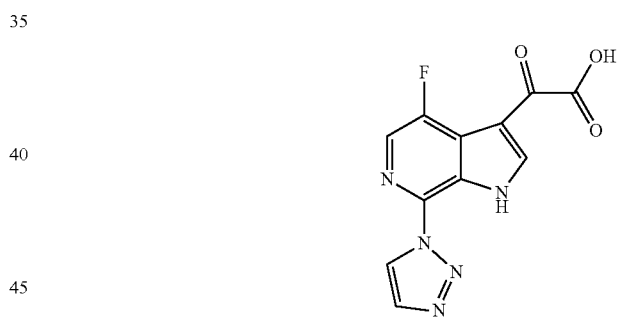

8-80

Ethyl methylimidazolium chloride (4.3 g, 29.6 mmol, 3 eq) was placed in a 250 ml flask. AlCl₃ (11.8 g, 88.6 mmol, 9 eq) was added into the flask in one portion. A liquid suspension was formed (some of AlCl₃ remained as solid). After stirring for 5-10 min. compound (1) (2.0 g, 9.85 mmol) was added in one portion followed by slow addition (via a syringe) of ethyl chlorooxalacetate (3.3 ml, 29.6 mmol, 3 eq). The reaction was stirred at room temperature for 20 hr. LCMS indicated compound 8-80:compound 7-80=6:2. (Compound I has strong UV absorption). The reaction was quenched by carefully adding ice water (~75 ml) at 0° C. A yellow solid precipitated at this point. The resulting suspension was filtered and the solid was washed with water. MeOH and ethyl acetate (to remove unreacted SM) and the solid was dried in air. (LCMS purity 70%~80%) 2 g of solid containing 8-80 was obtained and taken to the next step without further purification. LCMS (M+1)⁺=276; rt=0.97 min.

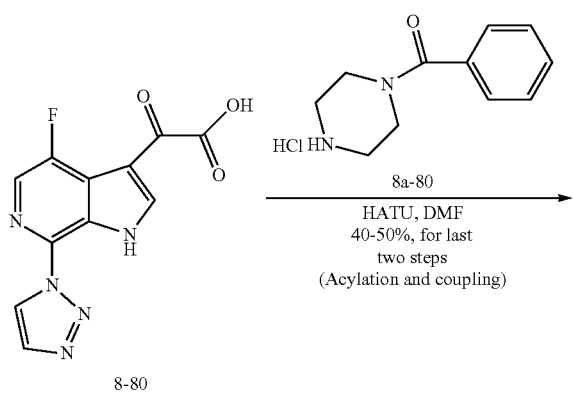

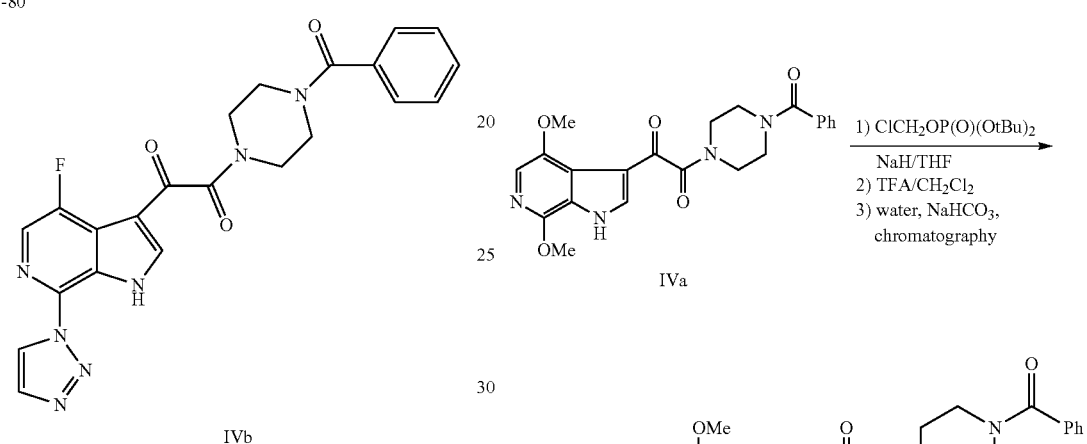

A mixture of compound 8-80 (4.9 g, 17.8 mmol) & N-benzoylpiperazine hydrochloride 8a-80 (HCl salt; 6.0 g, 26.7 mmol, 1.5 eq) in DMF (30 ml) was stirred at RT overnight (16 hr). A slurry was formed. An additional 20 ml of DMF was added into the slurry. Then HATU (12.2 g, 26.7 mmol, 1.5 eq) was added followed by DMAP (4.3 g, 35.6 mmol, 2 eq). The reaction mixture was stirred for 30 min. LCMS indicated the starting material 8-80 was completely converted to product (EXAMPLE 216). The resulting mixture was filtered and the solid washed with water. The filtrate was concentrated in vacuo. Water was added to the residue and the solid was collected by filtration. The solids were combined and washed with water, MeOH and EtOAc. Then the solid was dried in air. LCMS & HPLC showed IVb, >99% pure. The solid product was further purified by precipitation and crystallization in 5~10% $CH_3OH/CHCl_3$.

Purification of IVb

Crude compound IVb obtained as above (15.3 g) was dissolved in 10% $MeOH/CHCl_3$ (600 ml). A light brown suspension was formed, filtered through filter paper and washed with MeOH a twice. The brownish solid was discarded (~1.2 g). Compound IVb was crystallized in the filtrate, the solid was collected by filtration and the white solid was dried in air. The filtrate was used to repeat the crystallization several times. The solid obtained from each filtration was analyzed by HPLC. All the pure fractions were combined. The not so pure fractions were resubjected to crystallization with MeOH & $CHCl_3$. A total of 12.7 g of Compound IVb was obtained from recrystallization and precipitation. The mother liquid was concentrated and purified on silica gel column (EtOAc, then $CHC_3/MeOH$ (0-2%)) to provide 506 mg of product) as a white solid.

$^1$HNMR (d, DMSO) 13.1 (bs, 1H), 9.0 (s, 1H), 8.4 (s, 1H), 8.3 (s, 1H), 8.2 (s, 1H), 7.4 (bs, 5H), 3.7 (bs, 4H), 3.5 (bs, 4H); MS m/z 448 (MH). Anal: Calc for $C_{22}H_{18}FN_7O_3$; C, 59.05, H, 4.05, N, 21.91, F, 4.24. Found; C, 57.28, H, 4.14, N, 21.22; F, 4.07%.

Examples 1-4

Preparation of Prodrugs I from Parent Compounds IV

Synthetic Scheme for Examples 1-4

-continued

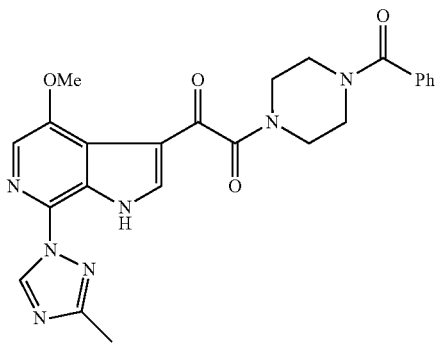

IVc

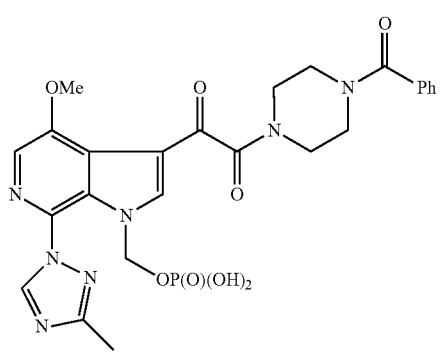

Id

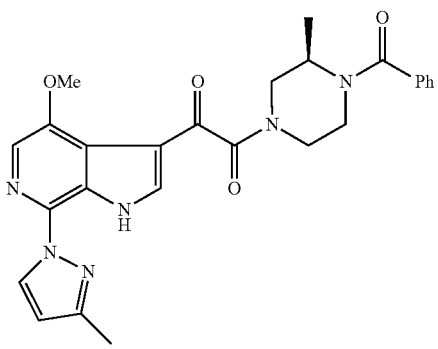

Example 1

Preparation of Ia

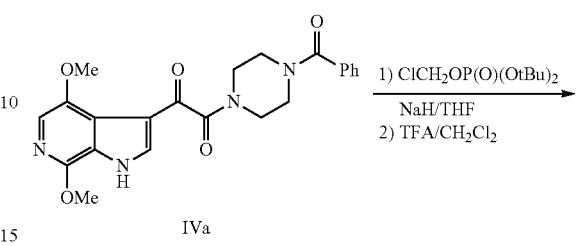

IVa

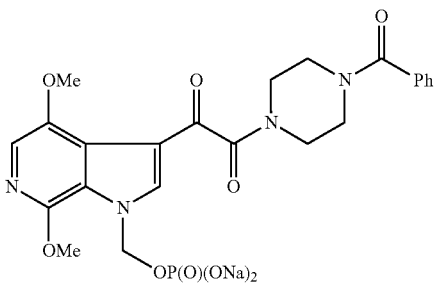

Ia

Procedure: A suspension of IVa (211 mg, 0.5 mmol) in THF (2 mL; Sure Seal) under anhydrous $N_2$ atmosphere was treated with NaH (86 mg, 2.2 mmol; 4.4 eq.; 60% oil dispersion). After a few minutes stirring at room temperature, di-tert-butyl chloromethyl phosphate (782 mg, 3.0 mmol; preparation, see U.S. Pat. No. 6,362,172) was added and the mixture stirred for 1-5 days, monitoring the completion of the reaction by HPLC (additional 1-2 eq. of each NaH and the phosphate may be required to bring the reaction to near completion). After the staring material was consumed, the mixture was concentrated in vacuo to dryness and the residue, which appeared to be a mixture of N-alkylated indole mono- and bis-t-butyl phosphate, was dissolved in $CH_2Cl_2$ (5 mL) was treated with TFA (5 mL) at room temperature for 2 h. The mixture was concentrated in vacuo and the residue was purified by C-18 reverse phase silica gel, eluting with 5-10% $CH_3CN$ in water containing $NaHCO_3$, to obtain 75 mg (0.13 mmol; Y. 26%) of the title compound Ia as an off-white powder (disodium salt): HPLC >99% (AP at 254 nm); LC/MS (ESI+) m/z 533 (M+H minus 2Na)$^+$; HRMS (ESI) m/z calcd for $C_{23}H_{26}N_4O_9P$ (M+H minus 2Na)$^+$ 533.1437, found 533.1426 (Δ −2.1 ppm); $^1$H NMR ($D_2O$, 500 MHz) δ ppm 3.51 (2H, m), 3.67 (2H, m), 3.73-3.79 (2H, m), 3.89-3.95 (2H, m), 3.94, 3.95 (3H, 2s), 4.05, 4.07 (3H, 2s), 6.02-6.04-6.05-6.07 (2H, ABq.), 7.43, 7.44 (1H, 2s), 7.45-7.56 (5H, m), 8.49, 8.52 (1H, 2s).

By using a similar procedure and conditions, Ib was prepared from IVb. Ic and Id were prepared from IVc, and IVd, respectively, but water rather than sodium bicarbonate solution was utilized in the purification.

Example 2

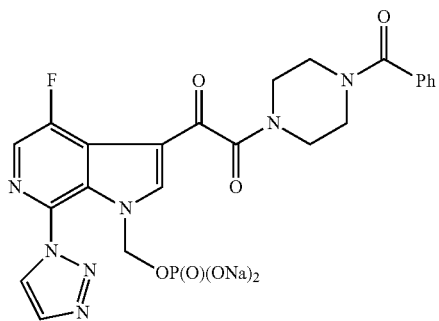

Ib: Yield 13% (disodium salt); HPLC >96% (AP at 254 nm); LC/MS (ESI+) m/z 558 (M+H minus 2Na)$^+$; $^1$H NMR (D$_2$O, 500 MHz) δ ppm 3.59 (2H, m), 3.70-3.84 (4H, m), 3.93-3.95 (2H, m), 5.28-5.29-5.30-5.32 (2H, ABq.), 7.4-7.6 (5H, m), 8.09, 8.10 (1H, 2s), 8.34, 8.36 (1H, 2s), 8.59, 8.61 (1H, 2s), 8.72, 8.75 (1H, 2s).

Example 3

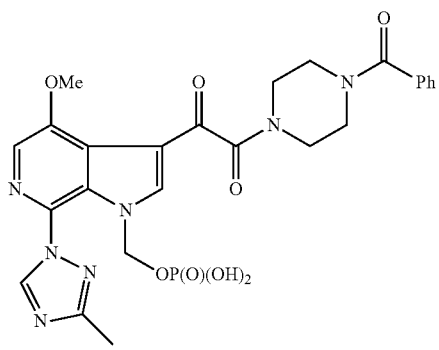

Ic: Yield 37% (acid form. Water was used in place of aqueous sodium bicarbonate during the purification; HPLC >98% (AP at 254 nm); LC/MS (ESI+) m/z 584 (M+H); $^1$H NMR (DMSO-d6, 500 MHz) δ ppm 2.40 (3H, s), 3.44 (4H, br.s), 3.66 (4H, brs), 4.04 (3H, s), 5.79 (1H, s), 5.82 (1H, s), 7.46 (5H, brs), 8.07 (1H, s), 8.41 (1H, s), 8.88 (1H, s).

Example 4

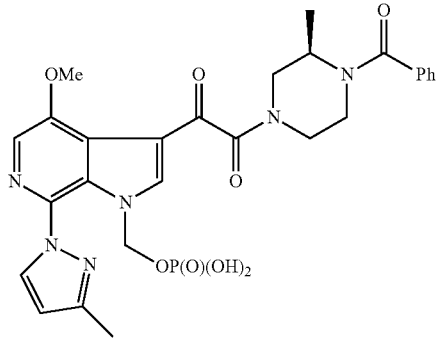

Id: Yield 7% (acid form). Water was used in place of aqueous sodium bicarbonate during the purification; LC/MS (ESI+) m/z 597 (M+H); H NMR (DMSO-d6, 500 MHz) δ ppm 1.16, 1.21 (3H, 2d, J=6.5 Hz), 2.29 (3H, s), 2.3-4.5 (7H, m), 4.00, 4.01 (3H, 2s), 5.79-5.85 (2H, m), 6.36 (1H, t, J=2 Hz), 7.42-7.47 (5H, m), 7.99 (1H, s), 8.08, 8.09 (H, 2s), 8.34, 8.44 (1H, 2s).

Example 5

Preparation of Ica, (Disodium Salt)

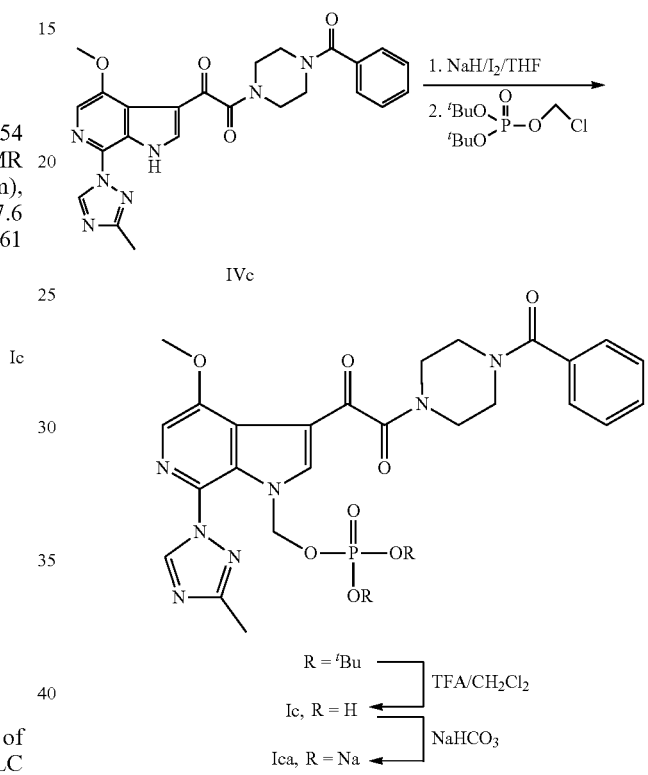

General Procedure: A suspension of IVc (0.24 g, 0.5 mmol) in anhydrous THF (4 mL) under nitrogen atmosphere was treated with sodium hydride (60% oil dispersion, 0.08 g, 2.0 mmol), and stirred until gas evolution ceased (approximately 5 minutes). The reaction mixture was treated with iodine (0.13 g, 0.5 mmol) and stirred for 2-3 minutes followed by addition of di-tert-butyl chloromethyl phosphate (1.6 g, 6.0 mmol, crude). A stream of nitrogen was allowed to pass over the reaction to facilitate the removal of much or all of the THF. The reaction mixture was stirred overnight. HPLC analysis of crude indicated starting IVc (ca. 56%) and desired adduct (ca. 32%).

Several crude reaction mixtures (a total of 6.7 mmol based on starting material IVc) were re-dissolved in dichloromethane, combined, concentrated in vacuo to remove any remaining THF. The residue was suspended in dichloromethane and TFA (1:1, approximately 40 mL total volume). The mixture was stirred for 1.5-2 hours and then solvent was removed in vacuo. The residue was suspended in dichloromethane and extracted into water (approximately 60 mL) made weakly basic with solid or aqueous sodium bicarbonate. The aqueous layer was reduced in volume by rotary evaporator if required and the solution was loaded onto a C-18 reverse phase column (approximately 80 g of C-18, YMC ODS-Aq, 50 micron) and eluted with water, followed by water containing 2.5% acetonitrile. Fractions containing pure product were pooled and organic solvent was removed by rotary evaporator. Purified product was recovered after lyophilization to give 1.00 g (1.30 mmol, 19% over 2 steps) of the title compound Ica (disodium salt) as an off-white powder: HPLC purity >99% AP at 254 nm (gradient 0-100% B/A; A 10% CH$_3$CN-90% H$_2$O-0.1% TFA, B 90% CH$_3$CN-10% H$_2$O-0.1% TFA, gradient time 4 min, column YMC ODS-Aq 4.6×50 mm 3 micron); MS-ESI– m/z 482 (M–H minus 2Na)$^-$; HRMS (ESI) m/z calcd for C$_{25}$H$_{27}$N$_7$O$_8$P (M+H minus 2Na)$^+$ 584.1659, found 584.1651 (Δ –1.3 ppm); $^1$H NMR (D$_2$O, 500 MHz) δ ppm 2.53, 2.54 (3H, 2s), 3.56 (2H, s, CH$_2$N), 3.72 (2H, br.s, CH$_2$N), 3.78, 3.83 (2H, 2br.s, CH$_2$N), 3.94, 3.96 (2H, 2br.s, CH$_2$N), 4.14 (3H, s, CH$_{3O}$), 5.38, 5.40 (2H, 2d, J=11 Hz), 7.45-7.59 (5H, m, Ar—Hs), 8.07, 8.09 (1H, 2s, indole-H-5), 8.64, 8.67 (1H, 2s, indole-H-2), 8.87, 8.89 (1H, 2s, triazole-H-5); $^{13}$C-NMR (125.7 MHz, D$_2$O) δ ppm 15.43 (N-Me), 44.03, 44.47, 44.66, 45.05, 48.20, 48.82, 49.60, 50.23, 59.78 (OMe), 75.81 (NCH$_2$O), 115.6, 126.0, 127.2, 129.6, 131.0, 131.7, 132.1, 133.5, 136.8, 147.6, 150.1, 154.2, 164.8, 170.4, 175.8, 189.2; UV (H$_2$O) λmax 220 nm (ε 3.91×10$^4$), 249 nm (ε 2.00×104), 303 nm (ε 1.60×104); Anal: Calc for C$_{25}$H$_{24}$N$_7$O$_8$PNa$_2$. 8H$_2$O. 0.2NaHCO$_3$; C, 38.39, H, 5.14, N, 12.44, P, 3.93, Na, 6.42 Found; C, 38.16, H, 4.81, N, 12.43, P, 3.72, Na, 6.05; KF (H$_2$O) 17.3%.

A less pure fractions were collected to obtain 0.22 g (0.29 mmol, Y. 4%) of the title compound Ica (disodium salt): HPLC purity >95% (AP at 254 nm).

Example 6

Preparation of Iab (Hydrated Lysine Salt)

Step One

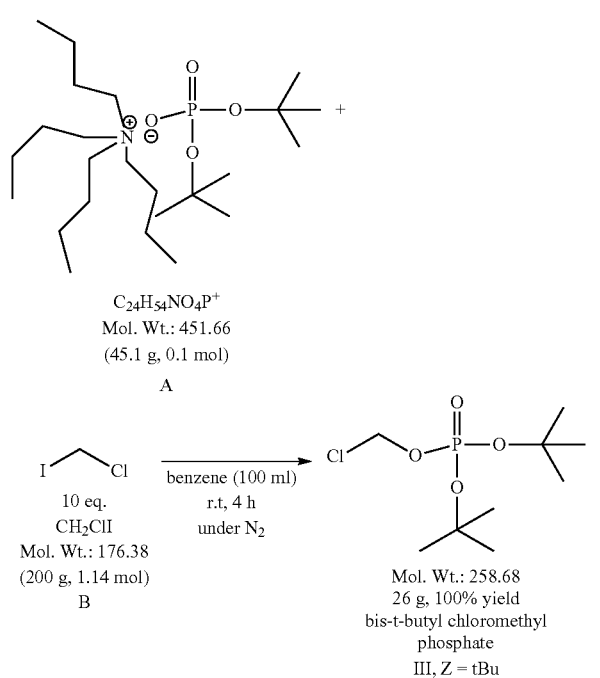

Phosphate ester A (45.1 g, 0.1 mol) and chloroiodomethane B (200 g, 1.14 mol) were combined in 100 ml of benzene and the mixture was stirred at room temperature for four hours before benzene was removed under vacuum. Then, 500 ml of ethyl ether was added to the residue and insoluble solid was filtered away. Concentration of the filtrate provided di-tert-butyl chloromethyl phosphate, which was utilized in the next step without any purification.

Step Two

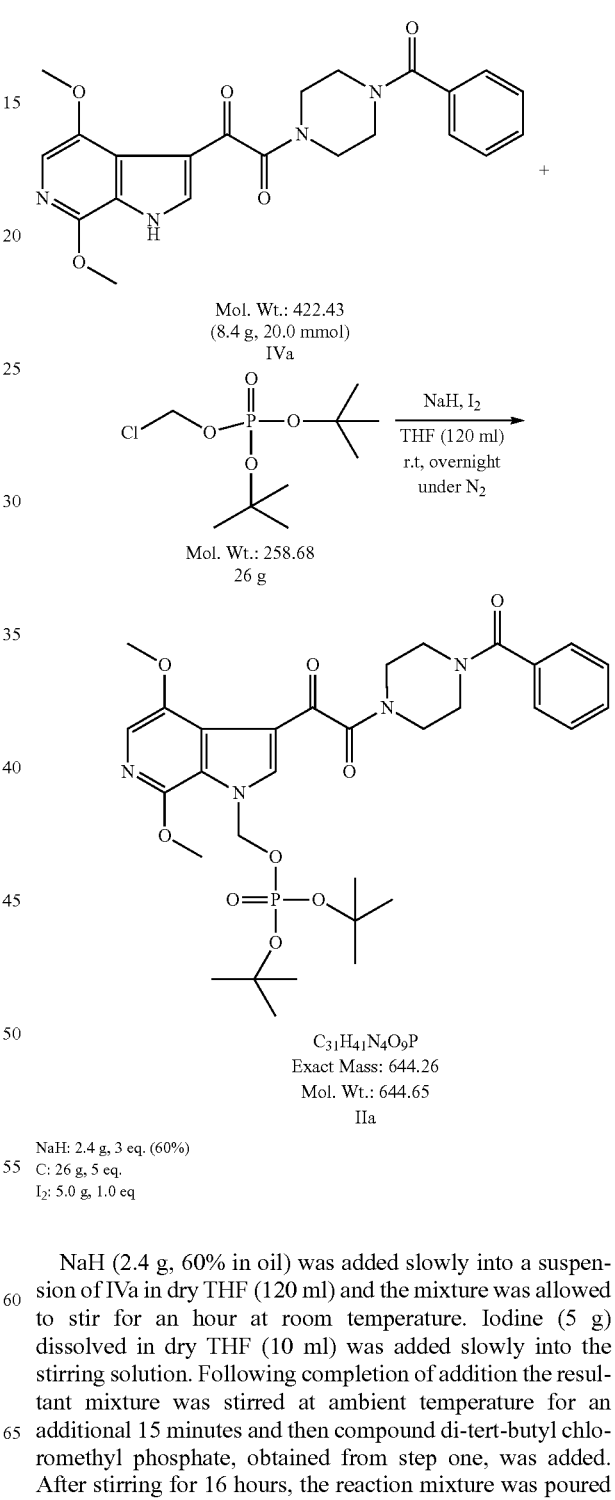

NaH: 2.4 g, 3 eq. (60%)
C: 26 g, 5 eq.
I$_2$: 5.0 g, 1.0 eq

NaH (2.4 g, 60% in oil) was added slowly into a suspension of IVa in dry THF (120 ml) and the mixture was allowed to stir for an hour at room temperature. Iodine (5 g) dissolved in dry THF (10 ml) was added slowly into the stirring solution. Following completion of addition the resultant mixture was stirred at ambient temperature for an additional 15 minutes and then compound di-tert-butyl chloromethyl phosphate, obtained from step one, was added. After stirring for 16 hours, the reaction mixture was poured into ice water (120 ml), followed by extraction with EtOAc (3×300 ml). The combined organic extracts were washed with water (100 ml) and then brine (100 ml), dried over Na$_2$SO$_4$, and concentrated under vacuum to afford a residue, which was purified by silica gel chromatography (elution with EtOAc/Et$_3$N (100/1) and then EtOAc/MeOH (100/1)) to give diester IIa in yields of 70-80%.

Step Three

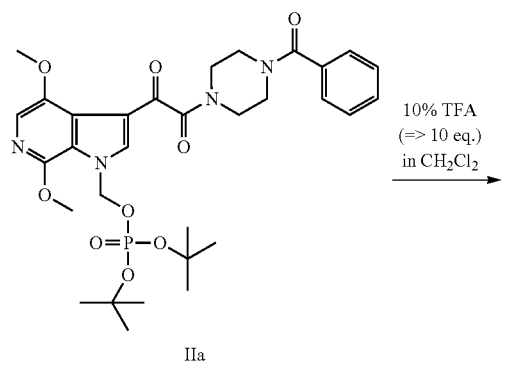

IIa

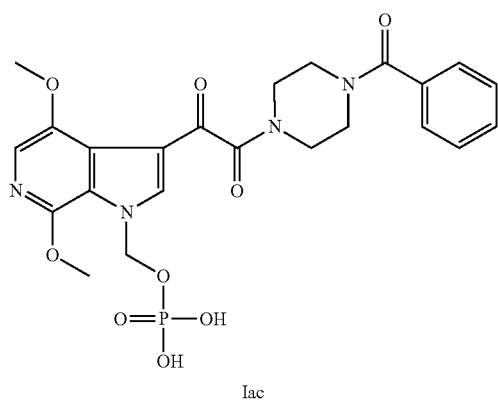

Iac

A mixed solution of TFA (50 ml) and dichloromethane (450 ml) was added into a round bottom flask containing 43.3 g of diester IIa. After stirring at room temperature for 16 hours, the reaction mixture was concentrated under vacuum to offer a residue of Iac which was used in further steps without any purification.

Step Four

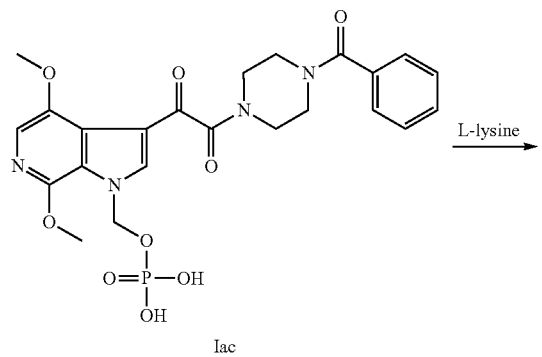

Iac

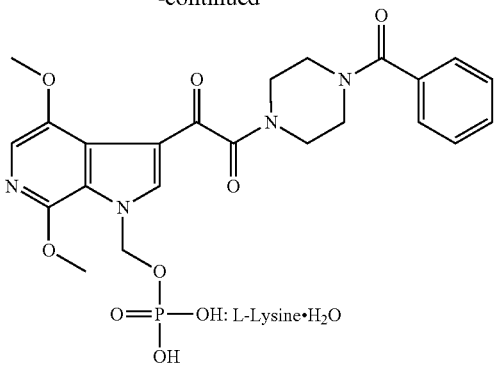

Iab

The above 55 g crude product Iac was added to an aqueous solution of L-lysine (1.36M, 70 mL) at room temperature. The resulting suspension (pH=1.83) was added to a lysine solution (1.36 M, ~40 mL) to pH 4.88. The resulting suspension was filtered through a pad of Celite. The clear light yellow filtrate (~200 mL) was mixed with acetone (200 mL) and heated to 45° C. Acetone (1400 mL) was added over 2 h at 45° C. The clear solution was seeded and stirred at 45° C. for 2 h, and slowly cooled to room temperature (5 h) and the suspension stirred overnight. The white solid was collected by filtration and dried under house vac. at 50° C. over 24 h to afford 41.2 g of Iab as an off-white solid.

The above solid was dissolved in 1:1 water-acetone (560 mL) at 45° C. Acetone (700 mL) was added over a period of 1 h at 45° C. The clear solution was seeded and stirred at 45° C. for 2 h. Slowly cooled to room temperature (5 h) and the suspension stirred at room temperature overnight. The white solid was collected by filtration and dried under house vac. at 50° C. over 36 h to afford 33 g of Iab as an off-white solid. The AP was >99% by HPLC.

$^1$H NMR (500 MHz, D$_2$O) δ 8.42 (s, ½H), 8.39 (s, ½H), 7.52 (m, 6H), 6.12 (m, 2H), 4.07 (s, 3H), 3.93 (m, 5H), 3.72 (m, 3H), 3.67 (m, 2H), 3.52 (m, 2H), 3.05 (m, 2H), 1.93 (m, 2H), 1.74 (m, 2H), 1.50 (m, 2H); MS m/z: (M+H-lysine)$^+$ calcd for C$_{23}$H$_{26}$N$_4$O$_9$P 533.14, found 533.03. M.P. 166.7 to 172.2 degrees. Using comparative 1H NMR integration of several different peaks, the ratio of lysine to IVa is calculated to range from 1.05:1 to 1.2:1 equivalents of lysine to parent prodrug. The salt form was determined to be a hydrate. Based on DSC (diffraction scanning calorimetry) and TGA (thermal gravity analysis), the observed water content is 2.80%. Theoretical calculation for a monohydrate is 2.58%. Thus, the ratio of water to parent molecule in the hydrate could be in the range 1:1 to ~1.5:1.

Example 7

Preparation of Crystalline Ic (Free Acid Mono-Hydrate)

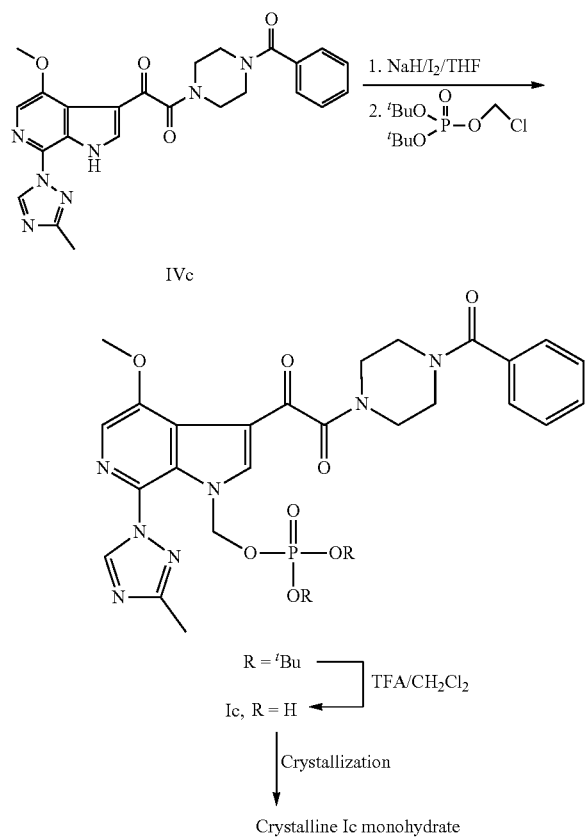

To a mixture of IVc (600 mg, 1.27 mmol) in anhydrous THF (10 ml) in an oven-dried round bottle flask under nitrogen at r.t. was added NaH (153 mg, 6.38 mmol, dry powder, 95%), and the white suspension stirred until no gas evolution was observed. The mixture was then added 2 (375 mg, 1.48 mmol), and stirred at r.t. for 3 h. To the reaction mixture was added NaH (153 mg, 6.38 mmol, dry powder, 95%), and the mixture stirred for about 5 to 10 min. The crude chloromethyl di-tert-butylphosphate (2.0 g, about 1.6 ml, 7.79 mmol) was added to the mixture, which was then stirred at r.t. for 15 h. LCMS analysis of the reaction showed a >97% conversion of the starting material. After evaporation of the volatiles, the residue was added $CH_2Cl_2$ (10 ml), cooled in an ice-water bath, slowly added TFA (10 ml) and stirred at r.t. for 3 h. The reaction mixture was then evaporated, and the residue partitioned between $CH_2Cl_2$ (50 ml) and $H_2O$ (50 ml). The $CH_2Cl_2$ layer was poured into the reaction flask that contained some undissolved brownish solid, and this mixture was extracted with a dilute aqueous $NaHCO_3$ solution (50 ml). The aqueous mixture was purified by reverse phase preparative HPLC (solvent A: 10% MeOH-90% $H_2O$-0.1% TFA; solvent B: 90% MeOH-10% $H_2O$-0.1% TFA; start % B=0, final % B=100; gradient time=6 min; flow rate=45 ml/min; column: phenomenex-Luna 30×50 mm, S5; fraction collected: 3.65 to 4.05 min). The fractions collected were evaporated to dryness, and the residue dried under high vacuum to obtain the acid Ic as a pale yellow solid (356.6 mg); $^1H$ NMR: (500 MHz, $CD_3OD$) δ 9.05 (s, 1H), 8.46 (s, 1H), 8.04 (s, 1H), 7.47 (b s, 5H), 5.93 (d, J=12, 2H), 4.10 (s, 3H), 4.00-3.40 (b s, 8H), 2.53 (s, 3H); $^{19}F$ NMR analysis showed that the material contained residual TFA, (the percentage was not quantified); Analytical HPLC method: Start % B=0, Final % B=100, Gradient time=2 min, Flow Rate=5 mL/min, Column: Xterra MS C18 7u 3.0×50 mm, LC/MS: (ES+) m/z $(M+H)^+$=584, HPLC $R_f$=0.983.

172.2 mg of the purified acid Ic was dissolved in 1 ml of $H_2O$ and then about 0.3 ml of absolute EtOH (200 proof) was added. The mixture was left standing in a refrigerator (temperature about 3° C.) overnight, after which time, crystalline material was observed. The mixture was then warmed to ambient temperature, diluted with $H_2O$ to a volume of 3 mL, and then 20 mL of MeCN was added slowly. Following the completion of addition, the mixture was stirred at r.t. for 2 h and then filtered. The solid collected (90 mg) was dried in vacuo, and then under high vacuum. This material was shown by powder x-ray studies to be crystalline; Elemental Analysis calculated for $C_{25}H_{26}N_7O_8P.H_2O$: C, 49.92; H, 4.69; N, 16.30; observed: C, 49.66; H, 4.62; N, 15.99; mp=205° C. (measured by differential scanning calorimetry). The 1H NMR pattern for crystalline material was compared with that from the purified acid and both were consistent with the structure.

Example 8

Preparation of Iab (Mono L Lysine Salt): {3-[(4-benzoylpiperazin-1-yl)(oxo)acetyl]-4,7-dimethoxy-1H-pyrrolo[2,3-c]pyridin-1-yl}methyl Dihydrogen Phosphate, L-Lysine Salt (1:1). The Sequence of Reactions is Described in Scheme for Example 8

Scheme for Example 8

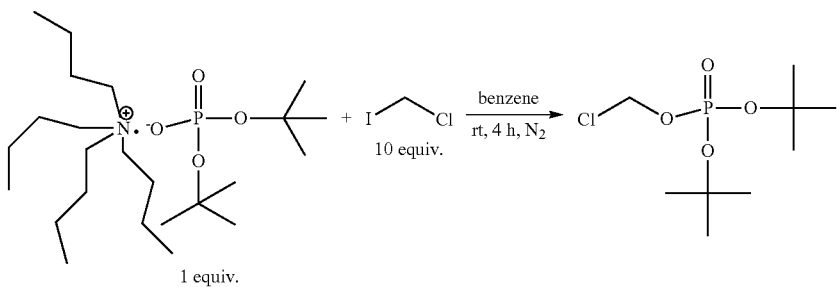

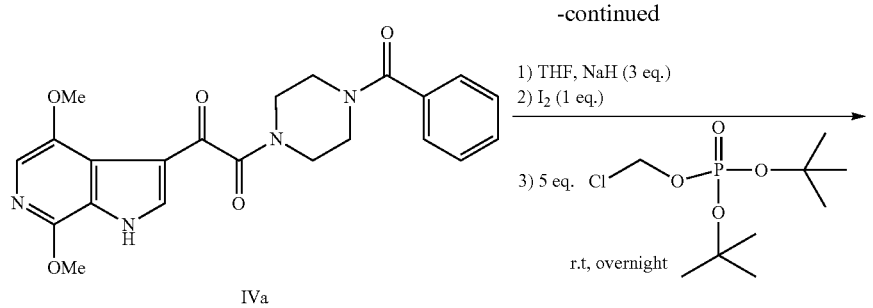

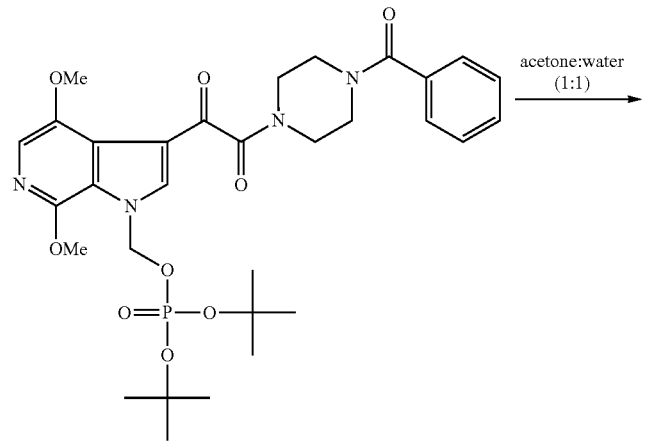

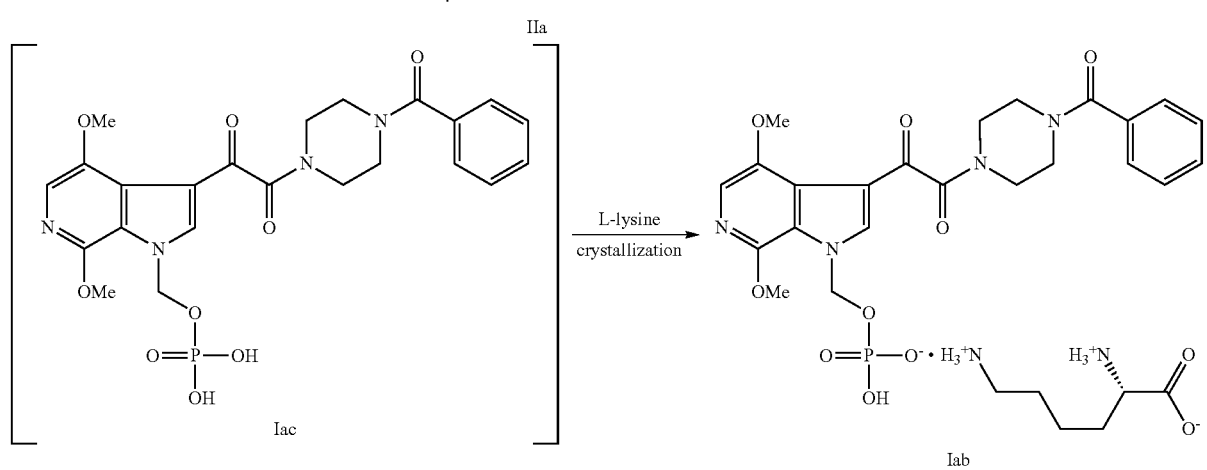

Preparation of Di-Tert-Butyl Chloromethyl Phosphate

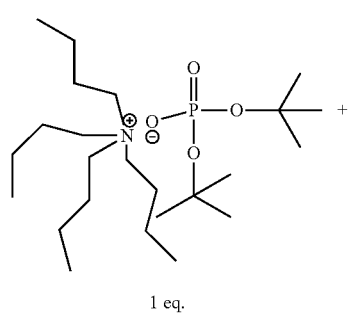

1 eq.

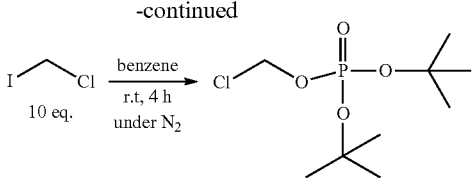

The tetrabutylammonium salt of bis-tert butyl phosphate (45.1 g, 0.1 mol) and chloroiodomethane (200 g, 1.14 mol) were combined in 100 ml of benzene and the mixture was stirred at room temperature for four hours and then the benzene was removed under vacuum. A portion of 500 ml of ethyl ether was added to the residue and insoluble solid was filtered away. Concentration of the filtrate in vacuo and removal of the volitiles on a vacuum pump provided di-tertbutyl chloromethyl phosphate, as a light yellow or light brown oil which was utilized in the next step without further purification.

Preparation of IIa: (3-(2-(4-benzoylpiperazin-1-yl)-2-oxoacetyl)-4,7-dimethoxy-1H-pyrrolo[2,3-c]pyridin-1-yl)methyl di-tert-butyl Phosphate

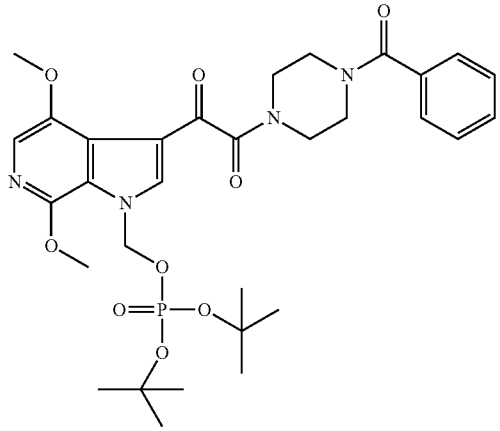

IIa

NaH (2.4 g, 60 mmol, 60% in oil) was added slowly to a suspension of (8.4 g, 20 mmol) IVa in dry THF (120 ml) and the mixture was allowed to stir for an hour at room temperature. Iodine (5 g, 20 mmol) dissolved in dry THF (10 ml) was added slowly and cautiously to the stirring solution at a rate to keep foaming under control. Following completion of addition, the resultant mixture was stirred at ambient temperature for an additional 15 minutes and then the ~0.1 mol di-tert-butyl chloromethyl phosphate, obtained as described in step one, was added. After stirring for 16 hours, the reaction mixture was poured into iced NH$_4$OAc (30%) (120 ml), followed by extraction with EtOAc (3×300 ml). The combined organic extracts were washed with water (100 ml) and then brine (100 ml), dried over Na$_2$SO$_4$, and concentrated invacuo to afford a residue, which was purified by silica gel chromatography (elution with EtOAc/Et$_3$N (100/1) and then EtOAc/MeOH (100/1) to give diester IIa (9.0-10.3 gs, AP ~75%) as a light yellow solid in yields of 70-80% over several runs.

$^1$H NMR (500 MHz, CDCl$_3$) δ 8.09 (s, 1H), 7.48 (s, 1H), 7.40 (b, 5H), 6.15 (d, 2H, J=11.5 Hz), 4.05 (s, 3H), 3.90 (s, 3H), 3.90-3.30 (b, 8H), 1.39 (s, 18H); $^{13}$C NMR (125 MHz, CDCl$_3$) δ 185.5, 170.7, 166.5, 146.9, 146.2, 139.6, 135.3, 130.2, 128.7, 128.4, 127.2, 124.5, 122.0, 120.8, 115.8, 83.8, 73.2, 57.3, 53.5, 46.1, 41.7, 29.8; MS m/z: (M+H)$^+$ calcd for C$_{31}$H$_{42}$N$_4$O$_9$P 645.27, found 645.10.

Preparation of Iab: {3-[(4-benzoylpiperazin-1-yl)(oxo)acetyl]-4,7-dimethoxy-1H-pyrrolo[2,3-c]pyridin-1-yl}methyl Dihydrogen Phosphate, L-Lysine Salt (1:1)

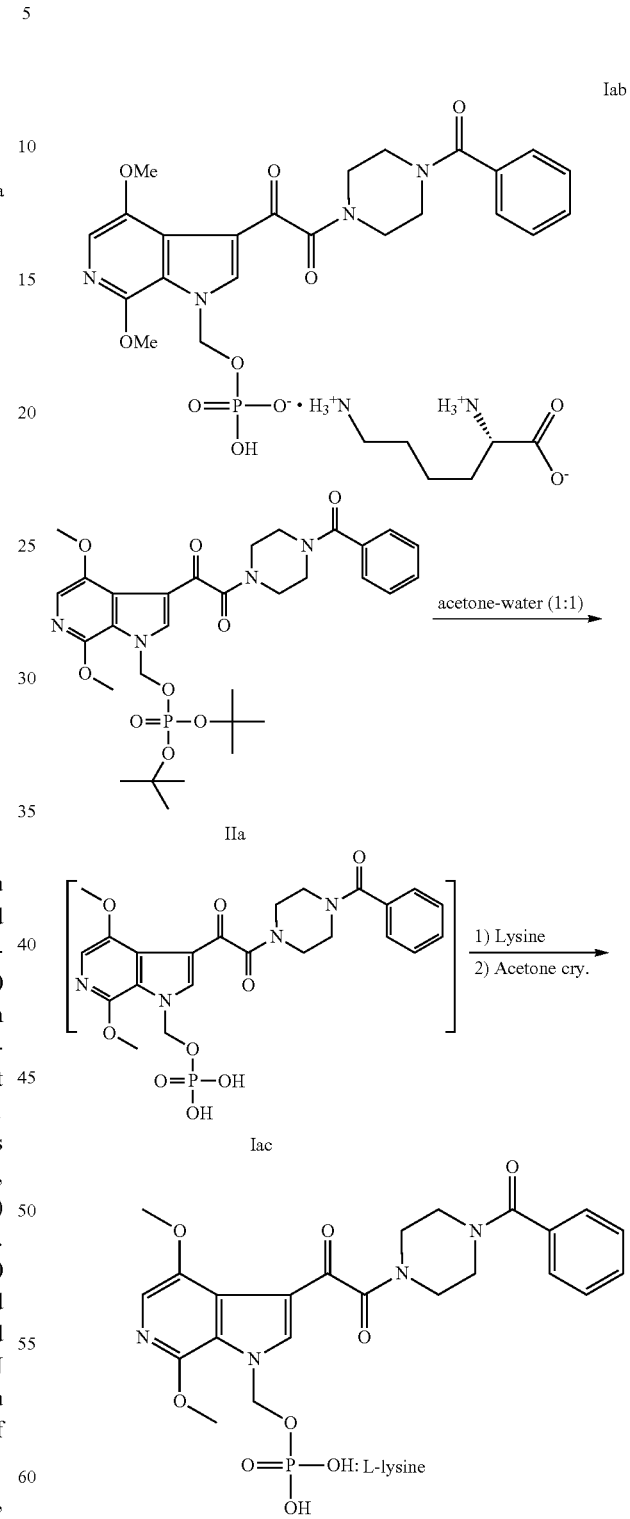

500 mg of diester IIa was dissolved in a mixture of water (3 ml) and acetone (3 ml). The resulting mixture was stirred at 40° C. for 16 hours to allow the solvolysis to reach completion. To this reaction mixture (~69 AP) was added 4M aqueous lysine solution to adjust pH to 4.83. Acetone (35 ml) was slowly added into the reaction mixture in 30 min at 45-50° C. At 45° C., the clear solution was seeded with crystalline Iab and kept stirred at this temperature for 45 min. After complete addition of acetone, the solution was cooled to room temperature in 4 hours and the crystallization of Iab completed overnight. The solid was collected by filtration and suction under nitrogen for 2 hours. The white crystalline solid was dried under house vacuum at 50-55° C. for 24 h to afford 343 mg of Iab.

Iab obtained in the above operation: $^1$H NMR (500 MHz, CD$_3$OD) δ 8.38 (s, 1H), 7.49 (m, 6H), 6.13 (d, 2H, J=10.5 Hz), 4.06 (s, 3H), 3.92 (s, 3H), 4.00-3.40 (m, 8H), 3.58 (t, 1H, J=6 Hz), 2.92 (t, 2H, J=7.5 Hz), 1.90-1.40 (m, 6H); $^{13}$C NMR (125 MHz, CD$_3$OD) δ186.1, 173.2, 171.8, 167.8, 147.4, 146.4, 141.0, 135.4, 130.4, 128.8, 127.2, 124.6, 122.3, 120.2, 114.6, 73.2, 56.6, 54.7, 53.1, 46.0, 41.6, 39.2, 30.5, 27.0, 22.0. HRMS m/z: (M-lysine+H)$^+$ calcd for C$_{23}$H$_{26}$N$_4$O$_9$P 533.1437, found 533.1437. Anal. Calcd. C, 51.32; H, 5.79; N, 12.38; P, 4.56. found: C, 48.54; H, 5.32; N, 11.76; P, 4.04. Melting Point 170° C.

Obtained via other process (hydrolysis with TFA in methylene chloride), Iab was a 1.70 molar hydrate and 1.14 molar lysine salt. $^1$H NMR (500 MHz, D$_2$O, 60° C.) δ8.72 (s, 1H), 7.84 (m, 6H), 6.44 (d, 2H, J=10 Hz), 4.41 (s, 3H), 4.27 (s, 3H), 4.3-3.7 (m, 8H), 4.10 (t, 1H, J=5 Hz), 3.39 (t, 2H, J=5 Hz), 2.30-1.80 (m, 6H); $^{13}$C NMR (125 MHz, D$_2$O, 27° C.) δ186.7, 174.9, 173.2, 167.9, 147.7, 145.7, 142.6, 134.3, 131.1, 129.2, 127.1, 124.3, 122.4, 120.1, 113.8, 73.5, 57.1, 54.9, 54.4, 47.7, 47.1, 46.3, 45.7, 42.6, 42.1, 42.0, 41.5, 39.5, 30.2, 26.8, 21.8. HRMS m/z: (M-lysine+H)$^+$ calcd for C$_{23}$H$_{26}$N$_4$O$_9$P 533.1437, found 533.1425. Anal. Calcd. C, 49.11; H, 6.13; N, 12.05. found: C, 48.93; H, 6.26; N, 12.07. M.P. 168-172° C.

Example 9

Preparation of Ibb (Mono L Lysine Salt): [3-[(4-benzoylpiperazin-1-yl)(oxo)acetyl]-4-fluoro-7-(H-1,2,3-triazol-1-yl)-1H-pyrrolo[2,3-c]pyridin-1-yl] methyl Dihydrogen Phosphate, L-Lysine Salt (1:1). The Sequence of Reactions is Described in the Scheme for Example 9

Scheme for Example 9

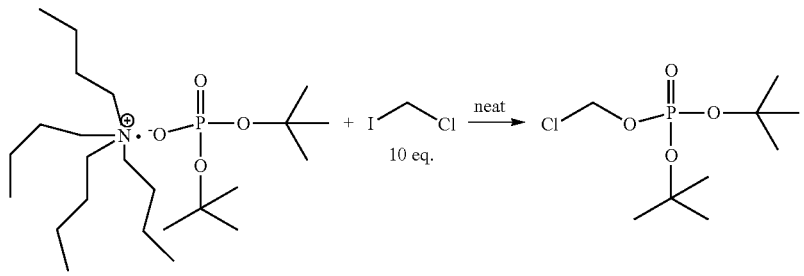

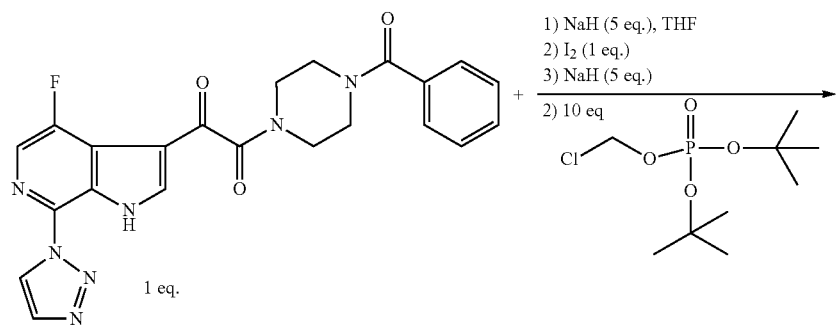

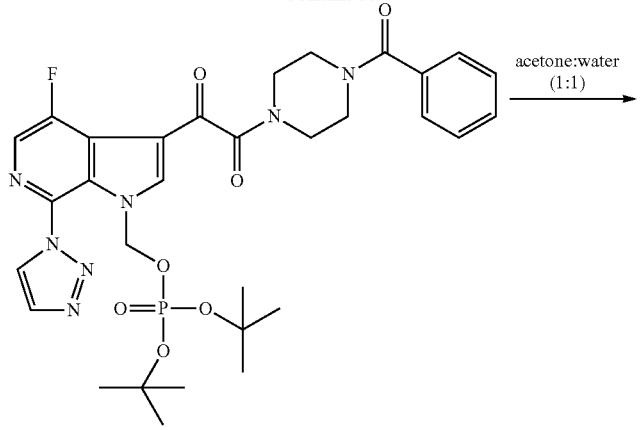

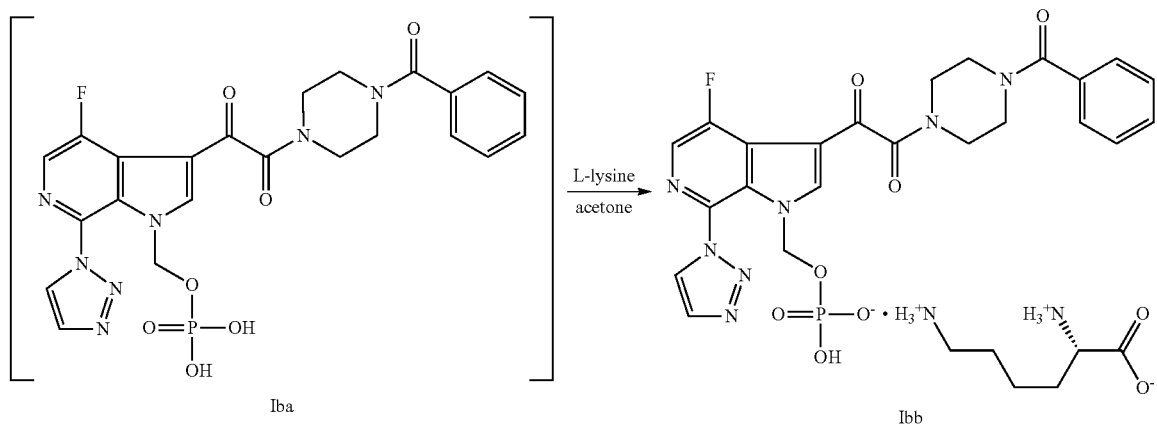

Preparation of Di-Tert-Butyl Chloromethyl Phosphate

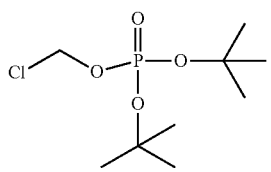

The tetrabutylammonium salt of bis-tert butyl phosphate (57 g, 0.126 mol, Digital Specialty Chemicals) and chloroiodomethane (221 g, 1.26 mol) were stirred at room temperature for four hours and then the volatiles were removed in vacuo. 500 ml of ethyl ether was added to the residue and insoluble solid was filtered away. Concentration of the filtrate and final removal of volatiles using a vacuum pump provided di-tert-butyl chloromethyl phosphate (112 g), typically as a light yellow or brown oil, which was utilized in the next step without any further purification.

Preparation of IIb: (3-(2-(4-benzoylpiperazin-1-yl)-2-oxoacetyl)-4-fluoro-7-(H-1,2,3-triazol-1-yl)-1H-pyrrolo[2,3-c]pyridin-1-yl)methyl di-tert-butyl Phosphate

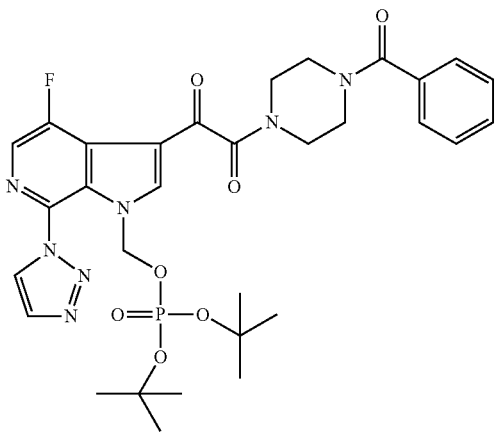

NaH (5.65 g, 95% dispersion in mineral oil, 0.224 mol) was added slowly into a suspension of IVb (20 g, 44.7 mmol) in dry THF (400 ml) and the mixture was allowed to stir for 0.5 hour at room temperature. A solution of iodine (11.3 g, 44.5 mmol) dissolved in dry THF (20 ml) was added slowly into the stirring solution at a rate which kept the reaction from becoming violent. The resultant mixture was stirred for an additional 3 hours before a second portion of 95% NaH (5.65 g, 0.224 mol) was introduced. After 15 minutes at ambient temperature, di-tert-butyl chloromethyl phosphate, (112 g), obtained from step one, was added in one portion. After stirring for 16 hours at ambient temperature, the reaction mixture was poured into iced $NH_4OAc$ (30%) (200 ml) and then extracted with EtOAc (3×500 ml). The combined organic extracts were washed with water (200 ml) and then brine (200 ml), dried over $Na_2SO_4$, and concentrated under vacuum to afford a residue, which was purified by silica gel chromatography (elution with EtOAc/ $MeOH/Et_3N$ (100/1/1) to give 15.0 gs (43% yield corrected for 85% AP) of diester IIb as a light yellow solid.

$^1$H NMR (500 MHz, $CDCl_3$) δ 8.36 (s, 1H), 8.25 (s, 1H), 8.21 (s, 1H), 7.88 (s, 1H), 7.41 (b, 5H), 5.90 (d, 2H, J=14.5 Hz), 3.90-3.40 (b, 8H), 1.23 (s, 18H); $^{13}$C NMR (125 MHz, $CDCl_3$) δ 182.9, 170.7, 165.1, 154.6, 152.5, 144.1, 135.1, 134.0, 131.9, 130.3, 128.7, 128.3, 127.2, 125.9, 124.3, 114.0, 84.1, 74.1, 46.2, 41.9, 29.6; HRMS m/z: $(M+H)^+$ calcd for $C_{31}H_{38}FN_7O_7P$ 670.26, found 670.34.

Preparation of Ibb (Mono L Lysine Salt): [3-[(4-benzoylpiperazin-1-yl)(oxo)acetyl]-4-fluoro-7-(H-1,2,3-triazol-1-yl)-1H-pyrrolo[2,3-c]pyridin-1-yl] methyl Dihydrogen Phosphate, L-Lysine Salt (1:1)

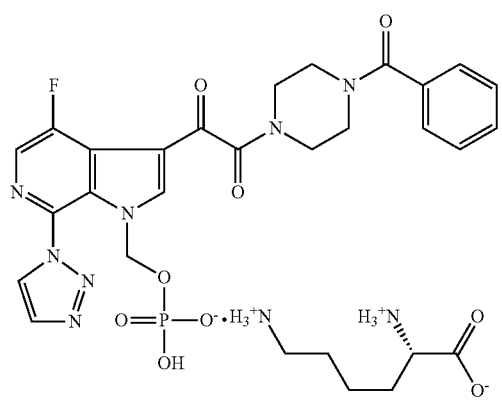

Ibb

Diester IIb (27 g) was dissolved in a mixture of water (55 ml) and acetone (55 ml). The resulting mixture (pH: not determined) was stirred at 40° C. for 16 hours to complete the solvolysis. To this reaction mixture was added 4M aqueous lysine solution to adjust pH to 3.51. EtOH (500 ml) was added into the solution and the flask wall was coated with some product after overnight. The clear solution was then transferred to another flask and EtOH (1500 ml) was slowly added to the reaction mixture in ~3 h. After complete addition of ethanol, the solution was stirred at room temperature for 48 hours and the resultant solid (Ibb) was collected by filtration and rinsed with ethanol. The white crystalline solid was dried under house vacuum at 55° C. for 24 h to afford 10.92 g of Ibb (98 AP).

This solid was further mixed with 12.5 g of salt obtained from other operations in 70 ml of water. EtOH (1000 ml) was then added and the resultant solution was stirred at r.t. for over 20 hours. The solid was collected by filtration, rinsed with EtOH (2×80 ml) and dried under house vacuum at 50° C. under nitrogen atmosphere for 44 hours to afford 21.5 g of Ibb in AP of 98.7.

Ibb obtained in the above procedure was ~1 molar lysine salt with 1.12% of water, 0.8% of TFA and 0.05% of ethanol. $^1$H NMR (500 MHz, $CD_3OD$, 50° C.) δ 8.94 (s, 1H), 8.87 (s, 1H), 8.69 (s, 1H), 8.42 (s, 1H), 7.83 (m, 5H), 5.81 (d, 2H, J=12.5 Hz), 4.30-3.70 (m, 8H), 4.08 (t, 1H, J=6.5 Hz), 3.67 (t, 2H, J=10 Hz), 2.26 (m, 2H), 2.07 (m, 2H), 1.88 (m, 2H); $^{13}$C NMR (125 MHz, $D_2O$, 30° C.) δ 185.2, 174.9, 173.3, 166.8, 153.1, 146.8, 134.8, 134.3, 131.3, 131.1, 130.3, 129.3, 128.9, 128.7, 128.5, 127.2, 124.2, 112.6, 74.0, 54.9, 47.9, 47.2, 46.4, 45.9, 42.7, 42.2, 42.0, 41.7, 39.5, 30.3, 26.8, 21.8. MS m/z: $(M-lysine+H)^+$ calcd for $C_{23}H_{22}FN_7O_7P$ 558.1302, found 558.1293. Anal. Calcd. C, 48.75; H, 5.07; N, 17.63; P, 4.33. found: C, 49.02; H, 4.90; N, 17.90; P, 4.37. M.P. 193° C. pKa (potentiometric) 6.1, 9.1.

Example 10

Preparation of Icb (Mono Tromethamine Salt): [3-[(4-benzoylpiperazin-1-yl)(oxo)acetyl]-4-methoxy-7-(3-methyl-1H-1,2,4-triazol-1-yl)-1H-pyrrolo[2,3-c]pyridin-1-yl]methyl Dihydrogen Phosphate, 2-amino-2-(hydroxymethyl)propane-1,3-diol Salt (1:1). The Sequence of Reactions is Described in Scheme for Example 10

Scheme for Example 10

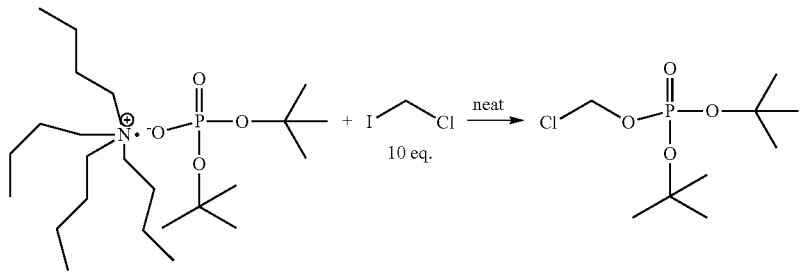

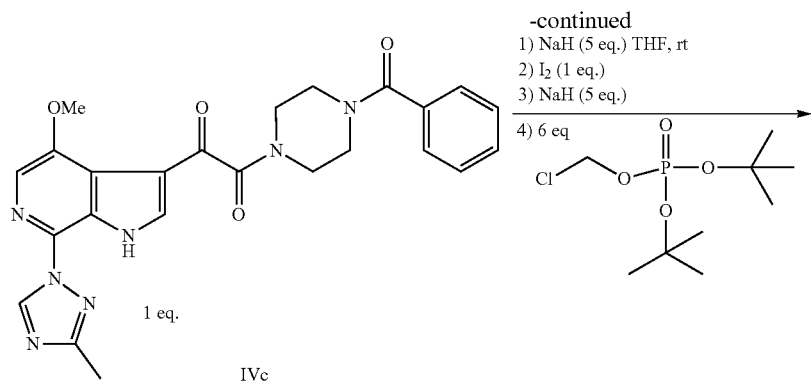

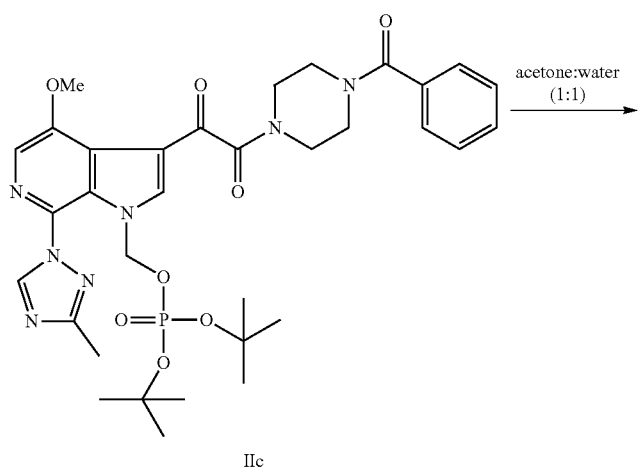

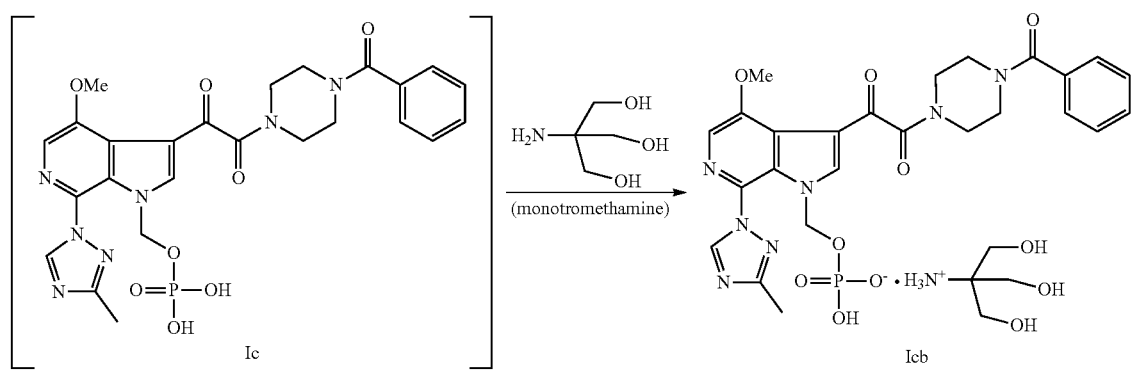

Preparation of Di-Tert-Butyl Chloromethyl Phosphate

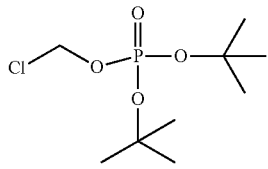

A mixture of tetrabutylammonium di-tert-butyl phosphate (57 g, 0.126 mol, Digital Specialty Chemicals) and chloroiodomethane (221 g, 1.26 mol) was stirred at room temperature for four hours before the volatiles were removed under vacuum. 500 ml of ethyl ether was added to the residue and insoluble solid was filtered away. Concentration of the filtrate in vacuo and removal of remaining volatiles using a vacuum pump provided di-tert-butyl chloromethyl phosphate as a light brown or yellow oil, which was utilized in the next step without further purification.

Preparation of IIc: (3-(2-(4-benzoylpiperazin-1-yl)-2-oxoacetyl)-4-methoxy-7-(3-methyl-1H-1,2,4-triazol-1-yl)-1H-pyrrolo[2,3-c]pyridin-1-yl)methyl di-tert-butyl Phosphate

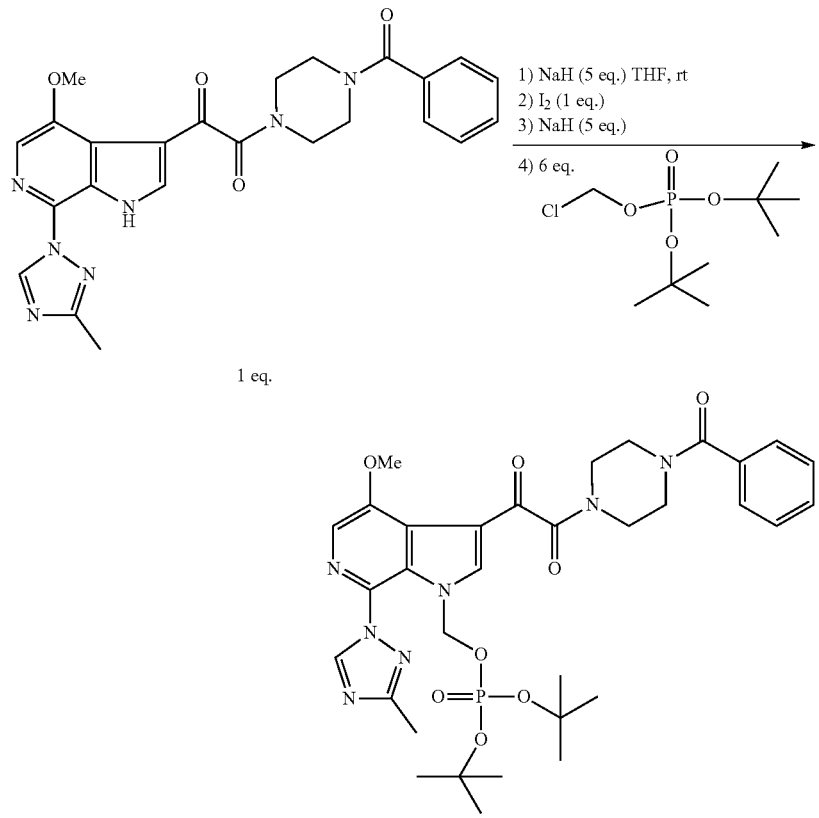

NaH (2.6 g, 10.3 mmol, 95% in oil, 5 eq.) was added slowly into a suspension of IVc (10.0 g, 21.1 mmol) in dry THF (100 ml) and the mixture was allowed to stir for 0.5 hour at room temperature. A solution of iodine (5.27 g, 20.8 mmol) dissolved in dry THF (10 ml) was added slowly into the stirring solution at a rate which prevented foaming or a violent reaction. The resultant mixture was stirred for an additional 3 hours before a second 2.6 g portion of NaH was introduced. After 15 minutes at ambient temperature di-tert-butyl chloromethyl phosphate, the entire batch of di-tert-butyl chloromethyl phosphate, obtained from step one, was added. After stirring for 16 hours, the reaction mixture was poured into iced NH$_4$OAc (30%) (120 ml), followed by extraction with EtOAc (3×300 ml). The combined organic extracts were washed with water (100 ml) and then brine (100 ml), dried over Na$_2$SO$_4$, and concentrated under vacuum to afford a residue, which was purified by silica gel chromatography (elution with EtOAc/Et$_3$N (50/1) and then EtOAc/MeOH (100/1)) to give 8.0 g (~75% AP, ~41% yield) of diester IIc as a light yellow solid.

$^1$H NMR (500 MHz, CD$_3$OD) δ 8.82 (s, 1H), 8.41 (s, 1H), 8.04 (s, 1H), 7.47 (b, 5H), 6.00 (d, 2H, J=14.5 Hz), 4.10 (s, 3H), 4.00-3.40 (b, 8H), 2.49 (s, 3H), 1.28 (s, 18H); $^{13}$C NMR (125 MHz, CD$_3$OD) δ 18.6, 176.4, 172.9, 168.0, 162.6, 152.6, 147.5, 144.0, 136.5, 131.5, 130.8, 129.9, 129.1, 128.3, 126.1, 124.0, 116.2, 85.8, 75.4, 61.6, 57.7, 30.1, 22.2, 13.7; HRMS m/z: (M+H)$^+$ calcd for C$_{33}$H$_{43}$N$_7$O$_8$P 696.29, found 696.34.

Preparation of Icb (Mono L Tromethamine Salt): [3-[(4-benzoylpiperazin-1-yl)(oxo)acetyl]-4-methoxy-7-(3-methyl-1H-1,2,4-triazol-1-yl)-1H-pyrrolo[2,3-c]pyridin-1-yl]methyl Dihydrogen Phosphate, 2-amino-2-(hydroxymethyl)propane-1,3-diol Salt (1:1)

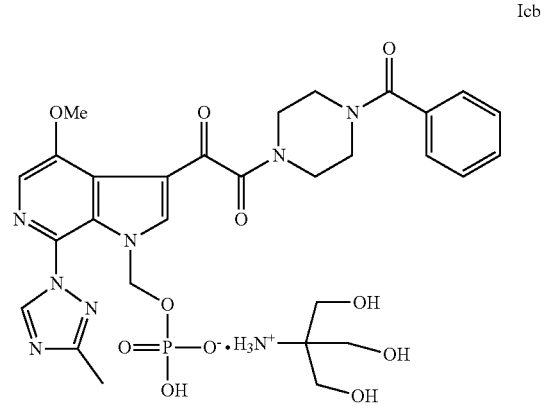 [SMILES: COc1cnc(-n2cnc(C)n2)c2c1c(C(=O)C(=O)N1CCN(C(=O)c3ccccc3)CC1)cn2COP(=O)([O-])O ; [NH3+]C(CO)(CO)CO]

Icb 500 mg (~75 AP, 0.54 mmol) of diester IIc was dissolved in a mixture of water (2.5 ml) and acetone (2.5 ml). The resulting mixture was stirred at 40° C. for 16 hours to complete the solvolysis. To this reaction mixture was added 3.0M aqueous TRIS (mono tromethamine) solution to adjust pH to 3.32. Acetone (30 ml) was slowly added to the reaction mixture in 1 hour.* After complete addition of acetone, the solution was stirred overnight to complete the crystallization of Icb. The solid was collected by filtration and rinsed with 20:1 acetone-water (2×5 mL). The white crystalline solid was dried under house vacuum under nitrogen atmosphere at 50° C. for 24 h to afford 290 mg of Icb (>98.5 AP).

* After adding about 15 and 20 ml of acetone, the reaction mixture was seeded with crystalline Icb.

Icb obtained in the above operation: $^1$H NMR (500 MHz, CD$_3$OD) δ 8.83 (s, 1H), 8.52 (s, 1H), 8.02 (s, 1H) 7.49 (b, 5H), 5.469 (d, 2H, J=13 Hz), 4.11 (s, 3H), 4.00-3.40 (m, 8H), 3.66 (s, 6H), 2.50 (s, 3H); $^{13}$C NMR (125 MHz, CD$_3$OD) δ 185.6, 171.9, 167.4, 161.4, 151.7, 146.9, 143.8, 135.4, 130.3, 129.7, 128.8, 127.2, 124.9, 122.6, 114.3, 73.5, 61.8, 59.9, 56.5, 46.0, 41.7, 12.6. HRMS m/z: (M-trisamine+H)$^+$ calcd for C$_{25}$H$_{27}$N$_7$O$_8$P 584.1659, found 584.1664. Anal. Calcd. C, 49.43; H, 5.29; N, 15.90; P, 4.39. found: C, 49.18; H, 5.38; N, 15.59; P, 4.26. Melting Point 203° C.

Obtained via other process (hydrolysis with TFA in methylene chloride), salt Icb is ~1 molar mono tromethamine salt with 0.47% of water, 0.1% of acetone and 0.05% of methanol. $^1$H NMR (500 MHz, d$_6$-DMSO, 30° C.) δ8.77 (s, 1H), 8.48 (s, 1H), 8.00 (s, 1H) 7.44 (b, 5H), 5.42 (d, 2H, J=15 Hz), 4.02 (s, 3H), 3.70-3.30 (m, 8H), 3.41 (s, 6H), 2.38 (s, 3H); $^{13}$C NMR (125 MHz, CDCl$_3$, 30° C.) δ 184.8, 169.0, 165.8, 160.3, 150.4, 146.2, 143.2, 135.4, 129.4, 128.9, 128.2, 127.7, 126.9, 123.2, 122.2, 112.9, 72.3, 60.7, 59.0, 56.7, 13.4. MS m/z: (M-trisamine+H)$^+$ calcd for C$_{25}$H$_{27}$N$_7$O$_8$P 584.2, found 584.0. Anal. Calcd. C, 49.11; H, 5.37; N, 15.76; P, 4.32. found: C, 48.88; H, 5.28; N, 15.71; P, 4.16. M.P. 201-205° C.

General Procedure to Form Additional Salts of Iac

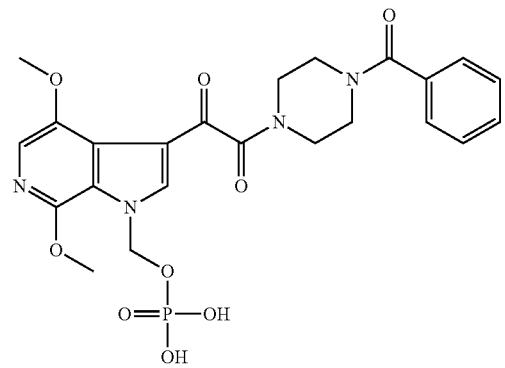

Iac

Procedure A:
1.2 eq. of metal alkoxide was added into a solution of phosphoric acid in THF and precipitate was collected as salt form.

Procedure B:
2.2 eq. (for Na, K) or 1.2 eq. (for Mg) of metal alkoxide was added into a solution of phosphoric acid in THF. After 2 hours, solvent was evaporated and MeOH was added to provide a clear solution. EtOH or iPrOH was then added into the solution until it became cloudy. Then, MeOH was added cautiously to let solution become just clear again. The mixed solution was left open to air for 16 hours and resultant precipitate was collected as the salt form.

Procedure C:
2.2 eq. of amine was added into a solution of phosphoric acid in THF. After 2 hours, solvent was evaporated and MeOH was added to provide a clear solution. EtOH or iPrOH was then added into the solution until it became cloudy. Then, MeOH was added cautiously to let solution become just clear again. The mixed solution was left open to air for 16 hours and resultant precipitate was collected as salt form.

| Compound | Parent Molecule | Element Analysis (Theoretical Comp.) | Element Analysis (Observed Comp. %) | Procedure Used |
|---|---|---|---|---|
| Iac | | C 51.88%<br>H 4.73%<br>N 10.52%<br>P 5.82% | | |

-continued

| Salt Form | | Element Analysis (Theoretical Comp.) | Element Analysis (Observed Comp. %) | |
|---|---|---|---|---|
| Mix of Iad with small amount of Ia | 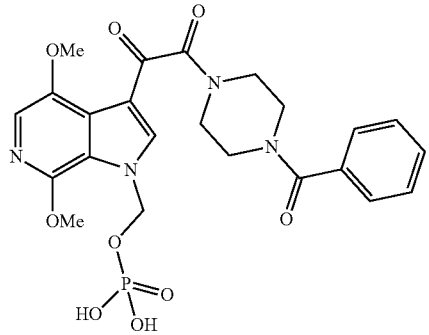 [SMILES: COc1cnc(OC)c2c1c(C(=O)C(=O)N1CCN(C(=O)c3ccccc3)CC1)cn2COP(=O)(O)O] xNa | Mono Na salt<br>C 49.83%<br>H 4.36%<br>N 10.11%<br>P 5.59%<br>Na 4.15%<br>Di Na salt<br>C 47.93%<br>H 4.02%<br>N 9.72%<br>P 5.37%<br>Na 7.89% | C 47.43%<br>H 4.59%<br>N 9.24%<br>P 5.72%<br>Na 4.48%<br>Mainly mono Na salt | Procedure B<br>NaOMe used |
| Mix of Iae And Iac | 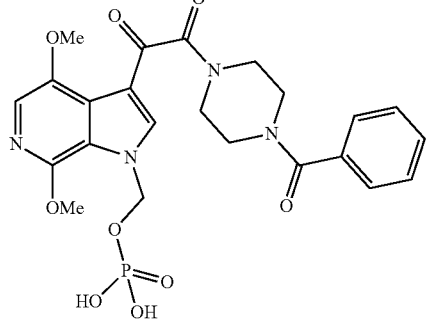 xK | Mono K salt<br>C 48.42%<br>H 4.24%<br>N 9.82%<br>P 5.43%<br>K 6.85%<br>Di K salt<br>C 45.39%<br>H 3.81%<br>N 9.21%<br>P 5.09%<br>K 12.85% | C 49.36%<br>H 5.25%<br>N 9.56%<br>P 4.25%<br>(4.33%)<br>K 3.31%<br>(3.18%)<br>Mixture of K salt and free acid | Procedure B<br>KOMe used |
| ~1.1 mix of Iaf and Iag | 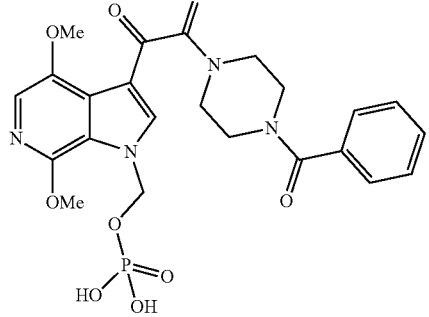 xCa | 0.5 Ca salt<br>C 50.09%<br>H 4.39%<br>N 10.16%<br>P 5.62%<br>Ca 3.63%<br>Mono Ca salt<br>C 48.42%<br>H 4.06%<br>N 9.82%<br>P 5.43%<br>Ca 7.03% | C 46.77%<br>H 4.22%<br>N 9.33%<br>P 5.52%<br>(5.70%)<br>Ca 4.95%<br>(5.30%)<br>Mixture of 0.5 Ca salt and mono Ca salt (~1:1) | Procedure A<br>Ca(OMe)$_2$ used |
| Iaj | 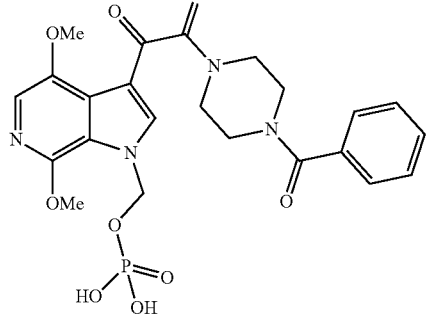 xZn | 0.5 Zn salt<br>C 48.97%<br>H 4.29%<br>N 9.93%<br>P 5.49%<br>Zn 5.80%<br>Mono Zn salt<br>C 46.36%<br>H 3.89%<br>N 9.40%<br>P 5.20%<br>Zn 10.97% | C 44.87%<br>H 4.08%<br>N 9.00%<br>P 5.54%<br>(5.45%)<br>Zn 9.18%<br>(9.47%)<br>Mainly mono Zn salt | Procedure A<br>Zn(O-tBu)$_2$ used |

| | | | |
|---|---|---|---|
| Mainlly Iak | 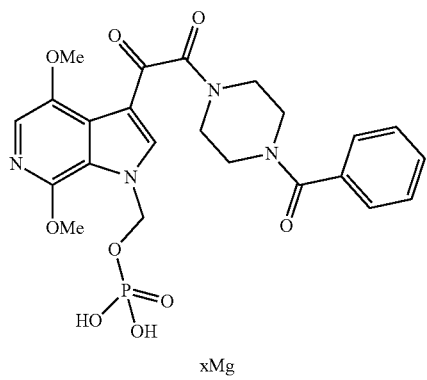 [SMILES: COc1cnc(OC)c2c1c(C(=O)C(=O)N1CCN(C(=O)c3ccccc3)CC1)cn2COP(=O)(O)O] xMg | 0.5 Mg salt<br>C 50.82%<br>H 4.45%<br>N 10.31%<br>P 5.70%<br>Mg 2.24%<br>MonoMg salt<br>C 49.80%<br>H 4.18%<br>N 10.10%<br>P 5.58%<br>Mg 4.38% | C 46.22%<br>H 4.48%<br>N 8.90%<br>P 3.88%<br>Mg 3.60%<br>Mainly mono Mg salt | Procedure B<br>Mg(OEt)$_2$ used |
| Mix of Iam and Ian | 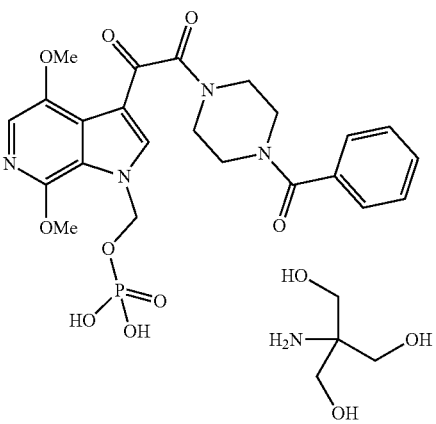 x | Mono Tris salt<br>C 49.62%<br>H 5.55%<br>N 10.72%<br>P 4.74%<br>Di Tris salt<br>C 48.06%<br>H 6.11%<br>N 10.85%<br>P 4.00% | C 45.30%<br>H 5.60%<br>N 9.59%<br>P 2.98%<br>Mainly di Tris salt mixed with Tris | Procedure C<br>Trometh-amine used |

Example 11

Preparation of Compound II'a from IIa

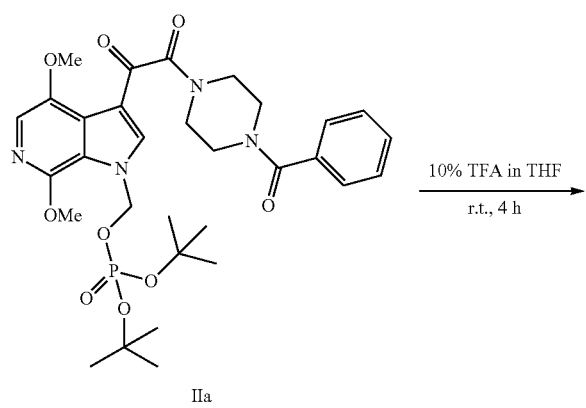

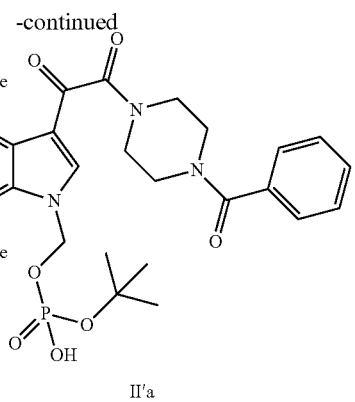

II'a

Di-phosphate ester IIa (500 mg) was dissolved in 5 m of 10% TFA in THF. The reaction mixture was stirred at room temperature for 4 hours before being quenched by 10% aqueous Na$_2$CO$_3$ solution (30 ml). After being washed with EtOAc (50 ml), the aqueous phase was concentrated under vacuum to provide a residue which was purified using Shimadzu automated preparative HPLC System to afford the desired mono-phosphate II'a (26.5 mg)).

$^1$H NMR (500 MHz, CDCl$_3$) d 8.13 (s, 1H), 7.40 (b, 6H), 6.13 (d, 2H, J=11.5 Hz), 4.05 (s, 3H), 3.88 (s, 3H), 3.90-3.40 (m, 8H), 1.39 (s, 9H); MS m/z (M+H)$^+$ calcd for C27H$_{34}$N$_4$O9P 589.21, found 589.13; LC retention time 1.32 min (column: Xterra 4.6×50 mmC18 5 um).

Alternate Preparation of Di-Tert-Butyl Chloromethyl Phosphate

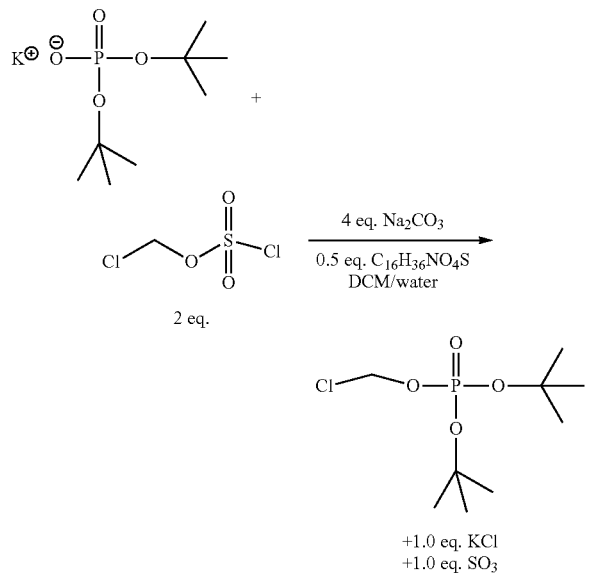

Reaction

To the inerted reactor, di-tert-butyl potassium phosphate (1.69 kg), 4.0 eq. of sodium carbonate and 0.05 eq of tetrabutyl ammonium hydrogen sulfate were added through the manway. Methylene chloride (7.7 L/kg) was then pumped through the sprayball to wash down the reactor walls. With the jacket temperature below 10° C., the exothermic water charge was added over the course of ten minutes (7.6 L/kg). The associated exotherm was minor with a batch temperature rising from 11.1 to 16.2° C. over the course of the addition. With the jacket and batch temperature near 7 and 15° C., respectively, 2.0 eq. of chloromethyl-sulfonylchloride (CMCS) was charged via addition funnel. The charge continued for 2 hours while the jacket temperature was slowly raised to 20° C. during the charge. The maximum batch temperature during the CMCS charge was 25.3° C. The jacket temperature was slowly raised during the charge to ensure that the exotherm started as preliminary laboratory data indicated that the exotherm may be slowed at lower batch temperatures. The reaction mixture was agitated and after 3.5 hours, an NMR sample indicated that the reaction had progressed 72%. The reaction was allowed to proceed overnight with a batch temperature between 19.7 and 23.6° C. (Delta V historian). An NMR sample taken after 16 hours indicated a reaction conversion of 76%. Laboratory batches ranged in conversion from 60 to 80%.

Work-Up

After the reaction was deemed complete, additional water at 9.3 L/kg was added to the batch to affect a phase split. The product rich lower phase was transferred to a carboy and the upper aqueous phase was sent to waste. A small rag layer was kept with the product rich organic. The organic phase was returned to R-1A and additional water at 5.1 L/kg was added as a wash. The phases were split with the product rich organic, approximately 18.5 kg, being sent to a carboy while the upper aqueous phase was sent to waste. No rag layer or solids were observed in the second split. However, it is recommended to polish filter the product rich organic to remove precipitated salts.

Methylene Chloride Distillation

The product rich organic was transferred to the rotovap bowl of EV APO-1A. Distillation of the methylene chloride was initiated with a jacket temperature of approximately 22° C. The distillation rate slowed after 4.5 hours and a batch sample was taken to analyze the methylene chloride content. NMR analysis indicated a 4:1 ratio of di-tert-butyl chloromethyl phosphate to methylene chloride. Typical laboratory results of this stream would indicate a 10:1 ratio so the distillation was continued with an increase in the rotovap jacket temperature. After an additional 2.5 hours, the distillation rate stopped. An NMR sample of the batch indicated that the ratio had increased to 5:1 di-tert-butyl chloromethyl phosphate to methylene chloride. The maximum rotovap jacket temperature was 28.4° C.

Purity of the Di-Tert-Butyl Chloromethyl Phosphate Oil

NMR analysis of the di-tert-butyl chloromethyl phosphate oil indicated the potency to be greater than 100%. Development work typically produced material with a potency of 100±10%. Karl-Fischer analysis measured water content at 0.02 wt % and GC analysis measured methylene chloride at 10.69 wt %. Thus, the reported potency is 89.29 wt % accounting for the methylene chloride and water contribution in the oil.

Storage of Di-Tert-Butyl Chloromethyl Phosphate

The di-tert-butyl chloromethyl phosphate oil was placed in cold room and the temperature was monitored with a stripchart recorder. Laboratory batches were typically held between 0 to 5° C. An NMR of the product after the 104 hour hold in the cold room indicated that the material had not lost potency. (Safety testing conducted during the campaign indicates that upon holding the oil self-heats with a subsequent pressure build-up).

NMR Standard Prep and Sample Prep

Preparation of Trimethyl Phosphate (TMPO$_4$) Standard Solution:

A standard solution of TMPO$_4$ should be prepared based on a 100 M % theoretical yield. For example: a 10 g input of the di-t-butyl potassium phosphate salt should yield 10.41 g (0.402 mols) of di-tert-butyl chloromethyl phosphate. The volume of dichloromethane in the reaction mixture will be 75 mL. The molarity of the solution is 0.536. A TMPO$_4$ solution should be prepared in that molarity and 0.5 mL of that solution should be combined with 0.5 mL of the dichloromethane layer from the reaction. The integrals found in the $^{31}$P NMR can be directly compared and will give the % conversion of di-tert-butyl chloromethyl phosphate.

Determination of % Unreacted Starting Material in the Reaction Aqueous Phase

After recording the volume of the reaction aqueous phase, accurately transfer 0.500 mL into a 1-dram vial containing a known weight of internal standard TMPO$_4$. Add approximately 0.24 mL of D$_2$O. Shake to mix thoroughly. Obtain $^{31}$P-quant spectra.

Calculation % Unreacted Starting Material:

$$\frac{\text{sp. aq. vol.}}{G\ \text{act. inpt.}} \times \frac{TMPO_4}{\text{vol. sample (0.5 mL)}} \times \frac{248.30\ \text{MW st. mat.}}{140.08\ \text{MW}\ TMPO_4} \times \frac{^{31}P\ \text{NMR integration st. mat.}}{^{31}P\ \text{NMR integration}\ TMPO_4} \times \frac{10}{10\ 00} = \begin{bmatrix}\%\ \text{unreacted starting material in the rxn. aq.}\end{bmatrix}$$

$$\frac{212 \text{ mL}}{11.0 \text{ g act.}} \times \frac{13.4 \text{ mg } TMPO_4}{0.500 \text{ mL}} \times \frac{248.30 \text{ MW st. mat.}}{140.08 \text{ MW } TMPO_4} \times \frac{9.617}{270.392} \times \frac{010}{1000} = \boxed{3.26\% \text{ unreacted starting material}}$$

Determination of the %-Potency of the Product Oil:

After recording the net weight of the distilled product oil, tare a 1-dram, screw-top vial containing a known weight of internal standard TMPO$_4$. Transfer approximately 0.02 mL of product oil into the vial and record the net weight of product oil. Add approximately 0.7 mL of CDCl$_3$. Shake to mix thoroughly. Obtain $^{31}$P-quant spectra. Inspect the $^1$H NMR spectra for the presence of residual phase-transfer catalyst (tetra-n-butyl-ammonium bisulfate) and methylene chloride. Report these as mol % relative to product. Calculation of %-Potency:

$$\frac{\text{mg } TMPO_4}{\text{mg sample}} \times \frac{258.68 \text{ MW product}}{140.08 \text{ MW } TMPO_4} \times \frac{^{31}P \text{ NMR integration product}}{^{31}P \text{ NMR integration } TMPO_4} \times 100 = \boxed{\% \text{ potency (w/w) of the product oil}}$$

$$\frac{13.7 \text{ mg } TMPO_4}{22.3 \text{ mg sample}} \times \frac{258.68 \text{ MW product}}{140.08 \text{ MW } TMPO_4} \times \frac{44.744}{55.256} \times 100 = \boxed{91.9\% \text{ potency (w/w) of the product oil}}$$

NMR Data for Di-Tert-Butyl Chloromethyl Phosphate $^1$H NMR (300.13 MHz, CDCl$_3$): δ 1.52 (s, 18H), δ 5.67 (d, J=15.5, 2H) $^{13}$C NMR (75.47 MHz, CDCl$_3$): δ 29.77 (d, J=4.5, 6C), δ 73.34 (d, J=7.5, 1C), δ 84.16 (d, J=1.5, 2C) $^{31}$P NMR (121.49 MHz, CDCl$_3$): δ −10.51 (s, 1P)

Example 12: Alternate Preparation of Iab (Pro-Drug of IVa)

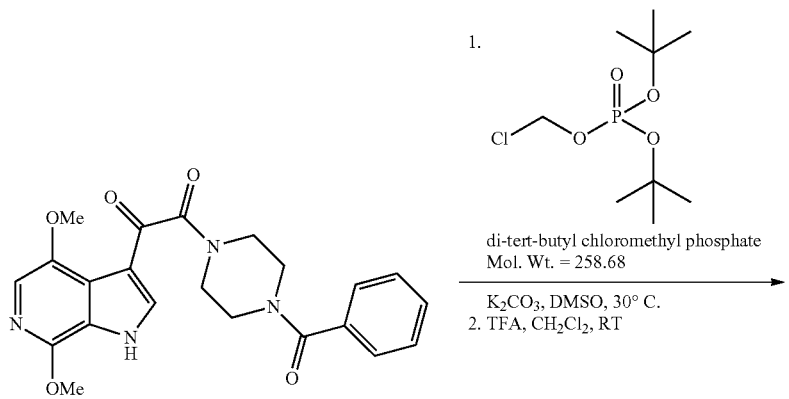

IVa
Mol. Wt. = 422.43

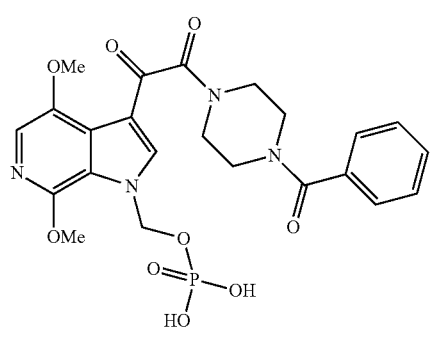

Iac
Mol. Wt. = 532.44

A 500 ml 4-neck round bottom flask equipped with an overhead stirrer, thermocouple, addition funnel, a nitrogen inlet and a septa was charged IVa (20.01 g, 47.37 mmol), K₂CO₃ (13.13 g, 95.00 mmol) and DMSO (100 ml, 1.41 moles) and the reaction was stirred at room temperature resulting in a light brown heterogeneous suspension. Di-tert-butyl chloromethyl phosphate (14.83 g, 57.32 mmol) was added via addition funnel and the reaction was heated to 30° C. for 16-24 hours after which time the reaction was cooled to 10° C. To the reaction was added DCM (200 ml) then was slowly quenched with water (200 ml) maintaining the reaction temperature under 20° C. resulting in a biphasic mixture. The product rich bottom layer was separated, washed with water (200 ml), then transferred to a 500 ml 4-neck round bottom flask equipped with an overhead stirrer, thermocouple, addition funnel, and nitrogen inlet. Trifluoroacetic acid (53.0 ml, 700.94 mmol) was added via addition funnel resulting in a slight exotherm. The reaction was stirred for 1-3 hours then cooled to 0° C. Methanol (300 ml) was added keeping the reaction temperature under 20° C., and then the cooled to 0° C. The reaction flask was fitted with a distillation apparatus and concentrated under vacuum to a volume of 200 ml (200 torr, <30° C.). The reaction was seeded with Iac (0.200 g) then stirred overnight at room temperature resulting in a slurry. The slurry was filtered then the wet cake was washed with THF (300 ml) then dried in a vacuum oven at 50° C. overnight resulting in a pale yellow to white powder (23.94 g, 95%). ¹H NMR (400 MHz, DMSO-d6) δ 8.30 (s, 1H), 7.55 (s, 1H), 7.44 (s, 5H), 6.12 (d, J=10.6 Hz, 2H), 3.97 (s, 3H), 3.85 (s, 3H), 3.80-3.22 (m, 8H); ¹³C NMR (100 MHz, DMSO-d6) δ 185.49, 169.26, 166.06, 146.20, 145.60, 140.64, 135.50, 129.68, 128.41, 127.04, 123.46, 121.17, 120.08, 114.32, 72.43, 56.92, 53.32, 45.22, 40.50; ES⁺ MS m/z (rel. intensity) 533 (MH⁺, 100), 453 (MH⁺—H3PO4, 15).

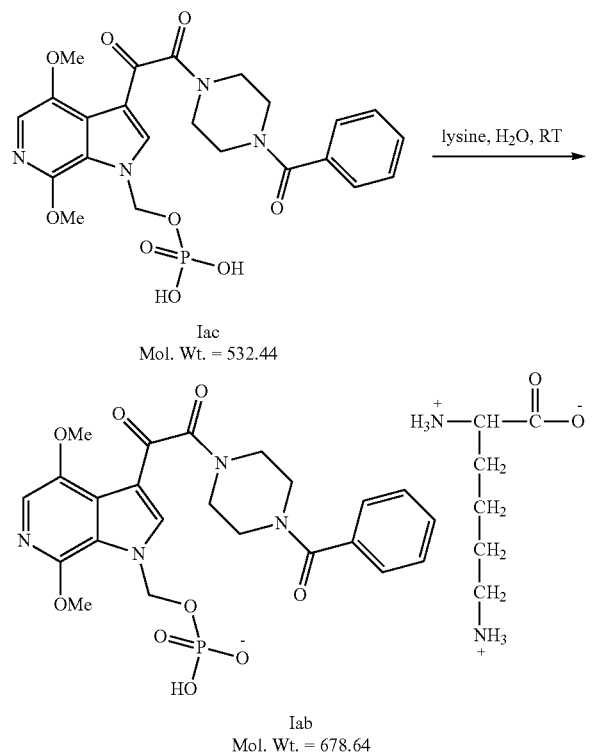

To a 10 L 4 neck reactor equipped with a thermocouple, overhead stirrer, condenser and nitrogen inlet was added Iac (611 g, 1.15 mol) and water (3875 ml). To the resulting suspension was added lysine (168 g, 1.15 mol). The reaction was stirred for one hour at RT, heated to 50° C. then maintained at 50° C. with stirring for an additional hour. The resulting hazy solution (pH=4.55) was filtered through a 10 micron cuno filter into a 20 L 4 neck reactor equipped with a thermocouple, overhead stirrer, condenser and nitrogen inlet. The reaction was heated to 50° C. then acetone (8 L) was added rapidly. The reaction was allowed to warm to 50° C. then acetone (4 L) was added at a moderate rate keeping the reaction temperature above 45° C. The reaction was seeded with Iab (0.200 g) then cooled to room temperature over 5 hours resulting in a slurry. The slurry was stirred overnight at room temperature then filtered. The wet cake was washed with acetone (4 L) then dried in a vacuum oven at 25° C. overnight with a bleed of moist air resulting in a fluffy white powder (751 g, 96%).

Example 13: Alternate Preparation of Icb (Pro-Drug of IVc)

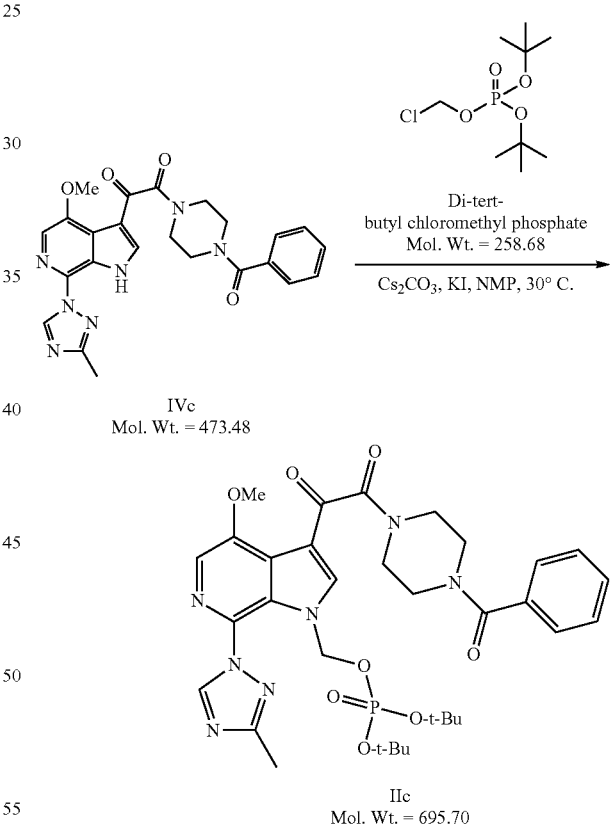

To a 10 L reactor equipped with an overhead stirrer, thermocouple, distillation apparatus, and nitrogen inlet was charged IVc (200.00 g, 422.39 mmol), Cs₂CO₃ (344.06 g, 1.06 mol), KI (140.24 g, 844.81 mmol) and NMP (1.00 L, 10.38 mol). The reaction was stirred at room temperature resulting in a light brown heterogeneous suspension. Di-tert-butyl chloromethyl phosphate (273.16 g, 1.06 mol) was added via addition funnel and the reaction mixture was heated to 30° C. for 16-24 hours with stirring after which time the reaction was cooled to 5° C. To the reaction was added DCM (1.5 L) then the reaction was slowly quenched with water (3.5 L) maintaining the reaction temperature under 20° C. resulting in a biphasic mixture. The product rich bottom layer was separated, washed with water (3.5 L×3), then transferred back to the reactor. The solution was concentrated under vacuum to a volume of 1 L keeping the temperature below 25° C. IPA was added (2 L) then the reaction was concentrated under vacuum to a volume of 2 L keeping the temperature below 25° C. The reaction was then seeded with IIc (0.200 g), stirred overnight at room temperature resulting in a slurry. The slurry was filtered and the wet cake was washed with MTBE (1 L), dried in a vacuum oven at 50° C. overnight resulting in a yellow/white powder (207.1 g, 70%). $^1$H NMR (400 MHz, CDCl$_3$) δ 8.54 (s, 1H), 8.18 (s, 1H), 7.91 (s, 1H), 7.42 (s, 5H), 5.95 (d, J=14.2 Hz, 2H), 4.06 (s, 3H), 3.97-3.36 (m, 8H), 2.50 (s, 3H), 1.27 (s, 18H); $^{13}$C NMR (100 MHz, CDCl$_3$) δ 184.64, 170.65, 165.91, 161.60, 150.82, 145.38, 141.89, 134.96, 130.20, 129.59, 128.68, 127.58, 127.10, 124.77, 122.64, 115.22, 83.90, 83.83, 73.69, 73.63, 56.95, 46.04, 41.66, 29.61, 29.56, 13.90; ES$^+$ MS m/z (rel. intensity) 696 (MH$^+$, 10), 640 (MH$^+$-isobutylene, 30), 584 (MH$^+$-2 isobutylene, 100).

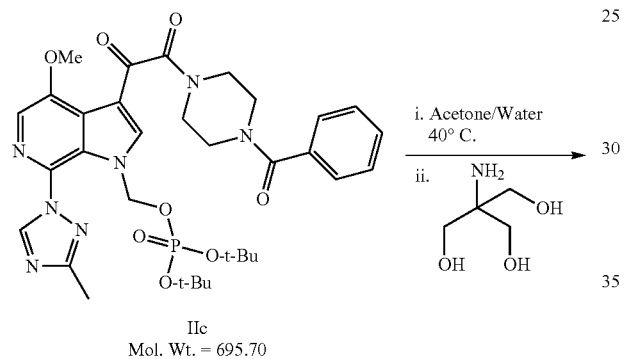

IIc
Mol. Wt. = 695.70

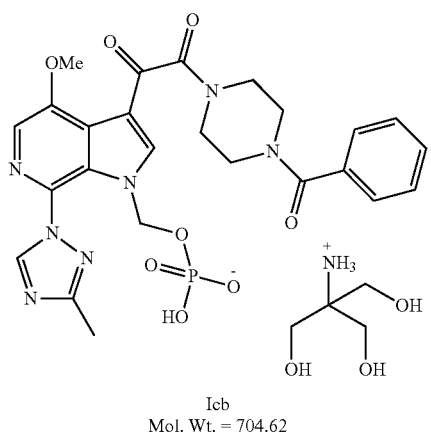

Icb
Mol. Wt. = 704.62

To a 10 L 4 neck reactor equipped with a thermocouple, overhead stirrer, condenser and nitrogen inlet was added IIc (200.24 g, 287.82 mmol), acetone (800.00 ml, 10.88 mol) and water (800.00 ml, 44.41 mol). The reaction was heated to 40° C. and stirred for 18-24 hours. The reaction was cooled to 20° C. then tromethamine (33.62 g, 277.54 mmol) was added. The reaction was heated to 40° C. then stirred for an additional hour until all solids were dissolved. The reaction was cooled to 20° C. then filtered through a 10 micron cuno filter into a 10 L 4 neck reactor equipped with a thermocouple, overhead stirrer, and nitrogen inlet. Acetone (3 L) was added rapidly, followed by seeding with Icb (0.500 g), then additional acetone (3 L) was added. The reaction was stirred at room temperature overnight resulting in a slurry then filtered. The wet cake was washed with acetone (800 ml) then dried in a vacuum oven at 50° C. overnight resulting in a fluffy white powder (165.91 g, 82%).

Supplementary Information:

Isolation of the Free-Acid Intermediate Ic:

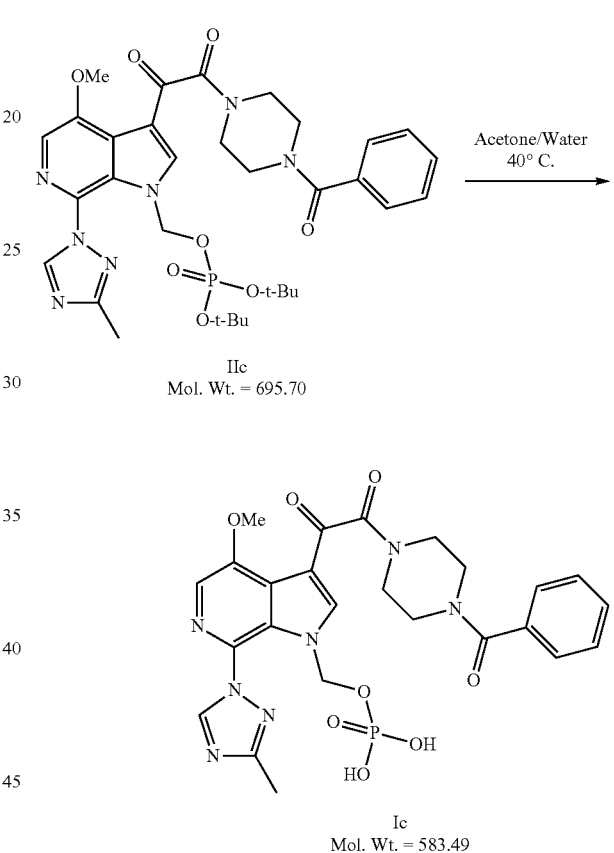

In a 250 mL 3 neck reactor equipped with a thermocouple, overhead stirrer, condenser and nitrogen inlet was added IIc (10.0 g, 14.37 mmol), acetone (40.00 ml, 544.15 mmol) and water (40.00 ml, 2.22 mol). The reaction was heated to 40° C. and stirred for 14-24 hours. The reaction was cooled to 20° C. then stirred for three hours, resulting in a slurry. The slurry was filtered, then the wet cake washed with acetone (40.00 ml) then dried in a vacuum oven at 50° C. overnight resulting in a fluffy white powder (7.00 g, 83%). NMR (400 MHz, DMSO-d6) δ 8.84 (s, 1H), 8.47 (s, 1H), 8.06 (s, 1H), 7.45 (s, 5H), 5.81 (d, J=12.3 Hz, 2H), 4.03 (s, 3H), 3.91-3.19 (m, 8H), 2.39 (s, 3H); $^{13}$C NMR (500 MHz, DMSO-d6) δ 185.20, 169.32, 165.85, 160.75, 150.51, 146.30, 143.24, 135.53, 129.74, 129.22, 128.46, 127.34, 127.09, 123.67, 122.73, 113.94, 72.90 (d, $^2J_{C-P}$=5 Hz), 57.01, 45.2 (bs), 40.8 (bs), 13.66. ES$^+$ MS m/z (rel. intensity) 486 (MH$^+$-H$_3$PO$_4$, 100).

Example 14: Alternate Preparation of Ibb
(Pro-Drug of IVb)

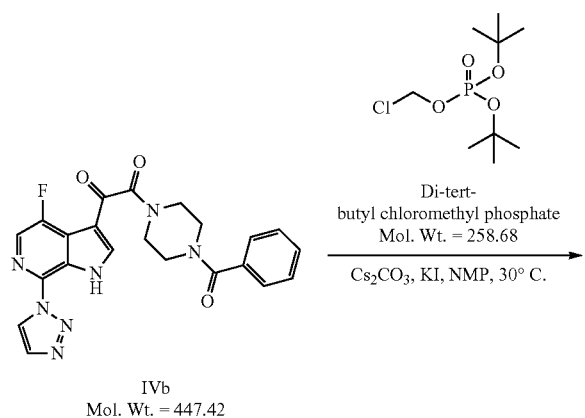

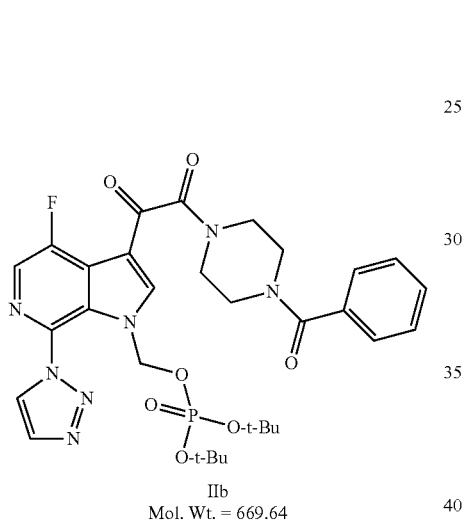

To a 10 L reactor equipped with an overhead stirrer, thermocouple, and nitrogen inlet was charged IVb (400.00 g, 894.73 mmol), $Cs_2CO_3$ (873.70 g, 2.68 mol), KI (297.70 g, 1.79 mol) and NMP (1.00 L, 10.38 mol). The reaction mixture was stirred at room temperature resulting in a light brown heterogeneous suspension. Di-tert-butyl chloromethyl phosphate (460.50 g, 1.78 mol) was added via addition funnel and the reaction was heated to 30° C. for 16-24 hours at which time the reaction was cooled to 5° C. To the reaction was added n-BuOAc (2.4 L) then the reaction was slowly quenched with water (4 L) maintaining the reaction temperature under 20° C. resulting in a biphasic mixture. The bottom aqueous layer was removed from the reactor, then the product rich top layer was seeded with IIc, (0.40 g) then stirred 3 hours at room temperature resulting in a slurry. The slurry was filtered then the wet cake was washed with MTBE (1.6 L) then dried in a vacuum oven at 50° C. overnight resulting in a yellow/white powder (483.2 g, 81%). $^1$H NMR (400 MHz, $CDCl_3$) δ 8.35 (s, 1H), 8.27 (s, 1H), 8.22 (s, 1H), 7.90 (s, 1H), 7.42, (s, 5H), 5.92, (d, J=14.9 Hz, 2H), 4.02-3.40 (m, 8H), 1.24 (s, 18H); $^{13}$C NMR (100 MHz, $CDCl_3$) δ 182.75, 170.64, 152.07, 144.03, 134.91, 133.96, 131.82, 130.21, 128.68, 128.27, 128.00, 127.07, 125.81, 124.01, 113.82, 84.00, 83.93, 73.97, 46.12, 41.90, 29.57, 29.53; ES$^+$ MS m/z (rel. intensity) 558 (MH$^+$, 100).

To a 300 ml 4 neck reactor equipped with a thermocouple, overhead stirrer, condenser, and nitrogen inlet was added IIb (18.0 g, 26.87 mmol), IPA (36.00 ml, 470.92 mol) and water (36.00 ml, 2.0 mol). The reaction was heated to 40° C. and stirred for 18-24 hours. The reaction was cooled to 20° C. then lysine (3.73, 25.54 mmol) was added. The reaction was stirred for 1 hour until all solids were dissolved. IPA (54 ml) was added over 30 minutes followed by seeding with Ibb (0.180 g) and stirring for an additional 30 minutes. IPA was added (18 ml) over 1 hour then the reaction was heated to 50° C. resulting in a thin slurry. The reaction was seeded with Ibb (0.180 g) then IPA (36 ml) was added over 2 hours then stirred for 12 hours resulting in a slurry. The reaction was heated to 70-80° C. for 2 to 3 hours then cooled to 50° C. IPA (59 ml) was added over 1 hour then additional IPA (121 ml) was added over 1 hour. The reaction was cooled to 20° C. over 2 hours then stirred for an additional 2 hours then filtered. The wet cake was washed with IPA (180 ml) then dried in a vacuum oven at 50° C. overnight resulting in a white powder (15.43 g, 82%).

Supplementary Information:

Procedure for the Isolation of the Free-Acid Intermediate Ibc:

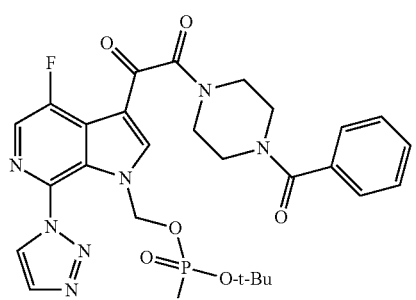

IIb
Mol. Wt. = 669.64

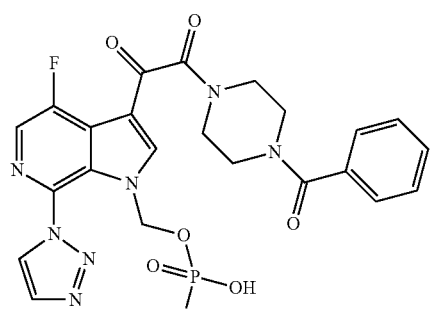

Ibc
Mol. Wt. = 557.43

In a 500 ml 3 neck flask equipped with a thermocouple, overhead stirrer, condenser, and nitrogen inlet was added IIb (50.00 g, 74.76 mmol), Acetone (100.00 ml, 1.36 mol) and water (100.00 ml, 5.55 mol). The reaction was heated to 40° C. and stirred for 18-24 hours.

In a 250 ml 3 neck flask equipped with a pH probe, magnetic stirbar, and nitrogen inlet was added 150 ml of the above Ibc solution then the pH was adjusted to pH=6.2 with 10 N NaOH. The solution was transferred to a separatory funnel, then washed with EtOAc (100 ml) then DCM (100 ml), then transferred back the 250 ml 3 neck flask. The pH was adjusted to pH=1.3 with 2 N HCl followed by stirring for three hours, resulting in a slurry which was filtered. The wet cake was re-slurried in MTBE (150 ml) then filtered, followed by re-slurrying in THF/Water (100:1, 130 ml) for 45 minutes, then filtered and dried in a vacuum oven at 50° C. overnight resulting in a white powder (10.0 g, 33%). NMR (400 MHz, DMSO-d6) δ 8.69 (s, 1H), 8.62 (s, 1H), 8.42 (s, 1H), 7.98 (s, 1H), 7.41 (s, 5H), 5.47 (d, J=13.3 Hz, 2H), 3.99-3.18 (m, 8H); $^{13}$C NMR (100 MHz, DMSO-d6) δ 183.97, 169.23, 165.20, 151.69, 145.91, 135.48, 133.83, 131.59, 129.65, 129.11, 129.03, 128.42, 127.77, 127.49, 127.03, 122.62, 112.08, 72.57. ES$^+$ MS m/z (rel. intensity) 558 (MH$^+$, 100).

Example 15: Preparation of Prodrug Ie

Step One

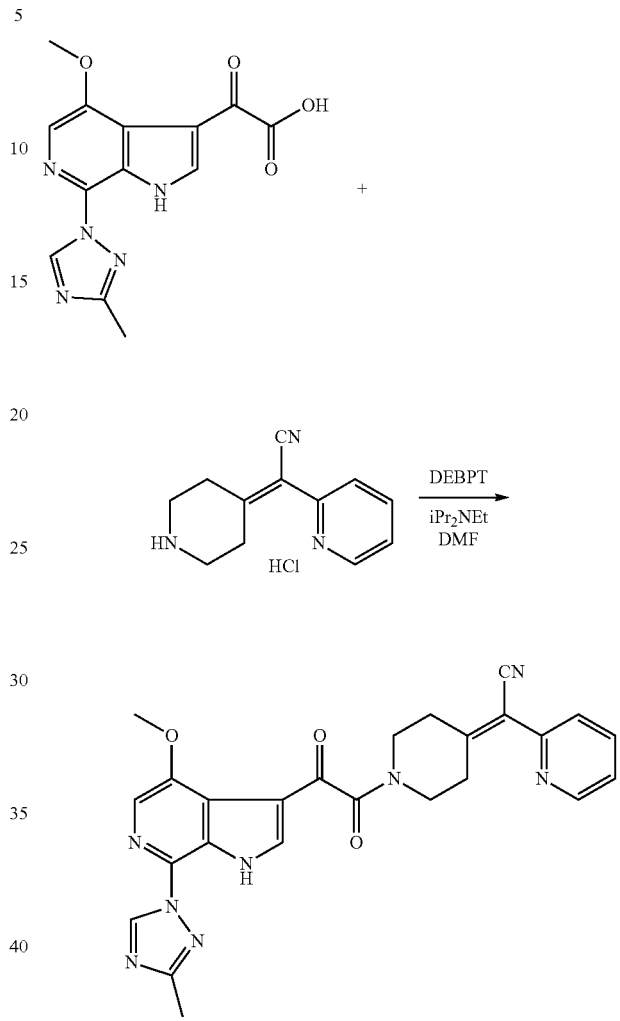

Preparation of 2-(1-(2-(4-methoxy-7-(3-methyl-1H-1,2,4-triazol-1-yl)-1H-pyrrolo[2,3-c]pyridin-3-yl)-2-oxoacetyl)piperidin-4-ylidene)-2-(pyridin-2-yl)acetonitrile (IVe): 2-(4-methoxy-7-(3-methyl-1H-1,2,4-triazol-1-yl)-1H-pyrrolo[2,3-c]pyridin-3-yl)-2-oxoacetic acid (1.5 g), 2-(piperidin-4-ylidene)-2-(pyridin-2-yl)acetonitrile hydrochloride (1.5 g), 3-(diethoxyphosphoryloxy)-1,2,3-benzotriazin-4(3H)-one (DEPBT) (2.1 g) and Hunig's Base (2 ml) were combined in 20 ml of DMF. The mixture was stirred at room temperature for 16 hours.

DMF was removed via evaporation at reduced pressure and the residue was partitioned with MeOH (80 ml). The precipitate was collected via filtration to provide 0.85 g of the product, 2-(1-(2-(4-methoxy-7-(3-methyl-1H-1,2,4-triazol-1-yl)-1H-pyrrolo[2,3-c]pyridin-3-yl)-2-oxoacetyl)piperidin-4-ylidene)-2-(pyridin-2-yl)acetonitrile (IVe). $^1$H NMR (500 MHz, DMSO-d6) 12.42 (s, 1H), 9.23 (m, 1H), 8.69 (m, 1H), 8.27 (m, 1H), 7.89 (m, 2H), 7.58 (m, 1H), 7.52 (m, 1H), 3.98 (s, 3H), 3.99-2.70 (m, 8H), 2.60 (m, 3H). MS m/z: (M+H)$^+$ calcd for $C_{25}H_{23}N_8O_3$ 483.19, found 483.18.

Step Two

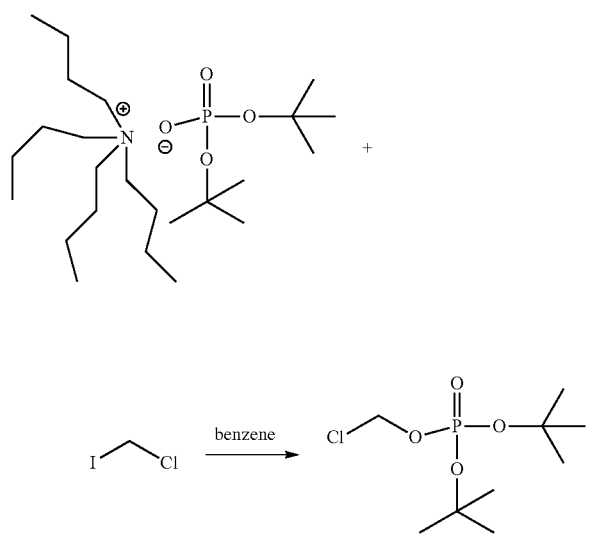

Phosphate ester (45.1 g, 0.1 mol) and chloroiodomethane (200 g, 1.14 mol) were combined in 100 ml of benzene and the mixture was stirred at room temperature for four hours before benzene was removed under vacuum. Then, 500 ml of ethyl ether was added to the residue and insoluble solid was filtered away. Concentration of the filtrate provided di-tert-butyl chloromethyl phosphate, which was utilized in the next step without any further purification.

Step Three

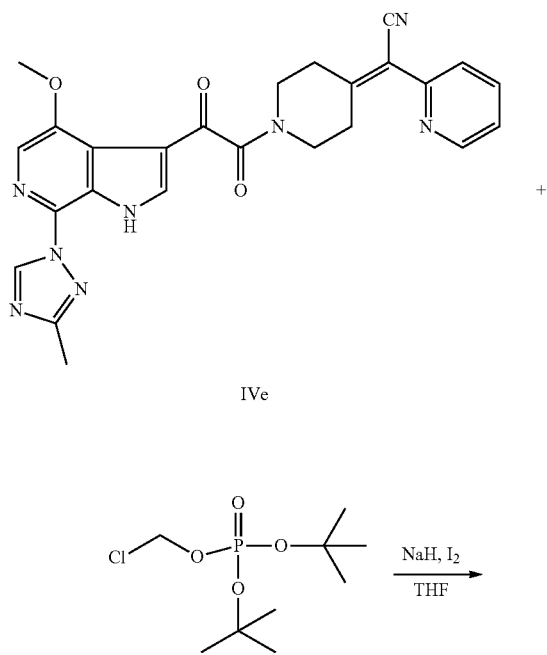

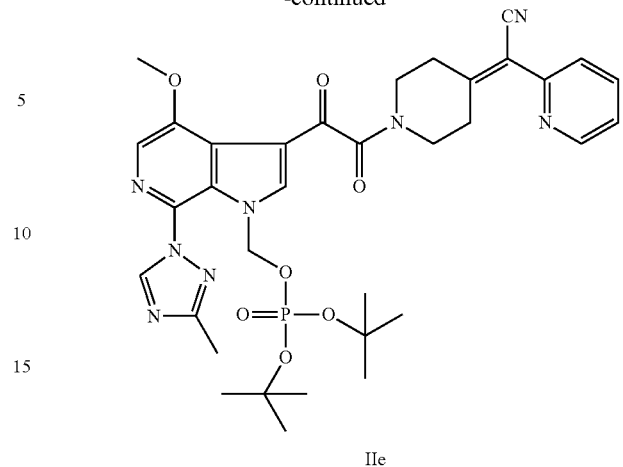

NaH (0.2 g, 95%) was added slowly into a suspension of 2-(1-(2-(4-methoxy-7-(3-methyl-1H-1,2,4-triazol-1-yl)-1H-pyrrolo[2,3-c]pyridin-3-yl)-2-oxoacetyl)piperidin-4-ylidene)-2-(pyridin-2-yl)acetonitrile (IVe) in dry THF (20 m) and the mixture was allowed to stir for an hour at room temperature. Iodine (0.4 g) dissolved in dry THF (2 ml) was added slowly into the stirring solution. The mixture was stirred for additional 3 hours before 0.2 g of NaH was charged. Following completion of addition the resultant mixture was stirred at ambient temperature for an additional 15 minutes and then di-tert-butyl chloromethyl phosphate, obtained from step two, was added. After stirring for 16 hours, the reaction mixture was poured into iced NH$_4$OAc (30%) (50 ml), followed by extraction with EtOAc (3×100 ml). The combined organic extracts were washed with water (50 ml) and then brine (50 m), dried over Na$_2$SO$_4$, and concentrated under vacuum to afford a residue, which was purified by silica gel chromatography (elution with EtOAc/Et$_3$N (100/1)) to give 330 mg of di-tert-butyl (3-(2-(4-(cyano(pyridin-2-yl)methylene)piperidin-1-yl)-2-oxoacetyl)-4-methoxy-7-(3-methyl-1H-1,2,4-triazol-1-yl)-1H-pyrrolo[2,3-c]pyridin-1-yl)methyl phosphate (IIe). $^1$H NMR (500 MHz, CD$_3$OD) δ 8.85 (m, 1H), 8.66 (m, 1H), 8.45 (m, 1H), 8.06 (m, 1H), 7.92 (m, 1H), 7.60 (m, 1H), 7.43 (m, 1H), 6.05 (m, 2H), 4.11 (s, 3H), 4.00 (m, 1H), 3.82 (m, 1H), 3.76 (m, 1H), 3.60 (m, 1H), 3.04 (m, 1H), 2.95 (m, 1H), 2.85 (m, 1H), 2.80 (m, 1H), 2.52 (s, 3H), 1.30 (m, 18H). MS m/z: (M+H)$^+$ calcd for C$_{34}$H$_{42}$N$_8$O$_7$P 705.29, found 605.30.

Step Four

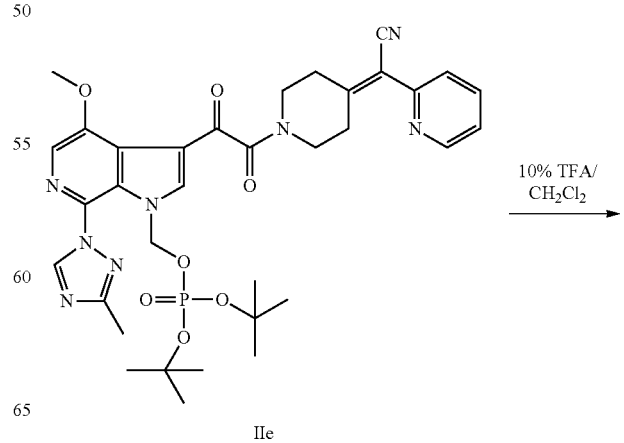

-continued

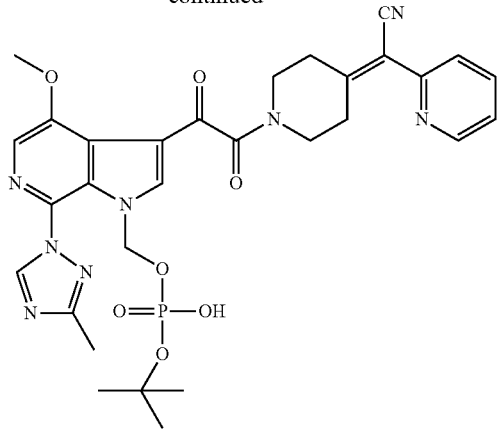

II'e

+

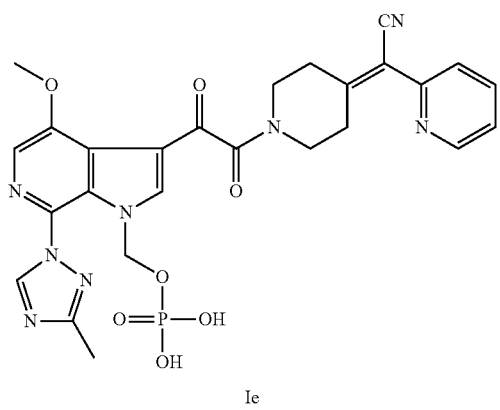

Ie

Di-tert-butyl (3-(2-(4-(cyano(pyridin-2-yl)methylene)piperidin-1-yl)-2-oxoacetyl)-4-methoxy-7-(3-methyl-1H-1,2,4-triazol-1-yl)-1H-pyrrolo[2,3-c]pyridin-1-yl)methyl phosphate (IIe) was dissolved in 8 ml of a mixed solution of TFA and dichloromethane (10% TFA/CH2Cl2) and the mixture was stirred for three hours. All the solvents were removed under vacuum and the residue was purified using a Shimadzu automated preparative HPLC System to give 25 mg of tert-butyl (3-(2-(4-(cyano(pyridin-2-yl)methylene)piperidin-1-yl)-2-oxoacetyl)-4-methoxy-7-(3-methyl-1H-1,2,4-triazol-1-yl)-1H-pyrrolo[2,3-c]pyridin-1-yl)methyl hydrogen phosphate (II'e) and 33 mg of (3-(2-(4-(cyano(pyridin-2-yl)methylene)piperidin-1-yl)-2-oxoacetyl)-4-methoxy-7-(3-methyl-1H-1,2,4-triazol-1-yl)-1H-pyrrolo[2,3-c]pyridin-1-yl)methyl dihydrogen phosphate (Ie). tert-Butyl (3-(2-(4-(cyano(pyridin-2-yl)methylene)piperidin-1-yl)-2-oxoacetyl)-4-methoxy-7-(3-methyl-1H-1,2,4-triazol-1-yl)-1H-pyrrolo[2,3-c]pyridin-1-yl)methyl hydrogen phosphate (II'e): $^1$HNMR (500 MHz, CD$_3$OD) δ 8.83 (m, 1H), 8.55 (m, 1H), 8.35 (m, 1H), 7.92 (m, 2H), 7.54 (m, 1H), 7.41 (m, 1H), 5.86 (m, 2H), 3.98 (s, 3H), 3.96 (m, 1H), 3.72 (n, 1H), 3.65 (m, 1H), 3.47 (m, 1H), 2.92 (m, 1H), 2.85 (m, 1H), 2.71 (m, 1H), 2.65 (m, 1H), 2.40 (s, 3H), 1.15 (m, 9H). MS m/z: (M+H)$^+$ calcd for C$_{30}$H$_{34}$N$_8$O$_7$P 649.23, found 649.22.

(3-(2-(4-(Cyano(pyridin-2-yl)methylene)piperidin-1-yl)-2-oxoacetyl)-4-methoxy-7-(3-methyl-1H-1,2,4-triazol-1-yl)-1H-pyrrolo[2,3-c]pyridin-1-yl)methyl dihydrogen phosphate (Ie): $^1$H NMR (500 MHz, DMSO-d6) δ 8.88 (m, 1H), 8.65 (m, 1H), 8.50 (m, 1H), 8.06 (m, 1H), 7.90 (m, 1H), 7.49 (m, 2H), 5.82 (m, 2H), 4.04 (s, 3H), 3.96 (m, 1H), 3.88 (m, 1H), 3.72 (m, 1H), 3.46 (m, 1H), 2.94 (m, 1H), 2.82 (m, 2H), 2.73 (m, 1H), 2.40 (m, 3H); $^{13}$C NMR (125 MHz, DMSO-d6) δ185.2, 165.6, 160.6, 159.1, 151.0, 150.4, 149.5, 146.2, 143.1, 137.4, 129.1, 127.2, 124.4, 123.6, 122.6, 117.4, 116.3, 113.9, 110.0, 72.8, 56.9, 48.4, 44.4, 36.4, 34.0, 13.6. MS m/z: (M+H)$^+$ calcd for C$_{26}$H$_{26}$N$_8$O$_7$P 593.17, found 593.14.

Example 16: Preparation of Prodrug If

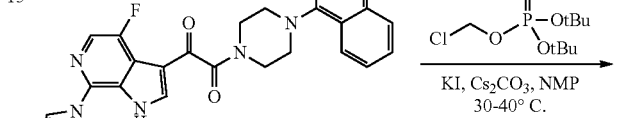

IVf

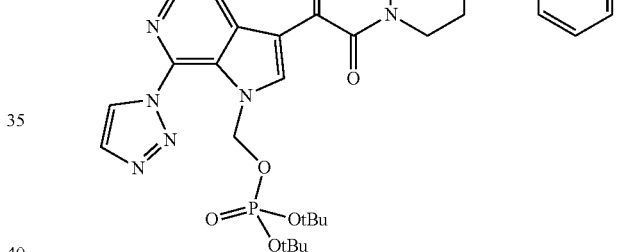

IIf

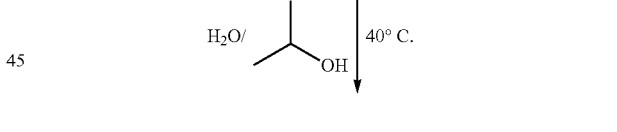

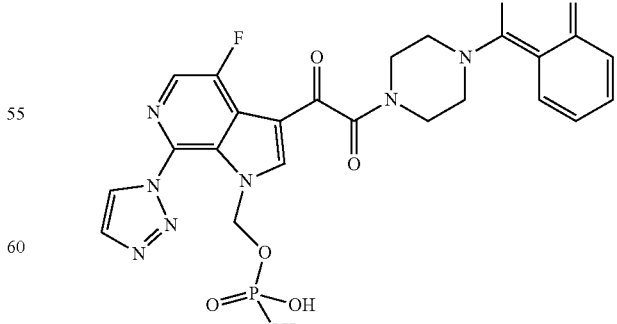

If

To a mixture of IVf (99.5 mg, 0.21 mmol) in 1-methyl-2-pyrrolidinone (1.0 ml) at r.t. in a capped vial was added KI (144 mg, 0.87 mmol) and $Cs_2CO_3$ (416 mg, 1.28 mmol)), and the mixture was stirred for about 5 min. Di-tertbutyl chloromethyl phosphate reagent (218 mg, 0.84 mmol) was then added dropwise. The resulting mixture was then stirred at 35 to 40° C. for 20 hours. The mixture was then diluted with $H_2O$ (about 8 ml) and extracted with EtOAc (about 8 ml). The organic extract was separated and evaporated to give the di-t-butyl chloromethyl phosphate; Analytical HPLC method: Solvent A 10% MeOH-90% $H_2O$-0.1% TFA; Solvent B 90% MeOH-10% $H_2O$-0.1% TFA; Start % B=0, Final % B=100, Gradient time=2 min, Flow Rate=5 mL/min, Column: Xterra MS C18 S7 3.0×50 mm; LC/MS: (ES☐) m/z $(M+H)^+$=694.22, HPLC $R_t$=1.243.

A mixture of Intermediate IIf in $H_2O$/isopropanol (1.0 ml/1.0 ml) in a stoppered round bottom flask was stirred at 40° C. for 9.5 hours. The mixture was then cooled to r.t., and the solution transferred to a vial by using a pipette. MeCN (1.0 ml) was added to this solution, which was then added isopropanol slowly and with intermittent stirring using a spatula. The off white precipitates were then filtered, washed with isopropanol (2×1.0 ml) and then dried under high vacuum to give the prodrug If; $^1$H NMR (500 MHz): (DMSO-$d_6$) δ 8.76 (s, 1H), 8.71 (s, 1H), 8.69 (s, 1H), 8.49 (s, 1H), 8.09 (d, J=8, 1H), 8.06 (s, 1H), 7.89 (d, J=7, 1H), 7.85 (app t, 1H), 7.59 (app t, 1H), 5.68 (d, J=13, 2H), 4.00 (b m, 2H), 3.90 (b m, 2H), 3.85 (b m, 2H), 3.65 (b m, 2H); Analytical HPLC method: Solvent A 10% MeOH-90% $H_2O$-0.1% TFA; Solvent B 90% MeOH-10% $H_2O$-0.1% TFA; Start % B=0, Final % B=100, Gradient time=2 min, Flow Rate=5 mL/min, Column: Xterra MS C18 S7 3.0×50 mm; LC/MS: (ES☐) m/z $(M+H)^+$=582.00, HPLC $R_t$=1.797.

To be successful, the conversion of the prodrug into parent must be initiated by alkaline phosphatases in man. Qualitative in vitro studies using human placental alkaline phosphatase and in vivo studies in rats showed that conversion of prodrug was rapid both in vitro with human enzymes and in in vivo in rats. Ideally, the rate of conversion will be rapid so that only limited exposure to prodrug occurs and maximum exposure to active parent antiviral agent will result. Data from studies (below) shows that in all three prodrug examples evaluated in rats, the prodrug is rapidly converted to active parent drug and that plasma levels of prodrug are very low in comparison to parent drug at all data points. These studies were done at doses in which doses of parent drug and the dose equivalent from phosphate prodrug were low and approximately equal, ~5 mg/kg. Since the advantages of prodrugs are to overcome dissolution limited absorption, at low doses the advantages of the prodrugs over less soluble parent molecules for clinical use in patients will not be obvious. The low dose in vivo studies were used to determine if the prodrugs were generating parent molecule. The solubility of the parent molecules IV, is dependent on crystalline form. A crystalline form is preferred for drug development. The data for all of the parent molecules can be summarized by saying that the aqueous solubility of crystalline material for all the parent molecules IV is <50 μg/mL and in some cases much less. Thus, the intrinsic aqueous solubility of the parent molecules is low and plays a major role in causing dissolution-limited absorption at higher doses.

TABLE 1

Biological and Pharmaceutical Properties of N-methyl dihydrogen phosphate (or salts) Azaindoleoxoacetic Piperazine Derivatives

| | Compound Ia (disodium salt) | Compound Ib (disodium salt) | Compound Ic (acid form) |
|---|---|---|---|
| Solubility (mg/mL), pH 6.5 | >18 | >8 | 1 |
| In vitro conversion in Alkaline phosphatase (note 1) | Complete and rapid conversion to parent without any intermediate formation | Complete and rapid conversion to parent without any intermediate formation | Complete and rapid conversion to parent without any intermediate formation |
| In vivo conversion in Rats-oral (note 2) MAP study | Rapid generation of parent in plasma | Rapid generation of parent in plasma | Rapid generation of parent in plasma |
| In vivo conversion in Rats-iv (note 2) MAP study | Rapid generation of parent in plasma | Rapid generation of parent in plasma | Rapid generation of parent in plasma |

Note 1:
The prodrug derivative (conc.~0.2 mM) was incubated with alkaline phosphatase (human placenta, Sigma, ~1.4 unit) in pH 8 Tris buffer (conc.~0.03M, 1 mL), and disappearance of the prodrug and formation of the parent were monitored by HPLC and LC/MS. In most cases, the prodrug completely disappeared, corresponding with formation of the parent within an hour or two, and no other intermediate was detected.

Note 2:
The prodrug was administered in rats by the oral (at the dose equiv. to 5 mg/Kg of the parent) or intravenous route (at the dose equiv. to 1 mg/Kg of the parent). The plasma levels indicate rapid conversion to the parent with no detectable amount of the prodrug (po).

In the tables below the term "LLQ" means lower limit of quantitation (i.e., not detected).

TABLE 2

MAP Study A: Summary of PK after PO and IV Administration of Prodrug Ia to Rats. Comparison to Historic PO of Compound IVa in Rats

| PK (5 mg/kg po) | Ia After prodrug dosing | IVa After prodrug dosing | Historic IVa After dosing of parent IVa (Study A1) |
|---|---|---|---|
| | *(structure: dimethoxy-pyrrolopyridine with phosphate prodrug, disodium salt)* | *(structure: dimethoxy-pyrrolopyridine parent IVa)* | *(structure: dimethoxy-pyrrolopyridine parent IVa)* |
| Dose PO (mpk) | 6.3 mpk | equivalent to 5 mpk of IVa) | 5 mpk |
| Cmax (um) | LLQ | 1.4 ± 0.6 | 4.5 ± 1.5 |
| Tmax (hr) | LLQ | 1.7 | 2 |
| AUC 0-24 h (μM * hr) | LLQ | 5.9 ± 1 | 14.9 ± 6.2 |
| Cp @ 24 hr p.o. (nM) | LLQ | 35.2 (n = 1) | 9.2 (n = 1) |
| Dose IV (mpk) | 1.26 mpk | equivalent to 1 mpk of 'IVa) | 1 |
| CL i.v. (ml/min/kg) | 16 ± 0.95 | — | 13 ± 4.6 |
| Vss i.v. (L/kg) | 0.095 ± 0.001 | — | 1.4 ± 0.4 |
| T½ i.v. (hr) | 0.14 ± 0.02 | 2.8 ± 1.5 | 4 ± 2.6 |
| T½ p.o. (hr) | | 3.3 ± 2.2 | 1.9 ± 0.8 |
| AUC0 tot ratio after IV administration* | | 0.534 | |
| AUCtot ratio after PO administration** | | 0.39 | |

TABLE 3

MAP Study B: Summary of PK after PO and IV Administration of Prodrug Ib to Rats. Comparison to Historic PO of Compound IVb in Rats

| PK (5 g/kg po) | Ib After prodrug dosing | IVb After prodrug dosing | Historic IVb After dosing of parent IVb (Study B1) |
|---|---|---|---|
| | *(structure: fluoro-pyrrolopyridine with triazole and phosphate prodrug, disodium salt)* | *(structure: fluoro-pyrrolopyridine with triazole parent IVb)* | |
| Dose PO (mpk) | 7 mpk | equivalent to 5 mpk of IVb) | 5 |
| Cmax (uM) | LLQ | 3.9 ± 0.8 | 9.5 ± 2.8 |

TABLE 3-continued

MAP Study B: Summary of PK after PO and IV Administration of Prodrug Ib to Rats. Comparison to Historic PO of Compound IVb in Rats

| PK (5 g/kg po) | Ib After prodrug dosing | IVb After prodrug dosing | Historic IVb After dosing of parent IVb (Study B1) |
|---|---|---|---|
| | 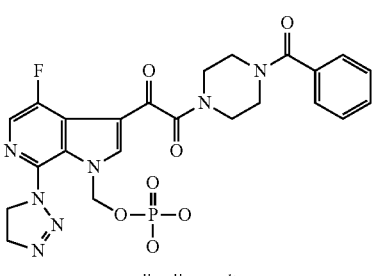 disodium salt | | |
| Tmax (hr) | LLQ | 1.1 | 4.6 |
| AUC 0-24 h (μM * hr) | LLQ | 13.7 ± 2.6 | 86 ± 33 |
| Cp @ 24 hr p.o. (nM) | LLQ | 7.5 (n = 1) | 161 |
| Dose IV (mpk) | 1.4 | equivalent to 1 mpk of 'IVa) | 1 |
| CL i.v. (ml/min/kg) | 46 ± 10 | — | 1.6 ± 0.2 |
| Vss i.v. (L/kg) | 0.97 ± 0.47 | — | 0.49 ± 0.26 |
| T½ i.v. (hr) | 1.8 ± 1.2 | 1.5 ± 0.2 | 5.9 ± 4.9 |
| T½ p.o. (hr) | | 2.4 ± 0.5 | 3.7 ± 0.9 |
| AUC0 tot ratio after IV administration* | | 0.10 | |
| AUCtot ratio after PO administration** | 0.14 | | |

TABLE 4

MAP Study C: Summary of PK after PO and IV Administration of Prodrug Ic to Rats. Comparison to Historic PO of Compound IVc in Rats

| PK (5 mg/kg po) | Ic After prodrug dosing | IVc After prodrug dosing | Historic IVc After dosing of parent IVc (Study C1) |
|---|---|---|---|
| | 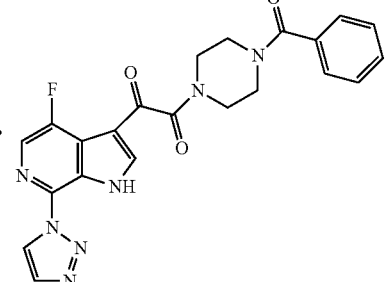 | | |
| Dose PO (mpk) | 6.5 mpk | equivalent to 5 mpk of IVc) | 5 |
| Cmax (uM) | LLQ | 10.2 ± 2.1 | 13.4 ± 3.6 |

TABLE 4-continued

MAP Study C: Summary of PK after PO and IV Administration of Prodrug Ic to Rats. Comparison to Historic PO of Compound IVc in Rats

| PK (5 mg/kg po) | Ic After prodrug dosing | IVc After prodrug dosing | Historic IVc After dosing of parent IVc (Study C1) |
|---|---|---|---|
| Tmax (hr) | LLQ | 0.8 ± 0.1 | 4 |
| AUC 0-24 h (μM * hr) | LLQ | 56 ± 7.5 | 110 ± 25 |
| Cp @ 24 hr p.o. (nM) | LLQ | 84.3 (n = 2) | 61 |
| Dose IV (mpk) | 1.3 | equivalent to 1 mpk of 'IVa) | 1 |
| CL i.v. (ml/min/kg) | 77.9 ± 44.3 | — | 1.3 ± 0.2 |
| Vss i.v. (L/kg) | 1.8 ± 2.6 | — | 0.4 ± 0.09 |
| T½ i.v. (hr) | 1.2 ± 1 | 3.2 ± 0.2 | 4.3 ± 1.1 |
| T½ p.o. (hr) | | 2.7 ± 1 | 3.0 ± 0.3 |
| AUC0 tot ratio after IV administration* | | 0.54 | |
| AUCtot ratio after PO administration** | | 0.43 | |

Key for all three tables-2, 3 and 4:

$$*AUCtot\ ratio = \frac{Total\ AUC\ of\ parent\ after\ IV\ administration\ of\ Prodrug}{Total\ AUC\ of\ parent\ after\ IV\ administration\ of\ parent\ (historic\ data)}$$

$$**AUCtot\ ratio = \frac{Total\ AUC\ of\ parent\ after\ PO\ administration\ of\ Prodrug}{Total\ AUC\ of\ parent\ after\ PO\ administration\ of\ parent\ (historic\ data)}$$

A dose escalation study D of one of the prodrugs (Ica) was carried out in rats in order to demonstrate the significant advantages of prodrugs over the parent for potential use in the treatment of HIV-1 patients after oral dosing. The exposure data and measured parameters from the prodrug dose escalation study were compared to similar data from historical studies conducted with parent molecules.

Figure 3:
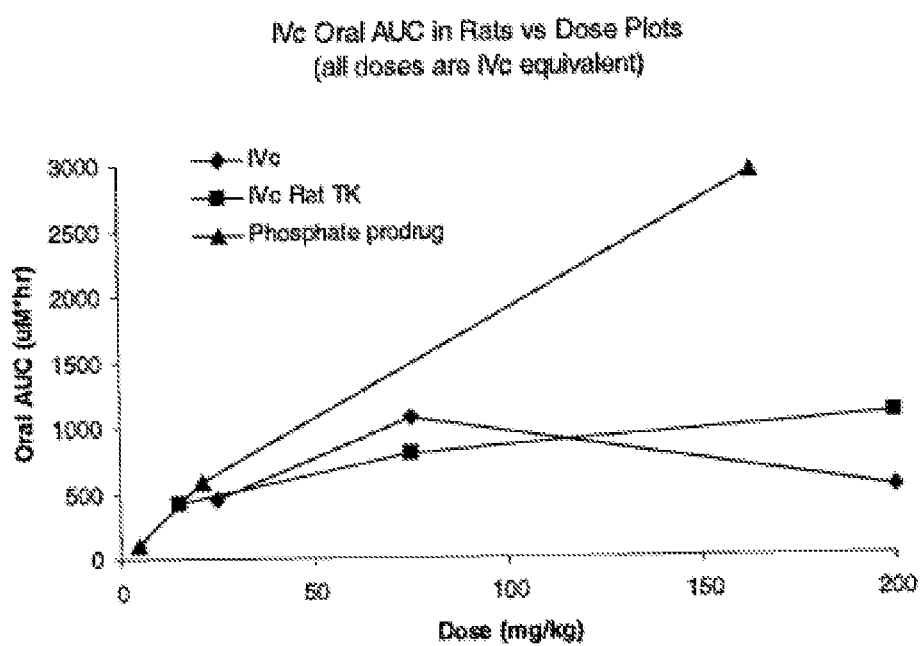
FIG. 3 illustrates IVc Oral AUC in Rats versus Dose Plots.
Figure 4:
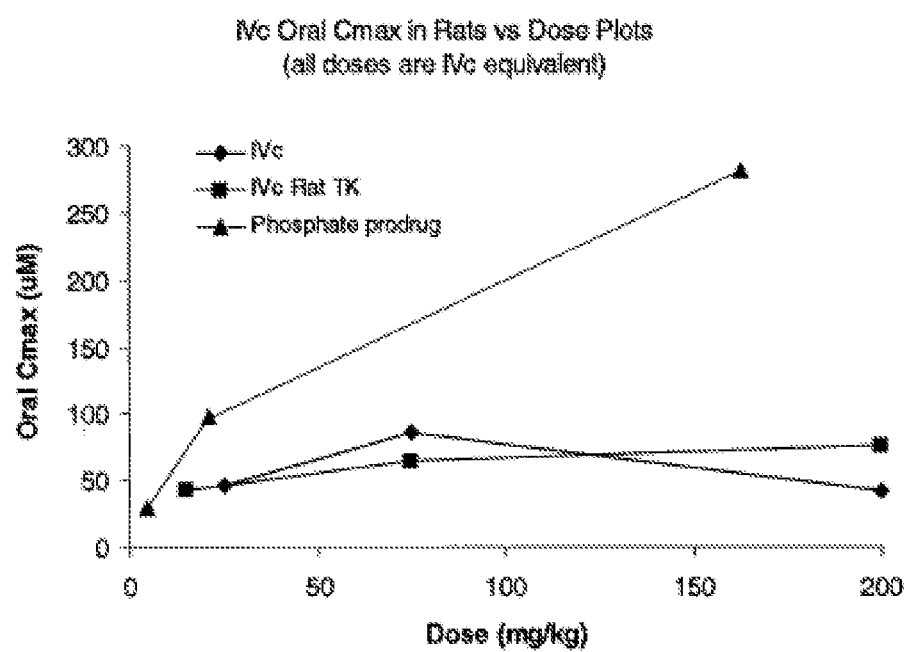
FIG. 4 illustrates IVc Oral Cmax in Rats versus Dose Plots.

FIGS. 3 and 4 compare the AUC (the area under the curve, a measure of exposure to drug in the rat) of IVc from oral dosing of prodrug Ica (study D) to that obtained from dosing parent molecule IVc (Study E) and a rat toxicokinetic study (TK). Details for the historical IVc dose escalation (Study E) and the rat TK study (F) are shown in these figures.

As can be seen from FIGS. 3 and 4, the AUC and Cmax of parent molecule after oral administration of the prodrug (triangles) is greater than that which resulted from administration of the parent drug in two separate studies. Clearly, the data shows that in order to maximize exposure multiples of drug in plasma, the prodrug offers a surprising advantage. Since the chemical structures of this class of molecules are similar, prodrugs of the class are expected to show enhancement in exposure from administration of prodrugs rather than parent. Given the uncertainty of improving oral exposure with phosphate prodrugs and the novelty of the new compounds, this result was not obvious and is surprising in its magnitude.

TABLE 5

Rat TK Study; Study F;
Historical Study of PO IVc in Rats at Three Doses

| | Compound IVc (Historical Data) | | |
|---|---|---|---|
| Dose (mg/kg) | 15 (soln) | 75 (susp) | 200 (susp) |
| Vehicle | 80/10/10 PEG-400/Ethanol/ 0.1N NaOH | | |

TABLE 5-continued

Rat TK Study; Study F;
Historical Study of PO IVc in Rats at Three Doses

| | Compound IVc (Historical Data) | | |
|---|---|---|---|
| Dose (mg/kg) | 15 (soln) | 75 (susp) | 200 (susp) |
| Mean Cmax (μM) | 42 | 65 | 76 |
| Mean AUC0-24 hr (μM*hr) | 418 | 792 | 1077 |
| Dose Ratio | | 1:5:13 | |
| Cmax Ratio | | | 1:1.5:1.8 |
| AUC Ratio | | | 1:1.9:2.6 |

IV and Oral Rat PK Study Protocol of Phosphate Prodrugs Studies A, B, and C

Compounds Ic (phosphate prodrug of IVc), Ib (phosphate prodrug of IVb), and Ia (phosphate prodrug of IVa) were administered separately to groups of three male Sprague-Dawley rats by IV bolus (1 mg/kg; all doses listed in this document were parent compound equivalent) or oral gavage (5 mg/kg). The rats for oral dosing studies were fasted overnight. Compound Ic was administered as a free acid, whereas the other two were as sodium salts. The dosing solutions of all three prodrugs for both IV and oral administration were prepared in 100% normal saline at 1 mg/mL (dosing solution concentrations were parent compound equivalent). Plasma samples were collected in EDTA vacutainers over 24 hrs, and analyzed by LC/MS/MS for both the prodrugs and parent molecules. Pharmacokinetic analysis was performed on Kinetica™.

Procedures for LC/MS/MS analysis are shown in the protocols below.

The results of this study are shown in Tables 2-4, middle two columns.

Oral Dose Escalation Study Protocol of Ica in Rats (Study D)

Groups of three fasted male Sprague-Dawley rats were orally administered compound Ica (disodium salt) at 4.5, 21, and 163 mg/kg (doses were IVc equivalent). The dosing solutions were prepared in water at 1, 5, and 20 mg (compound Ic (free acid) equivalent)/mL for the doses of 4.5, 21, and 163 mg (compound IVc equivalent)/kg, respectively. Plasma samples were collected in EDTA vacutainers over 24 hrs, and analyzed by LC/MS/MS for both Ic and IVc. Pharmacokinetic analysis was performed on Kinetica™.

Figure 5:
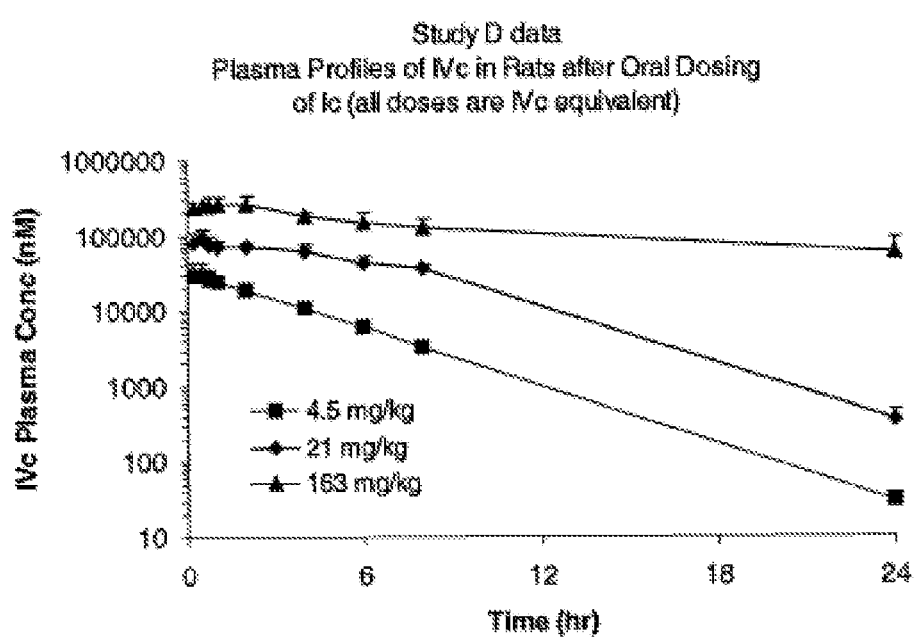
FIG. 5 illustrates Plasma Profiles of IVc in Rats After Oral Dosing of Ic.

The results of this study are shown in Table 46 and FIGS. 3-5.

TABLE 46

Oral Rat Dose Escalation Study

| | Dosing of Ica | | | | | |
|---|---|---|---|---|---|---|
| | IVc after phosphate prodrug Ica (Na salt) (all doses are IVc equivalent) (n = 3) | | | IVc (n = 2) Historical Data | | |
| Dose (mg/kg) | 5 (soln) | 25 (soln) | 200 (soln) | 25 (soln) | 75 (susp) | 200 (susp) |
| Vehicle | Water | | | 80/10/10 PEG-400/Ethanol/ 0.1N NaOH | | |
| Particle size (μM) | Soln | Soln | Soln | Soln | 27 | 31 |
| Mean Cmax (μM) | 29 ± 14 | 98 ± 21 | 281 ± 55 | 46 | 86 | 42 |
| C-24 hr (μM) | 0.029 ± 0.008 | 0.35 ± 0.13 | 58 ± 36 | 0.61 | 5.2 | 10 (n =1) |
| Mean AUCtot (μM*hr) | 109 ± 15 | 586 ± 53 | 2925 ± 304 * | 458 | 1071 | 518 * |
| Mean Tmax (hr) | 0.50 ± 0.25 | 1.7 ± 2.0 | 1.1 ± 0.80 | 4.0 | 5.0 | 4.0 |
| Mean T1/2 (hr) | 2.3 ± 0.07 | 2.5 ± 0.15 | 13 ± 7.5 | 3.4 | 6.8 | 20 |
| Dose Ratio | | 1:5:40 | | | 1:3:8 | |
| Avg. Cmax Ratio | | 1:3.4:9.7 | | | 1:1.9:0.91 | |
| Avg. AUC Ratio | | 1:5.4:27 | | | 1:2.6:1.1* | |

1. * The AUC was from 0-24 hr since the AUC (24 hr-infinity) was at least greater than 35% of the total AUC (0-infinity). This portion was too great to have an accurate measure of the total AUC.
2. The AUC conversion ratio at 5 mg/kg of IVc from Ica, calculated as the ratio of IVc AUC after Ica dosing divided by IVc AUC after direct dosing of IVc, was 0.99.
3. The prodrug Ica was only detected at ~20-40 nM in one to two samples in each rat in the 200 mg/kg dose group.

In Vivo Methods
Procedure for Study A: PO and IV Administration of IVa to Rats; PO Dose was 5 mg/kg Compound IVa was administered in a polyethylene glycol 400 (PEG400)/ethanol (EtOH) solution (90/10, v/v) unless noted otherwise. Plasma and tissue samples were collected and stored at −20° C. until analysis. Male Sprague-Dawley rats (300-350 g, Hilltop Lab Animals, Inc., Scottdale, Pa. 15683) with cannulas implanted in the jugular vein and/or bile duct were used in the pharmacokinetic studies of compound IVa. Rats were fasted overnight in PO studies. Blood samples (0.3 mL) were collected from the jugular vein in EDTA-containing
microtainer tubes (Becton Dickinson, Franklin Lakes, N.J. 07147) to obtain plasma. In the IV studies, a dose of 1 mg/kg was administered to 3 rats over 0.5 min, and serial plasma samples were collected before dosing and 2, 10, 15, 30, 45, 60, 120, 240, 360, 480, and 1440 min after dosing. In the PO studies, rats (n=3) received PO doses of 5 and 100 mg/kg. Serial plasma samples were taken before dosing and 15, 30, 45, 60, 120, 240, 360, 480, and 1440 min after dosing.

The oral (PO) results of this study are shown in the last right most column of Table 2.

Parent Drug Study B1

For the IV and PO pharmacokinetic studies of COMPOUND IVb in rats, COMPOUND IVb was dissolved in PEG-400/ethanol (90/10) as a solution. For the IV and PO pharmacokinetic studies of COMPOUND IVB in dogs, COMPOUND IVb was dissolved in PEG-400/ethanol (90/10) with pH adjustment with 0.1 N NaOH. Details of the formulations are provided in Table 6.

Rat. Male Sprague-Dawley rats (300-350 g, Hilltop Lab Animals, Inc., Scottdale, Pa.) with cannulas implanted in the jugular vein and/or bile duct were used. The rats were fasted overnight in the PO pharmacokinetic studies. Blood samples of 0.3 ml were collected from the jugular vein in EDTA-containing microtainer tubes (Becton Dickinson, Franklin Lakes, N.J.), and centrifuged to separate plasma.

In the IV study, COMPOUND IVb was delivered at 1 mg/kg as a bolus over 0.5 min (n=3). Serial blood samples were collected before dosing and 2, 10, 15, 30, 45, 60, 120, 240, 360, 480, and 1440 min after dosing.

In the PO study of COMPOUND IVb, the rats (n=3) received an oral dose of 5 mg/kg of COMPOUND IVB. Serial blood samples were collected before dosing and 15, 30, 45, 60, 120, 240, 360, 480, and 1440 min after dosing.

The results of this oral (PO) study are shown in Table 3, right most column.

TABLE 6

Formulations of IVb for in vivo Studies

| Compound IVb Studies | Form | Vehicle | Conc. (mg/ml) | Particle Size |
|---|---|---|---|---|
| Rat PK (Study B1) | amorphous | 90:10, PEG400/EtOH adj. to pH 8.6-9.0 | 3 | NA (soln) |

Bioanalytical Methods for In Vivo Studies Analyzing for IVb

This refers to method for analyzing for concentration levels of IVb in rat plasma samples (used for studies B and B1).

Quantitation of COMPOUND IVb by LC/MS/MS in Plasma. Aliquots of plasma samples from rat, dog, monkey or chimpanzee studies were prepared for analysis by precipitating plasma proteins with two volumes of acetonitrile containing the internal standard, COMPOUND IVa. The resulting supernates were separated from the precipitated proteins by centrifugation for 10 minutes and transferred to autosampler vials. Samples were either prepared manually, or with the use of the Tomtec automated liquid handler. An aliquot of 5 μL was injected for analysis.

The HPLC system consisted of two Shimadzu LC10AD pumps (Columbia, Md.), a Shimadzu SIL-HTC autosampler (Columbia, Md.), and a Hewlett Packard Series 1100 column compartment (Palo Alto, Calif.). The column was a YMC Pro C18 (2.0×50 mm, 3 m particles, Waters Co., Milford, Mass.), maintained at 60° C. and a flow rate of 0.3 ml/min. The mobile phase consisted of 10 mM ammonium formate and 0.1% formic acid in water (A) and 100% 10 mM ammonium formate and 0.1% formic acid in methanol (B). The initial mobile phase composition was 95% A. After sample injection, the mobile phase was changed to 15% A/85% B over 2 minutes and held at that composition for an additional 1 minute. The mobile phase was then returned to initial conditions and the column re-equilibrated for 1 minute. Total analysis time was 4 minutes.

The HPLC was interfaced to a Micromass Quattro LC. Ultra high purity nitrogen was used as the nebulizing and desolvation gas at flow rates of 100 L/hr for nebulization and 1100 L/hr for desolvation. The desolvation temperature was 300° C. and the source temperature was 150° C. Data acquisition utilized selected reaction monitoring (SRM). Ions representing the $(M+H)^+$ species for IVb and the internal standard were selected in MS1 and collisionally dissociated with argon at a pressure of $2 \times 10^{-3}$ torr to form specific product ions which were subsequently monitored by MS2. The transitions, voltages and retention times are summarized in Table 7.

TABLE 7

Parameters for MS/MS Analysis of COMPOUND IVB and COMPOUND IVa (IS)

| | COMPOUND IVB | COMPOUND IVa |
|---|---|---|
| SRM transition | mz 448 > 105 | 423 > 205 |
| Cone Voltage (V) | 22 | 30 |
| Collision Energy (V) | 16 | 30 |
| Retention time (minutes) | 2.6 | 2.4 |

The plasma standard curve ranged from 4 to 8000 ng/ml, the brain curve from 1-1000 ng/ml. The curves were fitted with a quadratic regression weighted by reciprocal concentration (1/x). Standards were analyzed in duplicate. Quality control (QC) samples, prepared in blank plasma, at three concentrations within the range of the calibration curve were also analyzed in triplicate with each plasma analytical set. For this compound, the predicted concentrations of 90% of the plasma QCs were within 20% of nominal concentration, indicating acceptable assay performance.

Vehicles and Formulations. Referring to Table 8, when the vehicle used contains NaOH, Compound IVc solution formulations were pH adjusted using NaOH to obtain a pH of 8.6-9.0, where the compound is partially ionized, based on it's pKa at 8.4.

TABLE 8

Formulations of Compound IVc for In Vivo Studies

| Compound IVc Studies | Form-Lot | State | Vehicle | Conc. (mg/ml) | Particle Size |
|---|---|---|---|---|---|
| Rat PK (Study C1) | 02-001 02-003 | unknown | 90:10, PEG400/EtOH adj. to pH 8.6-9.0 | 3 | NA |
| Pre-Tox Escalating Dose (Study E) | 02-004 | crystalline | 80:10:10 PEG400/EtOH/0.1N NaOH | 2.5 7.5 20 | NA mean = 27.22 µm (95% <84.4 µm) Multi-Modal Distribution, 3 peaks Overall mean = 31.07 µm (95% < 157.7 µm) |
| Pre-ECN Rat Tox (Rat TK) (Study F) | 02-005 | unknown | 80:10:10 PEG400/EtOH/0.1N NaOH | 3 15 40 | NA Multi-Modal Distribution, 2 peaks Overall mean = 19.251.1 m(95% < 52.3 µm) Multi-Modal Distribution, 2 peaks Overall mean = 21.78 µm (95% <57.5 µm) |

Quantitation of Compound IVc by LC/MS/MS in Plasma (Used in Studies C, Cl and D).

Aliquots of plasma samples from rat, dog, monkey and chimpanzee studies were prepared for analysis by precipitating plasma proteins with two volumes of acetonitrile containing the internal standard, compound IVa. The resulting supernates were separated from the precipitated proteins by centrifugation for 10 minutes and transferred to autosampler vials. Samples were either prepared manually, or with the use of the Tomtec automated liquid handler. The HPLC system consisted of two Shimadzu LC10AD pumps (Columbia, Md.), a Shimadzu SIL-HTC autosampler Columbia, Md.), and a Hewlett Packard Series 1100 column compartment (Palo Alto, Calif.). The column was a YMC Pro C18 (2.0×50 mm, 3 m particles, Waters Co., Milford, Mass.), maintained at 60° C. and a flow rate of 0.3 ml/min. The mobile phase consisted of 10 mM ammonium formate and 0.1% formic acid in water (A) and 100% 10 mM ammonium formate and 0.1% formic acid in methanol (B). The initial mobile phase composition was 95% A. After sample injection, the mobile phase was changed to 15% A/85% B over 2 minutes and held at that composition for an additional 1 minute. The mobile phase was then returned to initial conditions and the column re-equilibrated for 1 minute. Total analysis time was 4 minutes.

The HPLC was interfaced to a Micromass Quattro LC. Ultra high purity nitrogen was used as the nebulizing and desolvation gas at flow rates of 100 L/h for nebulization and 1100 L/h for desolvation. The desolvation temperature was 300° C. and the source temperature was 150° C. Data acquisition utilized selected reaction monitoring (SRM). Ions representing the (M+H)$^+$ species for IVc and the internal standard were selected in MS1 and collisionally dissociated with argon at a pressure of $2 \times 10^{-3}$ torr to form specific product ions which were subsequently monitored by MS2. The transitions, voltages and retention times are summarized in Table 9.

TABLE 9

Parameters for MS/MS Analysis of IVc and IVa (IS)

|  | IVc | IVa |
|---|---|---|
| SRM transition | mz 474 > 256 | m/z 423 > 205 |
| Cone Voltage (V) | 22 | 30 |
| Collision Energy (V) | 22 | 30 |
| Retention time (minutes) | 2.5 | 2.4 |

The plasma standard curve ranged from 4 to 8000 ng/ml, the brain curve from 1-1000 ng/ml. The curves were fitted with a quadratic regression weighted by reciprocal concentration (1/x). Standards were analyzed in duplicate. Quality control (QC) samples, prepared in blank plasma, at three concentrations within the range of the calibration curve were also analyzed in triplicate with each plasma analytical set. For this compound, the predicted concentrations of 90% of the plasma QCs were within 20% of nominal concentration, indicating acceptable assay performance.

Quantitation of Three Pro-Drugs and their Parent Compounds by LC/MS/MS in Biological Matrices This LC/MS/MS assay was developed to investigate three pro-drug compounds and their respective parent molecules in biological matrices. The three pro-drug compounds were: Compounds Ia, Ic, and Ib and their other respectives salts or free acids. Note this assay is used for the free acid and salt forms of the three prodrugs as molecular ion detected is independent of salt counterion. Their respective parent compounds were: IVa, IVc, and IVb.

The HPLC system consisted of Shimadzu LC10ADvp pumps (Columbia, Md.) and HTC PAL autosampler (Leap Technologies, Cary, N.C.) linked to a Synergi Hydro-RP analytical column (2.0×50 mm, Phenomenex, Torrance, Calif.). Mobile phase A consisted of 0.1% Formic Acid in water; mobile phase B was 0.1% formic acid in acetonitrile. LC flow rate was 0.4 mL/min into the mass spectrometer. The initial mobile phase composition was 10% B ramped to 75% B over 1.75 min, held at that composition for 0.25 min, ramped to 100% B over 0.1 min, held for 0.6 min, returned to initial conditions over the next 0.1 minute and then re-equilibrated. Total analysis time was 4 min. Retention times for all analytes ranged between 1.5 and 2.6 min.

The HPLC was interfaced to a Sciex API3000 triple quadrupole mass spectrometer (Toronto, Canada)

equipped with the Turboionspray source set at 450° C. and ionspray voltage set to 4.5 kV. UHP nitrogen was used as nebulizer and auxiliary gases with pressures of 80 psi and 7 L/min, respectively. The analysis was performed in positive ion mode. The transitions monitored for all compounds and their collision energies (CE) were: m/z 533.41>435.24 for Ia (CE=19); m/z 584.46>486.29 for Ic (CE=23); m/z 558.31>432.13 for Ib (CE=19); 423.39>204.96 for IVa (CE=31); 474.36>255.97 for IVc (CE=29); 448.35>105.20 for IVb (CE=35).

To accommodate a wide variety of biological sample matrices, acetonitrile precipitation was used in sample preparation. Test samples and standards were transferred to a 96 well plate using the Packard Multiprobe II (Packard Instruments, Downers Grove, Ill.). 200 μL of acetonitrile containing the internal standard (BMS-647257, 500 nM) was added to 100 μL aliquots of both test samples and standards in the 96 well plate using the Tomtec Quadra 96. The plate was then vortexed for approximately 3 minutes and centrifuged at 3000 rpm for 15 minutes. Using the Tomtec Quadra 96, 150 μL of supernatant was transferred from the plate to a clean 96 deep well plate. 150 μL of 0.2% formic acid in water was then added to each well using the Tomtec Quadra 96 and the plate was vortexed before analysis.

Standard curves at eight concentration points from 5 nM to 10 μM were prepared from stock solutions in acetonitrile and serially diluted in matrix for both pro-drug and parent compounds. Standard curves were transferred in duplicate 100 uL aliquots to a 96 well plate containing the test samples, extracted with the test samples as described above, and injected at the beginning, middle, and end of the analytical sequence. The standard curves were fitted with a linear regression weighted $1/x^2$. Data and chromatographic peaks were processed and concentrations of standards and unknowns were quantitated using PEBiosystems Analyst™ 1.1.

In Vivo Methods
Conditions for Study C1, E and F (Rat PK. MAP and TK Studies)

For the IV and PO pharmacokinetic studies of compound IVc in rats, compound IVc was dissolved in PEG-400/ethanol (90/10) as a solution. Please refer to Table 8.

Rat. Male Sprague-Dawley rats (300-350 g, Hilltop Lab Animals, Inc., Scottdale, Pa.) with cannulas implanted in the jugular vein and/or bile duct were used. The rats were fasted overnight in the PO pharmacokinetic studies. Blood samples of 0.3 ml were collected from the jugular vein in EDTA-containing microtainer tubes (Becton Dickinson, Franklin Lakes, N.J.), and centrifuged to separate plasma.

In an IV study, compound IVc was delivered at 1 mg/kg as a bolus over 0.5 min (n=3). Serial blood samples were collected before dosing and 2, 10, 15, 30, 45, 60, 120, 240, 360, 480, and 1440 min after dosing.

PO Single Dose Study C1

In the PO study C1 of Compound IVc, the rats (n=3) received an oral dose of 5 mg/kg of Compound IVc. Serial blood samples were collected before dosing and 15, 30, 45, 60, 120, 240, 360, 480, and 1440 min after dosing. The oral (PO) results from Study C1 are in Table 4, right most column.

Oral (PO) Dose Escalation Study E

In the oral dose escalation study E of Compound IVc, groups of rats (n=2 per group) received oral doses of 25, 75, and 200 mg/kg. At 25 mg/kg, the dosing solution was in solution; at the higher doses, the dosing solutions were suspensions. Serial blood samples were collected before dosing and 15, 30, 45, 60, 120, 240, 360, 480, and 1440 min after dosing. Brain samples were collected at 1440 min to assess brain penetration. The brain samples were blotted dry and the wet weights were recorded. The oral (PO) results from Study E are in Table 46.

2-Week Oral Dose Rat Toxicology Study F

In the 2-week oral rat study F (n=six/sex/group), Compound IVc was administered at daily doses of 15, 75, or 200 mg/kg. Toxicokinetic evaluations on days 1 and 14 indicated that systemic exposures ($AUC_{0-24}$ h) of Compound IVc were generally dose related but were not dose proportional (see Table 5), with no evidence of autoinduction or accumulation. On Day 14, $AUC_{0-24h}$ values were slightly higher in females (≤644 μg*hr/ml) compared to males (≤526.88 μg*hr/ml) at dosages 200 mg/kg/day. The oral (PO) results from Study F are in Table 5.

Map Study G: PO and IV Dosing Study of Diester IIa in Rats Structure of Compound IIa

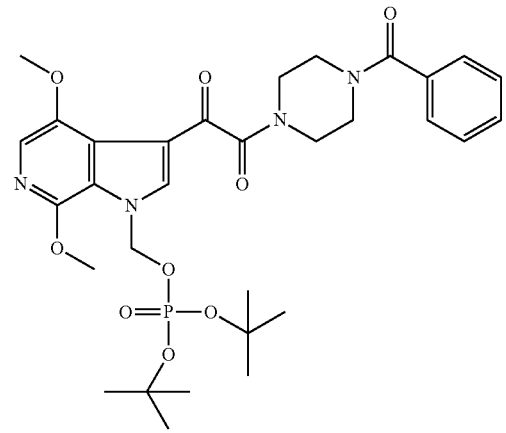 [SMILES: COc1cnc(OC)c2c1c(C(=O)C(=O)N1CCN(C(=O)c3ccccc3)CC1)cn2COP(=O)(OC(C)(C)C)OC(C)(C)C]

The procedure for the oral dosing leg of MAP study A1 was followed except that diester IIa was utilized in place of Compound IVa. Analysis for compound IVa showed that dosing of the diester IIa by oral route produced substantial IVa. The data is described in Table 10 below:

TABLE 10

| for Map Study G | |
|---|---|
| Dose and Route: | Data measured for IVa following PO dosing of |
| PO 5 mg/kg | diester IIa (di-tert butyl ester prodrug of IVa) |
| Cmax p.o. (nM) | 1123 ± 270 |
| | (IVa conc) |
| Tmax p.o. (hr) | 2.7 ± 1.2 (IVa) |
| F (%) | 33 (IVa) |
| AUC p.o. (μM*hr) | 4.0 ± 1.0 (IVa) |
| Cp @ 24 hr p.o. (nM) | Not detected |
| T½ p.o. (hr) | 1.3 ± 0.26 (IVa) |

Map Study H: PO and IV Dosing Study of
Monoester II'a in Rats Structure of Compound II'a

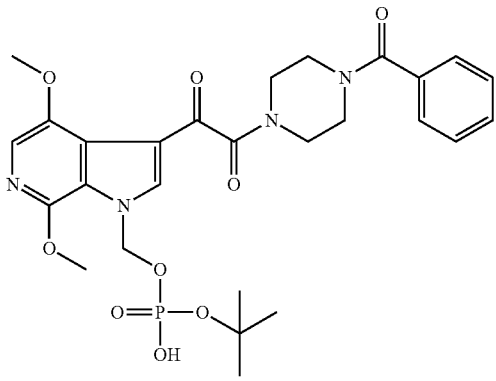 [SMILES: COc1cnc(OC)c2c1c(C(=O)C(=O)N1CCN(C(=O)c3ccccc3)CC1)cn2COP(=O)(O)OC(C)(C)C]

The procedure for the oral dosing leg of MAP study A1 was followed except that monoester II'a was utilized in place of Compound IVa. Analysis for compound IVa showed that dosing of the monoester II'a by oral route produced substantial IVa. The data is described in the table below:

TABLE 11 for Map Study H

| Dose and Route: PO 5 mg/kg | Data measured for IVa following PO dosing of monester II'a (mono-tert butyl ester prodrug of IVa) |
|---|---|
| Cmax p.o. (nM) | 1586 ± 615 (IVa conc) |
| Tmax p.o. (hr) | 2.0 ± 1.7 (IVa) |
| F (%) | 44 (of IVa) |
| AUC p.o. (µM*hr) | 5.9 ± 2.2 (IVa) |
| Cp @ 24 hr p.o. (nM) | 3.61 (n = 2/3) |
| T½ p.o. (hr) | 2.8 ± 1.6 (IVa) |

A significant number of studies were done to demonstrate and characterize the surprising utility of the prodrugs I. Dose escalation exposure experiments comparing exposure of parent molecules after dosing prodrug and parent were carried out in rats and dogs for prodrugs I of parent molecules IVa, IVb, and IVc. The effect of food and dose on exposure of IVa after dosing prodrug Iab or parent IVa was compared in dogs. The prodrug showed suprising ability to improve exposure and avoid effects of feed as compared to parent. Low dosage full pharmacokinetic studies (oral and IV dosing) were carried out in rats dogs and monkeys for prodrugs Iab, Ibb, and Icb to show conversion to parent compounds IVa, IVb, and IVc respectively. Oral dosing studies in rats were carried out for prodrug Ie (free acid), and for parent compound IVf to demonstrate conversion and systemic exposure of parents IVe and IVf respectively. Data is shown above or below in this application.

Additional Profiling Section 1

Additional Studies with Iab:

Iac is the free acid phosphate prodrug of the N-hydroxymethyl adduct of IVa and is hydrolyzed by alkaline phosphatase (ALP) to form IVa. Iab, a mono-lysine salt of Iac, was used for all of the following studies.

IV and PO pharmacokinetic studies of Iab were conducted in rats, dogs and monkeys. In all cases, blood samples were collected in the presence of EDTA. The presence of EDTA, a known ALP inhibitor, minimized significant ex vivo conversion of Iab during sample processing. IVa was rapidly formed following IV administration of Iab. Good oral bioavailabilities (62-94%) of IVa were observed after administration of Iab in rats, dogs and monkeys with very little or no Iab present in plasma. Since there are high levels of ALP expression in the gut, it is likely that following oral administration of Iab, Iab is hydrolyzed by ALP present at the brush border membranes of the intestinal lumen to form IVa, which is rapidly absorbed due to its high permeability.

In vitro incubation studies were conducted for a qualitative assessment of ALP-dependent hydrolysis of Iab in different tissues. Iab was hydrolyzed in the presence of serum and hepatocytes from rat, dog, monkey and human, as well as human placental ALP. On the occasions where Iab and IVa were measured, the conversion of Iab to IVa was near stoichiometric. Due to hydrolysis in serum, the protein binding of Iab could not be determined. Based on the in vitro data, it is anticipated that Iab will be hydrolyzed by human ALP and that IVa will be formed after oral administration of Iab to human subjects.

The crystalline solubility of Iab at room temperature increases from 0.22 mg/ml at pH 1.4 to >12 mg/ml at pH 5.4 and pH 8.9; aqueous solutions containing >100 mg/mL have been prepared for in vivo toxicology studies. In comparison, the aqueous solubility of the parent compound, IVa, at room temperature as crystalline material was determined to be 0.04-0.9 mg/mL (pH range of 1.5-10). Iab exhibits acceptable solution and solid stabilities.

The higher aqueous solubility of Iab provides a means to overcome the dissolution-rate limited absorption of IVa below certain doses and thereby increased the exposures of IVa in oral dose escalation and toxicokinetic studies. Iab, when dosed orally at ~200 mg/kg of IVa equivalent, provided 2-fold higher AUC of IVa in rats and dogs, without significant plasma exposure to the prodrug, as compared to the AUC from the historical IVa suspension studies at the similar dose. Moreover, the AUC and Cmax values of IVa in fasted dogs receiving Iab dry-filled capsules (200 mg/dog of IVa equivalent) were 38 and 58 times, respectively, those attained in fasted dogs given the IVa clinical capsule formulation, and 4 and 6 times, respectively, those attained in fed dogs given the IVa clinical capsule formulation.

No significant differences in AUC and Cmax of IVa were observed between fasted and fed dogs receiving Iab, whereas a 9-fold improvement was observed in fed dogs as compared to fasted dogs receiving IVa. These data suggest that efficacious blood levels of IVa may be achieved in HIV-infected patients without the requirement for a high fat meal. The spray dried form of IVa gave rise to similar exposure levels of IVa as that observed from Iab in dogs.

Single-Dose Toxicokinetic Tolerability Study in CD Rats

A 1-day oral toxicokinetic study in rats was conducted using the prodrug Iab (monolysine salt). Iab was administered at dosages of 16, 72, and 267 mg/kg (free acid) by oral gavage to three male rats/group using water as the vehicle (solution formulation). The dosages of prodrug free acid correspond to IVa (parent) molar equivalent dosages of 13, 57, and 211 mg/kg, respectively. The endpoint evaluated was plasma toxicokinetics of Iab and IVa in the individual rats.

The mean toxicokinetic values are provided in Table 12.

TABLE 12

Mean toxicokinetic values for Iab and IVa in male rats given ≤267 mg/kg of Iab as a single oral dose

| | Dosages (mg/kg) Iab | | | | | |
|---|---|---|---|---|---|---|
| | 16 | | 72 | | 267 | |
| | IVa molar equiv. | | | | | |
| | 13 | | 57 | | 211 | |
| | Iab | IVa | Iab | IVa | Iab | IVa |
| $C_{max}$ (µM) | 0.068 | 26 | 0.095 | 104 | 0.11 | 214 |
| $C_{24h}$ (µM) | <LLQ[1] | 0.090 | <LLQ | 0.027 | <LLQ | 1.9 |
| AUC (µM · h) | 0.020[2] | 67[3] | 0.049[2] | 261[3] | 0.057[2] | 1161[3] |
| T1/2 (h) | 0.64 | 3.2 | 0.37 | 2.3 | 0.045 | 3.4 |

Values represent means from 1-3 rats/group for Iab data and 3 rats/group for IVa data.
[1]Below the lower limit of quantification.
[2]AUC from zero to time of last quantifiable sample
[3]AUC from zero to ∞

Figure 6A:
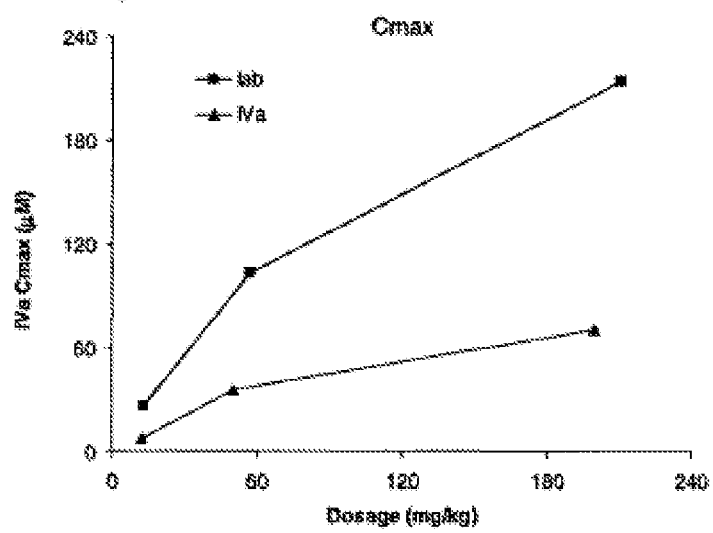
FIGS. 6A and 6B illustrates Comparison of IVa Cmax and AUC in Male Rats Given Either IVa or Iab.
Figure 6B:
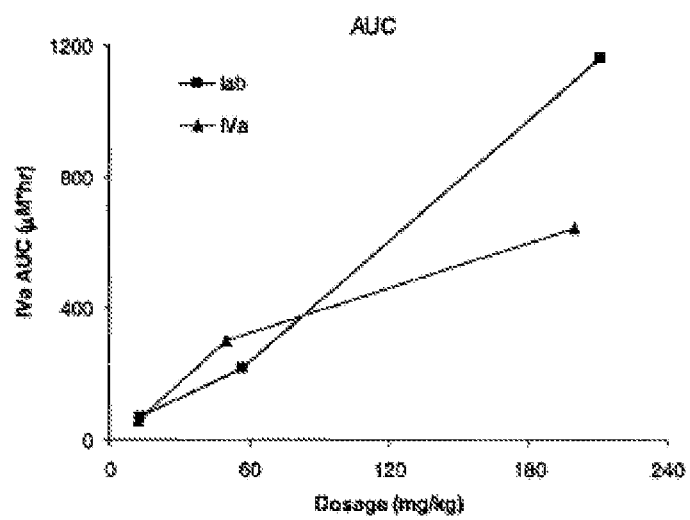

Mean maximum plasma concentration ($C_{max}$) of both Iab (prodrug) and IVa (parent) was achieved within 1.1 hour post-dose. The plasma area under the plasma concentration-time curve (AUC) of the prodrug was ≤0.03% that of the parent. (In rats given ≤267 mg/kg of Iab, the AUC of IVa increased proportionally with Iab dosage, and $C_{max}$ increased in a less than dosage-proportional manner between 72 and 267 mg/kg of Iab. A comparison of IVa AUC obtained in rats given either IVa (2) or Iab, is shown in FIGS. 6A and 6B.

Solubility in preclinical formulations has been an issue. The AUC of IVa is equivalent for both parent and prodrug at lower dosages (e.g., 550 mg/kg) because both were formulated as solutions (PEG-400 for parent and water for prodrug) but at a high dosage (e.g., 200 mg/kg) the neutral parent was formulated as a suspension whereas the prodrug salt was formulated as an aqueous solution.

A 2-week rat toxicity study using dosages of 5, 50, or 500 mg/kg BID to support the IND is ongoing (3). The in-life phase of the study has been completed, and there were no noteworthy in-life observations.

Single-Dose Toxicokinetic and Tolerability Study in Dogs

A multi-phase study was conducted to evaluate the tolerability of the prodrug, Iab (monolysine salt) at dosages of 24, 90, or 240 mg/kg (free acid, molar equivalent to 19, 71, or 190 mg/kg of parent IVa, respectively) and the toxicokinetics of Iab and IVa (4). Iab was administered to two female dogs/group once daily either as an aqueous solution (24 or 90 mg/kg) or dry-filled capsules (24, 90 [once and twice daily] or 240 mg/kg). The endpoints were: clinical signs, body weight, food consumption, and plasma toxicokinetics of Iab and IVa. In all cases, a 1-week washout period was used between doses for all phases of the study.

The plasma toxicokinetic values from the initial phase of the study are shown in Table 13.

TABLE 13

Toxicokinetic values for IVa in female dogs given ≤90 mg/kg of Iab as a single oral dose

| | Dosages (mg/kg) Ibb | | | | | |
|---|---|---|---|---|---|---|
| | 24 | | 90 | | 24 | |
| | IVa molar equiv. | | | | | |
| | 19 | | 71 | | 19 | |
| | Formulation | | | | | |
| | Solution | | Solution | | Dry-filled capsule | |
| | Dog #1201 | Dog #1202 | Dog #3201 | Dog #3202 | Dog #4201 | Dog #4202 |
| $C_{max}$ (µM) | 72.3 | 66.5 | 124 | 125 | 79.7 | 85.6 |
| $C_{24h}$ (µM) | 0.61 | 0.33 | 3.2 | 2.2 | 1.4 | 0.87 |
| $AUC_{0-\infty}$ (µM · h) | 465 | 330 | 844 | 838 | 486 | 514 |
| T1/2 (h) | 3.2 | 3.1 | 4.4 | 3.9 | 4.2 | 3.4 |

Iab was not detected in the plasma samples. Mean maximum plasma concentration ($C_{max}$) of IVa was achieved between 1-2 hours post-dose. When Iab was given as a solution, both the $C_{max}$ and AUC increased in less than dosage proportional manner between 24 and 90 mg/kg. Emesis was observed at about 30 minutes after dosing in both dogs given 90 mg/kg. The $C_{max}$ and AUC of IVa were equivalent following Iab administration at 24 mg/kg using either dry-filled capsules or an aqueous solution.

Other than emesis, there were no clinical signs observed, and there no effects on body weight and food consumption.

To determine whether emesis could be eliminated/reduced by administration of Iab as a dry-filled capsules, the next phase of the study was conducted using dosages of 90 or 240 mg/kg, and 90 mg/kg given twice 4 h apart (BID). The toxicokinetic values are shown in Table 14.

TABLE 14

Toxicokinetic values for IVa in female dogs given ≤240 mg/kg of Iab as a single oral dose or with twice daily dosing (BID)

| | Dosages (mg/kg) Ibb | | | | | |
|---|---|---|---|---|---|---|
| | 90 | | 240 | | 180 (90 BID) | |
| | IVa molar equiv. | | | | | |
| | 71 | | 190 | | 142 (71 BID) | |
| | Formulation | | | | | |
| | Solution | | Solution | | Dry-filled capsule | |
| | Dog #1201 | Dog #1202 | Dog #2201 | Dog #2202 | Dog #3201 | Dog #3202 |
| $C_{max}$ (µM) | 214 | 152 | 172 | 189 | 311 | 248 |
| $C_{24h}$ (µM) | 4.6 | 0.89 | 2.8 | 6.6 | 34 | 50 |
| $AUC_{0-\infty}$ (µM · h) | 1740 | 960 | 1186 | 1584 | 3305[1] | 2485 |
| T1/2 (h) | 3.6 | 2.9 | 3.7 | 4.5 | 6.1 | 13 |

[1]AUC from zero to 24 h

There was no difference in $C_{max}$ or AUC between dogs given 90 or 240 mg/kg of Iab administered by dry-filled capsules. Emesis was observed in Dogs #1201, #2201, and #2202 about 1 hour after dosing. The vomit was collected and assayed for Iab content to estimate the amount of the total dose that was lost; the percentage of estimated total dose lost was <1% for #1201, ≈90% for #2201, ≈9% for #2202. Although the estimations of "dose lost" do not appear to be quantitatively consistent with the plasma AUC data, it does indicate that test article can be found in vomit within a short time after dosing. Iab was detected in plasma of the dogs, 0.005-0.049 µM at 1 hour post dose and 0.005-0.006 µM at 2 hours post dose; the prodrug was not detectable at later time points.

Figure 7A:
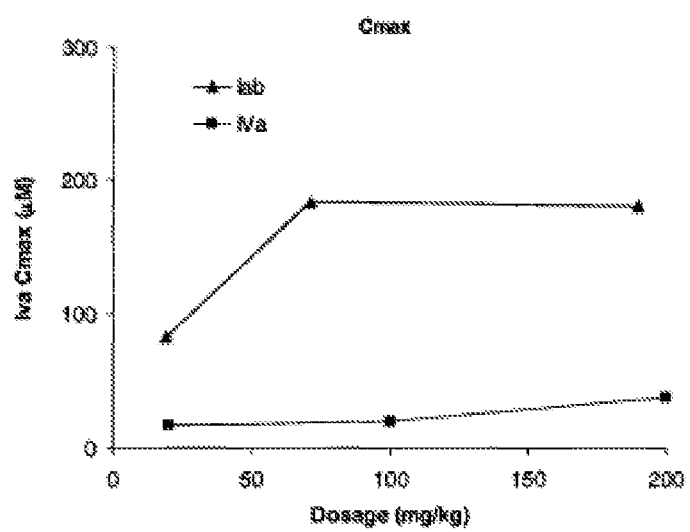
FIGS. 7A and 7B illustrates Comparison of IVa Cmax and AUC in Dogs Given Either IVa or Iab.
Figure 7B:
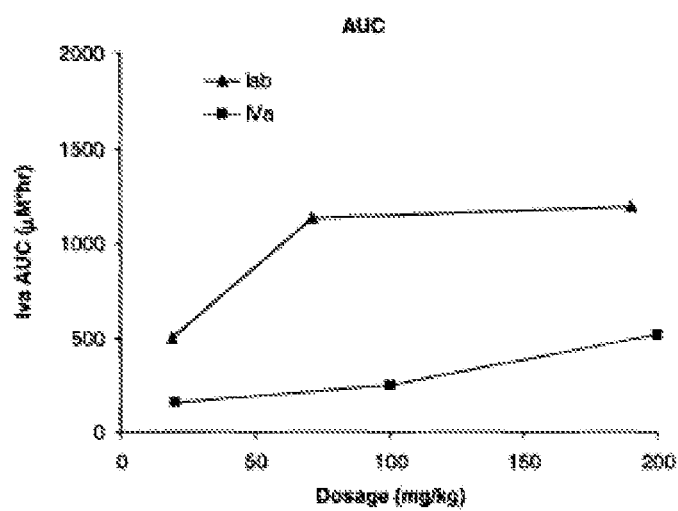

A comparison of IVa AUC obtained in dogs given either IVa (5, 6) or Iab, is shown in FIGS. 7A and 7B.

Vehicles and Formulations

Summary of Formulations Used for Key PK and Safety Studies

All in vivo PK studies in rats, dogs, and monkeys were performed using aqueous solutions for PO and IV dosing. Toxicology and exposure studies in dogs were performed with aqueous solutions at dosages of 24 and 90 mg/kg and drug in capsule formulations at dosages of 24, 90, and 240 mg/kg of Iab, mono-lysine salt.

In the rat oral dose escalation study, Iab was dosed as aqueous solutions at concentrations of 4.5, 20.0, and 73.5 mg/mL (mono-lysine salt form of prodrug). A significant improvement in AUC and Cmax for IVa, parent, after oral dosing of Iab, prodrug, were observed compared to the historical data of IVa oral dosing.

Drug in capsule formulations of Iab at doses of 20 mg/kg of IVa equivalent were used for food effect studies in dogs. The prodrug was compared to the clinical capsule formulation of the parent compound, IVa, at 20 mg/kg. When IVa clinical capsule was dosed, a 9-fold increase in exposure was seen in dogs fed a high fat meal compared to fasted dogs. Upon dosing of the prodrug, Iab, the exposure of IVa was significantly higher and as expected, the exposure was not significantly different between fasted and fed dogs.

Metabolism and Pharmacokinetics Summary

Summary of Findings and Interpretation

Iab is the phosphate prodrug of the N-hydroxymethyl adduct of IVa and is hydrolyzed by alkaline phosphatase (ALP) to form IVa. After administration of Iab to animals, therefore, plasma samples were prepared from blood collected in the presence of EDTA, a known ALP inhibitor. Conversion of Iab to IVa was minimal (<2%) in rat, monkey and human blood containing EDTA, and approximately 6% in dog blood containing EDTA. No significant ex vivo conversion of Iab is expected during sample storage (−20° C.) and analysis of Iab.

The hydrolysis of Iab was studied in animal and human in vitro systems. Since multiple ALP isoforms are widely distributed in various tissues, quantitative in vitro to in vivo correlations were not attempted (Fishman et al., 1968; Komoda et al., 1981; Moss, 1983; Yora and Sakagishi, 1986; Sumikawa et al., 1990). Therefore, the studies were limited to a qualitative assessment of ALP-dependent hydrolysis in different tissues. Iab was hydrolyzed in the presence of serum and hepatocytes from rat, dog, monkey and human, as well as in human placental ALP. On the occasions where Iab and IVa were measured, the conversion of Iab to IVa was near stoichiometric. Due to hydrolysis in serum, the protein binding of Iab could not be determined.

None or very low levels of Iab were detected in rat, dog and monkey plasma after oral administration of Iab. IVa was rapidly formed following IV administration of Iab in rats, dogs and monkeys. The IV AUC conversion ratios were 1.5 in rats, 0.80 in dogs and 0.70 in monkeys, suggesting good conversion from Iab to IVa.

Good oral bioavailabilies (62-94%) of IVa were observed after administration of Iab in rats, dogs and monkeys. More significantly, the higher aqueous solubility of Iab lessened the dissolution-rate limited absorption of IVa below certain doses and thereby increased the exposures of IVa in oral dose escalation and toxicokinetic studies (Tables 12-14 and FIG. 6-7). The AUC levels of IVa in fasted dogs receiving Iab capsules were about 40 times the levels in fasted dogs given IVa clinical form capsules. Although a 40-fold difference is likely an over-prediction of the clinical situation, based on the development experience with IVa, Iab clearly demonstrated the potential to improve the dissolution-rate limited absorption seen with parent IVa.

To investigate the effect of food on the oral absorption of IVa in dogs, Iab and IVa were administered in capsules under fasting and fed conditions. No significant differences in AUC and Cmax were observed with Iab, whereas a 9-fold improvement was observed with IVa upon feeding. These data suggest potential clinical benefits for HIV-infected patients, in whom efficacious blood levels of IVa may be achieved without the requirement for a high fat meal.

Methods

The studies described in this report used the mono-lysine salt of Iab, unless stated otherwise.

Quantitation of Iab and IVa by LC/MS/MS

An LC/MS/MS method was developed for the analysis of Iab and IVa in plasma samples from the animal pharmacokinetic studies as well as in acetonitrile supernatant from in vitro incubation studies. For the analysis in plasma, a Packard Multiprobe instrument was used to transfer 50 µL of each standard, QC, and plasma sample to a clean 96-well plate for protein precipitation extraction. After the addition of 200 µL of acetonitrile containing the internal standard IVc, the samples were vortex mixed and the resulting supernatant was separated from the precipitated proteins by centrifugation for 10 min. For the analysis in the supernatant generated from the in vitro studies, an equal volume of the supernatant and acetonitrile containing the internal standard was mixed. An aliquot of the above supernatant was transferred using a Tomtec automated liquid handler to a second clean 96-well plate. An equal volume of water was added, and the plate was capped and vortex mixed.

The HPLC system consisted of Shimadzu LC10ADvp pumps (Columbia, Md.) and a HTC PAL autosampler (Leap Technologies, Cary, N.C.) linked to a Phenomenex Synergi Fusion-RP analytical column (2.0×50 mm, 5µ; Torrance, Calif.). Mobile phase A consisted of 5 mM ammonium formate in water; mobile phase B was 100% acetonitrile. LC flow rate was 0.38 mL/min. The initial mobile phase composition was 3% B, ramped to 60% B over 1.75 min and held for 0.25 min, ramped to 100% B over 0.1 min and held for 0.8 min, returned to initial conditions over the next 0.1 min, and re-equilibrated. Total analysis time was 4.0 min. The retention time for Iab, IVa and IVc was 1.50, 1.67 and 1.73 min, respectively.

The HPLC system was interfaced to a Sciex API4000 triple quadrupole mass spectrometer (Toronto, Canada) equipped with the Turboionspray source set at 550° C. and the ionspray voltage set to 4.5 kV. UHP nitrogen was used as nebulizer and auxiliary gas with the pressure of 80 psi and 7 L/min, respectively. The collision energies for Iab, IVa and IVc were 21, 29 and 31 volts, respectively. Data acquisition utilized selected reaction monitoring (SRM). Ions representing the positive ion mode (M+H)® species for Iab, IVa and the internal standard were selected in MS1 and collisionally dissociated with nitrogen and optimized collision energies to form specific product ions subsequently monitored by MS2.

The SRM transitions for Iab, IVa and IVc were m/z 533→435, 423→205 and 474→256, respectively.

Standard curves ranging from 5 nM to 10 µM were prepared from stock solutions and serially diluted in matrix for both Iab and IVa. Standard curves were aliquoted in duplicate, extracted with the samples, and injected at the beginning, middle, and end of the analytical sequence. The standard curves were fitted with a linear regression weighted by reciprocal concentration $1/x^2$. Data and chromatographic peaks were processed and concentrations of standards and unknowns were quantitated using PEBiosystems Analyst™ 1.1.

In Vitro Methods (1) Stability of Iab in EDTA Blood Serum and Tris-HCl Buffer

The stability of Iab was studied in fresh blood and serum from rat, dog, monkey and human (n=2). The blood was collected in vacutainers containing $K_2EDTA$ (Becton Dickinson, Franklin Lakes, N.J.). The serum was collected in vacutainers containing no anticoagulant. Iab was incubated at a starting concentration of approximately 10 µM for 60-90 min at 37° C. Serial samples were taken at the pre-determined times. Aliquots of blood samples (200 µL) were first mixed with 100 µL of water followed by 400 µL of acetonitrile. The serum samples (50 µL) were added into microtainers containing $K_2EDTA$ (Becton Dickinson, Franklin Lakes, N.J.) followed by the addition of 100 µL of acetonitrile. The supernatant was analyzed for both Iab and IVa by LC/MS/MS.

The stability of Iab was also evaluated, as described above, in Tris-HCl buffer (0.1 M, pH 7.5).

(2) Hydrolysis of Iab in the Presence of Human Placental ALP

Solid human placental ALP was obtained from Sigma (P-3895, St. Louis, Mo.). A solution of 1000 units/L was prepared in Tris-HCl buffer (0.1 M, pH 7.5). Solutions of 100 and 10 units/L were obtained by serial dilution. Iab was incubated in the 10, 100 and 1000 units/L solutions (n=2) at 37° C. for 2 hr. The starting concentration of Iab in the incubation was 10 µM. Aliquots of 100 µL samples were taken at pre-determined times and added into $K_2EDTA$ microtainers followed by the addition of 200 µL of acetonitrile. The supernatant was analyzed for both Iab and IVa by LC/MS/MS.

In Vivo Studies

All blood samples (0.3 mL) were collected in microtainers containing $K_2EDTA$ (Becton Dickinson, Franklin Lakes, N.J.) and placed on chipped ice. After centrifugation, plasma was separated and stored at −20° C. until analysis. The mono-lysine salt of Iab (Form 3, Lot 1) was used for the pharmacokinetic studies. The dosing solutions of Iab were prepared in either sterile water (for IV administration in dogs and monkeys) or distilled water (for all other dose administration).

(1) In Vivo Studies in the Rat

Male Sprague-Dawley rats (300-350 g, Hilltop Lab Animals, Inc., Scottsdale, Pa.) with cannulas implanted in the jugular vein were used. The rats were fasted overnight in the PO pharmacokinetic studies. Blood samples were collected from the jugular vein.

In the IV study, Iab was delivered at 1.4 mg/kg (free acid, or 1.1 mg/kg of IVa equivalent) as a bolus over 0.5 min (n=3). The concentration of the dosing solution was 1.4 mg/mL, and the dosing volume was 1 mL/kg. Serial blood samples were collected before dosing and at 2, 10, 15, 30, 45 min, 1, 2, 4, 6, 8 and 24 hr after dosing.

In the PO study, Iab was administered at 7.9 mg/kg (free acid, or 6.3 mg/kg of IVa equivalent) by oral gavage (n=3). The concentration of the dosing solution was 4.0 mg/mL, and the dosing volume was 2 mL/kg. Serial blood samples were collected before dosing and at 15, 30, 45 min, 1, 2, 4, 6, 8 and 24 hr after dosing.

(2) In Vivo Studies in the Dog

The IV and PO studies of Iab were conducted in a crossover fashion in three male beagle dogs (11±1.1 kg, Marshall Farms USA Inc., North Rose, N.Y.). There was a two-week washout period between the IV and PO studies.

In the IV study, Iab was infused via the cephalic vein at 1.2 mg/kg (free acid, or 0.95 mg/kg of IVa equivalent) over 5 min at a constant rate of 0.1 mL/kg/min. The concentration of the dosing solution was 2.4 mg/mL, and the dosing volume was 0.5 mL/kg. Serial blood samples were collected from the femoral artery before dosing and at 5, 10, 15, 30, 45 min, 1, 2, 4, 6, 8 and 24 hr after dosing.

In the PO study, the dogs were fasted overnight before dosing. Iab was administered by oral gavage at 6.6 mg/kg (free acid, or 5.2 mg/kg of IVa equivalent). The concentration of the dosing solution was 13.2 mg/mL, and the dosing volume was 0.5 mL/kg. Serial blood samples were collected before dosing and at 15, 30, 45 min, 1, 2, 4, 6, 8 and 24 hr after dosing.

To study the effect of food on the oral absorption of IVa after administration of Iab and IVa, these two compounds were administered in capsules as solid to a group of three dogs in a cross-over fashion under overnight fasting and fed conditions. There was a one-week washout period between each study. Iab was administered at 200 mg per dog (ca 20 mg/kg) of IVa equivalent; IVa was administered in a clinical capsule formulation at 200 mg per dog (ca 20 mg/kg). In the studies where the dogs were fed, the following meal was prepared: 2 slices of bacon, 2 eggs, 2 pieces of toast with butter and jelly, 4 oz. hash browns and 8 oz. of whole milk. After homogenization using a laboratory blender, the meal was equally divided into five portions and kept frozen. Before the study, the meals were thawed and each dog was fed one portion.

Additional formulation studies of IVa were conducted in fasted dogs (n=2 per dose group). The dogs were administered either the clinical form or the spray dried form of IVa in capsules. The clinical capsule form of IVa was administered at a single dose of 20 mg/kg. The spray dried form of IVa was administered at 20, 75 and 200 mg/kg.

(3) In Vivo Studies in the Monkey

The IV and PO studies of Iab were conducted in a crossover fashion in three male cynomolgus monkeys (11±1.2 kg, Charles River Biomedical Research Foundation, Houston, Tex.). There was a two-week washout period between the IV and PO studies.

In the IV study, Iab was infused via the femoral vein at 1.3 mg/kg (free acid, or 1.1 mg/kg of IVa equivalent) over 5 min at a constant rate of 0.1 mL/kg/min. The concentration of the dosing solution was 2.6 mg/mL, and the dosing volume was 0.5 mL/kg. Serial blood samples were collected from the femoral artery before dosing and at 5, 10, 15, 30, 45 min, 1, 2, 4, 6, 8 and 24 hr after dosing.

In the PO study, the monkeys were fasted overnight before dosing. Iab was administered by oral gavage at 7.1 mg/kg (free acid, or 5.6 mg/kg of IVa equivalent). The concentration of the dosing solution was 14.2 mg/mL, and the dosing volume was 0.5 mL/kg. Serial blood samples were collected before dosing and at 15, 30, 45 min, 1, 2, 4, 6, 8 and 24 hr after dosing.

(4) Data Analysis

All results are expressed as mean±SD, unless specified otherwise.

The pharmacokinetic parameters of Iab and IVa were calculated by Non-Compartmental Analysis using the KINETICA™ software program (version 4.0.2, InnaPhase Co., Philadelphia, Pa.). The Cmax and Tmax values were recorded directly from experimental observations. The AUC0-n and AUCtot values were calculated using the mixed log-linear trapezoidal summations. The total body clearance (Cl), mean residence time (MRT), and the steady state volume of distribution (Vss) were also calculated after intravenous administration. The absolute oral bioavailability (expressed as %) was estimated by taking the ratio of dose-normalized AUC values after oral doses to those after intravenous doses.

The hepatic clearance $Cl_H$ was calculated from the following equation using the well-stirred model:

$$Cl_H \text{ (mL/min/kg)} = \frac{Qh \times Cl_{int.in\ vivo}}{Qh + Cl_{int.in\ vivo}}$$

where Qh is the liver blood flow of 55, 31, 44 and 21 mL/min/kg for the rat, dog, monkey and human, respectively (Davis and Morris, 1993).

The hepatic extraction ration (ER) was calculated at follows:

$$ER = Cl_H/Qh$$

Student's t-test was used for statistical analysis (Microsoft Excel, Redmond, Wash.). Differences were considered statistically significant at the level of $P<0.05$.

In Vitro Studies

Stability of Iab in EDTA Blood Serum and Tris-HCl Buffer

As part of the analytical assay validation, the stability of Iab was studied in blood containing EDTA, which is known to be an inhibitor of alkaline phosphatases (Bowers, Jr. and McComb, 1966; Yora and Sakagishi, 1986). After incubation at 37° C. for 60 min, there was 1.2% conversion from the initial concentration of Iab to Ia in the rat blood (Table 15), and less than 1% conversion in the monkey and human blood (Tables 15 and 16). There was approximately 6% conversion in the dog blood, and the percentages of conversion were similar between two different dogs, as well as in the same dog on two different test occasions (Tables 15 and 16). Under the sample storage condition of −20° C., the above small percentages of conversion observed at 37° C. are not expected to introduce any significant ex vivo conversion during the analysis of Iab.

Iab was stable in the Tris-HCl buffer at 37° C. during the 60-min study period (Table 17).

TABLE 15

Stability of Iab in the Fresh EDTA Blood from Rat, Dog and Monkey

| | Rat Blood (n = 2) | | | Dog A Blood (n = 2) | | | Monkey Blood (n = 2) | | |
|---|---|---|---|---|---|---|---|---|---|
| Time (min) | Iab (μM) | IVa Formed (μM) | % IVa Formed* | Iab (μM) | IVa Formed (μM) | % IVa Formed* | Iab (μM) | IVa Formed (μM) | % IVa Formed* |
| 0 | 8.0 | 0.019 | 0.24 | 12 | 0.036 | 0.30 | 8.5 | 0.011 | 0.13 |
| 20 | 8.8 | 0.056 | 0.70 | 12 | 0.29 | 2.4 | 9.2 | 0.024 | 0.28 |
| 40 | 10 | 0.072 | 0.90 | 11 | 0.49 | 4.1 | 9.2 | 0.041 | 0.48 |
| 60 | 10 | 0.093 | 1.2 | 11 | 0.74 | 6.2 | 8.7 | 0.048 | 0.56 |

*Percentage formed as the starting concentration of Iab.

TABLE 16

Stability of Iab in the Fresh EDTA Blood from Dog (Repeat) and Human

| | Dog A Blood (n = 2) | | | Dog B Blood (n = 2) | | | Human Blood (n = 2) | | |
|---|---|---|---|---|---|---|---|---|---|
| Time (min) | Iab (μM) | IVa Formed (μM) | % IVa Formed* | Iab (μM) | IVa Formed (μM) | % IVa Formed* | Iab (μM) | IVa Formed (μM) | % IVa Formed* |
| 0 | 11 | 0.069 | 0.63 | 12 | 0.084 | 0.68 | 11 | 0.061 | 0.55 |
| 15 | 11 | 0.25 | 2.3 | 11 | 0.25 | 2.0 | 11 | 0.067 | 0.59 |
| 30 | 11 | 0.37 | 3.4 | 11 | 0.43 | 3.5 | 7.1 | 0.057 | 0.50 |
| 45 | 11 | 0.53 | 4.8 | 13 | 0.56 | 4.5 | 9.8 | 0.073 | 0.65 |
| 60 | 10 | 0.67 | 6.1 | 14 | 0.72 | 5.8 | 9.8 | 0.084 | 0.75 |

*Percentage formed as the starting concentration of Iab.

TABLE 17

Stability of Iab in Tris-HCl Buffer

| | Tris-HCl (n = 2) | | |
|---|---|---|---|
| Time (min) | Iab (μM) | IVa Formed (μM) | % IVa Formed * |
| 0 | 10 | 0.011 | 0.11 |
| 20 | 10 | 0.008 | 0.081 |
| 40 | 7.6 | 0.008 | 0.076 |
| 60 | 10 | 0.009 | 0.088 |

* Percentage formed as the starting concentration of Iab.

To investigate the hydrolysis of Iab in the systemic circulation, Iab was incubated in fresh serum (rat, dog, monkey and human) at 37° C. for 90 min. The rate of hydrolysis was the most rapid in the rat serum, followed by dog, monkey and human sera (Table 18). The conversion of Iab to IVa was near stoichiometric.

Serum contains lower ALP activities as compared to tissues (McComb et al., 1979a). In addition, serum also contains ALP isoforms from tissue sources such as bone, liver and intestine, which are attributed to leakage through the blood vessels (Moss, 1983). Therefore, the hydrolysis of Iab in serum was probably mediated by multiple isoforms of ALP.

formed from Iab vs. from the historical IVa study was 1.5 (theoretical value for complete conversion=1), suggesting complete conversion of Iab to IVa.

With the exception of one sample (5 nM; Table 20), Iab was not detected in any samples after oral administration. The Tmax of IVa after oral administration of Iab was 0.83 hr, which is shorter than the historical Tmax of IVa of 2.0 hr, indicating more rapid absorption of IVa following the oral administration of the prodrug. The more rapid absorption of

TABLE 18

Stability of Iab in the Fresh Serum from Rat, Dog, Monkey and Human

| Time (min) | Rat Serum (n = 2) | | Dog Serum (n = 2) | | Monkey Serum (n = 2) | | Human Serum (n = 2) | |
|---|---|---|---|---|---|---|---|---|
| | Iab (μM) | IVa Formed (μM) | Iab (μM) | IVa Formed (μM) | Iab (μM) | IVa Formed (μM) | Iab (μM) | IVa Formed (μM) |
| 0 | 6.8 | 0.25 | 9.2 | 0.066 | 9.0 | 0.20 | 9.5 | 0.10 |
| 15 | 5.8 | 1.1 | 9.0 | 0.85 | 7.3 | 0.48 | 9.2 | 0.10 |
| 30 | 5.4 | 1.8 | 7.8 | 1.6 | 6.8 | 0.75 | 9.0 | 0.15 |
| 45 | 4.9 | 2.8 | 7.8 | 2.5 | 6.5 | 1.2 | 9.6 | 0.20 |
| 60 | 4.3 | 3.7 | 7.1 | 3.2 | 6.3 | 1.5 | 9.1 | 0.24 |
| 90 | 3.3 | 5.4 | 6.7 | 4.4 | 6.3 | 2.0 | 9.4 | 0.32 |
| $t_{1/2}$ (min)* | 80 | | 182** | | 365** | | >2000 | |

*Calculated as the disappearance of Iab.
**The half-lives are greater than the incubation period.

Hydrolysis of Iab in the Presence of Human Placental ALP

Figure 8:
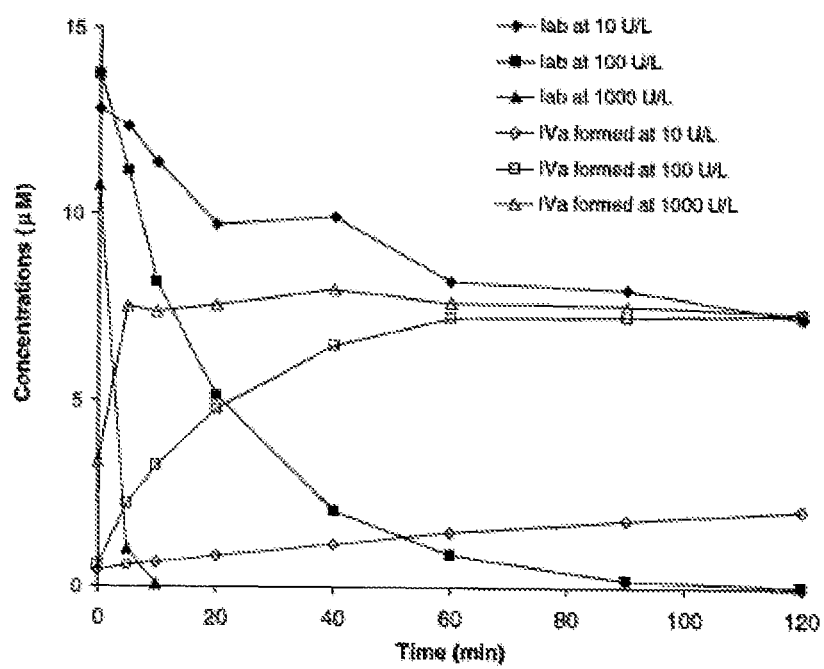
FIG. 8 illustrates Hydrolysis of Iab in Human Placental ALP Solutions and the Formation of IVa.

To study the hydrolysis of Iab in a purified form of human ALP, Iab was incubated in human placental ALP solutions at 10, 100 and 1000 units/L at 37° C. for 2 hr. The disappearance $t_{1/2}$ of Iab was determined and reported in Table 19. As expected, the rate of hydrolysis was faster in the solutions with higher ALP activities. IVa was also formed accordingly (FIG. 8). This indicates that Iab is hydrolyzed by the ALP derived from humans to form IVa.

TABLE 19

Hydrolysis of Iab in Human Placental ALP Solutions

| | ALP Activity (Units/L) (n = 2) | | |
|---|---|---|---|
| | 10 | 100 | 1000 |
| $t_{1/2}$ (min) | 186 | 14 | 1.4 |

Note:
Iab was incubated at a starting concentration of ~10 μM at 37° C. for 120 min.

In Vivo Studies
In Vivo Studies in the Rat

Figure 9:
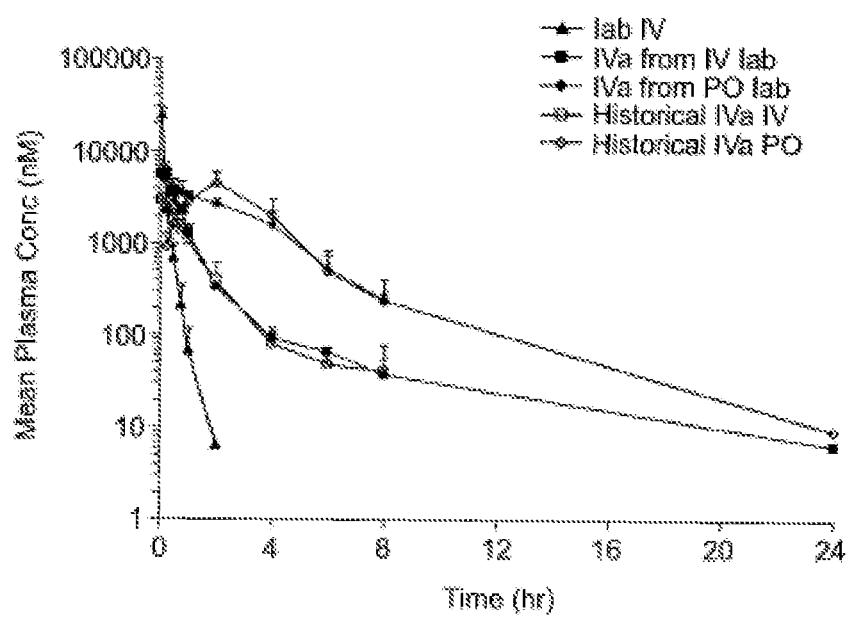
FIG. 9 illustrates Plasma Concentration Versus Time Profiles of Iab and IVa Following IV and Oral Administration of Iab in Rats and from the Historical Data of IVa in Rats.

The pharmacokinetic parameters of Iab and IVa in rats after IV and oral administration of Iab are summarized in Table 20. The plasma concentration versus time profiles are shown in FIG. 9. For comparison, the historical data from the pharmacokinetic studies of IVa in rats are also shown.

The total body clearance (Cl) of Iab following IV administration was 14 mL/min/kg, suggesting that Iab is a low clearance compound in rats. The elimination half-life (tin) and mean residence time (MRT) after IV administration were 0.16 hr and 0.14 hr, respectively. Iab was not detected beyond 2 hr. The volume of distribution of Iab at steady state (Vss) was 0.12 L/kg, suggesting very limited tissue distribution. The formation of IVa from Iab after IV administration was rapid; IVa was detected at the first sampling time point of 2 min (data not shown). The IV AUC ratio of IVa IVa from the prodrug is likely the result of better aqueous solubility of Iab as well as rapid hydrolysis of Iab to form IVa in the intestine. Although the absolute oral bioavailability of IVa from Iab was 62%, lower than the historical IVa data, the exposure of IVa from the Iab rat oral dose escalation study was superior as compared to the historical data with IVa (Table 16 and FIG. 8).

The terminal plasma concentration vs. time profiles of IVa formed from Iab are similar to the historical IVa profiles.

TABLE 20

Pharmacokinetic Parameters of Iab and IVa Following IV and Oral Administration of Iab in Rats (Mean ± SD, n = 3)

| PK Parameters | Iab | IVa Formed after Dosing with Iab | Historical IVa |
|---|---|---|---|
| | IV | | |
| Dose (mg/kg) | 1.4 free acid or 1.1 of IVa equivalent | | 1 |
| AUC$_{tot}$ (μM · hr) | 3.3 ± 1.0 | 5.4 ± 0.93 | 3.3 ± 1.1 |
| CL$_{tot}$ (mL/min/kg) | 14 ± 4.2 | NA | 13 ± 4.0 |
| $t_{1/2}$ (hr) | 0.16 ± 0.052 | 4.4 ± 1.9 | 2.4 ± 0.32 |
| MRT (hr) | 0.14 ± 0.020 | NA | 2.2 ± 1.5 |
| Vdss (L/kg) | 0.12 ± 0.019 | NA | 1.5 ± 0.25 |
| IV AUC Ratio of IVa | NA | 1.5* | NA |
| | PO | | |
| Dose (mg/kg) | 7.9 free acid or 6.3 of IVa equivalent | | 5 |
| Tmax (hr) | ND | 0.83 ± 0.29 | 2.0 |
| Cmax (μM) | ND** | 3.9 ± 0.98 | 4.5 ± 1.5 |
| C-24 hr (μM) | ND | ND | 9 (n = 1) |

TABLE 20-continued

Pharmacokinetic Parameters of Iab and IVa Following IV and Oral Administration of Iab in Rats (Mean ± SD, n = 3)

| PK Parameters | Iab | IVa Formed after Dosing with Iab | Historical IVa |
|---|---|---|---|
| $AUC_{tot}$ (µM · hr) | ND | 13 ± 1.4 | 15 ± 6.3 |
| $t_{1/2}$ (hr) | ND | 1.5 ± 0.24 | 1.7 ± 0.92 |
| Bioavailability (%) | ND | 62*** | 90 |
| PO AUC Ratio of IVa | NA | 0.69* | NA |

NA—not applicable;
ND—not detected (<5 nM).
*The ratios were calculated from $$\frac{\text{'043 } AUC \text{ after prodrug dosing}}{\text{'043 } AUC \text{ after '043 dosing}}$$

for IV and PO, respectively
**Iab was detected in one rat only at 15 min (5 nM).
***Calculated from historical IV data of IVa.

31. In Vivo Studies in the Dog

Figure 10:
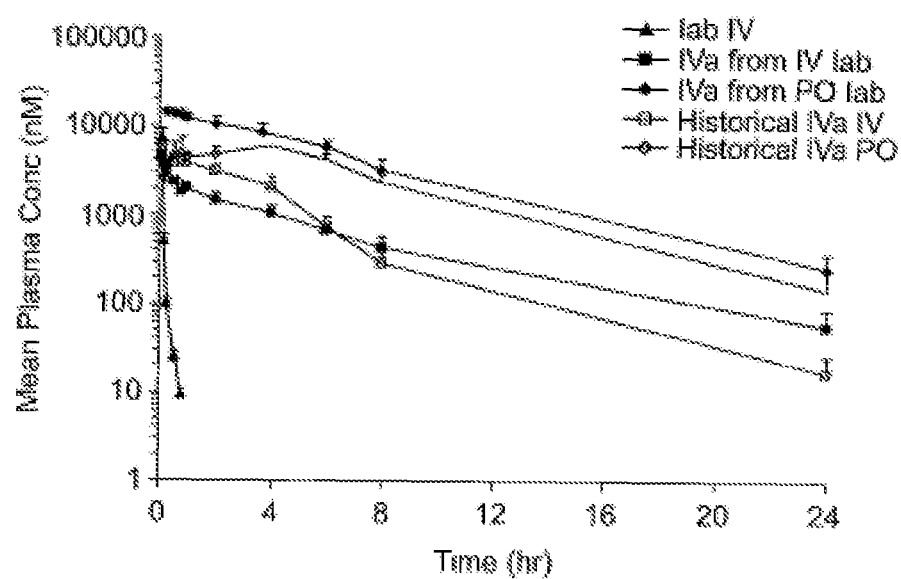
FIG. 10 illustrates Plasma Concentration Versus Time Profiles of Iab and IVa Following IV and Oral Administration of Iab in Dogs and from the Historical Data of IVa in Dogs.

The pharmacokinetic parameters of Iab and IVa in dogs after IV and oral administration of Iab are summarized in Table 21. The plasma concentration versus time profiles are shown in FIG. 10. For comparison, the historical data from the pharmacokinetic studies of IVa in dogs are also shown.

The Cl of Iab after IV administration was 70 mL/min/kg, which is significantly higher than the liver blood flow of 31 mL/min/kg in dogs, suggestive of potential involvement of extrahepatic hydrolysis and/or other route(s) of elimination (e.g., renal excretion). The t1/2 and MRT after IV administration were 0.15 hr and 0.07 hr, respectively. Iab was not detected beyond 45 min. The Vss of Iab was 0.30 L/kg, suggesting low potential for tissue distribution. The formation of IVa from Iab after IV administration was rapid; IVa was detected at the first sampling time point of 5 min (data not shown). The IV AUC ratio of IVa formed from Iab vs. from the historical IVa study was 0.80, suggesting good conversion of Iab to IVa.

Iab was detected at 5 nM (LLQ) only at 15 min and 30 min in one dog after oral administration. The Tmax of IVa after oral administration of Iab was 0.25 hr, which is shorter than the historical Tmax of IVa of 2.9 hr, indicating more rapid absorption of IVa following the oral administration of the prodrug. The absolute oral bioavailability of IVa from Iab was 94%, higher than the historical IVa data of 57%. The terminal plasma concentration vs. time profiles of IVa formed from Iab are similar to the historical IVa profiles.

TABLE 21

Pharmacokinetic Parameters of Iab and IVa Following IV and Oral Administration of Iab in Dogs (Mean ± SD, n = 3)

| PK Parameters | Iab | IVa Formed after Dosing with Iab | Historical IVa |
|---|---|---|---|
| IV | | | |
| Dose (mg/kg) | 1.2 free acid or 0.95 of IVa equivalent | | 1 |
| $AUC_{tot}$ (µM · hr) | 0.56 ± 0.12 | 13 ± 2.2 | 17 ± 3.5 |
| $CL_{tot}$ (mL/min/kg) | 70 ± 16 | NA | 2.4 ± 0.43 |
| $t_{1/2}$ (hr) | 0.15 ± 0.010 | 5.2 ± 1.0 | 2.6 ± 1.2 |
| MRT (hr) | 0.07 ± 0.006 | NA | 3.3 ± 0.71 |
| Vdss (L/kg) | 0.30 ± 0.094 | NA | 0.45 ± 0.083 |
| IV AUC Ratio of IVa | NA | 0.80 | NA |

TABLE 21-continued

Pharmacokinetic Parameters of Iab and IVa Following IV and Oral Administration of Iab in Dogs (Mean ± SD, n = 3)

| PK Parameters | Iab | IVa Formed after Dosing with Iab | Historical IVa |
|---|---|---|---|
| PO | | | |
| Dose (mg/kg) | 6.6 free acid or 5.2 of IVa equivalent | | 5 |
| Tmax (hr) | ND | 0.25 | 2.9 ± 1.9 |
| Cmax (µM) | ND* | 14 ± 1.3 | 6.5 ± 1.2 |
| C-24 hr (µM) | ND | 0.26 ± 0.12 | 0.15 ± 0.093 |
| $AUC_{tot}$ (µM · hr) | ND | 83 ± 16 | 47 ± 7.2 |
| $t_{1/2}$ (hr) | ND | 4.1 ± 0.52 | 3.8 ± 0.81 |
| Bioavailability (%) | ND | 94 | 57 ± 17 |
| PO AUC Ratio of IVa | NA | 1.7 | NA |

*Iab was detected at 5 nM (LLQ) only at 15 min and 30 min in one dog.

To study the effect of food on the oral absorption of IVa after administration of Iab and IVa, the dogs were administered either Iab or IVa in capsules under fasting and fed conditions. The study was conducted in across-over fashion, with a one-week washout period between each study. No significant differences in the AUC and Cmax were observed between the fasting and fed conditions after administration of Iab (Table 22), whereas a 9-fold improvement in AUC and Cmax was observed after administration of IVa with feeding (Table 23). Overall, the effect of feeding was more pronounced in dogs (Table 23) than in human subjects (Table 24) receiving IVa. This is suggestive of quantitative species differences in the effect of food on the oral absorption of IVa.

The oral absorption of IVa was shown to be dissolution-rate limited in humans and animal species. The improvement of IVa exposure in humans upon feeding with a high fat meal was presumably due to the increased secretion of bile salts which facilitated the dissolution of IVa. In dogs, the lack of the effect of food on the oral absorption of IVa after Iab administration suggests potential benefits in humans, for whom diet modification may not be required.

TABLE 22

Effect of Food on the Oral Exposure of IVa in Dogs Following Oral Administration of Iab in Dry-Filled Capsules (20 mg/kg of IVa equivalent) (Mean ± SD, n = 3)

| Parameters | Fasting | Fed |
|---|---|---|
| $AUC_{tot}$ (µM · hr) | 414 ± 70 | 422 ± 57 |
| Cmax (µM) | 70 ± 12 | 130 ± 102 |
| Tmax (hr) | 2.0 | 1.5 ± 0.87 |
| $t_{1/2}$ (hr) | 4.2 ± 0.42 | 3.2 ± 1.0 |

Note:
Iab was detected at <200 nM in a few samples at the early time points.

TABLE 23

Effect of Food on the Oral Exposure of IVa in Dogs Following Oral Administration of IVa in Clinical Form Capsules (20 mg/kg) (Mean ± SD, n = 3)

| Parameters | Fasting | Fed | Fed/Fasting Ratio |
|---|---|---|---|
| $AUC_{tot}$ (µM · hr) | 11 ± 1.4 | 96 ± 10* | 9.0 ± 2.2 |
| Cmax (µM) | 1.2 ± 0.22 | 11 ± 0.99* | 9.1 ± 0.92 |
| Tmax (hr) | 3.3 ± 1.2 | 4.0 | |
| $t_{1/2}$ (hr) | 5.3 ± 2.7 | 8.0 ± 3.1 | |

*Significantly different from the values under fasting condition.

TABLE 24

Effect of Food on the Oral Exposure of IVa in the First-in-Human Study (Mean ± SD, n = 6)

| | 800 mg | | | 1800 mg | | |
|---|---|---|---|---|---|---|
| | Fasting | Fed | Fed/Fasting Ratio | Fasting | Fed | Fed/Fasting Ratio |
| $AUC_{total}$ ($\mu M \cdot hr$) | 22 ± 12 | 53 ± 10 | 2.4 | 19 ± 5.8 | 82 ± 16 | 4.3 |

TABLE 24-continued

Effect of Food on the Oral Exposure of IVa in the First-in-Human Study (Mean ± SD, n = 6)

| | 800 mg | | | 1800 mg | | |
|---|---|---|---|---|---|---|
| | Fasting | Fed | Fed/Fasting Ratio | Fasting | Fed | Fed/Fasting Ratio |
| $C_{max}$ ($\mu M$) | 3.7 ± 1.1 | 9.8 ± 1.3 | 2.6 | 3.3 ± 0.84 | 15 ± 5.0 | 4.5 |

Additional capsule formulation studies were conducted in the same fasted dogs with the clinical and spray dried forms of IVa to compare with ab. As shown in Table 25, at 20 mg/kg of IVa equivalent, similar exposure of IVa was observed following administration of Iab and the spray dried form of IVa. However, Iab provided significantly higher exposure of IVa as compared to the clinical form of IVa. The AUC and Cmax of IVa from the prodrug were 37 times and 45 times higher, respectively, than the values from the clinical form of IVa. The fold increase in dogs is likely an over-prediction of the clinical situation based on the experience with IVa in development (data not shown).

In the dose escalation study of the spray-dry form of IVa in dogs, the increases of AUC and Cmax from 20 mg/kg to 75 mg/kg were less than proportional to dose increase (Table 26). No significant further increases in exposure were observed from 75 mg/kg to 200 mg/kg.

TABLE 25

Oral Exposure of IVa in Dogs After Oral Administration of Iab and Different Formulations of IVa in Capsules (Cross-Over Studies)

| | Parameters | | | | | |
|---|---|---|---|---|---|---|
| Formulation | Dog# 4201 Iab | Dog# 4202 Iab | Dog# 4201 IVa spray-dry | Dog# 4202 IVa spray-dry | Dog# 4201 'IVa clinical form | Dog# 4202 'IVa clinical form |
| Dose (mg/kg; 'IVa eq.) | 19 | 19 | 20 | 20 | 20 | 20 |
| $AUC_{tot}$ ($\mu M \cdot hr$) | 486 | 514 | 303* | 338 | 11 | 16 |
| Cmax ($\mu M$) | 80 | 86 | 46 | 81 | 1.3 | 2.4 |
| Tmax (hr) | 1.0 | 1.0 | 2.0 | 1.0 | 1.0 | 4.0 |
| $t_{1/2}$ (hr) | 4.2 | 3.4 | 57 | 4.2 | 7.1 | 4.5 |

*AUC was 0-24 hr.

TABLE 26

Oral Exposure of IVa in Dogs After Oral Administration of the Spray-Dry form of IVa in Capsules

| Parameters | Dog# 4201* | Dog# 4202* | Dog# 1201 | Dog# 1202 | Dog# 2201 | Dog# 2202 |
|---|---|---|---|---|---|---|
| Dose (mg/kg) | 20 | 20 | 75 | 75 | 200 | 200 |
| $AUC_{tot}$ ($\mu M \cdot hr$) | 303** | 338 | 759 | 923 | 935** | 1209 |
| Cmax ($\mu M$) | 46 | 81 | 156 | 192 | 178 | 210 |
| Tmax (hr) | 2.0 | 1.0 | 1.0 | 1.0 | 1.0 | 2.0 |
| $t_{1/2}$ (hr) | 57 | 4.2` | 2.1 | 1.9 | 3.0 | 2.3 |
| Dose ratio | | | 1:3.8:10 | | | |
| Average AUC ratio | | | 1:2.6:3.4 | | | |
| Average Cmax ratio | | | 1:2.7:3.0 | | | |

*As in Table 25.
**AUC was 0-24 hr.

In Vivo Studies in the Monkey

Figure 11:
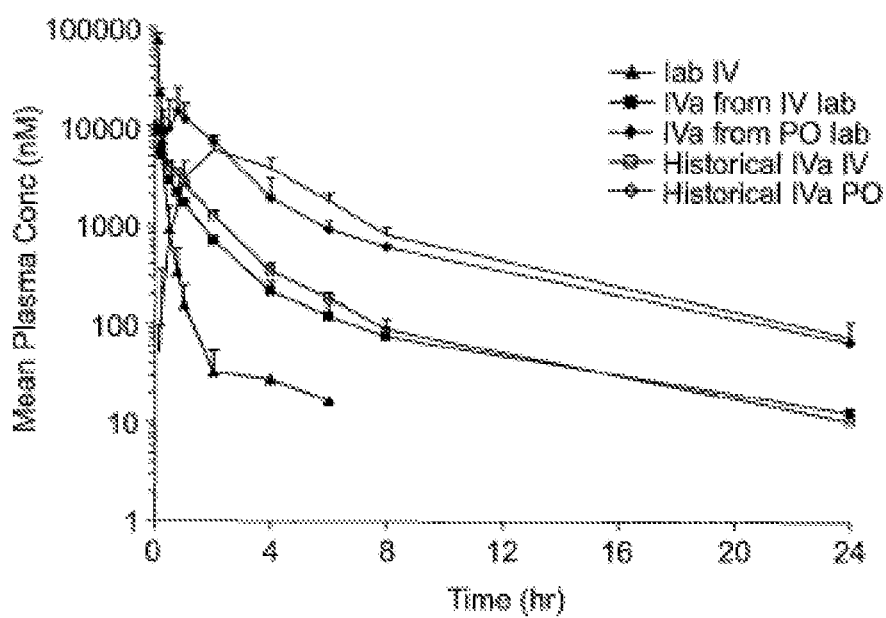
FIG. 11 illustrates Plasma Concentration Versus Time Profiles of Iab and IVa Following IV and Oral Administration of Iab in Monkeys and from the Historical Data of IVa in Monkeys.

The pharmacokinetic parameters of Iab and IVa in monkeys after IV and oral administration of Iab are summarized in Table 27. The plasma concentration versus time profiles are shown in FIG. 11. For comparison, the historical data from the pharmacokinetic studies of IVa in monkeys are also shown.

The Cl of Iab after IV administration was 4.4 mL/min/kg, suggesting that Iab is a low clearance compound in monkeys. The tin and MRT after IV administration were 1.0 hr and 0.18 hr, respectively. The MRT reflected a more realistic estimate of the duration of Iab in the plasma since the plasma concentrations of Iab in the terminal phase were low (FIG. 11). Iab was not detected beyond 6 hr. The Vss of Iab was 0.048 L/kg, suggesting very limited tissue distribution. The formation of IVa from Iab after IV administration was rapid;

IVa was detected at the first sampling time point of 5 min (data not shown). The IV AUC ratio of IVa formed from Iab vs. from the historical IVa study was 0.70, suggesting good conversion of Iab to IVa.

Iab was detected at a concentration of 18 nM at 15 min in only one monkey after oral administration. The Tmax of IVa after oral administration of Iab was 0.83 hr, which is shorter than the historical Tmax of IVa of 2.7 hr, indicating more rapid absorption of IVa following the oral administration of the prodrug. The absolute oral bioavailability of IVa from Iab was 66%, similar to the historical IVa data of 60%.

The terminal plasma concentration vs. time profiles of IVa formed from Iab are similar to the historical IVa profiles.

TABLE 27

Pharmacokinetic Parameters of Iab and IVa Following IV and Oral Administration of Iab in Monkeys (Mean ± SD, n = 3)

| PK Parameters | Iab | IVa Formed after Dosing with Iab | Historical IVa |
|---|---|---|---|
| IV | | | |
| Dose (mg/kg) | 1.3 free acid or 1.1 of IVa eqv. | | 1 |
| $AUC_{tot}$ (μM · hr) | 9.5 ± 0.38 | 7.1 ± 1.0 | 9.2 ± 0.53 |
| $CL_{tot}$ (mL/min/kg) | 4.4 ± 0.18 | NA | 4.3 ± 0.26 |
| $t_{1/2}$ (hr) | 1.0 ± 0.78 | 4.8 ± 1.9 | 4.7 ± 0.31 |
| MRT (hr) | 0.18 ± 0.059 | NA | 2.4 ± 0.15 |
| Vdss (L/kg) | 0.048 ± 0.017 | NA | 0.63 ± 0.39 |
| IV AUC Ratio of IVa | NA | 0.70 | NA |
| PO | | | |
| Dose (mg/kg) | 7.1 free acid or 5.6 of IVa eqv. | | 5 |
| Tmax (hr) | ND | 0.83 ± 0.14 | 2.7 ± 1.2 |
| Cmax (μM) | ND* | 16 ± 6.4 | 5.8 ± 1.2 |
| C-24 hr (μM) | ND | 0.067 ± 0.039 | 0.074 ± 0.032 |
| $AUC_{tot}$ (μM · hr) | ND | 34 ± 2.7 | 27 ± 2.9 |
| $t_{1/2}$ (hr) | ND | 4.8 ± 1.3 | 4.2 ± 0.64 |
| Bioavailability (%) | ND | 66 | 60 ± 4 |
| PO AUC Ratio of IVa | NA | 1.1 | NA |

*Iab was detected at 18 nM at 15 min in only one monkey.

Additional Profiling Section 2
Additional Studies with Prodrug Ibb

IV and PO pharmacokinetic studies of Ibb were conducted in rats, dogs and monkeys. In all cases, blood samples were collected in the presence of EDTA. The presence of EDTA, a known ALP inhibitor, minimized significant ex vivo conversion of Ibb during sample processing. IVb was rapidly formed following IV administration of Ibb. Good oral bioavailabilities of IVb (50-310%; calculated using the historical IV AUC of IVb) were observed after administration of Ibb in rats, dogs and monkeys with very low levels of Ibb present in plasma. Since there are high levels of ALP expression in the gut, it is likely that following oral administration of Ibb, Ibb is hydrolyzed by ALP present at the brush border membranes of the intestinal lumen to form IVb, which is rapidly absorbed due to its high permeability.

In vitro incubation studies were conducted for a qualitative assessment of ALP-dependent hydrolysis of Ibb in different tissues. Ibb was hydrolyzed in the presence of serum and hepatocytes from rat, dog, monkey and human, as well as human placental ALP. On the occasions where Ibb and IVb were measured, the conversion of Ibb to IVb was near stoichiometric. Due to hydrolysis in serum, the protein binding of Ibb could not be determined. Based on the in vitro data, it is anticipated that Ibb will be hydrolyzed by human ALP and that IVb will be formed after oral administration of Ibb to human subjects.

The crystalline solubility of Ibb-03 at room temperature is >11 mg/mL in the pH range of 1.5 to 8.7; aqueous solutions containing >75 mg/mL have been prepared for in vivo toxicology studies. In comparison, the aqueous solubility of the parent compound, IVb, at room temperature as crystalline material was determined to be 0.007-0.19 mg/mL (pH range of 1.0-9.6). Ibb-03 exhibits acceptable solution and solid stabilities.

The higher aqueous solubility of Ibb provides a means to overcome the dissolution-rate limited absorption of IVb below certain doses and thereby increased the exposures of IVb in oral dose escalation and toxicokinetic studies. Ibb, when dosed orally up to 200 mg/kg of IVb bmsequivalent, provided 11- and 2.6-fold (BID) higher AUC of IVb in rats and dogs, respectively, with relatively low plasma exposure to the prodrug (<0.9 μM), as compared to the AUC from the historical IVb suspension studies at the similar dose.

Single-Dose Toxicokinetic Study in Sprague Dawley Rats

A 1-day oral toxicokinetic study in rats was conducted by using the prodrug Ibb (monolysine salt). Ibb was administered at dosages of 19, 64, and 236 mg/kg (free acid) by oral gavage to three male rats/group using water as the vehicle (solution formulation). The dosages of prodrug free acid correspond to IVb (parent) molar equivalent dosages of 15, 51, and 190 mg/kg, respectively. The endpoint evaluated was plasma toxicokinetics of Ibb and IVb in the individual rats.

The mean toxicokinetic values are provided in Table 28.

TABLE 28

Mean toxicokinetic values for Ibb and IVb in male rats given ≤200 mg/kg of Ibb as a single oral dose

| | Dosages (mg/kg) Ibb | | | | | |
|---|---|---|---|---|---|---|
| | 19 | | 64 | | 236 | |
| | IVb molar equiv. | | | | | |
| | 15 | | 51 | | 190 | |
| | Ibb | IVb | Ibb | IVb | Ibb | IVb |
| Cmax (μM) | 0.027 | 58 | 0.14 | 135 | 0.25 | 290 |
| $C_{24h}$ (μM) | <LLQ | 0.048 | <LLQ | 0.29 | <LLQ | 29 |
| AUC (μM · h) | 0.030[1] | 283[2] | 0.18[1] | 997[2] | 0.49[1] | 3700[2] |
| T1/2 (h) | 1.3 | 2.1 | 4.6 | 2.1 | 3.6 | 5.8 |

Values represent means from one to three rats/group for Ibb data and 3 rats/group for IVb data. LLQ is the lower limit of quantification.
[1]AUC from zero to last time point.
[2]AUC from zero to ∞

Mean maximum plasma concentration (Cmax) of IVb (parent) was achieved within ≈1-3 hours post-dose. In rats given ≤236 mg/kg of Ibb, the increase in AUC of IVb was nearly proportional with Ibb dosage, and Cmax increased in a less than dosage-proportional manner between 19 and 236 mg/kg of Ibb. Ibb was detected in plasma of rats given ≥19 mg/kg of Ibb but at very low concentrations relative to those of IVb.

Figure 12A:
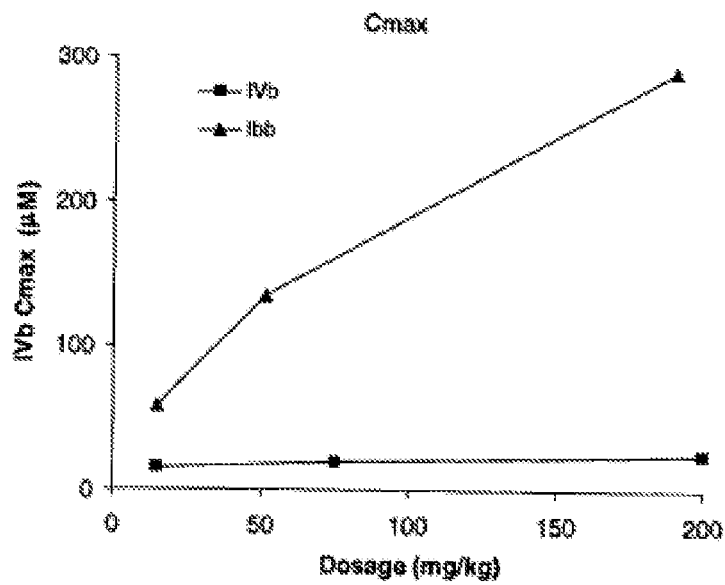
FIGS. 12A and 12B illustrates Comparison of IVb Cmax and AUC in Male Rats Given Either IVb or Ibb.
Figure 12B:
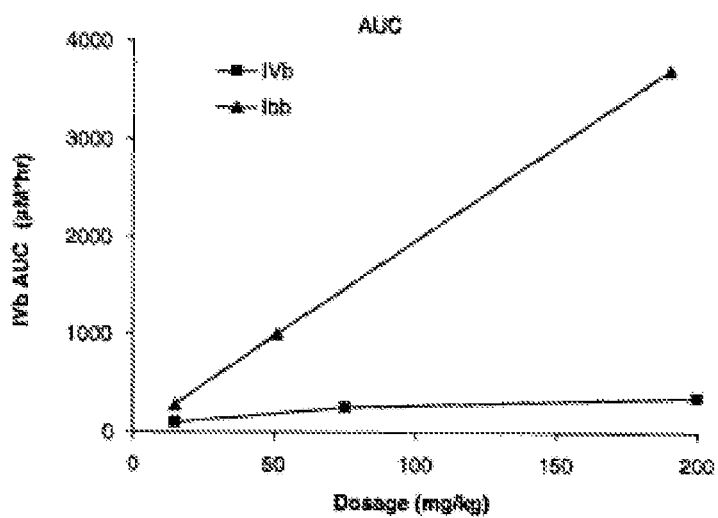

A comparison of IVb Cmax and AUC obtained in rats given either IVb or Ibb, is shown in FIGS. 12A and 12B.

The exposure to IVb is substantially increased following administration of Ibb compared to that achieved after dosing IVb.

Single-Dose Toxicokinetic and Tolerability Study in Dogs

A two-phase study was conducted to evaluate the tolerability of the prodrug, Ibb (monolysine salt) at dosages of 25, 92, or 250 mg/kg (free acid, molar equivalent to 20, 74, or 201 mg/kg of parent IVb, respectively) and the toxicokinetics of Ibb and IVb (1). On day 1, Ibb was administered to one dog/sex/group once daily in dry-filled capsules at the above dosages. A 1-week washout period was used between doses in the study. On day 8, Ibb was administered to one dog/sex/group once daily as an aqueous solution at 25 mg/kg or twice daily in dry-filled capsules at 46 or 125 mg/kg BID. The endpoints were: clinical signs, body weight, food consumption, serum chemistry, hematology and plasma toxicokinetics of Ibb and IVb.

The plasma toxicokinetic values from individual dogs are shown in Table 29.

Figure 13A:
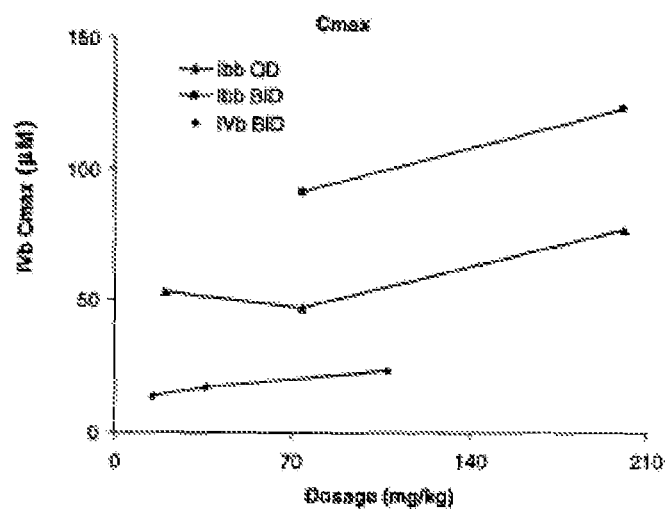
FIGS. 13A and 13B illustrates Comparison of IVb Cmax and AUC in Dogs Given Either IVb or Ibb.
Figure 13B:
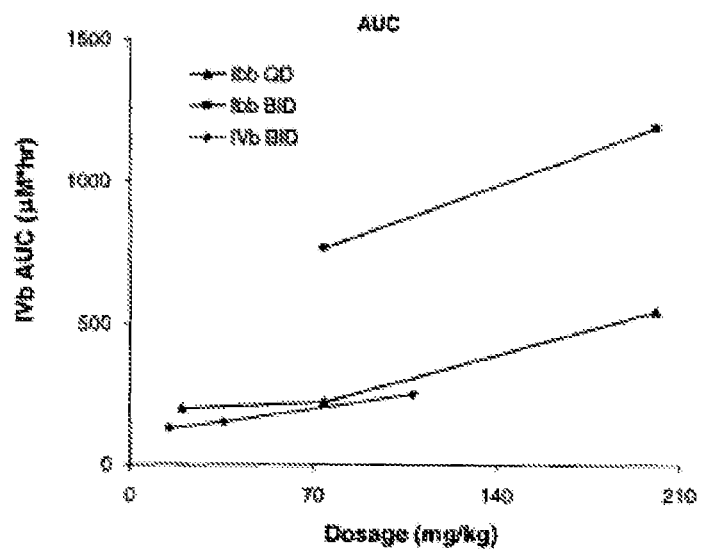

A comparison of IVb AUC obtained in dogs given either Ibb or IVb (2), is shown in FIGS. 13A and 13B.

The absolute oral bioavailability of IVb, parent compound, after administration of aqueous solutions of Ibb-03, the phosphate prodrug, ranged from 50% to 310% in rats, dogs, and monkeys. These calculations are based on historical IV data. The exposure of IVb, after oral administration of aqueous solutions of the prodrug, Ibb-03, dosed up to 190 mg/kg of IVb equivalent is 3-10 fold higher in the rat oral dose escalation study as compared to the historical data with IVb. When Ibb-03 is dosed BID as drug in capsule in dogs, 2-3 fold improvement in exposure is achieved compared to historical data from pre-ECN toxicology studies with BID dosing of IVb as suspensions. The in vivo exposure data from drug in capsule formulations suggests that oral expo-

TABLE 29

Toxicokinetic values for IVb in dogs given ≤250 mg/kg of Ibb

| | Dosages (mg/kg) | | | | | |
|---|---|---|---|---|---|---|
| Ibb | 25[1] | | 92[2] | | 250[3] | |
| IVb molar equiv. | 20 | | 75 | | 203 | |
| Animal | 2101M | 2201F | 3101M | 3201F | 4101M | 4201F |
| Cmax (µM) | | | | | | |
| day 1 | 72 | 34 | 28[4] | 66[4] | 61[4] | 93[4] |
| day 8 | 56 | 33 | 74[4] | 108[5] | 158[5] | 88[4,5] |
| $C_{24h}$ (µM) | | | | | | |
| day 1 | 0.008 | 0.688 | 1.90 | 0.202 | 2.61 | 0.704 |
| day 8 | 0.547 | 0.107 | 10.6 | 0.307 | 54.2 | 1.96 |
| $AUC_{0-\infty}$ (µM · h) | | | | | | |
| day 1 | 259 | 136 | 111[4] | 329[4] | 334[4] | 745[4] |
| day 8 | 324 | 139 | 478[4] | 1053[5] | 1393[5] | 978[4,5] |
| T1/2 (h) | | | | | | |
| day 1 | 1.5 | 4.5 | 3.6 | 2.3 | 4.1 | 3.2 |
| day 8 | 3.3 | 3.4 | 5.2 | 2.4 | 8.0 | 3.3 |

[1]Formulated as dry-filled capsules on day 1 and as an aqueous solution on day 8 formulated (QD dosing on both days)
[2]As 92 mg/kg QD on day 1 and as 46 mg/kg BID on day 8; formulated as dry-filled capsules on both days
[3]As 250 mg/kg QD on day 1 and as 125 mg/kg BID on day 8; formulated as dry-filled capsules on both days
[4]Emesis observed within 2 hours of dosing with capsule remnant present
[5]Emesis observed within 2 hours of dosing with no capsule remnant Low levels (0.9 µM) of Ibb were detected in some plasma samples on days 1 and 8. Mean maximum plasma concentration (Cmax) of IVb was achieved between 1-4 hours post-dose for QD dosing, and 1-2 hours post-second dose for BID dosing. At 25 mg/kg QD, equivalent Cmax and AUC of IVb was observed when Ibb was administered as either dry-filled capsules or an aqueous solution. On day 1, emesis (white, streaked with red that contained capsule remnants) was observed at about 0.5-1.25 hours after dosing in all dogs given ≥92 mg/kg QD (3101M, 3201F, 4101M, and 4201F), which likely contributed to the flat exposure between 92 and 250 mg/kg. On day 8, emesis (white or brown) was observed within 2 hours after dosing in all dogs given 46 mg/kg BID; capsule remnants were only observed in vomitus of two dogs (3101M post-first dose and 4201F post second dose). Twice-daily dosing provided greater exposure to IVb in dogs than once daily dosing.

Other than emesis, there were no clinical signs observed, and there were no effects on body weight and food consumption.

Despite the emesis observed in dogs, a higher IVb AUC is observed in dogs given Ibb than that in dogs given IVb.

sure of IVb in humans could be significantly improved by administration of traditional solid oral dosage forms of Ibb.

Ibb is the phosphate prodrug of the N-hydroxymethyl adduct of IVb and is hydrolyzed by alkaline phosphatase (ALP) to form IVb. After administration of Ibb to animals, therefore, plasma samples were prepared from blood collected in the presence of EDTA, a known ALP inhibitor. Conversion of Ibb to IVb was minimal (<2%) in the blood containing EDTA (rat, dog, monkey and human). No significant ex vivo conversion of Ibb is expected during sample storage (−20° C.) and analysis of Ibb.

The hydrolysis of Ibb was studied in animal and human in vitro systems. Since multiple ALP isoforms are widely distributed in various tissues, quantitative in vitro to in vivo correlations were not attempted (Fishman et al., 1968; Komoda et al., 1981; Moss, 1983; Yora and Sakagishi, 1986; Sumikawa et al., 1990). Therefore, the studies were limited to a qualitative assessment of ALP-dependent hydrolysis in different tissues. Ibb was hydrolyzed in the presence of serum (rat, dog, monkey and human), hepatocytes (rat, dog and human) as well as in human placental ALP. No turnover was observed in monkey hepatocytes. The conversion of Ibb to IVb was near stoichiometric. Due to hydrolysis in serum, the protein binding of Ibb could not be determined.

Ibb was completely hydrolyzed to form IVb in Caco-2 cells and, as expected, very low levels of Ibb were detected in rat, dog and monkey plasma after oral administration of Ibb. These data are consistent with reports describing the high levels of ALP expression in the gut (McComb et al., 1979a; Butterworth, 1983). The membrane-bound ALP is mostly localized in the brush border membranes of the microvilli lining the intestinal lumen (Butterworth, 1983; Testa and Mayer, 2003). It is likely that following oral administration of Ibb, Ibb is hydrolyzed by ALP present at the brush border membranes of the intestinal lumen to form IVb, which is rapidly absorbed due to its high permeability.

Although different isoforms of ALP exist in different tissues and species, the substrate specificity for ALP is relatively broad (Heimbach et al., 2003), which is consistent with the above findings for Ibb.

IVb was rapidly formed following IV administration of Ibb in rats, dogs and monkeys. The IV AUC conversion ratios were 0.62 in rats, 1.6 in dogs and 1.7 in monkeys, suggesting satisfactory to good conversion from Ibb to IVb.

Good oral bioavailabilities (50-310%; calculated using the historical IV AUC of IVb) of IVb were observed after administration of Ibb in rats, dogs and monkeys. More significantly, the higher aqueous solubility of Ibb lessened the dissolution-rate limited absorption of IVb and thereby increased the exposures of IVb in oral dose escalation and toxicokinetic studies as compared to the exposures from the historical IVb studies (Discovery Toxicology section Tables 28-29 and FIG. 12-13).

Methods

The studies described in this report used the mono-lysine salt of Ibb.

Quantitation of Ibb and IVb by LC/MS/MS

An LC/MS/MS method was developed for the analysis of Ibb and IVb in plasma samples from the animal pharmacokinetic studies as well as in acetonitrile supernatant from in vitro incubation studies. For the analysis in plasma, a Packard Multiprobe instrument was used to transfer 50 μL of each standard, QC, and plasma sample to a clean 96-well plate for protein precipitation extraction. After the addition of 200 μL of acetonitrile containing the internal standard IVc, the samples were vortex mixed and the resulting supernatant was separated from the precipitated proteins by centrifugation for 10 min. For the analysis in the supernatant generated from the in vitro studies, an equal volume of the supernatant and acetonitrile containing the internal standard was mixed. An aliquot of the above supernatant was transferred using a Tomtec automated liquid handler to a second clean 96-well plate. An equal volume of water was added, and the plate was capped and vortex mixed.

The HPLC system consisted of Shimadzu LC10ADvp pumps (Columbia, Md.) and a HTC PAL autosampler (Leap Technologies, Cary, N.C.) linked to a Phenomenex Synergi Fusion-RP analytical column (2.0×50 mm, 5 s; Torrance, Calif.). Mobile phase A consisted of 5 mM ammonium formate in water; mobile phase B was 100% acetonitrile. LC flow rate was 0.38 mL/min. The initial mobile phase composition was 2% B, ramped to 50% B over 1.8 min and held for 0.5 min, ramped to 100% B over 0.1 min and held for 0.5 min, returned to initial conditions over the next 0.1 min, and re-equilibrated. Total analysis time was 4.0 min. The retention time for Ibb, IVb and IVc was 1.42, 2.21 and 1.73 min, respectively.

The HPLC system was interfaced to a Sciex API4000 triple quadrupole mass spectrometer (Toronto, Canada) equipped with the Turboionspray source set at 550° C. and the ionspray voltage set to 4.5 kV. UHP nitrogen was used as nebulizer and auxiliary gas with the pressure of 80 psi and 7 L/min, respectively. The collision energies for Ibb, IVb and IVc were 19, 25 and 29 volts, respectively. Data acquisition utilized selected reaction monitoring (SRM). Ions representing the positive ion mode $(M+H)^+$ species for Ibb, IVb and the internal standard were selected in MS1 and collisionally dissociated with nitrogen and optimized collision energies to form specific product ions subsequently monitored by MS2. The SRM transitions for Ibb, IVb and IVc were m/z 558→432, 448→202 and 474→256, respectively.

Standard curves ranging from 5 nM to 10 μM were prepared from stock solutions and serially diluted in matrix for both Ibb and IVb. Standard curves were aliquoted in duplicate, extracted with the samples, and injected at the beginning, middle, and end of the analytical sequence. The standard curves were fitted with a linear regression weighted by reciprocal concentration $1/x^2$. Data and chromatographic peaks were processed and concentrations of standards and unknowns were quantitated using PEBiosystems Analyst™ 1.1.

In Vitro Methods (1) Stability of Ibb in EDTA Blood Serum and Tris-HCl Buffer

The stability of Ibb was studied in fresh blood and serum from rat, dog, monkey and human (n=2). The blood was collected in vacutainers containing $K_2EDTA$ (Becton Dickinson, Franklin Lakes, N.J.). The serum was collected in vacutainers containing no anticoagulant. Ibb was incubated at a starting concentration of approximately 15 μM for 90 min at 37° C. Serial samples were taken at the pre-determined times. Aliquots of blood samples (200 μL) were first mixed with 100 μL of water followed by 400 μL of acetonitrile. The serum samples (50 μL) were added into microtainers containing $K_2EDTA$ (Becton Dickinson, Franklin Lakes, N.J.) followed by the addition of 100 μL of acetonitrile. The supernatant was analyzed for both Ibb and IVb by LC/MS/MS.

The stability of Ibb was also evaluated, as described above, in Tris-HCl buffer (0.1 M, pH 7.5).

(2) Hydrolysis of Ibb in the Presence of Human Placental ALP

Solid human placental ALP was obtained from Sigma (P-3895, St. Louis, Mo.). A solution of 1000 units/L was prepared in Tris-HCl buffer (0.1 M, pH 7.5). Solutions of 100 and 10 units/L were obtained by serial dilution. Ibb was incubated in the 10, 100 and 1000 units/L solutions (n=2) at 37° C. for 2 hr. The starting concentration of Ibb in the incubation was 10 μM. Aliquots of 100 μL samples were taken at pre-determined times and added into $K_2EDTA$ microtainers followed by the addition of 200 μL of acetonitrile. The supernatant was analyzed for both Ibb and IVb by LC/MS/MS.

In Vivo Studies

All blood samples (0.3 mL) were collected in microtainers containing $K_2EDTA$ (Becton Dickinson, Franklin Lakes, N.J.) and placed on chipped ice. After centrifugation, plasma was separated and stored at −20° C. until analysis. The mono-lysine salt of Ibb (Form 3) was used for the pharmacokinetic studies. The dosing solutions of Ibb were prepared in either sterile water (for IV administration in dogs and monkeys) or distilled water (for all other dose administration).

(1) In Vivo Studies in the Rat

Male Sprague-Dawley rats (300-350 g, Hilltop Lab Animals, Inc., Scottsdale, Pa.) with cannulas implanted in the jugular vein were used. The rats were fasted overnight in the PO pharmacokinetic studies. Blood samples were collected from the jugular vein.

In the IV study, Ibb was delivered at 1.3 mg/kg (free acid, or 1.0 mg/kg of IVb equivalent) as a bolus over 0.5 min (n=3). The concentration of the dosing solution was 1.3 mg/mL, and the dosing volume was 1 mL/kg. Serial blood samples were collected before dosing and at 2, 10, 15, 30, 45 min, 1, 2, 4, 6, 8 and 24 hr after dosing.

In the PO study, Ibb was administered at 6.6 mg/kg (free acid, or 5.2 mg/kg of IVb equivalent) by oral gavage (n=3). The concentration of the dosing solution was 1.3 mg/mL, and the dosing volume was 5 mL/kg. Serial blood samples were collected before dosing and at 15, 30, 45 min, 1, 2, 4, 6, 8 and 24 hr after dosing.

(2) In Vivo Studies in the Dog

The IV and PO studies of Ibb were conducted in male beagle dogs (10±0.78 kg, Marshall Farms USA Inc., North Rose, N.Y.). Three dogs were used in each study. Of the three dogs, two same dogs were used for both IV and PO studies. There was a two-week washout period between the IV and PO studies.

In the IV study, Ibb was infused via the cephalic vein at 1.3 mg/kg (free acid, or 1.0 mg/kg of IVb equivalent) over 5 min at a constant rate of 0.1 mL/kg/min. The concentration of the dosing solution was 2.6 mg/mL, and the dosing volume was 0.5 mL/kg. Serial blood samples were collected from the femoral artery before dosing and at 5, 10, 15, 30, 45 min, 1, 2, 4, 6, 8 and 24 hr after dosing.

In the PO study, the dogs were fasted overnight before dosing. Ibb was administered by oral gavage at 7.0 mg/kg (free acid, or 5.6 mg/kg of IVb equivalent). The concentration of the dosing solution was 7.0 mg/mL, and the dosing volume was 1 mL/kg. Serial blood samples were collected before dosing and at 15, 30, 45 min, 1, 2, 4, 6, 8 and 24 hr after dosing.

(3) In Vivo Studies in the Monkey

The IV and PO studies of Ibb were conducted in a crossover fashion in three male cynomolgus monkeys (9.9±2.4 kg, Charles River Biomedical Research Foundation, Houston, Tex.). There was a two-week washout period between the IV and PO studies.

In the IV study, Ibb was infused via the femoral vein at 1.3 mg/kg (free acid, or 1.1 mg/kg of IVb equivalent) over 5 min at a constant rate of 0.1 mL/kg/min. The concentration of the dosing solution was 2.7 mg/mL, and the dosing volume was 0.5 mL/kg. Serial blood samples were collected from the femoral artery before dosing and at 5, 10, 15, 30, 45 min, 1, 2, 4, 6, 8 and 24 hr after dosing.

In the PO study, the monkeys were fasted overnight before dosing. Ibb was administered by oral gavage at 5.8 mg/kg (free acid, or 4.7 mg/kg of IVb equivalent). The concentration of the dosing solution was 5.8 mg/mL, and the dosing volume was 1 mL/kg. Serial blood samples were collected before dosing and at 15, 30, 45 min, 1, 2, 4, 6, 8 and 24 hr after dosing.

(4) Data Analysis

All results are expressed as mean±SD, unless specified otherwise.

The pharmacokinetic parameters of Ibb and IVb were calculated by Non-Compartmental Analysis using the KINETICA™ software program (version 4.0.2, InnaPhase Co., Philadelphia, Pa.). The Cmax and Tmax values were recorded directly from experimental observations. The $AUC_{0-n}$ and $AUC_{tot}$ values were calculated using the mixed log-linear trapezoidal summations. The total body clearance (Cl), mean residence time (MRT), and the steady state volume of distribution (Vss) were also calculated after intravenous administration. The absolute oral bioavailability (expressed as %) was estimated by taking the ratio of dose-normalized AUC values after oral doses to those after intravenous doses.

The in vitro intrinsic clearance of Ibb in hepatocytes ($Cl_{int}$) was calculated as follows:

$$Cl_{int} \text{ (µL/min/million cells)} = \text{Rate}/C_E$$

where Rate is the rate of metabolism in hepatocytes (pmol/min/million cells), and CE is the concentration of Ibb in the incubation.

The in vivo intrinsic hepatic clearance of Ibb ($Cl_{int,in\ vivo}$) was calculated as follows:

$$Cl_{int,in\ vivo} \text{ (mL/min/kg)} = Cl_{int} \times \frac{120 \text{ (million cells)}}{\text{g liver}} \times \frac{\chi \text{ g liver}}{\text{kg body weight}} \times \frac{1}{1000}$$

where χ is 40, 32, 30 and 26 g liver/kg body weight for the rat, dog, monkey and human, respectively (Davis and Morris, 1993).

The hepatic clearance $Cl_H$ was calculated from the following equation using the well-stirred model:

$$Cl_H \text{ (mL/min/kg)} = \frac{Qh \times Cl_{int,in\ vivo}}{Qh + Cl_{int,in\ vivo}}$$

where Qh is the liver blood flow of 55, 31, 44 and 21 mL/min/kg for the rat, dog, monkey and human, respectively (Davis and Morris, 1993).

The hepatic extraction ration (ER) was calculated at follows:

$$ER = Cl_H/Qh$$

Student's t-test was used for statistical analysis (Microsoft® Excel, Redmond, Wash.). Differences were considered statistically significant at the level of P<0.05.

In Vitro Studies

Stability of Ibb in EDTA Blood Serum and Tris-HCl Buffer

As part of the analytical assay validation, the stability of Ibb was studied in blood containing EDTA, which is known to be an inhibitor of ALP (Bowers, Jr. and McComb, 1966; Yora and Sakagishi, 1986). After incubation at 37° C. for 90 min, there was less than 2% conversion of Ibb to IVb in blood containing EDTA and in the presence of Tris-HCl buffer (Tables 30 and 31). The above small percentages of conversion observed at 37° C. indicate that conversion under the sample storage conditions (−20° C.) is unlikely. Therefore, relatively minimal ex vivo conversion to IVb is expected during the analysis of Ibb.

TABLE 30

Stability of Ibb in the Fresh EDTA Blood from Rat, Dog and Monkey

| Time (min) | Rat Blood (n = 2) | | | Dog Blood (n = 2) | | | Monkey Blood (n = 2) | | |
|---|---|---|---|---|---|---|---|---|---|
| | Ibb (μM) | IVb Formed (μM) | % IVb Formed * | Ibb (μM) | IVb Formed (μM) | % IVb Formed * | Ibb (μM) | IVb Formed (μM) | % IVb Formed * |
| 0 | 15 | 0.23 | 1.6 | 13 | 0.089 | 0.68 | 16 | 0.075 | 0.47 |
| 15 | 15 | 0.22 | 1.5 | 12 | 0.079 | 0.60 | 19 | 0.12 | 0.76 |
| 30 | 18 | 0.26 | 1.7 | 15 | 0.085 | 0.65 | 18 | 0.13 | 0.80 |
| 45 | 15 | 0.29 | 1.9 | 16 | 0.095 | 0.73 | 18 | 0.13 | 0.82 |
| 60 | 16 | 0.31 | 2.0 | 13 | 0.088 | 0.67 | 19 | 0.14 | 0.86 |
| 90 | 17 | 0.32 | 2.1 | 16 | 0.11 | 0.82 | 17 | 0.14 | 0.89 |

* Percentage formed as the starting concentration of Ibb.

TABLE 31

Stability of Ibb in the Fresh EDTA Blood from Human, and Tris-HCl Buffer

| Time (min) | Human Blood (n = 2) | | | Tris-HCl Buffer (n = 2) | | |
|---|---|---|---|---|---|---|
| | Ibb (μM) | IVb Formed (μM) | % IVb Formed * | Ibb (μM) | IVb Formed (μM) | % IVb Formed * |
| 0 | 16 | 0.099 | 0.62 | 14 | 0.30 | 2.2 |
| 15 | 15 | 0.093 | 0.58 | 12 | 0.30 | 2.1 |
| 30 | 16 | 0.097 | 0.60 | 13 | 0.33 | 2.3 |
| 45 | 16 | 0.11 | 0.67 | 12 | 0.41 | 2.9 |
| 60 | 16 | 0.10 | 0.65 | 13 | 0.51 | 3.7 |
| 90 | 18 | 0.12 | 0.73 | 12 | 0.51 | 3.6 |

* Percentage formed as the starting concentration of Ibb.

To investigate the hydrolysis of Ibb in the systemic circulation, Ibb was incubated in fresh serum (rat, dog, monkey and human) at 37° C. for 90 min. The rate of hydrolysis was most rapid in the monkey serum, followed by human, dog and rat sera (Table 3). The conversion of Ibb to IVb was near stoichiometric.

Serum contains lower ALP activities as compared to tissues (McComb et al., 1979a). In addition, serum also contains ALP isoforms from tissue sources such as bone, liver and intestine, as a result of enzyme leakage through the blood vessels (Moss, 1983). Therefore, the hydrolysis of Ibb in serum was probably mediated by multiple isoforms of ALP.

Hydrolysis of Ibb in the Presence of Human Placental ALP

Figure 14:
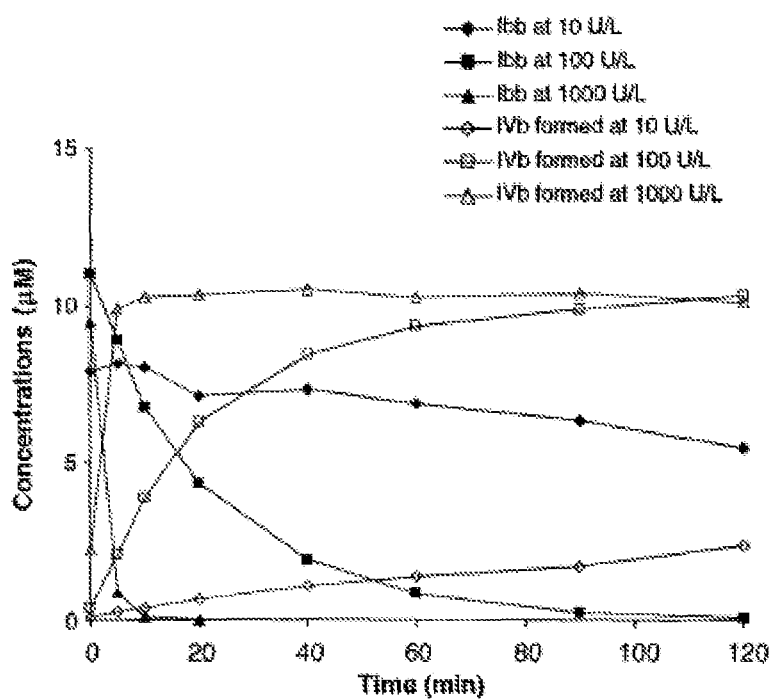
FIG. 14 illustrates Hydrolysis of Ibb in Human Placental ALP Solutions and the Formation of IVb.

To study the hydrolysis of Ibb in a purified form of human ALP, Ibb was incubated at 37° C. (2 hr) with solutions containing human placental ALP (10, 100 and 1000 units/L). The disappearance $t_{1/2}$ of Ibb was determined (Table 4). As expected, the rate of hydrolysis was faster in the solutions with higher ALP activities. IVb was also formed accordingly (FIG. 14). This indicates that Ibb is hydrolyzed by the ALP derived from humans to form IVb.

TABLE 32

Stability of Ibb in the Fresh Serum from Rat, Dog, Monkey and Human

| Time (mm) | Rat Serum (n = 2) | | Dog Serum (n = 2) | | Monkey Serum (n = 2) | | Human Serum (n = 2) | |
|---|---|---|---|---|---|---|---|---|
| | Ibb (μM) | IVb Formed (μM) | Ibb (μM) | IVb Formed (μM) | Ibb (μM) | IVb Formed (μM) | Ibb (μM) | IVb Formed (μM) |
| 0 | 12 | 0.095 | 13 | 0.13 | 14 | 0.34 | 13 | 0.14 |
| 15 | 9.4 | 0.33 | 12 | 0.66 | 6.6 | 6.5 | 9.0 | 0.96 |
| 30 | 9.2 | 0.60 | 11 | 1.2 | 3.1 | 8.5 | 10 | 2.0 |
| 45 | 9.4 | 0.92 | 10 | 1.7 | 1.7 | 10 | 10 | 3.1 |
| 60 | 9.3 | 1.3 | 10 | 2.4 | 0.85 | 11 | 8.0 | 3.6 |
| 90 | 9.0 | 2.2 | 8.9 | 3.6 | 0.22 | 13 | 6.5 | 5.0 |
| $t_{1/2}$ (min)* | 704** | | 167** | | 15 | | 75 | |

*Calculated as the disappearance of Ibb.
**The half-lives are greater than the incubation period.

TABLE 33

Hydrolysis of Ibb in Human Placental ALP Solutions

|  | ALP Activity (Units/L) (n = 2) | | |
| --- | --- | --- | --- |
|  | 10 | 100 | 1000 |
| $t_{1/2}$ (min) | 198 | 16 | 2.0 |

Note:
Ibb was incubated at a starting concentration of 10 μM at 37° C. for 120 min.

In Vivo Studies
In Vivo Studies in the Rat

Figure 15:
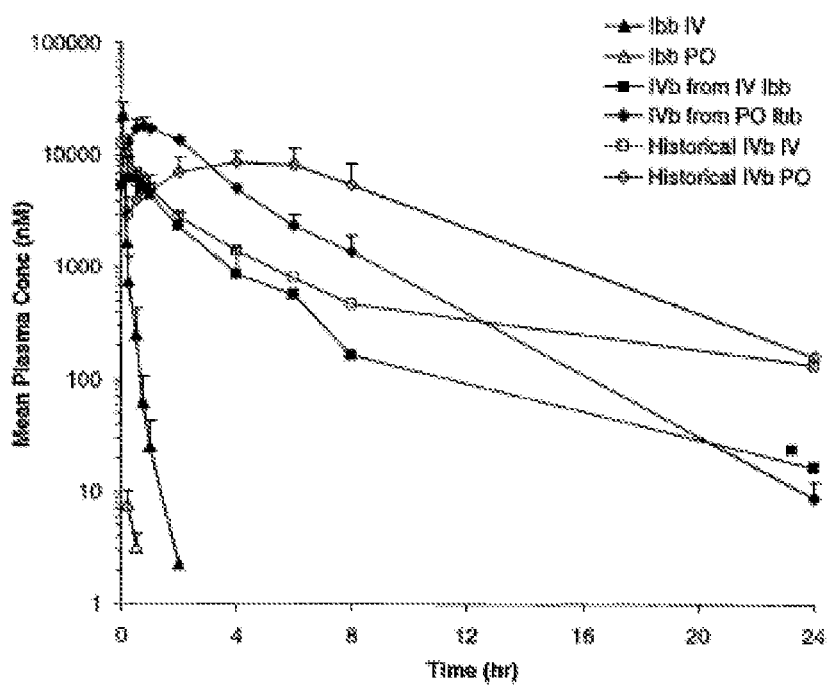
FIG. 15 illustrates Plasma Concentration Versus Time Profiles of Ibb and IVb Following IV and Oral Administration of Ibb in the Rat and the Historical Data of IVb in the Rat.

The pharmacokinetic parameters of Ibb and IVb in rats after IV and oral administration of Ibb are summarized in Table 34. The plasma concentration versus time profiles are shown in FIG. 15. For comparison, the historical data from the pharmacokinetic studies of IVb in rats are also shown.

The total body clearance (Cl) of Ibb following IV administration was 19 mL/min/kg, suggesting that Ibb is a low to moderate clearance compound in rats. The elimination half-life ($t_{1/2}$) and mean residence time (MRT) after IV administration were 0.18 hr and 0.079 hr, respectively. Iab was not detected beyond 2 hr. The volume of distribution of Ibb at steady state (Vss) was 0.10 L/kg, suggesting very limited tissue distribution. The formation of IVb from Ibb after IV administration was rapid; IVb was detected at the first sampling time point of 2 min (data not shown). The IV AUC ratio of IVb formed from Ibb vs. from the historical IVb study was 0.62 (theoretical value for complete conversion=1), indicating satisfactory conversion of Ibb to IVb in rats after IV dosing.

Ibb was detected (<10 nM) in the plasma (0.25 and 0.5 hr) after oral administration. The Tmax of IVb after oral administration of Ibb was 0.83 hr, which is shorter than the historical Tmax of IVb of 4.7 hr, indicating more rapid absorption of IVb following the oral administration of the prodrug. The more rapid absorption of IVb from the prodrug is likely the result of better aqueous solubility of Ibb as well as rapid hydrolysis of Ibb to form IVb in the intestine. The absolute oral bioavailability of IVb from Ibb was 50%, similar to the historical IVb value of 60% (Table 34). Moreover, the exposure of IVb from the Ibb rat oral dose escalation study was superior as compared to the historical data with IVb (Table 31 and FIG. 14).

TABLE 34

Pharmacokinetic Parameters of Ibb and IVb Following IV and Oral Administration of Ibb in the Rat (Mean ± SD, n = 3)

| PK Parameters | Ibb (03-002) | IVb Formed after Dosing with Ibb | Historical IVb |
| --- | --- | --- | --- |
| IV | | | |
| Dose (mg/kg) | 1.3 free acid or 1.0 of IVb eqv. | | 1 |
| $AUC_{tot}$ (μM * hr) | 2.5 ± 1.4 | 15 ± 5.4 | 24 ± 3.2 |
| $CL_{tot}$ (mL/min/kg) | 19 ± 8.9 | NA | 1.6 ± 0.20 |
| $T_{1/2}$ (hr) | 0.18 ± 0.050 | 3.0 ± 1.8 | 5.9 ± 4.9 |
| MRT (hr) | 0.079 ± 0.041 | NA | 5.6 ± 3.6 |
| Vdss (L/kg) | 0.10 ± 0.093 | NA | 0.49 ± 0.26 |
| IV IVb AUC Ratio | NA | 0.62 * | NA |
| PO | | | |
| Dose (mg/kg) | 6.6 free acid or 5.2 of IVb eqv. | | 5 |
| Tmax (hr) | 0.25 | 0.83 ± 0.14 | 4.7 ± 1.2 |
| Cmax (μM) | 0.008 ± 0.003 | 19 ± 1.8 | 9.5 ± 2.8 |

TABLE 34-continued

Pharmacokinetic Parameters of Ibb and IVb Following IV and Oral Administration of Ibb in the Rat (Mean ± SD, n = 3)

| PK Parameters | Ibb (03-002) | IVb Formed after Dosing with Ibb | Historical IVb |
| --- | --- | --- | --- |
| C-24 hr (μM) | ND | 0.009 ± 0.004 | 0.16 (n = 2) |
| $AUC_{tot}$ (μM * hr) | ND | 62 ± 3.3 | 86 ± 33 |
| $T_{1/2}$ (hr) | ND | 2.2 ± 0.11 | 3.7 ± 0.86 |
| Bioavailability (%) | ND | 50 ** | 60 |
| PO IVb AUC Ratio | NA | 0.69 * | NA |

NA—not applicable;
ND—not detected (<5 nM).
* The ratios were calculated from IVb AUC after prodrug dosing/IVb AUC after IVb dosing for IV and PO, respectively.
** Calculated from historical IV data of IVb.

In Vivo Studies in the Dog

Figure 16:
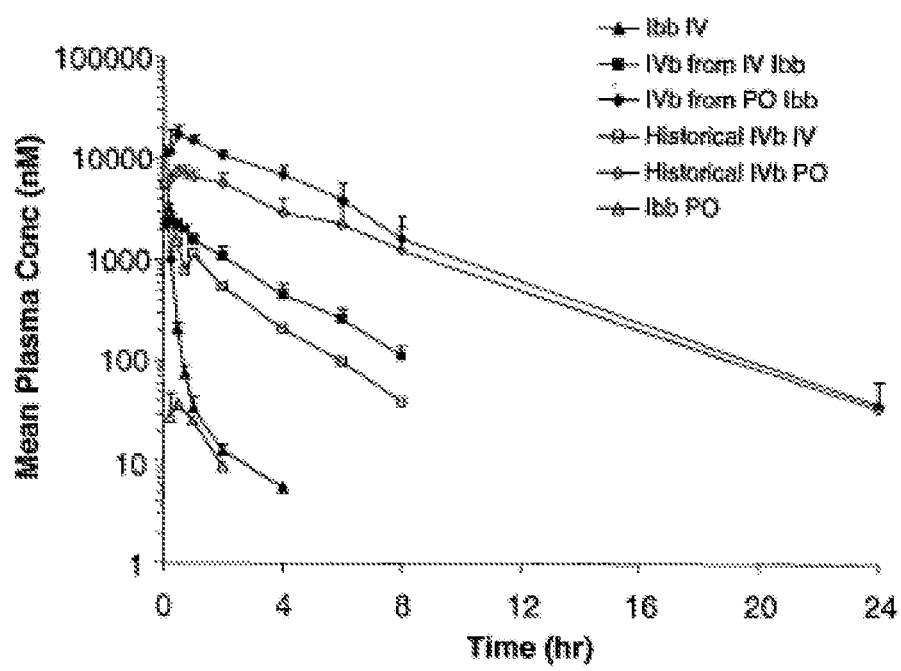
FIG. 16 illustrates Plasma Concentration Versus Time Profiles of Ibb and IVb Following IV and Oral Administration of Ibb in the Dog and the Historical Data of IVb in the Dog.

The pharmacokinetic parameters of Ibb and IVb in dogs after IV and oral administration of Ibb are summarized in Table 35. The plasma concentration versus time profiles are shown in FIG. 16. For comparison, the historical data from the pharmacokinetic studies of IVb in dogs are also shown.

The Cl of Ibb after IV administration was 27 mL/min/kg, similar to the liver blood flow of 31 mL/min/kg in dogs, suggesting that Ibb is a high clearance compound in dogs. The tin and MRT after IV administration were 0.83 hr and 0.21 hr, respectively. The MRT reflected a more realistic estimate of the duration of Ibb in the plasma since the plasma concentrations of Ibb in the terminal phase were low (FIG. 3). Ibb was not detected beyond 4 hr. The Vss of Ibb was 0.35 L/kg, suggesting limited tissue distribution. The formation of IVb from Ibb after IV administration was rapid; IVb was detected at the first sampling time point of 5 min (data not shown). The IV AUC ratio of IVb formed from Ibb vs. from the historical IVb study was 1.6, suggesting complete conversion of Ibb to IVb in dogs after IV administration.

Ibb was detected (Cmax=0.034 nM) in plasma samples at early time points (up to 2 hr in one dog) following oral administration. The Tmax of IVb after oral administration of Ibb was 0.40 hr, similar to the historical Tmax of IVb of 0.50 hr. The absolute oral bioavailability of IVb from Ibb was 310%, similar to the historical IVb data of 179%. Moreover, the exposure of IVb from the Ibb dog tolerability study (dose escalation) was greater when compared to the historical data with IVb (Table 31 and FIG. 15).

The terminal plasma concentration vs. time profiles of IVb formed from Ibb are similar to the historical IVb profiles (FIG. 16).

TABLE 35

Pharmacokinetic Parameters of Ibb and IVb Following IV and Oral Administration of Ibb in the Dog (Mean ± SD, n = 3)

| PK Parameters | Ibb | IVb Formed after Dosing with Ibb | Historical IVb |
| --- | --- | --- | --- |
| IV | | | |
| Dose (mg/kg) | 1.3 free acid (03-001) or 1.0 of IVb eqv. | | 1 (n = 2) |
| $AUC_{tot}$ (μM * hr) | 1.4 ± 0.18 | 6.2 ± 0.80 | 3.8 |
| $CL_{tot}$ (mL/min/kg) | 27 ± 3.2 | NA | 9.8 |
| $T_{1/2}$ (hr) | 0.83 ± 0.58 | 2.0 ± 0.21 | 1.6 |
| MRT (hr) | 0.21 ± 0.043 | NA | 1.8 |
| Vdss (L/kg) | 0.35 ± 0.091 | NA | 1.1 |
| IV IVb AUC Ratio | NA | 1.6* | NA |

TABLE 35-continued

Pharmacokinetic Parameters of Ibb and IVb Following IV and
Oral Administration of Ibb in the Dog (Mean ± SD, n = 3)

| PK Parameters | Ibb | IVb Formed after Dosing with Ibb | Historical IVb |
|---|---|---|---|
| PO | | | |
| Dose (mg/kg) | 7.0 free acid (03-002) or 5.6 of IVb eqv. | | 5 (n = 3) |
| Tmax (hr) | 0.33 ± 0.14 | 0.40 ± 0.13 | 0.50 ± 0.25 |
| Cmax (µM) | 0.034 ± 0.018 | 20 ± 2.4 | 7.7 ± 0.71 |
| C-24 hr (µM) | ND | 0.037 ± 0.026 | 0.034 (n = 2) |
| $AUC_{tot}$ (µM * hr) | 0.059 (n = 1) | 66 ± 17 | 30 ± 11 |
| $T_{1/2}$ (hr) | NA | 2.6 ± 0.21 | 2.7 ± 0.40 |
| Bioavailability (%) | NA | 310** | 179 ± 56 |
| PO IVb AUC Ratio | NA | 2.2* | NA |

Figure 17:
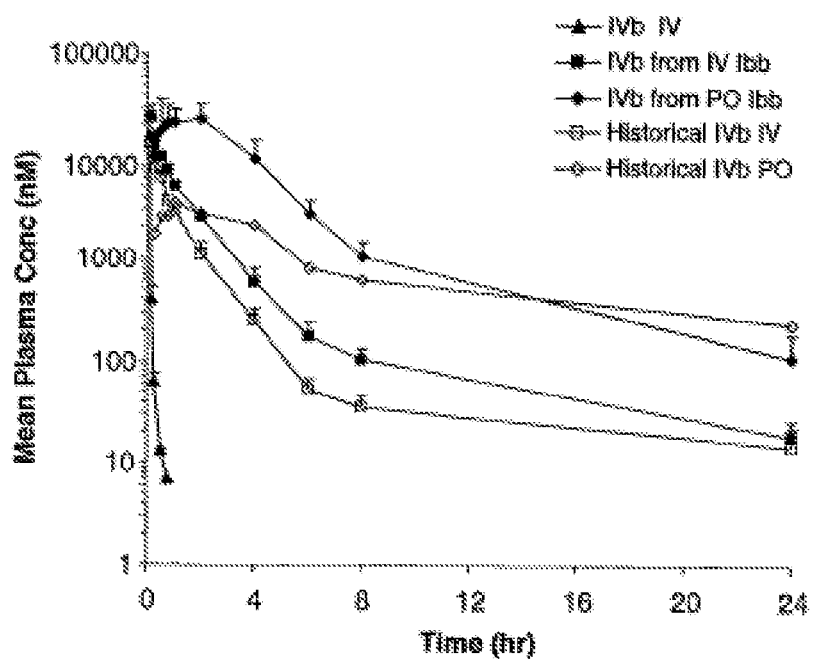
FIG. 17 illustrates Plasma Concentration Versus Time Profiles of Ibb and IVb Following IV and Oral Administration of Ibb in the Monkey and the Historical Data of IVb in the Monkey.

*The ratios were calculated from IVb AUC after prodrug dosing/IVb after IVb dosing for IV and PO, respectively.
**Calculated from historical IV data of IVb In Vivo Studies in the Monkey The pharmacokinetic parameters of Ibb and IVb in monkeys following IV and oral administration of Ibb are summarized in Table 36. The plasma concentration versus time profiles are shown in FIG. 17. For comparison, the historical data from the pharmacokinetic studies of IVb in monkeys are also shown.

The Cl of Ibb after IV administration was 28 mL/min/kg, suggesting that Ibb is a moderate to high clearance compound in monkeys. The tin and MRT after IV administration were 0.10 hr and 0.093 hr, respectively. The Vss of Ibb was 0.15 L/kg, suggesting very limited tissue distribution. The formation of IVb from Ibb after IV administration was rapid; IVb was detected at the first sampling time point of 5 min (data not shown). The IV AUC ratio of IVb formed from Ibb vs. from the historical IVb study was 1.7, suggesting complete conversion of Ibb to IVb in monkeys after IV dosing.

Ibb was not detected (LLQ=5 nM) in any plasma samples after oral administration. The Tmax of IVb after oral administration of Ibb was 1.5 hr, similar to the historical Tmax of IVb of 2.5 hr. The absolute oral bioavailability of IVb from Ibb was 187%, which is higher that the historical IVb data of 49% (Table 36).

The terminal plasma concentration vs. time profiles of IVb formed from Ibb are similar to the historical IVb profiles (FIG. 17).

TABLE 36

Pharmacokinetic Parameters of Ibb and IVb Following IV and
Oral Administration of Ibb in the Monkey (Mean ± SD, n = 3)

| PK Parameters | Ibb | IVb Formed after Dosing with Ibb | Historical IVb |
|---|---|---|---|
| IV | | | |
| Dose (mg/kg) | 1.3 free acid or 1.1 of IVb eqv. | | 1 (n = 3) |
| $AUC_{tot}$ (µM * hr) | 1.5 ± 0.40 | 19 ± 1.8 | 10 ± 1.2 |
| $CL_{tot}$ (mL/min/kg) | 28 ± 6.8 | NA | 3.7 ± 0.43 |
| $T_{1/2}$(hr) | 0.10 ± 0.042 | 6.5 ± 2.4 | 19 ± 20 |
| MRT (hr) | 0.093 ± 0.00076 | NA | 5.6 ± 6.3 |
| Vdss (L/kg) | 0.15 ± 0.039 | NA | 1.2 ± 1.4 |
| IV IVb AUC Ratio | NA | 1.7* | NA |
| PO | | | |
| Dose (mg/kg) | 5.8 free acid or 4.7 of IVb eqv. | | 5 (n = 2) |

TABLE 36-continued

Pharmacokinetic Parameters of Ibb and IVb Following IV and
Oral Administration of Ibb in the Monkey (Mean ± SD, n = 3)

| PK Parameters | Ibb | IVb Formed after Dosing with Ibb | Historical IVb |
|---|---|---|---|
| Tmax (hr) | NA | 1.5 ± 0.87 | 2.5 |
| Cmax (µM) | ND | 31 ± 11 | 4.2 |
| C-24 hr (µM) | ND | 0.11 ± 0.075 | 0.24 |
| $AUC_{tot}$ (µM * hr) | ND | 88 ± 4.6 | 24 |
| $T_{1/2}$ (hr) | NA | 4.1 ± 1.1 | 11 |
| Bioavailability (%) | NA | 187** | 49 |
| PO IVb AUC Ratio | NA | 3.4* | NA |

*The ratios were calculated from IVb AUC after prodrug dosing/IVb for AUC after IVb dosing IV and PO, respectively.
**Calculated from historical IV data of IVb Profiling Section 3:

Additional Studies with Prodrug Icb

Single-Dose Toxicokinetic Tolerability Study in CD Rats

A 1-day oral toxicokinetic study in rats was conducted using the prodrug Icb (disodium salt). Icb was administered at dosages of 5, 25, and 200 mg/kg (free acid) by oral gavage to three male rats/group using water as the vehicle (solution formulation). The dosages of prodrug free acid correspond to IVc (parent) molar equivalent dosages of 4.5, 21, and 163 mg/kg, respectively. The endpoint evaluated was plasma toxicokinetics of Icb and IVc in the individual rats.

The mean toxicokinetic values are provided in Table 37.

TABLE 37

Mean toxicokinetic values for Icb and IVc in male rats
given ≤200 mg/kg of Icb as a single oral dose

| | Dosages (mg/kg) | | |
|---|---|---|---|
| Icb | 5 | 25 | 200 |
| IVc molar equiv. | 4.5 | 21 | 163 |
| | IVc | IVc | IVc |
| Cmax (µM) | 29 | 98 | 281 |
| $C_{24h}$ (µM) | 0.029 | 0.35 | 58 |
| AUC (µM · h) | 109[1] | 586[1] | 2925[2] |
| T1/2 (h) | 3.2 | 2.3 | 3.4 |

Values represent means from three rats/group for Icb data and 3 rats/group for IVc data.
[1]AUC from zero to ∞
[2]AUC from zero to 24 h Mean maximum plasma concentration (Cmax) of IVc (parent) was achieved within ≈1.7 hour post-dose. In rats given ≤267 mg/kg of Icb, the increase in AUC of IVc was nearly proportional with Icb dosage, and Cmax increased in a less than dosage-proportional manner between 25 and 200 mg/kg of Icb. Icb was not detected in plasma of rats given ≤25 mg/kg of Icb, and very low concentrations (≈0.02-0.04 µM) were detected in plasma of rats given 200 mg/kg of Icb at a few time points.

Figure 18A:
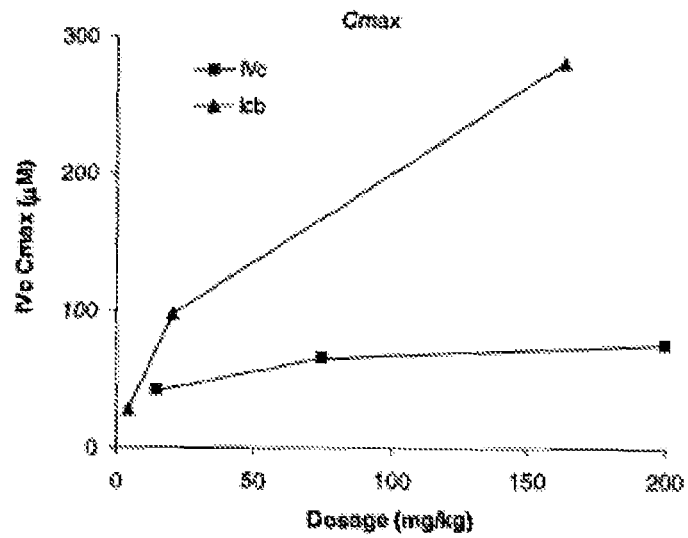
FIGS. 18A and 18B illustrates Comparison of IVc Cmax and AUC in Male Rats Given Either IVc or Icb.
Figure 18B:
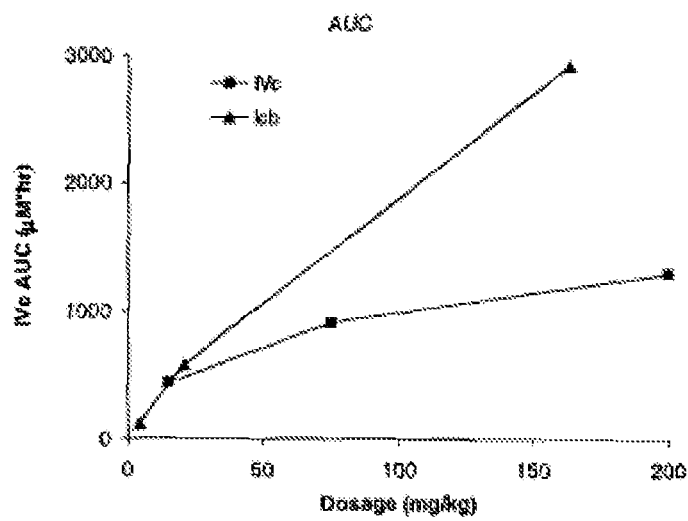

A comparison of IVc AUC obtained in rats given either IVc (1) or Icb, is shown in FIG. 18.

The AUC of IVc is similar after administration of either parent or prodrug at lower dosages (e.g., ≤25 mg/kg) because both can be formulated as solutions (PEG-400/ethanol/0.1N NaOH for parent and water for prodrug) but at a high dosage (e.g., 200 mg/kg) the neutral parent can only be formulated as a suspension whereas the prodrug salt can be formulated as an aqueous solution, which provides superior exposure of IVc.

Single-Dose Toxicokinetic and Tolerability Study in Dogs

A two-phase study was conducted to evaluate the tolerability of the prodrug, Icb (monotromethamine salt) at dosages of 25, 92, or 250 mg/kg (free acid, molar equivalent to 20, 75, or 203 mg/kg of parent IVc, respectively) and the toxicokinetics of Icb and IVc (2). On day 1, Icb was administered to one dog/sex/group once daily in dry-filled capsules at the above dosages. A 1-week washout period was used between doses in the study. On day 8, Icb was administered to one dog/sex/group once daily as an aqueous solution at 25 mg/kg or twice daily in dry-filled capsules at 46 or 125 mg/kg BID. The endpoints were: clinical signs, body weight, food consumption, serum chemistry, hematology and plasma toxicokinetics of Icb and IVc.

The plasma toxicokinetic values from individual dogs are shown in Table 38.

TABLE 38

Toxicokinetic values for IVc in dogs given ≤250 mg/kg of Icb

| | Dosages (mg/kg) | | | | | |
|---|---|---|---|---|---|---|
| Icb | 25[1] | | 92[2] | | 250[3] | |
| IVc molar equiv. | 20 | | 75 | | 203 | |
| Animal | 2101M | 2201F | 3101M | 3201F | 4101M | 4201F |
| Cmax (µM) | | | | | | |
| day 1 | 65.1 | 24.6 | 117[4] | 157 | 92.6[4] | 88.9[4] |
| day 8 | 59.4 | 46.8 | 121 | 104 | 226[5] | 96.9[4] |
| $C_{24\,h}$ (µM) | | | | | | |
| day 1 | 0.008 | 0.688 | 1.90 | 0.202 | 2.61 | 0.704 |
| day 8 | 0.547 | 0.107 | 10.6 | 0.307 | 54.2 | 1.96 |
| $AUC_{0-\infty}$ (µM · h) | | | | | | |
| day 1 | 365 | 122 | 820[4] | 730 | 739[4] | 523[4] |
| day 8 | 362 | 173 | 1137 | 490 | 3783[5] | 596[4,5] |
| T1/2 (h) | | | | | | |
| day 1 | 1.5 | 4.5 | 3.6 | 2.3 | 4.1 | 3.2 |
| day 8 | 3.3 | 3.4 | 5.2 | 2.4 | 8.0 | 3.3 |

[1]Formulated as dry-filled capsules on day 1 and as an aqueous solution on day 8 formulated (QD dosing on both days)
[2]As 92 mg/kg QD on day 1 and as 46 mg/kg BID on day 8; formulated as dry-filled capsules on both days
[3]As 250 mg/kg QD on day 1 and as 125 mg/kg BID on day 8; formulated as dry-filled capsules on both days
[4]Emesis observed within 2 hours of dosing with capsule remnant present
[5]Emesis observed within 2 hours of dosing with no capsule remnant Low levels (≤0.1 µM) of Icb were detected in some plasma samples on days 1 and 8. Mean maximum plasma concentration (Cmax) of IVc was achieved between 1-2 hours post-dose for QD dosing, and 1-2 hours post-second dose for BID dosing. At 25 mg/kg QD, equivalent Cmax and AUC of IVc was observed when Icb was administered as either dry-filled capsules or an aqueous solution. On day 1, emesis (white or brown, streaked with red that contained capsule remnants) was observed at about 1-1.25 hours after dosing in dogs given ≥92 mg/kg QD (3101M, 4101M, and 4201F), which likely contributed to the flat exposure between 92 and 250 mg/kg. On day 8, emesis was observed within 2 hours after dosing in both dogs given 125 mg/kg BID but with different results. Animal 4101M had substantial exposure despite emesis, consistent with the absence of capsule remnant in the vomitus.

Only low levels (≤0.1 µM) of Icb were detected in some plasma samples on days 1 and 8.

Other than emesis, there were no clinical signs observed, and there were no effects on body weight and food consumption.

Figure 19A:
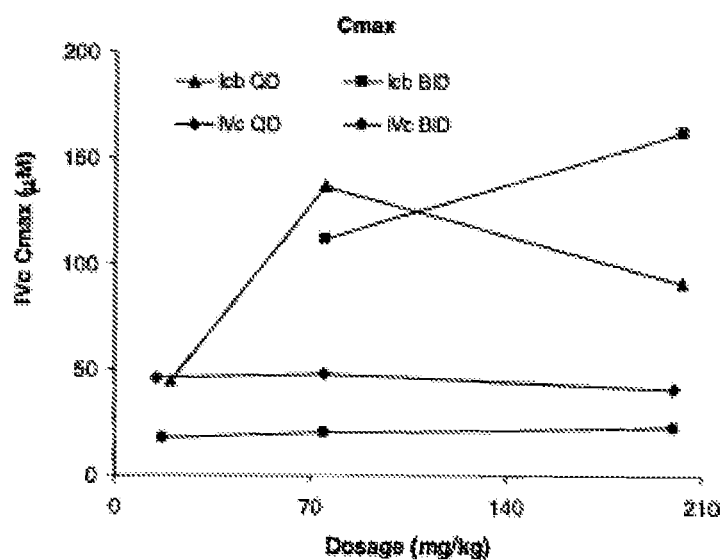
FIGS. 19A and 19B illustrates Comparison of IVc Cmax and AUC in Dogs Given Either IVc or Icb.
Figure 19B:
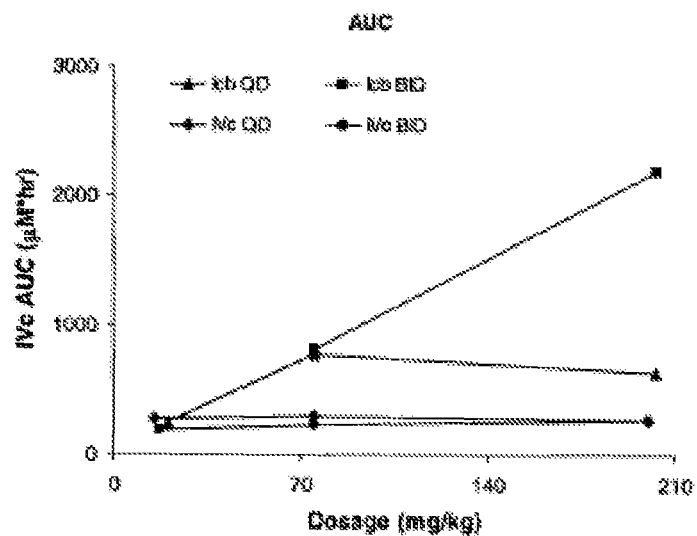

Despite the emesis observed in dogs, a higher IVc AUC is observed in dogs given Icb than that in dogs given IVc. A comparison of IVc AUC obtained in dogs given either Icb or IVc (3, 4), is shown in FIGS. 19A and B.

Vehicles and Formulations

Summary of Formulations Used for Key PK and Safety Studies

All in vivo PK studies in rats, dogs, and monkeys were performed using aqueous solutions for PO and IV dosing. Pre-ECN toxicology studies in dogs were performed with aqueous solutions prepared at 20 mg/kg IVc equivalent dose and as drug in capsule formulations at doses of 20, 75, and 203 mg/kg of IVc equivalents.

In rat oral dose escalation study, Icb-03 was dosed as aqueous solutions at doses of 4.5, 21, and 163 mg/kg of IVc equivalents. Significant improvements in AUC and Cmax of IVc, parent compound, after oral dosing of Icb, the prodrug, were observed compared to the historical data after IVc oral dosing.

Metabolism and Pharmacokinetics Summary

Summary of Findings and Interpretation

Icb is the phosphate prodrug of the N-hydroxymethyl adduct of IVc and is hydrolyzed by alkaline phosphatase (ALP) to form IVc. After administration of Icb to animals, therefore, plasma samples were prepared from blood collected in the presence of EDTA, a known ALP inhibitor. Conversion of Icb to IVc was minimal (<2%) in the blood containing EDTA (rat, dog, monkey and human). No significant ex vivo conversion of Icb is expected during sample storage (−20° C.) and analysis of Icb.

The hydrolysis of Icb was studied in animal and human in vitro systems. Since multiple ALP isoforms are widely distributed in various tissues, quantitative in vitro to in vivo correlations were not attempted (Fishman et al., 1968; Komoda et al., 1981; Moss, 1983; Yora and Sakagishi, 1986; Sumikawa et al., 1990). Therefore, the studies were limited to a qualitative assessment of ALP-dependent hydrolysis in different tissues. Icb was hydrolyzed in the presence of serum (rat, dog, monkey and human), hepatocytes (rat, dog and human) as well as in human placental ALP. No turnover was observed in monkey hepatocytes. The conversion of Icb to IVc was near stoichiometric. Due to hydrolysis in serum, the protein binding of Icb could not be determined.

IVc was rapidly formed following IV administration of Icb in rats, dogs and monkeys. The IV AUC conversion ratios were 1.0 in rats, 0.67 in dogs and 0.90 in monkeys, suggesting good conversion from Icb to IVc.

Good oral bioavailabilities (80-122%) of IVc were observed after administration of Icb in rats, dogs and monkeys. More significantly, the higher aqueous solubility of Icb lessened the dissolution-rate limited absorption of IVc below certain doses and thereby increased the exposures of IVc in oral dose escalation and toxicokinetic studies as compared to the exposures from the historical IVc studies.

Methods

The studies described in this report used the mono-tromethamine salt of Icb, unless stated otherwise.

Quantitation of Icb and IVc by LC/MS/MS

An LC/MS/MS method was developed for the analysis of Icb and IVc in plasma samples from the animal pharmacokinetic studies as well as in acetonitrile supernatant from in vitro incubation studies. For the analysis in plasma, a Packard Multiprobe instrument was used to transfer 50 µL of each standard, QC, and plasma sample to a clean 96-well plate for protein precipitation extraction. After the addition of 200 µL of acetonitrile containing the internal standard Compound X below, the samples were vortex mixed and the resulting supernatant was separated from the precipitated proteins by centrifugation for 10 min. For the analysis in the supernatant generated from the in vitro studies, an equal volume of the supernatant and acetonitrile containing the internal standard was mixed. An aliquot of the above supernatant was transferred using a Tomtec automated liquid handler to a second clean 96-well plate. An equal volume of water was added, and the plate was capped and vortex mixed.

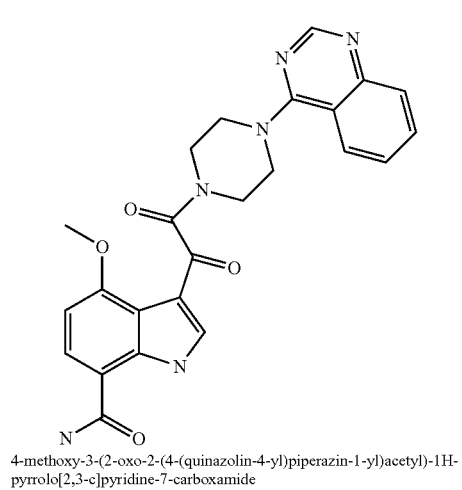

Compound X 4-methoxy-3-(2-oxo-2-(4-(quinazolin-4-yl)piperazin-1-yl)acetyl)-1H-pyrrolo[2,3-c]pyridine-7-carboxamide The HPLC system consisted of Shimadzu LC10ADvp pumps (Columbia, Md.) and a HTC PAL autosampler (Leap Technologies, Cary, N.C.) linked to a Phenomenex Synergi Fusion-RP analytical column (2.0×50 mm, 5µ; Torrance, Calif.). Mobile phase A consisted of 5 mM ammonium formate in water; mobile phase B was 100% acetonitrile. LC flow rate was 0.4 mL/min. The initial mobile phase composition was 3% B, ramped to 60% B over 1.75 min and held for 0.5 min, ramped to 100% B over 0.1 min and held for 0.5 min, returned to initial conditions over the next 0.1 min, and re-equilibrated. Total analysis time was 4.0 min. The retention time for Icb, IVc and Compound X was 1.2, 1.7 and 1.6 min, respectively.

The HPLC system was interfaced to a Sciex API4000 triple quadrupole mass spectrometer (Toronto, Canada) equipped with the Turboionspray source set at 550° C. and the ionspray voltage set to 4.5 kV. UHP nitrogen was used as nebulizer and auxiliary gas with the pressure of 80 psi and 7 L/min, respectively. The collision energies for Icb, IVc and Compound X were 23, 29 and 37 volts, respectively. Data acquisition utilized selected reaction monitoring (SRM). Ions representing the positive ion mode $(M+H)^+$ species for Icb, IVc and the internal standard were selected in MS1 and collisionally dissociated with nitrogen and optimized collision energies to form specific product ions subsequently monitored by MS2. The SRM transitions for Icb, IVc and Compound X were m/z 584→486, 474→256 and 460→218, respectively.

Standard curves ranging from 5 nM to 10 µM were prepared from stock solutions and serially diluted in matrix for both Icb and IVc. Standard curves were aliquoted in duplicate, extracted with the samples, and injected at the beginning, middle, and end of the analytical sequence. The standard curves were fitted with a linear regression weighted by reciprocal concentration $1/x^2$. Data and chromatographic peaks were processed and concentrations of standards and unknowns were quantitated using PEBiosystems Analyst™ 1.1.

In Vitro Methods (1) Stability of Icb in EDTA Blood. Serum and Tris-HCl Buffer

The stability of Icb was studied in fresh blood and serum from rat, dog, monkey and human (n=2). The blood was collected in vacutainers containing $K_2EDTA$ (Becton Dickinson, Franklin Lakes, N.J.). The serum was collected in vacutainers containing no anticoagulant. Icb was incubated at a starting concentration of approximately 10 µM for 90 min at 37° C. Serial samples were taken at the pre-determined times. Aliquots of blood samples (200 µL) were first mixed with 100 µL of water followed by 400 µL of acetonitrile. The serum samples (50 µL) were added into microtainers containing $K_2EDTA$ (Becton Dickinson, Franklin Lakes, N.J.) followed by the addition of 100 µL of acetonitrile. The supernatant was analyzed for both Icb and IVc by LC/MS/MS.

The stability of Icb was also evaluated, as described above, in Tris-HCl buffer (0.1 M, pH 7.5).

(2) Hydrolysis of Icb in the Presence of Human Placental ALP

Solid human placental ALP was obtained from Sigma (P-3895, St. Louis, Mo.). A solution of 1000 units/L was prepared in Tris-HCl buffer (0.1 M, pH 7.5). Solutions of 100 and 10 units/L were obtained by serial dilution. Icb was incubated in the 10, 100 and 1000 units/L solutions (n=2) at 37° C. for 2 hr. The starting concentration of Icb in the incubation was 10 µM. Aliquots of 100 µL samples were taken at pre-determined times and added into $K_2EDTA$ microtainers followed by the addition of 200 µL of acetonitrile. The supernatant was analyzed for both Icb and IVc by LC/MS/MS.

(1) In Vivo Studies in the Rat

Male Sprague-Dawley rats (300-350 g, Hilltop Lab Animals, Inc., Scottsdale, Pa.) with cannulas implanted in the jugular vein were used. The rats were fasted overnight in the PO pharmacokinetic studies. Blood samples were collected from the jugular vein.

In the IV study, Icb was delivered at 1.4 mg/kg (free acid, or 1.1 mg/kg of IVc equivalent) as a bolus over 0.5 min (n=3). The concentration of the dosing solution was 1.4 mg/mL, and the dosing volume was 1 mL/kg. Serial blood samples were collected before dosing and at 2, 10, 15, 30, 45 min, 1, 2, 4, 6, 8 and 24 hr after dosing.

In the PO study, Icb was administered at 6.9 mg/kg (free acid, or 5.6 mg/kg of IVc equivalent) by oral gavage (n=3). The concentration of the dosing solution was 1.4 mg/mL, and the dosing volume was 5 mL/kg. Serial blood samples were collected before dosing and at 15, 30, 45 min, 1, 2, 4, 6, 8 and 24 hr after dosing.

(2) In Vivo Studies in the Dog

The IV and PO studies of Icb were conducted in a crossover fashion in three male beagle dogs (12±2.8 kg, Marshall Farms USA Inc., North Rose, N.Y.). There was a two-week washout period between the IV and PO studies.

In the IV study, Icb was infused via the cephalic vein at 1.3 mg/kg (free acid, or 1.0 mg/kg of IVc equivalent) over 5 min at a constant rate of 0.1 mL/kg/min. The concentration of the dosing solution was 2.6 mg/mL, and the dosing volume was 0.5 mL/kg. Serial blood samples were collected from the femoral artery before dosing and at 5, 10, 15, 30, 45 min, 1, 2, 4, 6, 8 and 24 hr after dosing.

In the PO study, the dogs were fasted overnight before dosing. Icb was administered by oral gavage at 6.0 mg/kg (free acid, or 4.9 mg/kg of IVc equivalent). The concentration of the dosing solution was 12 mg/mL, and the dosing volume was 0.5 mL/kg. Serial blood samples were collected before dosing and at 15, 30, 45 min, 1, 2, 4, 6, 8 and 24 hr after dosing.

(3) In Vivo Studies in the Monkey

The IV and PO studies of Icb were conducted in a crossover fashion in three male cynomolgus monkeys (10±1.6 kg, Charles River Biomedical Research Foundation, Houston, Tex.). There was a two-week washout period between the IV and PO studies.

In the IV study, Icb was infused via the femoral vein at 1.4 mg/kg (free acid, or 1.1 mg/kg of IVc equivalent) over 5 min at a constant rate of 0.1 mL/kg/min. The concentration of the dosing solution was 2.8 mg/mL, and the dosing volume was 0.5 mL/kg. Serial blood samples were collected from the femoral artery before dosing and at 5, 10, 15, 30, 45 min, 1, 2, 4, 6, 8 and 24 hr after dosing.

In the PO study, the monkeys were fasted overnight before dosing. Icb was administered by oral gavage at 4.9 mg/kg (free acid, or 4.0 mg/kg of IVc equivalent). The concentration of the dosing solution was 9.8 mg/mL, and the dosing volume was 0.5 mL/kg. Serial blood samples were collected before dosing and at 15, 30, 45 min, 1, 2, 4, 6, 8 and 24 hr after dosing.

(4) Data Analysis

All results are expressed as mean±SD, unless specified otherwise.

The pharmacokinetic parameters of Icb and IVc were calculated by Non-Compartmental Analysis using the KINETICA™ software program (version 4.0.2, InnaPhase Co., Philadelphia, Pa.). The Cmax and Tmax values were recorded directly from experimental observations. The $AUC_{0-n}$ and $AUC_{tot}$ values were calculated using the mixed log-linear trapezoidal summations. The total body clearance (Cl), mean residence time (MRT), and the steady state volume of distribution (Vss) were also calculated after intravenous administration. The absolute oral bioavailability (expressed as %) was estimated by taking the ratio of dose-normalized AUC values after oral doses to those after intravenous doses.

The in vitro intrinsic clearance of Icb in hepatocytes ($Cl_{int}$) was calculated as follows:

$$Cl_{int} \text{ (µL/min/million cells)} = \text{Rate}/C_E$$

where Rate is the rate of metabolism in hepatocytes (pmol/min/million cells), and $C_E$ is the concentration of Icb in the incubation.

The in vivo intrinsic hepatic clearance of Icb ($Cl_{int,in\ vivo}$) was calculated as follows:

$$Cl_{int.in\ vivo} \text{ (mL/min/kg)} = Cl_{int} \times \frac{120 \text{ (million cells)}}{\text{g liver}} \times \frac{\chi \text{ g liver}}{\text{kg body weight}} \times \frac{1}{1000}$$

where $\chi$ is 40, 32, 30 and 26 g liver/kg body weight for the rat, dog, monkey and human, respectively (Davis and Morris, 1993).

The hepatic clearance $Cl_H$ was calculated from the following equation using the well-stirred model:

$$Cl_H \text{ (mL/min/kg)} = \frac{Qh \times Cl_{int.in\ vivo}}{Qh + Cl_{int.in\ vivo}}$$

where Qh is the liver blood flow of 55, 31, 44 and 21 mL/min/kg for the rat, dog, monkey and human, respectively (Davis and Morris, 1993).

The hepatic extraction ration (ER) was calculated at follows:

$$ER = Cl_H/Qh$$

Student's t-test was used for statistical analysis (Microsoft® Excel, Redmond, Wash.). Differences were considered statistically significant at the level of P<0.05.

In Vitro Studies

Stability of Icb in EDTA Blood Serum and Tris-HC Buffer

As part of the analytical assay validation, the stability of Icb was studied in blood containing EDTA, which is known to be an inhibitor of alkaline phosphatases (Bowers, Jr. and McComb, 1966; Yora and Sakagishi, 1986). After incubation at 37° C. for 90 min, there was less than 2% conversion of Icb to IVc in blood containing EDTA and in the presence of Tris-HCl buffer (Tables 39 and 40). Under the sample storage condition of −20° C., the above small percentages of conversion observed at 37° C. are not expected to introduce any significant ex vivo conversion during the analysis of Icb.

TABLE 39

Stability of Icb in the Fresh EDTA Blood from Rat, Dog and Monkey

| Time (min) | Rat Blood (n = 2) | | | Dog Blood (n = 2) | | | Monkey Blood (n = 2) | | |
|---|---|---|---|---|---|---|---|---|---|
| | Icb (μM) | IVc Formed (μM) | % IVc Formed * | Icb (μM) | IVc Formed (μM) | % IVc Formed * | Icb (μM) | IVc Formed (μM) | % IVc Formed * |
| 0 | 12 | 0.21 | 1.7 | 10 | 0.087 | 0.72 | 12 | 0.26 | 2.2 |
| 15 | 11 | 0.26 | 2.2 | 10 | 0.087 | 0.72 | 12 | 0.17 | 1.4 |
| 30 | 15 | 0.37 | 3.1 | 9.4 | 0.087 | 0.72 | 11 | 0.16 | 1.4 |
| 45 | 14 | 0.38 | 3.2 | 11 | 0.10 | 0.86 | 12 | 0.19 | 1.6 |
| 60 | 14 | 0.41 | 3.4 | 11 | 0.10 | 0.84 | 11 | 0.19 | 1.6 |
| 90 | 12 | 0.39 | 3.3 | 11 | 0.11 | 0.91 | 11 | 0.19 | 1.5 |

* Percentage formed as the starting concentration of Icb

TABLE 40

Stability of Icb in the Fresh EDTA Blood from Human, and Tris-HCl Buffer

| Time (min) | Human Blood (n = 2) | | | Tris-HCl Buffer (n = 2) | | |
|---|---|---|---|---|---|---|
| | Icb (μM) | IVc Formed (μM) | % IVc Formed * | Icb (μM) | IVc Formed (μM) | % IVc Formed * |
| 0 | 11 | 0.083 | 0.69 | 11 | 0.17 | 1.5 |
| 15 | 11 | 0.088 | 0.74 | 11 | 0.18 | 1.5 |
| 30 | 13 | 0.091 | 0.76 | 11 | 0.23 | 1.9 |
| 45 | 12 | 0.10 | 0.80 | 11 | 0.24 | 2.0 |
| 60 | 11 | 0.092 | 0.76 | 10 | 0.26 | 2.2 |
| 90 | 11 | 0.091 | 0.76 | 11 | 0.30 | 2.5 |

* Percentage formed as the starting concentration of Icb

To investigate the hydrolysis of Icb in the systemic circulation, Icb was incubated in fresh serum (rat, dog, monkey and human) at 37° C. for 90 min. The rate of hydrolysis was most rapid in the monkey serum, followed by rat, human and dog sera (Table 41). The conversion of Icb to IVc was near stoichiometric.

Serum contains lower ALP activities as compared to tissues (McComb et al., 1979a). In addition, serum also contains ALP isoforms from tissue sources such as bone, liver and intestine, as a result of enzyme leakage through the blood vessels (Moss, 1983). Therefore, the hydrolysis of Icb in serum was probably mediated by multiple isoforms of ALP.

Hydrolysis of Icb in the Presence of Human Placental ALP

Figure 20:
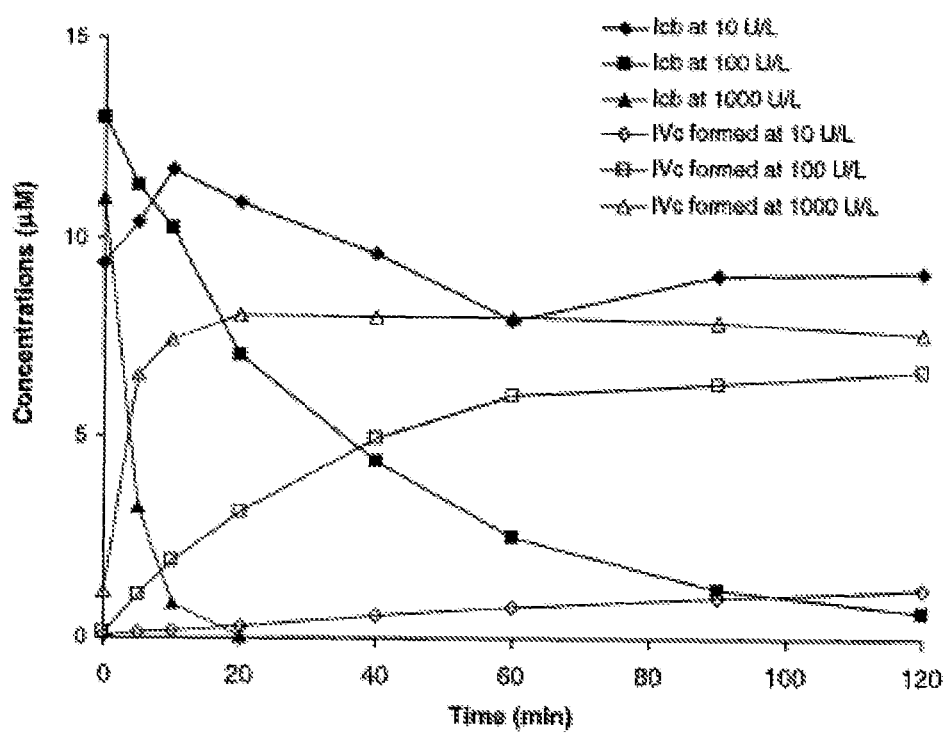
FIG. 20 illustrates Hydrolysis of Icb in Human Placental ALP Solutions and the Formation of IVc.

To study the hydrolysis of Icb in a purified form of human ALP, Icb was incubated at 37° C. (2 hr) with solutions containing human placental ALP (10, 100 and 1000 units/L). The disappearance $t_{1/2}$ of Icb was determined (Table 42). As expected, the rate of hydrolysis was faster in the solutions with higher ALP activities. IVc was also formed accordingly (FIG. 20). This indicates that Icb is hydrolyzed by the ALP derived from humans to form IVc.

TABLE 42

Hydrolysis of Icb in Human Placental ALP Solutions

| | ALP Activity (Units/L) (n = 2) | | |
|---|---|---|---|
| | 10 | 100 | 1000 |
| $t_{1/2}$ (min) | 250 | 29 | 2.4 |

Note:
Icb was incubated at a starting concentration of 10 μM at 37° C. for 120 min.

In Vivo Studies
In Vivo Studies in the Rat

Figure 21:
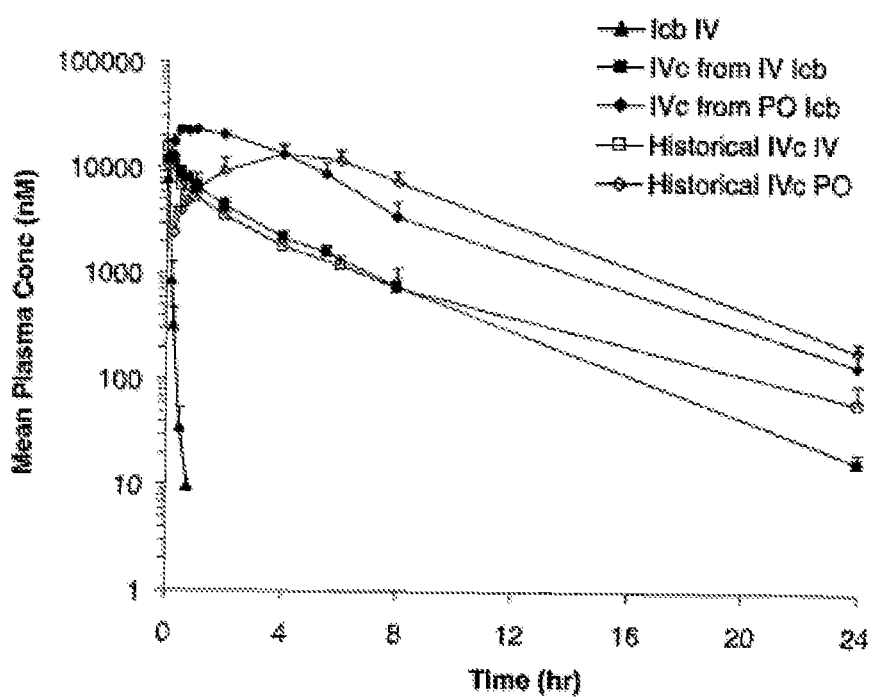
FIG. 21 illustrates Plasma Concentration Versus Time Profiles of Icb and IVc Following IV and Oral Administration of Icb in the Rat and the Historical Data of IVc in the Rat.

The pharmacokinetic parameters of Icb and IVc in rats after IV and oral administration of Icb are summarized in Table 43. The plasma concentration versus time profiles are shown in FIG. 21. For comparison, the historical data from the pharmacokinetic studies of IVc in rats are also shown.

The total body clearance (Cl) of Icb following IV administration was 49 mL/min/kg, suggesting that Icb is a high clearance compound in rats. The elimination half-life ($t_{1/2}$)

TABLE 41

Stability of Icb in the Fresh Serum from Rat, Dog, Monkey and Human

| Time (min) | Rat Serum (n = 2) | | Dog Serum (n = 2) | | Monkey Serum (n = 2) | | Human Serum (n = 2) | |
|---|---|---|---|---|---|---|---|---|
| | Icb (μM) | IVc Formed (μM) | Icb (μM) | IVc Formed (μM) | Icb (μM) | IVc Formed (μM) | Icb (μM) | IVc Formed (μM) |
| 0 | 7.6 | 0.23 | 10 | 0.046 | 9.3 | 0.15 | 10 | 0.087 |
| 15 | 6.5 | 1.4 | 9.7 | 0.52 | 7.1 | 2.4 | 8.8 | 1.2 |
| 30 | 4.9 | 3.4 | 9.1 | 1.5 | 4.5 | 4.8 | 7.7 | 2.7 |
| 45 | 4.4 | 5.6 | 8.5 | 2.3 | 3.3 | 7.2 | 6.6 | 3.9 |
| 60 | 3.4 | 7.1 | 8.1 | 3.0 | 2.3 | 8.4 | 5.9 | 4.6 |
| 90 | 2.1 | 8.7 | 6.9 | 4.0 | 1.1 | 9.6 | 4.7 | 6.1 |
| $t_{1/2}$ (min)* | 42 | | 156** | | 30 | | 89 | |

*Calculated as the disappearance of Icb.
**The half-lives are greater than the incubation period.

and mean residence time (MRT) after IV administration were 0.084 hr and 0.072 hr, respectively. The volume of distribution of Icb at steady state (Vss) was 0.21 L/kg, suggesting very limited tissue distribution. The formation of IVc from Icb after IV administration was rapid; IVc was detected at the first sampling time point of 2 min (data not shown). The IV AUC ratio of IVc formed from Icb vs. from the historical IVc study was 1.0 (theoretical value for complete conversion=1), suggesting complete conversion of Icb to IVc.

Icb was not detected (LLQ=5 nM) in any plasma samples after oral administration. The Tmax of IVc after oral administration of Icb was 0.80 hr, which is shorter than the historical Tmax of IVc of 4.0 hr, indicating more rapid absorption of IVc following the oral administration of the prodrug. The more rapid absorption of IVc from the prodrug is likely the result of better aqueous solubility of Icb as well as rapid hydrolysis of Icb to form IVc in the intestine. The absolute oral bioavailability of IVc from Icb was 80%, similar to the historical IVc value of 82% (Table 43). Moreover, the exposure of IVc from the Icb rat oral dose escalation study was superior as compared to the historical data with IVc (Table 37 and FIGS. 18A and B).

The terminal plasma concentration vs. time profiles of IVc formed from Icb are similar to the historical IVc profiles (FIG. 21).

TABLE 43

Pharmacokinetic Parameters of Icb and IVc Following IV and Oral Administration of Icb in the Rat (Mean ± SD, n = 3)

| PK Parameters | Icb (03-002) | IVc Formed after Dosing with Icb | Historical IVc |
|---|---|---|---|
| IV | | | |
| Dose (mg/kg) | 1.4 free acid or 1.1 of IVc eqv. | | 1 |
| $AUC_{tot}$ (µM * hr) | 0.84 ± 0.24 | 30 ± 4.1 | 27 ± 4.0 |
| $CL_{tot}$ (mL/min/kg) | 49 ± 12 | NA | 1.3 ± 0.19 |
| $T_{1/2}$ (hr) | 0.084 ± 0.012 | 2.9 ± 0.14 | 4.3 ± 1.1 |
| MRT (hr) | 0.072 ± 0.008 | NA | 4.5 ± 0.77 |
| Vdss (L/kg) | 0.21 ± 0.033 | NA | 0.36 ± 0.098 |
| IV IVc AUC Ratio | NA | 1.0* | NA |
| PO | | | |
| Dose (mg/kg) | 6.9 free acid or 5.6 of IVc eqv. | | 5 |
| Tmax (hr) | ND | 0.80 ± 0.30 | 4.0 |
| Cmax (µM) | ND | 23 ± 0.60 | 13 ± 3.6 |
| C-24 hr (µM) | ND | 0.14 ± 0.063 | 0.19 ± 0.048 |
| $AUC_{tot}$ (µM * hr) | ND | 122 ± 17 | 111 ± 25 |
| $T_{1/2}$ (hr) | ND | 3.1 ± 0.42 | 3.0 ± 0.28 |
| Bioavailability (%) | ND | 80** | 82 |
| PO IVc AUC Ratio | NA | 0.98* | NA |

Figure 22:
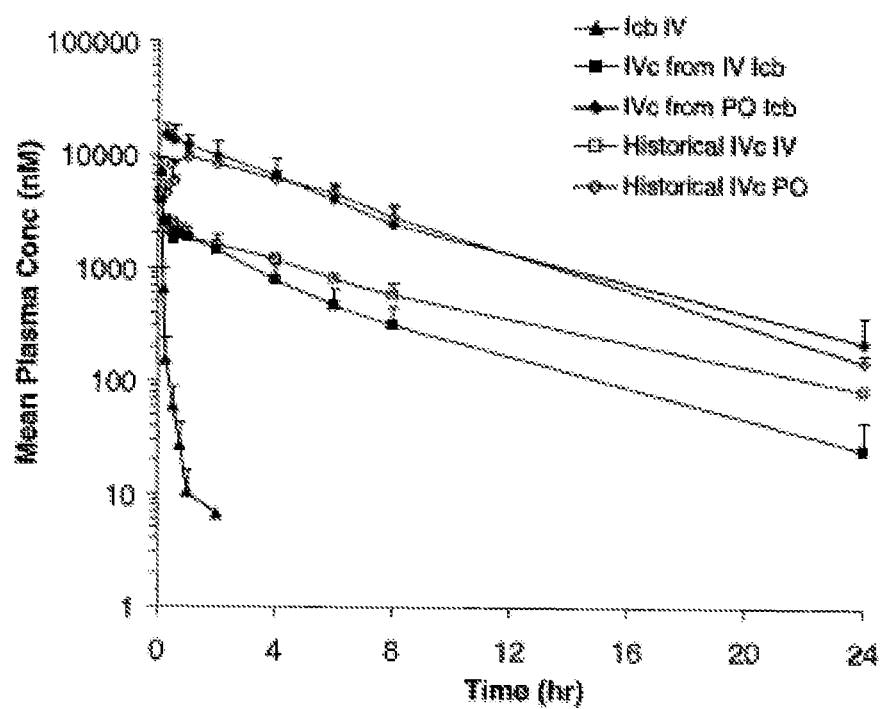
FIG. 22 illustrates Plasma Concentration Versus Time Profiles of Icb and IVc Following IV and Oral Administration of Icb in the Dog and the Historical Data of IVc in the Dog.

NA—not applicable;
ND—not detected (<5 nM).
*The ratios were calculated from IVc AUC after prodrug dosing/IVc AUC after IVc dosing for IV and PO, respectively.
**Calculated from historical IV data of IVc In Vivo Studies in the Dog The pharmacokinetic parameters of Icb and IVc in dogs after IV and oral administration of Icb are summarized in Table 44. The plasma concentration versus time profiles are shown in FIG. 22. For comparison, the historical data from the pharmacokinetic studies of IVc in dogs are also shown.

The Cl of Icb after IV administration was 64 mL/min/kg, significantly higher than the liver blood flow of 31 mL/min/kg in dogs, and suggests the involvement of extrahepatic hydrolysis and/or other route(s) of elimination (e.g., renal excretion). The t1n and MRT after IV administration were 0.25 hr and 0.14 hr, respectively. Icb was not detected beyond 2 hr. The Vss of Icb was 0.50 L/kg, suggesting low potential for tissue distribution. The formation of IVc from Icb after IV administration was rapid; IVc was detected at the first sampling time point of 5 min (data not shown). The IV AUC ratio of IVc formed from Icb vs. from the historical IVc study was 0.67, suggesting moderate conversion of Icb to IVc in dogs after IV administration.

Icb was not detected (LLQ=5 nM) in any plasma samples oral administration. The Tmax of IVc after oral administration of Icb was 0.58 hr, which is shorter than the historical Tmax of IVc of 1.3 hr, indicating more rapid absorption of IVc following the oral administration of the prodrug. The absolute oral bioavailability of IVc from Icb was 104%, similar to the historical IVc data of 89%. Moreover, the exposure of IVc from the Icb dog tolerability study (dose escalation) was better when compared to the historical data with IVc (Table 41 and FIG. 21).

The terminal plasma concentration vs. time profiles of IVc formed from Icb are similar to the historical IVc profiles (FIG. 22).

TABLE 44

Pharmacokinetic Parameters of Icb and IVc Following IV and Oral Administration of Icb in the Dog (Mean ± SD, n = 3)

| PK Parameters | Icb (03-002) | IVc Formed after Dosing with Icb | Historical IVc |
|---|---|---|---|
| IV | | | |
| Dose (mg/kg) | 1.28 free acid or 1.04 of IVc eqv. | | 1 |
| $AUC_{tot}$ (µM * hr) | 0.61 ± 0.20 | 9.8 ± 3.6 | 14 ± 2.5 |
| $CL_{tot}$ (mL/min/kg) | 64 ± 18 | NA | 2.6 ± 0.46 |
| $T_{1/2}$ (hr) | 0.25 ± 0.10 | 4.1 ± 0.54 | 4.6 ± 1.7 |
| MRT (hr) | 0.14 ± 0.021 | NA | 6.3 ± 1.9 |
| Vdss (L/kg) | 0.50 ± 0.088 | NA | 0.93 ± 0.14 |
| IV IVc AUC Ratio | NA | 0.67* | NA |
| PO | | | |
| Dose (mg/kg) | 6.05 free acid or 4.92 of IVc eqv. | | 5 |
| Tmax (hr) | ND | 0.58 ± 0.38 | 1.3 ± 0.58 |
| Cmax (µM) | ND | 16 ± 3.9 | 9.6 ± 0.87 |
| C-24 hr (µM) | ND | 0.22 ± 0.16 | 0.15 ± 0.027 |
| $AUC_{tot}$ (µM * hr) | ND | 72 ± 27 | 63 ± 2.4 |
| $T_{1/2}$ (hr) | ND | 4.2 ± 0.58 | 3.6 ± 0.042 |
| Bioavailability (%) | ND | 104** | 89 ± 12 |
| PO IVc AUC Ratio | NA | 1.2* | NA |

Figure 23:
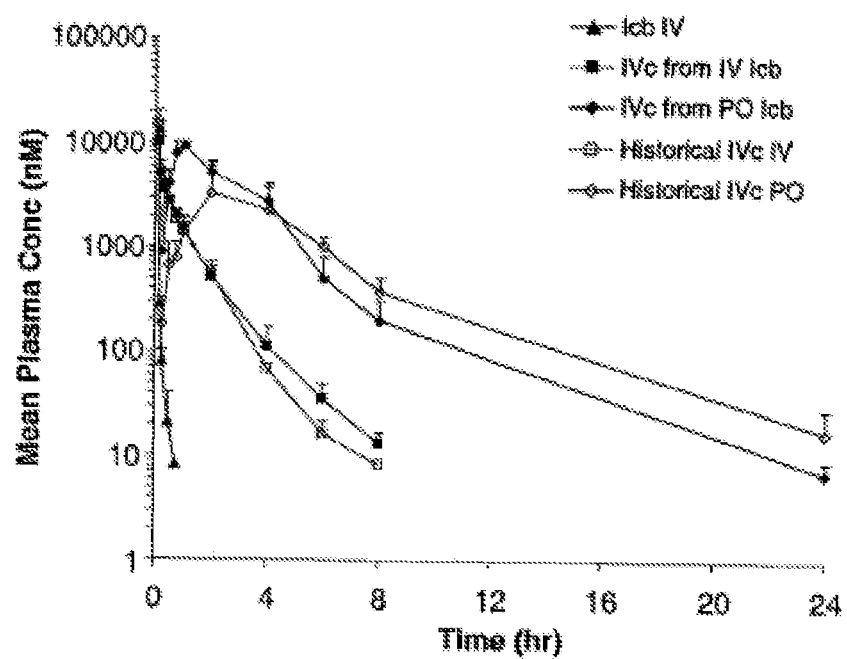
FIG. 23 illustrates Plasma Concentration Versus Time Profiles of Icb and IVc Following IV and Oral Administration of Icb in the Monkey and the Historical Data of IVc in the Monkey.

*The ratios were calculated from IVc AUC after prodrug dosing/IVc AUC after IVc dosing for IV and PO, respectively.
**Calculated from historical IV data of IVc In Vivo Studies in the Monkey The pharmacokinetic parameters of Icb and IVc in monkeys following IV and oral administration of Icb are summarized in Table 45. The plasma concentration versus time profiles are shown in FIG. 23. For comparison, the historical data from the pharmacokinetic studies of IVc in monkeys are also shown.

The Cl of Icb after IV administration was 47 mL/min/kg, similar to the liver blood flow of 44 mL/min/kg in monkeys, suggesting that Icb is a high clearance compound in monkeys. The t1n and MRT after IV administration were 0.089 hr and 0.097 hr, respectively. The Vss of Icb was 0.27 l/kg, suggesting limited tissue distribution. The formation of IVc from Icb after IV administration was rapid; IVc was detected at the first sampling time point of 5 min (data not shown).

The IV AUC ratio of IVc formed from Icb vs. from the historical IVc study was 0.90, suggesting good conversion of Icb to IVc.

Icb was not detected (LLQ=5 nM) in any plasma samples after oral administration. The Tmax of IVc after oral administration of Icb was 0.92 hr, which is shorter than the historical Tmax of IVc of 2.3 hr, indicating more rapid absorption of IVc following the oral administration of the prodrug. The absolute oral bioavailability of IVc from Icb was 122%, which is higher that the historical IVc data of 64% (Table 45).

The terminal plasma concentration vs. time profiles of IVc formed from Icb are similar to the historical IVc profiles (FIG. 23).

TABLE 45

Pharmacokinetic Parameters of Icb and IVc Following IV and Oral Administration of Icb in the Monkey (Mean ± SD, n = 3)

| PK Parameters | Icb (03-002) | IVc Formed after Dosing with Icb | Historical IVc |
|---|---|---|---|
| IV | | | |
| Dose (mg/kg) | 1.4 free acid or 1.1 of IVc eqv. | | 1 |
| $AUC_{tot}$ (μM * hr) | 0.87 ± 0.14 | 5.0 ± 0.57 | 5.0 ± 1.0 |
| $CL_{tot}$ (mL/min/kg) | 47 ± 8.1 | NA | 7.5 ± 1.5 |
| $T_{1/2}$ (hr) | 0.089 ± 0.031 | 1.2 ± 0.063 | 0.92 ± 0.30 |
| MRT (hr) | 0.097 ± 0.003 | NA | 0.87 ± 0.085 |
| Vdss (L/kg) | 0.27 ± 0.043 | NA | 0.40 ± 0.097 |
| IV IVc AUC Ratio | NA | 0.90* | NA |
| PO | | | |
| Dose (mg/kg) | 4.9 free acid or 4.0 of IVc eqv. | | 5 |
| Tmax (hr) | ND | 0.92 ± 0.14 | 2.3 ± 1.5 |
| Cmax (μM) | ND | 9.5 ± 1.2 | 4.2 ± 2.6 |
| C-24 hr (μM) | ND | 0.007 ± 0.002 | 0.017 ± 0.011 |
| $AUC_{tot}$ (μM * hr) | ND | 24 ± 4.6 | 14 ± 4.0 |
| $T_{1/2}$ (hr) | ND | 3.2 ± 0.37 | 3.3 ± 0.53 |
| Bioavailability (%) | ND | 122** | 64 ± 29 |
| PO IVc AUC Ratio | NA | 2.1* | NA |

*The ratios were calculated from IVc AUC after prodrug dosing/IVc AUC after oral dosing for IV and PO, respectively.
**Calculated from historical IV data of IVc Additional Profiling Section 4:
Additional Studies with Prodrug Ie
Prodrug Ie was dosed orally to rats using methodology similar to that described above for the other prodrugs. Following PO dosing, parent molecule IVe was detected in the plasma.

Additional Profiling Section 5:
Additional Studies with Prodrug if
Prodrug If was dosed orally to rats using methodology similar to that described above for the other prodrugs. Following PO dosing, parent molecule IVf was detected in the plasma.

The following Table 47 shows the data contained from oral dosing studies in rats as described in additional profiling sections 4 and 5.

| Compound dosed | If | Ie |
|---|---|---|
| Details and structure of Compound dosed | Phosphate prodrug of IVf<br>PO 1.3 mg/kg<br>(IVfeq)<br>PK of IVf only<br>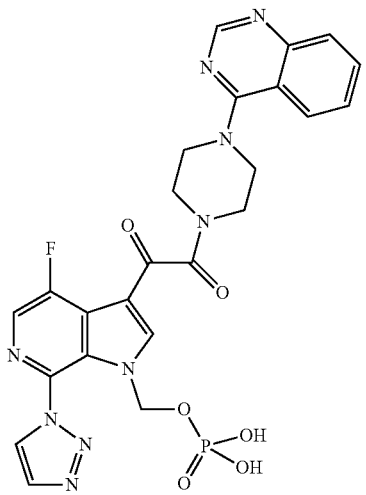 [SMILES: O=C(C(=O)N1CCN(c2ncnc3ccccc23)CC1)c1cn(COP(=O)(O)O)c2c(-n3ccnn3)ncc(F)c12] | Phosphate prodrug of IVe<br>PO 6.0 mg/kg (IVe eq)<br>PK of IVe only<br>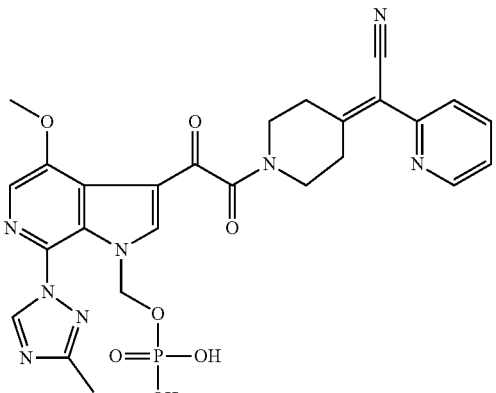 |
| Cmax p.o. (nM) | 2960 ± 859 | 10058 ± 2755 |
| Tmax p.o. (hr) | 1.3 ± 0.66 | 0.58 ± 0.14 |
| F (%) (calc on historical IV data for parent) | 91 | 28 |
| AUC p.o. (μM * hr) | 12.5 ± 5.1 | 22 ± 6.3 |

| | | |
|---|---|---|
| Cp @ 24 hr p.o. (nM) | None detected | 53.9 (1/3 rats) |
| CL i.v. (mL/min/kg) | No IV | No IV |
| Vss i.v. (L/kg) | No IV | No IV |
| T½ p.o. (hr) | 1.9 ± 0.66 | |
| T½ i.v. (hr) | No IV | No IV |
| Compound dosed | II″e | IIe |
| Details and structure of Compound dosed | Monoester prodrug of IVe<br>PO 6.0 mg/kg (IVe eq)<br>PK of IVe only | Diester prodrug of IVe<br>PO 7.0 mg/kg (IVe eq)<br>PK of IVe only |
| Cmax p.o. (nM) | 4678 ± 3295 | 1545 ± 332 |
| Tmax p.o. (hr) | 0.92 ± 0.95 | 3.3 ± 1.2 |
| F (%) (calc on historical IV data for parent) | 11 | 7.7 |
| AUC p.o. (μM * hr) | 8.7 ± 2.7 | 6.9 ± 1.8 |
| Cp @ 24 hr p.o. (nM) | Not detected | 8.17 (1/3 rats) |
| CL i.v. (mL/min/kg) | No IV | No IV |
| Vss i.v. (L/kg) | No IV | No IV |
| T½ p.o. (hr) | | |
| T½ i.v. (hr) | No IV | No IV |

Note
on detection of prodrugs in plasma and other tissues. Once a salt form of a prodrug is administered, it is understood that in the body, scrambling of the salt may occur. However the assays used to quantitate for prodrugs in the subject animal models detetcs by analysis the free acid of the phophate. This analyzing for example a lysine salt Iab or a free acid Iac is assumed to be analyzing for the same species and is not intended to imply that the species detected was actually the lysine salt. In this application, this convention applies to samples obtained from in vivo studies and samples only Biology
"μM" means micromolar;
"mL" means milliliter;
"μW" means microliter,
"mg" means milligram;
"DMSO" means dimethylsulfoxide
The materials and experimental procedures used to assess the anti-HIV activity of the parent compounds which are generated from the prodrugs in vivo are described below:
Cells:
The human T cell line MT-2 and PM1 (AIDS Research and Reference Reagent Program, National Institutes of Health) were maintained and propagated in Medium RPMI-1640 (Invitrogen, Carlsbad, Calif.), containing 10% fetal Bovine serum. (FBS, Sigma, St. Louis, Mo.).
Virus:
Laboratory strains of HIV-1—the T-tropic strain LAI was obtained through the AIDS Research and Reference Reagent Program, National Institutes of Health. It was amplified in MT-2 cells and titered using a virus yield assay (2). Detection was achieved through use of a reverse transcriptase assay (3), adapted for use with a Scintillation Proximity detection protocol (1) (Amersham Biosciences, Piscataway, N.J.).

Experiment
1. Compounds stocks were prepared by dissolving in DMSO to 30 mM. For dilution plates, compounds were serially diluted 3-fold into DMSO, using 96-well polypropylene plates, so that the concentrations were 100-fold greater than the final assay concentration. For antiviral and cytotoxicity assays, 2 μl was added per well (1% final DMSO concentration).
2. Compounds were added from dilution plates to 96 well tissue culture plates, containing 100 μl Medium RPMI-1640, containing 10% fetal bovine serum at a concentration of <20 μM.

3. For antiviral assays, cells were infected at a multiplicity of infection of 0.005. After 1 h at 37° C., infected cells were diluted to 200,000 cells per ml in Medium RPMI-1640, containing 10% fetal bovine serum. 100 µl of this solution was added per well, giving a final volume of 200 µl.
4. Plates were incubated at 37° C. in a humidified $CO_2$ incubator and harvested after 5 days.
5. Viral infections were monitored by measuring reverse transcriptase activity in the supernatants of infected wells as described above. The percent inhibition for each compound was calculated by quantifying the readout level in cells infected in the presence of each compound as a percentage of that observed for cells infected in the absence of compound and subtracting such a determined value from 100.
6. An $EC_{50}$ provides a method for comparing the antiviral potency of the compounds of this invention. The effective concentration for fifty percent inhibition ($EC_{50}$) was calculated with the Microsoft Excel Xlfit curve fitting software. For each compound, curves were generated from percent inhibition calculated at 8 different concentrations by using a four paramenter logistic model (model 205). The $EC_{50}$ data for the compounds is shown in Table 48.

Results

| Biological Data Key for $EC_{50}$s | | | |
|---|---|---|---|
| Compounds with $EC_{50}$s >5 µM | Compounds with $EC_{50}$s >1 uM but <5 µM | Compounds with EC50 >50 nM but not yet tested at higher concentrations | Compounds with EC50 <1 uM |
| Group C | Group B | Group A' | Group A |

TABLE 48

| Antiviral Activity of Compounds IV (Parent Molecules) | | | |
|---|---|---|---|
| Compound IVa | Compound IVb (sodium salt) | Compound IVc (acid form) | Compound IVd (acid form) |
| $EC_{50}$-LAI   A | A | A | A |

The anti-HIV activity of the prodrugs themselves are not relevant since the parent molecules, as shown by the studies below, are generated from the prodrugs in vivo and are the active ingredient and also the major species in the plasma. In addition, the prodrugs may slowly convert to parents in the in vitro assays at least to a limited extent thus complicating interpretation of the antiviral data.

Cytotoxicity

1. Cytotoxicity assays were conducted with the same MT-2 cells, using methodology well known in the art. This method has been described in the literature (4). In brief, cells were incubated in the presence of drug for six days, after which cell viability was measured using a redox-active dye reduction assay. 50 µl of XTT reagent (1 mg/ml 2,3-bis[2-methoxy-4-nitro-5-sulfophenyl]-2H-tetrazolium-5-carboxanilide, 10 µg/ml phenazine methosulfate dissolved in phosphate buffered saline) was added to each well and incubated for 3 hours. Color formation by actively respiring cells was quantitated in a plate reader at 450 nm, and used to determine a $CC_{50}$. The CC50 for IVa, IVb, IVc, and IVd parent molecules were greater than 10 µM when measured by this method. The cytotoxicity data is a secondary screen which shows the compounds are not nonspecifically killing the cells which were used in the antiviral assay and provides further support for the contention that the compounds possess antiviral activity.

Thus, in accordance with the present invention there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically-effective amount of a compound of the present invention.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

What is claimed is:
1. The compound
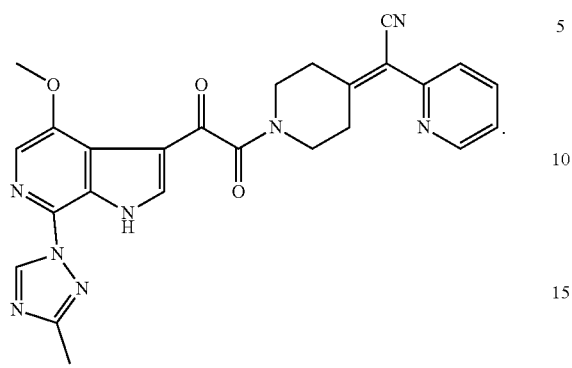

The compounds of this invention can be administered orally to humans in a dosage range of 1 to 100 mg/kg body weight in divided doses. One preferred dosage range is 1 to 10 mg/kg body weight orally in divided doses. Other preferred dosage ranges are 1 to 20 mg/kg and 1 to 30 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.